US008093273B2

(12) United States Patent
Wong et al.

(10) Patent No.: US 8,093,273 B2
(45) Date of Patent: Jan. 10, 2012

(54) FLAVANOIDS AND ISOFLAVANOIDS FOR THE PREVENTION AND TREATMENT OF CARDIOVASCULAR DISEASES

(75) Inventors: Norman C. W. Wong, Calgary (CA); Joseph E. L. Tucker, Calgary (CA); Henrik C. Hansen, Calgary (CA); Fabrizio S. Chiacchia, Calgary (CA); David McCaffrey, Lethbridge (CA)

(73) Assignee: Resverlogix Corp., Calgary, Alberta (CA)

( * ) Notice: Subject to any disclaimer, the term of this patent is extended or adjusted under 35 U.S.C. 154(b) by 1119 days.

(21) Appl. No.: 11/255,103

(22) Filed: Oct. 20, 2005

(65) Prior Publication Data
US 2006/0205767 A1    Sep. 14, 2006

Related U.S. Application Data

(60) Provisional application No. 60/620,888, filed on Oct. 20, 2004, provisional application No. 60/626,819, filed on Nov. 10, 2004, provisional application No. 60/665,859, filed on Mar. 29, 2005.

(51) Int. Cl.
*A01N 43/40* (2006.01)
*A01N 43/42* (2006.01)
*A61K 31/47* (2006.01)

(52) U.S. Cl. ......... 514/352; 514/337; 514/303; 514/309

(58) Field of Classification Search .................. 514/352
See application file for complete search history.

(56) References Cited

U.S. PATENT DOCUMENTS

| | | | |
|---|---|---|---|
| 2,065,593 A | 12/1936 | Lubs | |
| 2,065,900 A | 12/1936 | Laska et al. | |
| 2,071,329 A | 2/1937 | Brown | |
| 3,251,837 A | 5/1966 | Holland et al. | |
| 3,600,394 A | 8/1971 | Coyne et al. | |
| 3,773,946 A | 11/1973 | Creger | |
| 3,930,024 A | 12/1975 | Creger | |
| 4,613,593 A | 9/1986 | Yamatsu et al. | |
| 4,689,344 A | 8/1987 | Bar-Tana | |
| 4,711,896 A | 12/1987 | Bar-Tana et al. | |
| 4,825,005 A | 4/1989 | Frey et al. | |
| 5,124,337 A | 6/1992 | Dugar et al. | |
| 5,126,351 A | 6/1992 | Luzzio et al. | |
| 5,244,904 A | 9/1993 | Nagase et al. | |
| 5,354,749 A | 10/1994 | Dressel et al. | |
| 5,407,942 A | 4/1995 | Dressel et al. | |
| 5,446,071 A | 8/1995 | Grese et al. | |
| 5,480,883 A | 1/1996 | Spada et al. | |
| 5,539,119 A | 7/1996 | Nagase et al. | |
| 5,576,322 A | 11/1996 | Takase et al. | |
| 5,595,974 A | 1/1997 | Tomaru | |
| 5,693,652 A | 12/1997 | Takase et al. | |
| 5,707,987 A | 1/1998 | Nakagawa et al. | |
| 5,733,913 A | 3/1998 | Blankley et al. | |
| 5,756,344 A | 5/1998 | Onda et al. | |
| 5,756,544 A | 5/1998 | Bisgaier et al. | |
| 5,756,736 A | 5/1998 | Arzeno et al. | |
| 5,756,763 A | 5/1998 | Takeuchi et al. | |
| 5,763,414 A | 6/1998 | Bok et al. | |
| 5,783,577 A | 7/1998 | Houghten et al. | |
| 5,792,461 A | 8/1998 | Bok et al. | |
| 5,792,902 A | 8/1998 | Benoit et al. | |
| 5,798,344 A | 8/1998 | Kuroki et al. | |
| 5,801,180 A | 9/1998 | Takase et al. | |
| 5,854,264 A | 12/1998 | Anthony et al. | |
| 5,877,208 A | 3/1999 | Bok et al. | |
| 5,922,866 A | 7/1999 | Miyata et al. | |
| 5,965,556 A | 10/1999 | Takeuchi et al. | |
| 6,022,901 A | 2/2000 | Goodman | |
| 6,048,903 A | 4/2000 | Toppo | |
| 6,054,435 A | 4/2000 | Or et al. | |
| 6,133,241 A | 10/2000 | Bok et al. | |
| 6,165,984 A | 12/2000 | Bok et al. | |
| 6,168,776 B1 | 1/2001 | Klunk et al. | |
| 6,239,114 B1 | 5/2001 | Guthrie et al. | |
| 6,291,456 B1 | 9/2001 | Stein et al. | |
| 6,303,629 B1 | 10/2001 | Kun | |
| 6,414,037 B1 | 7/2002 | Pezzuto et al. | |
| 6,455,577 B2 | 9/2002 | Bok et al. | |
| 6,482,479 B1 | 11/2002 | Dübal et al. | |
| 6,512,161 B1 | 1/2003 | Rouy et al. | |
| 6,541,045 B1 | 4/2003 | Charters et al. | |
| 6,541,522 B2 | 4/2003 | Inman et al. | |

(Continued)

FOREIGN PATENT DOCUMENTS

AU        719140        7/1998

(Continued)

OTHER PUBLICATIONS

Ordovas, J.M., J.M. USDA Human Nutrition Research Center on Aging, Tufts University, Boston MA 02111, USA, see abstract, lines 1-17, p. 69, col. 1, last paragraph, col. 2, top portion, lines 1-18).*
Yamakoshi et al., Isoflavone aglycone-rich extract without soy protein cholesterol-fed rabbits, Journal of Nutrition (2000), 130(8), printed pp. 1-19.*
Schork, N. ( Genetics of Complex Disease, Am. J. Respir. Crit. Care Med., vol. 156, No. 4, Oct. 1997, S103-S109, Printed pp. 1-16).*
English Language Derwent Abstract of DE 197 56 388 A1.
English Language Derwent Abstract of DE 36 01 417.
English Language Derwent Abstract of EP 0 564 350.
English Language Derwent Abstract of EP 210 342 A2.
English Language Derwent Abstract of FR 2 244 493.
Jeong et al., "Hypocholesterolemic Activity of Hesperetin Derivatives," *Bioorganic & Medicinal Chemistry Letters* 13:2663-2665 (2003).

(Continued)

*Primary Examiner* — Sreeni Padmanabhan
*Assistant Examiner* — Timothy Betton
(74) *Attorney, Agent, or Firm* — Finnegan, Henderson, Farabow, Garrett & Dunner, LLP

(57) ABSTRACT

The present disclosure provides non-naturally occurring polyphenol compounds that upregulate the expression of Apolipoprotein A-I (ApoA-I). The disclosed compositions and methods can be used for treatment and prevention of cardiovascular disease and related disease states, including cholesterol or lipid related disorders, such as, e.g., atherosclerosis.

8 Claims, 5 Drawing Sheets

U.S. PATENT DOCUMENTS

| | | |
|---|---|---|
| 6,548,548 B2 | 4/2003 | Campbell et al. |
| 6,635,642 B1 | 10/2003 | Jackson et al. |
| 6,673,780 B2 | 1/2004 | Dasseaux et al. |
| 6,703,422 B2 | 3/2004 | Dasseaux et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 2002/0004608 A1 | 1/2002 | Alig et al. |
| 2002/0091263 A1 | 7/2002 | Trova |
| 2003/0064967 A1 | 4/2003 | Luchoomun |
| 2003/0068526 A1 | 4/2003 | Kamatani et al. |
| 2003/0072964 A1 | 4/2003 | Kwong et al. |
| 2003/0171429 A1 | 9/2003 | Chen et al. |
| 2004/0001834 A1 | 1/2004 | Kim et al. |
| 2004/0033480 A1 | 2/2004 | Wong et al. |
| 2004/0058903 A1 | 3/2004 | Takasugi et al. |
| 2004/0097493 A1 | 5/2004 | Chen et al. |
| 2004/0198750 A1 | 10/2004 | Green et al. |
| 2004/0235888 A1 | 11/2004 | Yamamori et al. |
| 2004/0242615 A1 | 12/2004 | Yamamori et al. |
| 2005/0043300 A1 | 2/2005 | Middleton et al. |
| 2005/0080021 A1 | 4/2005 | Tucker et al. |
| 2005/0080024 A1 | 4/2005 | Tucker et al. |
| 2005/0261319 A1 | 11/2005 | Deuschle et al. |
| 2006/0116364 A1 | 6/2006 | Hamaoka et al. |
| 2006/0205767 A1 | 9/2006 | Wong et al. |
| 2007/0218155 A1 | 9/2007 | Kuhrts |
| 2008/0275069 A1 | 11/2008 | Mizutani et al. |
| 2010/0004448 A1 | 1/2010 | Hansen et al. |
| 2011/0082176 A1 | 4/2011 | Wong et al. |

FOREIGN PATENT DOCUMENTS

| | | |
|---|---|---|
| CA | 2104981 | 3/1994 |
| CA | 2345406 | 4/2000 |
| CN | 1067070 | 2/1997 |
| DE | 637259 | 10/1936 |
| DE | 652772 | 11/1937 |
| DE | 36 01 417 | 7/1987 |
| DE | 42 15 588 | 11/1993 |
| DE | 196 51 099 | 6/1998 |
| DE | 197 56 388 A1 | 6/1999 |
| DE | 199 34 799 | 2/2002 |
| EP | 210 342 A2 | 4/1986 |
| EP | 182 213 | 9/1990 |
| EP | 0 407 217 A1 | 1/1991 |
| EP | 0 258 190 B1 | 11/1991 |
| EP | 488 602 | 6/1992 |
| EP | 272 455 | 2/1993 |
| EP | 0 564 350 | 10/1993 |
| EP | 375 404 | 2/1994 |
| EP | 333 175 | 6/1994 |
| EP | 343 499 | 7/1994 |
| EP | 409 413 | 8/1994 |
| EP | 420 511 | 8/1994 |
| EP | 0 633 022 | 1/1995 |
| EP | 569 795 | 4/1995 |
| EP | 330 108 | 12/1995 |
| EP | 0 747 051 | 12/1996 |
| EP | 643 119 | 4/2000 |
| EP | 1 125 908 A1 | 8/2001 |
| EP | 0 498 723 B1 | 9/2001 |
| EP | 0 607 439 | 1/2002 |
| EP | 776 893 | 2/2002 |
| EP | 1 195 378 | 4/2002 |
| EP | 1 398 032 A1 | 3/2004 |
| EP | 1 418 164 | 5/2004 |
| EP | 1 426 046 | 6/2004 |
| EP | 1 477 481 A1 | 11/2004 |
| EP | 1 637 523 A1 | 3/2006 |
| EP | 2 005 941 A2 | 12/2008 |
| FR | 803201 | 9/1936 |
| FR | 803619 | 10/1936 |
| FR | 2 244 492 | 4/1975 |
| FR | 2 244 493 | 4/1975 |
| GB | 472489 | 3/1936 |
| GB | 728767 | 4/1955 |
| GB | 1 175 808 | 12/1969 |
| GB | 1 179 019 | 1/1970 |
| GB | 2 292 149 | 2/1996 |
| JP | 6-80656 | 3/1994 |
| JP | 7-41442 | 2/1995 |
| JP | 7-61942 | 3/1995 |
| JP | 7-118241 | 5/1995 |
| JP | 7-179380 | 7/1995 |
| JP | 7-233109 | 9/1995 |
| JP | 7-247289 | 9/1995 |
| JP | 1995/247289 | 9/1995 |
| JP | 10-287678 A | 10/1998 |
| JP | 2001/131151 | 5/2001 |
| JP | 2001/139550 | 5/2001 |
| JP | 2001/335476 | 12/2001 |
| JP | 2002/249483 | 6/2002 |
| JP | 2004/307440 | 4/2004 |
| JP | 2004/203751 | 7/2004 |
| KR | 10-0707532 | 4/2007 |
| WO | WO 91/18901 | 12/1991 |
| WO | WO 92/09374 | 6/1992 |
| WO | WO 92/18123 | 10/1992 |
| WO | WO 92/20642 | 11/1992 |
| WO | WO 92/21661 | 12/1992 |
| WO | WO 93/07124 A1 | 4/1993 |
| WO | WO 93/08174 | 4/1993 |
| WO | WO 94/14763 | 7/1994 |
| WO | WO 95/03277 | 2/1995 |
| WO | WO 95/23150 | 8/1995 |
| WO | WO 96/15128 | 5/1996 |
| WO | WO 96/31206 | 10/1996 |
| WO | WO 97/10221 A1 | 3/1997 |
| WO | WO 97/15308 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 | 8/1997 |
| WO | WO 97/48694 | 12/1997 |
| WO | WO 98/11438 A1 | 3/1998 |
| WO | WO 98/26127 | 6/1998 |
| WO | WO 98/30530 | 7/1998 |
| WO | WO 98/50370 A1 | 11/1998 |
| WO | WO 98/51307 | 11/1998 |
| WO | WO 98/51308 | 11/1998 |
| WO | WO 98/55124 | 12/1998 |
| WO | WO 99/00116 | 1/1999 |
| WO | WO 99/11634 | 3/1999 |
| WO | WO 99/18077 | 4/1999 |
| WO | WO 99/29667 | 6/1999 |
| WO | WO00/17184 | 3/2000 |
| WO | WO 00/23075 | 4/2000 |
| WO | WO 00/35865 | 6/2000 |
| WO | WO 00/44362 | 8/2000 |
| WO | WO 00/55168 | 9/2000 |
| WO | WO 00/64888 | 11/2000 |
| WO | WO 01/00554 | 1/2001 |
| WO | WO 01/60775 A1 | 8/2001 |
| WO | WO 01/82916 | 11/2001 |
| WO | WO 01/83456 A1 | 11/2001 |
| WO | WO 02/44189 | 6/2002 |
| WO | WO 02/074307 | 9/2002 |
| WO | WO 02/087556 | 11/2002 |
| WO | WO 02/096426 | 12/2002 |
| WO | WO 03/007959 | 1/2003 |
| WO | WO 03/016292 A1 | 2/2003 |
| WO | WO 03/018008 | 3/2003 |
| WO | WO 03/040256 | 5/2003 |
| WO | WO 03/040257 | 5/2003 |
| WO | WO 03/070236 | 8/2003 |
| WO | WO 03/099274 | 12/2003 |
| WO | WO 03/106435 A1 | 12/2003 |
| WO | WO 2004/017920 | 3/2004 |
| WO | WO 2004/032846 | 4/2004 |
| WO | WO2004/037176 A2 | 5/2004 |
| WO | WO 2004/039795 | 5/2004 |
| WO | WO 2004/047755 | 6/2004 |
| WO | WO 2004/056355 | 7/2004 |
| WO | WO 2004/058717 | 7/2004 |
| WO | WO 2004/065392 A1 | 8/2004 |
| WO | WO 2004/072042 | 8/2004 |

| | | | |
|---|---|---|---|
| WO | WO 2004/092196 A2 | 10/2004 |
| WO | WO 2004/092196 A3 | 10/2004 |
| WO | WO 2004/094452 A2 | 11/2004 |
| WO | WO 2004/094452 A3 | 11/2004 |
| WO | WO 2004/112710 | 12/2004 |
| WO | WO 2005/034960 | 4/2005 |
| WO | WO 2005/065183 A2 | 7/2005 |
| WO | WO 2005/066162 A1 | 7/2005 |
| WO | WO 2005/075431 A1 | 8/2005 |
| WO | WO2005/115993 A1 | 12/2005 |
| WO | WO2006/012577 A2 | 2/2006 |
| WO | WO 2006/045096 A2 | 4/2006 |
| WO | WO 2006/045096 A3 | 4/2006 |
| WO | WO 2006/071095 A1 | 7/2006 |
| WO | WO 2006/105081 A2 | 10/2006 |
| WO | WO 2007/016525 A2 | 2/2007 |
| WO | WO 2007/071055 A1 | 6/2007 |
| WO | WO2010/079431 A2 | 7/2010 |

OTHER PUBLICATIONS

Lamon-Fava, "Genistein Activates Apolipoprotein A-1 Gene Expression in the Human Hepatoma Cell Line Hep G2," *Journal of Nutrition* 130:2489-2492 (2000).

Theriault et al., "Modulation of Hepatic Lipoprotein Synthesis and Secretion by Taxifolin, a Plant Flavonoid," *Journal of Lipid Research* 41:1969-1979 (2000).

Patent Abstracts of Japan English language abstract of JP 2001/131151.

Abstracts of Japan English language abstract of JP 2001/139550.

Patent Abstracts of Japan English language abstract of JP 2001/335476.

International Search Report for priority application PCT/US2005/038048, dated Jan. 31, 2007.

Barter et al., "Antiinflammatory Properties of HDL," *Circ. Res.* 95:764-772 (2004).

Fisher Center for Alzheimer's Research Foundation "Alzheimer's Disease: 'Good' Cholesterol May Help Keep Alzheimer's at Bay," The Ninth International Conference on Alzheimer's Disease and Related Disorders, Philadelphia, PA, Jul. 22, 2004. http://www.alzinfo.org/newsarticle/templates/archivenewstemplate.asp?articleid=156&zoneid=7.

Gaziano et al., "Relation Between Systemic Hypertension and Blood Lipids on the Risk of Myocardial Infarction," *Am. J. Cardiol.* 84(7):768-773 (1999).

Gordon et al., "High Density Lipoprotein As a Protective Factor Against Coronary Heart Disease," *Am. J. Med.* 62:707-714 (1977).

Grundy et al., "Definition of Metabolic Syndrome," *Circulation* 109:433-438 (2004).

Jensen et al., "Serum Lipids and Anthropometric Factors Related to the Prevalence of Intermittent Claudication," *Eur. J. Vasc. Endovasc. Surg.* 30:582-587 (2005).

Kawamatsu et al., "2-Amino-4-phenylthiazole derivatives as anti-atherogenic agents," *Eur. J. Med. Chem.—Chimica Therapeutica* 16(4):355-362 (1981).

Koudinov et al., "Alzheimer's amyloid beta and lipid metabolism: a missing link?," *FASEB* 12:1097-9 (1998).

Maher and Brown, "Lipoprotein (a) and coronary heart disease," *Curr. Opin. Lipidol.* 6:229-235 (1995).

Nissen et al., "Effect of Recombinant ApoA-I Milano on Coronary Atherosclerosis in Patients with Acute Coronary Syndroms: A Randomized Controlled Trial," *JAMA* 290(17):2292-300 (2003).

Plump et al., "Human apolipoprotein A-I gene expression increases high density lipoprotein and suppresses atherosclerosis in the apolipoprotein E-deficient mouse," *Proc. Natl. Acad. Sci. USA* 91:9607-9611 (1994).

Raun et al., "Apolipoprotein A-I possesses an anti-obesity effect associated with increase of energy expenditure and upregulation of UCP1 in brown fat," *J. Cell. Mol. Med.* (2010). "Postprint"; 10.1111/j.1582.4934.2010.01045.x.

Rubin et al., "Expression of human apolipoprotein A-I in transgenic mice results in reduced plasma levels of murine apolipoprotein A-I and the appearance of two new high density lipoprotein size sub-classes," *Proc. Natl. Acad. Sci USA* 88:434-438 (1991).

Rubin et al., "Inhibition of early atherogenesis in transgenic mice by human apolipoprotein AI," *Nature* 353(6341):265-7 (1991).

Rubins et al., "Reduction in Stroke with Gemfibrozil in Men with Coronary Heart Disease and Low HDL Cholesterol," *Circulation* 103:2828-2833 (2001).

Shah et al., "Effects of Recombinant Apolipoprotein A-I $_{Milano}$ on Aortic Atherosclerosis in Apolipoprotein E-Deficient Mice," *Circulation* 97(8):780-5 (1998).

Sharrett et al., "Associations of Lipoprotein Cholesterols, Apolipoproteins A-I and B, and Triglycerides with Carotid Atherosclerosis and Coronary Heart Disease," *Arterioscler. Thromb.* 14:1098-1104 (1994).

Tanne et al., "High-Density Lipoprotein Cholesterol and Risk of Ischemic Stroke Mortaility," *Stroke* 28:83-87 (1997).

Utermann, "The Mysteries of Lipoprotein(a)," *Science* 246:904-910 (1999).

Wei et al., "Total Cholesterol and High Density Lipoprotein Cholesterol as Important Predictors of Erectile Dysfunction," *Am. J. Epidemiol.* 140(10):930-937 (1994).

Welsh and Schultz, "Dyslipidemia In Diabetic Patients," *Prospectives in Cardiology*, Aug. 2002.

Abdul-Rahman, A. et al. "Dinuclear molybdenum complexes derived from diphenols: electrochemical interactions and reduced species" *Polyhedron* 16(24):4353-4362 (1997).

Bayly, S.R. et al. "Electronic and magnetic metal-metal interactions in dinuclear oxomolybdenum(V) complexes across bis-phenolate bridging ligands with different spacers between the pholate termini: ligand-centered vs. metal-centered redox activity" *J. Chem. Soc., Dalton Transactions* 9:1401-1414 (2001).

Bhilare, S.V. et al. "Ionic-Liquid-Influenced Expeditious and Stereoselective Synthesis of Olefins" *Synthetic Communications* 37(18):3111-3117 (2007).

Buhle, E.L. et al. "Trivalent carbon. II. Unsymmetrical hexaaryldimethylperoxides" *J. Am. Chem. Soc.* 65:584-586 (1943).

Clarkson et al. "Inhibition of Postmenopausal Atherosclerosis Progression: a Comparison of the Effects of Conjugated Equine Estrogens and Soy Phytoestrogens" *J. Clin. Endocrinol. Metab.* 86(1):41-47 (2001).

Co-pending U.S. Appl. No. 10/575,406, filed Nov. 1, 2006, entitled "Treatment of Diseases Associated With the Egr-1 Enhancer Element" Inventors: Norman C.W. Wong et al.

Eiden, F. et al. "1,2-Bisbenzopyranyl-ethane" *Archiv der Pharmazie* 313(2):120-128 (1980) (German), Abstract p. 120.

English language Derwent abstract for EP 2 005 941, 4 pages (2009).

English language Derwent abstract for JP 10-287678, 1 page (1999).

Fieser, L.F. "Potentials of some unstable oxidation-reduction systems" *J. Am. Chem. Soc.* 52:4915-4940 (1930).

Guillory, J.K. "Generation of Polymorphs, Hydrates, Solvates, and Amorphous Solids" Brittain, Harry G. (ed.) *Polymorphism in Pharmaceutical Solids* vol. 95, Marcel Dekker, Inc., New York; pp. 202-208 (1999).

Hakamata et al. "Differential effects of an acyl-coenzyme A: cholesterol acyltransferase inhibitor on HDL-induced cholesterol efflux from rat macrophage foam cells" *FEBS Letters* 363:29-32 (1995).

Hemingway, R.W. et al. "A Gas-liquid chromatographic examination of stilbene derivatives" *J. Chromatography* 50(3):391-399 (1970).

Laarhoven, W.H. et al. "Influence of non-planarity in styrene and stilbene derivatives. IV. Syntheses, infrared spectra, and molecular refractions of some sterically hindered p,p'-dimethoxystilbenes" *Recueil des Travaux Chimiques des Pays-Bas* 80:775-791 (1961).

Linnell, W.H. "Isomers of stilboestrol. Part II." *Q. J. Pharm. Pharmacol.* 15:384-388 (1942).

Melani, F. et al. "Tricyclic heterocyclic systems: pyrazolo[5',4':4,5]-and pyrazolo-[3',4':4,5]pyrano[2,3-*b*]pyridine derivatives" *J. Heterocyclic Chem.* 25:1367 (1988).

Office Action in pending U.S. Appl. No. 11/254,420 mailed Mar. 3, 2009.

Ohtomo et al. "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).

Rajakumar, P. et al. "TiCl$_4$-dioxane—A facile and efficient system for de-*O*-benzylation, de-*O*-allylation, and de-*O*-xylylation of phenolic ethers" *Synthetic Communications* 33(22):3891-3896 (2003).

Richtzenhain, H. "Estrogenic stilbene and diphenylethane derivatives. II." *Chemische Berichte* 82:405-407 (1949) (German) (No English abstract available).

Rodriguez et al. "Novel effects of the Acyl-Coenzyme A: cholesterol Acyltransferase Inhibitor 58-035 on Foam Cell Development in Primary Human Monocyte-Derived Macrophages" *Arterioscler. Thromb. Vasc. Biol.* 19:2199-2206 (1999).

Schultz, T.P. et al. "Role of stilbenes in the natural durability of wood: fungicidal structure-activity relationships" *Phytochemistry* 29(5):1501-1507 (1990).

Sieber, R.H. "Reactions of chloroacetaldehyde with aromatic hydrocarbons, phenols, and phenol ethers" *Justus Liebigs Annalen der Chemie* 730:31-46 (1969) (German), Abstract p. 31.

Sliwa, H. et al. "Tautomerie entre structures a-enaminocetone et b-ceto iminoether presentee par les piperidines resultant de la semihydrogenation d'alcoxy-2-acyl-3 pyridines" *J. Heterocyclic Chem.* 16:969 (1979) (French), Summary p. 944.

Smyth, M.S. et al. "Non-amine based analogs of lavendustin A as protein-tyrosine kinase inhibitors" *J. Med. Chem.* 36(20):3010-3014 (1993).

U.S. Appl. No. 11/670,238 entitled: "Compounds for the Prevention and Treatment of Cardiovascular Diseases" filed Feb. 1, 2007.

U.S. Appl. No. 11/990,162 entitled: "Pharmaceutical Compositions for the Prevention and Treatment of Complex Diseases and Delivery by Insertable Medical Devices" filed Feb. 7, 2008.

Vippagunta et al. "Crystalline solids" *Adv. Drug Delivery Rev.* 48:3-26 (2001).

Webster Ninth New Collegiate Dictionary, Definition of 'Prevent', 1 page (2000).

Yoshioka, N. et al. "Semiempirical Investigation of Stilbene-Linked Diradicals and Magnetic Study of Their Bis(N-tert-butylnitroxide) Variants" *J. Org. Chem.* 59(15):4272-4280 (1994).

Baba et al., "Continuous intake of polyphenolic compounds containing cocoa powder reduces LDL oxidative susceptibility and has beneficial effects on plasma HDL-cholesterol concentrations in humans," *Am. J. Clin. Nutr.* 85:709-717 (2007).

Cooper et al., "Wine polyphenols and promotion of cardiac health," *Nutrition Research Reviews* 17:111-129 (2004).

International Search Report and Written Opinion as issued in International Application No. PCT/CA2004/001818 mailed on Feb. 28, 2005.

Kawamatsu et al., "2-Amino-4-phenylthiazole derivatives as anit-atherogenic agents," *Eur. J. Med. Chem.* 16(4):355-362 (1981).

Maher et al., "Lipoprotein (a) and coronary heart disease," *Curr. Opin. Lipidol.* 6:229-235 (1995).

Quinones et al., "The EGR-1 gene is induced by DNA-damaging agents and non-genotoxic drugs in both normal and neoplastic human cells," *Life Sciences* 72(26):2975-2992 (2003).

Ragione et al., "Antioxidants induce different phenotypes by a distinct modulation of signal transduction," *FEBS Letters* 523:289-294 (2002).

Ragione et al., "p21cip1 Gene expression is modulated by Egr1," *J. Biol. Chem.* 278(26):23360-23368 (2003).

Rice-Evans, "Flavonoids and Isoflavones: Absorption, Metabolism, and Bioactivity," *Free Radical Biol. Med.* 36:827-828 (2004).

Abdel-Jalil et al., "Synthesis and Antitumor Activity of 2-Aryl1-7-fluoro-6-(4-methyl-1-piperazinyl)-4(3*H*)-quinazolinones", *Heterocycles* 65(9):2061-2070 (2005).

Chakrabarty et al., "Induction of apoptosis in human cancer cell lines by diospyrin, a plant-derived bisnaphthoquinonoid, and its synthetic derivatives," *Cancer Letters* 188(1-2):85-93 (2002).

Co-pending U.S. Appl. No. 11/254,420, filed Oct. 20, 2005, Inventors: Norman C.W. Wong et al.

Co-pending U.S. Appl. No. 11/670,238, filed Feb. 1, 2007, Inventors: Norman C.W. Wong et al.

Co-pending U.S. Appl. No. 11/990,162, filed Feb. 7, 2008, Inventors: Norman C.W. Wong et al.

Gerritsen et al., "Flavenoids inhibit cytokine-induced endothelial cell adhesion protein gene expression," *Am. J. Pathol.* 147(2):278-292 (1995).

Hazra et al., "New diospyrin derivatives with improved tumour inhibitory activity towards ehrlich ascites carcinoma," *Medical Science Research* 22(5):351-353 (1994).

Hazra et al., "Synthesis of an antitumor derivative of diospyrin," *IRCS Medical Science* 14(1):35-36 (1986).

International Search Report and Written Opinion as issued in International Application No. PCT/CA2007/000146 mailed on Oct. 29, 2007.

International Search Report and Written Opinion as issued in International Application No. PCT/US2006/029827 mailed on Apr. 16, 2007.

International Search Report and Written Opinion as issued in International Application No. PCT/US2005/037719 mailed on Mar. 9, 2007.

Jin et al., "Antiplatelet and antithrombotic activities of CP201, a newly synthesized 1,4-naphthoquinone derivative," *Vasc. Pharmacol.* 41(1):35-41 (2004).

Kawamatsu et al., "2-Amino-4-phenylthiazole derivatives as anit-atherogenic agents," *Eur. J. Med. Chem.* 16(4):355-362 (1981).

Kublak et al., "The preparation of the aza-spirobicyclic system of discorhabdin c via an intramolecular phenolate alkylation," *Tetrahedron Lett.* 31(27):3845-3848 (1990).

Lin et al. "Potential bioreductive alkylating agents. 7. Antitumor effects of phenyl-substituted 2-chloromethyl-3-phenyl-1,4-naphthoquinones," *J. Med. Chem.* 19(11):1336-1338 (1976).

Lopez et al., "The Synthesis of Substituted 2-Aryl-4(3*H*)-quinazolinones using NaHSO$_3$/DMA. Steric Effect Upon the Cyclisation-Dehydrogenation Step" *J. Chem. Research (S)* pp. 258-259 (2000).

Mahto et al., "Synthesis of 3-Aryl-7-hydroxy Isochromenes" *Asian J. Chem.* 11(2):431-435 (1999).

McKee et al., "Some Basically Substituted Quinazolines" *J. Am. Chem. Soc.* 68(10):1902-1903 (1946).

Meckes et al., "The effects of chrysin and pinostrobin, 2 flavonoids isolated from teloxys graveolens leaves, on isolated guinea-pig ileum," *Phytomedicine* 5(6):459-463 (1998).

Middleton et al., "Quercetin inhibits lipopolysaccharide-induced expression of endothelial cell intracellular adhesion molecule-1," *Int. Archives of Allergy and Immunology* 107(1/3):435-436 (1995).

Rimando et al., "Pterostilbene, a new agonist for the peroxisome proliferator-activated receptor alpha-isoform, lowers plasma lipoproteins and cholesterol in hyercholesterolemic hamsters," *J. Agri. Food Chem.* 53(9):3403-3407 (2005).

Tait et al., "Synthesis and Free Radical Scavenging Activity of 4-(2H-1,2,4-Benzothiadiazine-1,1-dioxide-3-yl)-2,6-bis(1,1-dimethylethyl)phenols," *Tetrahedron* 52(38):12587-12596 (1996).

Woelle et al., "Selective inhibition of tumor necrosis factor-induced vascular cell adhesion molecule-1 gene expression by a novel flavonoid: lack of effect on transcription factor NF-kappa-B," *Arterioscler. Thromb. Vasc. Biol.* 16(12):1501-1508 (1996).

Wurm et al., "1,4-Naphthoquinones, XXVI: Phenyl-1,4-naphthoquinone derivatives with the hydroxylation patterns of bioflavonoids," *Pharmazie* 52(10):739 (1997).

Wurm, "2-(3,5-Di-*tert*-butyl-4-hydroxyphenyl)-1,4-Naphthochinone Als 5-Lipoxygenasehemmer," *Archiv der Pharmazie* 324:491-495 (1991).

Yardley et al., "In vitro activity of diospyrin and derivatives against leishmania donovani, trypanosoma cruzi and trypanosoma brucei brucei," *Phytotherapy Research* 10(7):559-562 (1996).

"trans-Resveratrol [501-36-0]. Review of Toxicological Literature." Mar. 2002.

Acton et al., "Identification of Scavenger Receptor SR-BI as a High Density Lipoprotein Receptor," *Science* 271:518-520 (1996).

Asztalos, "High-Density Lipoprotein Metabolism and Progression of Atherosclerosis: New Insights from the HDL Atherosclerosis Treatment Study," *Curr Opin Cardiol* 19:385-391 (2004).

Badimon et al., "Role of High Density Lipoproteins in the Regression of Atherosclerosis," *Circulation* 86(Suppl. III):86-94 (1992).

Barrans et al., "Pre-β HDL: Structure and Metabolism," *Biochem Biophys Acta* 1300:73-85 (1996).

Barter et al., "High Density Lipoproteins and Coronary Heart Disease," *Atherosclerosis* 121:1-12 (1996).

Bertele et al., "Platelet Thromboxane Synthetase Inhibitors with Low Doses of Aspirin: Possible Resolution of the 'Aspirin Dilemma,'" *Science* 220:517-519 (1983).
Beugelmans et al., "Synthesis Via SRN1 Reactions: Part IV. One-pot Synthesis of 1-oxi-1,2-Dihydroisoquinolines (Isocarbostyrils) Via SRN1 (Ar) Reactions," *Synthesis* 9:729-731 (1981).
Bisagni et al., "A Convenient Way to Dibenzo[c,h]-1,5-Naphthyridines (11-Aza-Benzo[c]phenanthridines)," *Tetrahedron* 52:10427-10440 (1996).
Bisgaier et al., "A Novel Compound that Elevates High Density Lipoprotein and Activates the Peroxisome Proliferator Activated Receptor," *J Lipid Res* 39:17-30 (1998).
Boyce et al., "Acylation and Alkylation of O-Tolunitrile. A New Route to 3-Substituted Isocarbostyrils," *J Org Chem* 31:3807-3809 (1966).
Bradsher et al., "A New Isoquinoline Synthesis Via O-Substituted Benzylamines," *Tetrahedron Lett* 31:3149-3150 (1972).
Bradsher et al., "α-Acyl-o-Tolunitriles As Intermediates in the Preparation of 3-Substituted Isoquinolines and 1-Amino-2-Benzopyrylium Derivatives," *J Org Chem* 43:3817-3820 (1978).
Cherubini et al., "Role of antioxidants in Atherosclerosis: Epidemiological and Clinical Update," *Curr Pharm Des* 11:2017-2032 (2005).
Cho et al., "Molecular Modeling of 3-Arylisoquinoline Antitumor Agents Active Against A-549. A Comparative Molecular Field Analysis Study," *Bioorg Med Chem* 10:2953-2961 (2002).
Cho et al., "Synthesis and Biological Evaluation of 3-Arylisoquinolines As Antitumor Agents," *Bioorg Med Chem Lett* 8:41-46 (1998).
Cho et al., "Synthesis and Antitumor Activity of 3-Arylisoquinoline Derivatives," *Arch Pharm Res* 20:264-268 (1997).
Cho et al., "Synthesis and Comparative Molecular Field Analysis (CoMFA) of Antitumor 3-Arylisoquinoline Derivatives," *Bioorg Med Chem* 6(12):2449-2458 (1998).
Chyu et al., "Differential Effects of Green Tea-Derived Catechin on Developing Versus Established Atherosclerosis in Apolipoprotein E-Null Mice," *Circulation* 109:2448-2453 (2004).
Cramer et al., "New Syntheses of Aryl Fluorides and Aryl Fluorosulfonates from Oxyflourides of Sulfur," *J Org Chem* 26:4164-4165 (1961).
Dai et al., "Synthesis of 3,4-disubstitute Isoquinolines Via Palladium-Catalyzed Cross-Coupling of 2-(1-alkynyl)benzaldimines and Organic Halides," *Journal of Organic Chemistry* 68:920-928 (2003).
Dai et al., "Synthesis of 3-Substituted 4-Aroylisoquinolines Via Pd-Catalyzed Carbonylative Cyclization of 2-(1-Alkynyl)benzaldimines," *J Org Chem* 67:7042-7047 (2002).
Dansky et al., "High-Density Lipoprotein and Plaque Regression The Good Cholesterol Gets Even Better," *Circulation* 100:1762-1763 (1999).
Decossin et al., "Subclasses of LpA-I In Coronary Artery Disease: Distribution and Cholesterol Efflux Ability," *Eur J Clin Invest* 27:299-307 (1997).
Esterbauer et al., "Continuous Monitoring of In Vitro Oxidation of Human Low Density Lipoprotein," *Free Radical Res Commun* 6:67-75 (1989).
Ferreira et al., "Diversity of Structure and Function in Oligomeric Flavanoids," *Tetrahedron* 48:1743-1803 (1992).
Fielding et al., "Molecular Physiology of Reverse Cholesterol Transport," *J Lipid Res* 36:211-228 (1995).
Flammang et al., "2,3-Benzodiazepines: 2-Aminoisoquinolinones From Ring Contraction of 1-oxo-2,3-Benzodiazepines," *C R Acad Sci Paris, Series C* 290:361-363 (1980).
Fokialakis et al., "A New Class of Phytoestrogens: Evaluation of the Estrogenic Activity of Deoxybenzoins," *Chem Biol* 11:397-406 (2004).
Gidez et al., "Separation and Quantitation of Subclasses of Human Plasma High Density Lipoproteins by a Simple Precipitation Procedure," *J Lipid Res* 23:1206-1223 (1982).
Gordon et al., "High Density Lipoprotein As a Protective Factor Against Coronary Heart Disease," *Am J Med* 62(5):707-714 (1977).
Gugler et al., "Disposition of Quercetin in Man After Single Oral and Intravenous Doses," *Eur J Clin Pharmacol* 9:229-234 (1975), Abstract.
Heeg et al., "Plasma Levels of Probucol in Man After Single and Repeated Oral Doses," *La Nouvelle Presse Medicate* 9:2990-2994 (1980).
Hertog et al., "Dietary Antioxidant Flavonoids and Risk of Coronary Heart Disease: One Zutphen Elderly Study," *Lancet* 342:1007-1011 (1993).
Hidaka et al., "Affinity Purification of the Hepatic High-Density Lipoprotein Receptor Identifies Two Acidic Glycoproteins and Enables Further Characterization of Their Binding Properties," *Biochem J* 15:161-167 (1992).
Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity," *Arterioscler Thromb Vasc Biol* 17:1053-1059 (1997).
Huang et al., "Synthesis of Isoquinolines by Palladium-Catalyzed Cyclization, Followed by a Heck Reaction," *Tetrahedron Lett* 43:3557-3560 (2002).
Ishibashi et al., "Hypercholesterolemia in Low Density Lipoprotein Receptor Knockout Mice and its Reversal by Adenovirus-Mediated Gene Delivery," *J Clin Invest* 92:883-893 (1993).
Ishibashi et al., "Massive Xanthomatosis and Atherosclerosis in Cholesterol-Fed Low Density Lipoprotein Receptor-Negative Mice," *J Clin Invest* 93:1885-1893 (1994).
Jayatilake et al., "Kinase Inhibitors From Polygonum Cuspidatum," *J Nat Prod* 56:1805-1810 (1993).
Kilbourne et al., "Involvement of Early Growth Response Factor Egr-1 in Apolipoprotein AI Gene Transcription," *J Biol Chem* 270:7004-7010 (1995).
Kim et al., "Hypothetical Drug Binding Receptor Site Analysis Using CoMFA Method for 3-Arylisoquinolines Active Against SK-OV-3 Tumor Cell Line," *Yakhak Hoechi* 46(4):219-225 (2002).
Kulkarni et al., "Quantification of $HDL_2$ and $HDL_3$ Cholesterol by the Profile-II (VAP-II) Methodology," *J Lipid Res* 38:2353-2364 (1997).
Kurata et al., "A Candidate High Density Lipoprotein (HDL) Receptor, $HB_2$, With Possible Multiple Functions Shows Sequence Homology with Adhesion Molecules," *J Atheroscler Thromb* 4:112-117 (1998).
Kurowska, "Essential Amino Acids in Relation to Hypercholesterolemia Induced in Rabbits by Dietary Casein," *J Nutr* 120:831-836 (1990).
Kuzuyza et al., "Probucol Prevents Oxidative Injury to Endothelial Cells," *J Lipid Res* 32:197-204 (1991).
Lagrost et al., "Opposite Effects of Cholesteryl Ester Transfer Protein and Phospholipid Transfer Protein on the Size Distribution of Plasma High Density Lipoproteins," *J Biol Chem* 271:19058-19065 (1996).
Landshulz et al., "Regulation of Scavenger Receptor, Class B, Type I, a High Density Lipoprotein Receptor, in Liver and Steroidogenic Tissues of the Rat," *J Clin Invest* 98:984-995 (1996).
Lin et al., "Chemoprevention of Cancer and Cardiovascular Disease by Resveratrol," *Proc. Natl. Sci. Counc. ROC* (B) 23:99-106 (1999).
Lin et al., "Solvent Effects on Aza-Anionic Cycloaromatization of 2-(2-Substituted-Ethynyl)Benzonitriles," *J Chinese Chem Soc* 48:211-214 (2001).
Lin et al., "The Role of Absorption, Distribution, Metabolism, Excretion and Toxicity in Drug Recovery," *Curr Top Med Chem* 3:1125-1154 (2003).
Manach et al., "Polyphenols and prevention of cardiovascular diseases," *Curr Opin Lipidol* 1:77-84 (2005).
Marks, "Epidermal Growth Control Mechanisms, Hyperplasia, and Tumor Promotion in the Skin," *Cancer Res* 36:2636-2343 (1976).
Mondal et al., "Two-Stage Chemical Oncogenesis in Cultures of C3H/10T1/2 Cells," *Cancer Res* 36:2254-2260 (1976).
Noorouz-Zadeh, "Ferrous Ion Oxidation in Presence of Xylenol Orange for Detection of Lipid Hydroperoxides in Plasma," *Methods Enzymol* 300:58-62 (1999).
Parra et al., "A Case-Control Study of Lipoprotein Particles in Two Populations at Contrasting Risk for Coronary Heart Disease," *Artherioscler Thromb* 12:701-707 (1992).
Coronary Heart Disease, *Arterioscler Thromb* 12:701-707 (1992).
Pearson et al., "The *Ortho* Bromination of Phenols," *J Org Chem* 32:2358-2360 (1967).

Pettit et al., "Antineoplastic Agents. 465. Structural Modification of Resveratrol: Sodium Resverastatin Phosphate," *J Med Chem* 45:2534-2542 (2002).

Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland," *J Biol Chem* 271:33545-33549 (1996).

Rose et al., "Oxygen Heterocycles. XIII. From 3-Arylisocoumarins to 3-Arylisoquinolines and 4-Aryl-5H-2,3-Benzodiazepines," *J Chem Soc [Section] C: Organic* 17:2205-2208 (1968).

Rubin et al., "Expression of Human Apolipoprotein A-1 in Transgenic Mice Results in Reduced Plasma Levels of Murine Apolipoprotein A-1 and the Appearance of Two New High Density Lipoprotein Size Subclasses.," *Proc Natl Acad Sci USA* 88:434-438 (1991).

Rubin et al., "Inhibition of Early Atherogenesis in Transgenic Mice by Human Apolipoprotein AI.," *Nature* 353:265-267 (1991).

Sarkhel et al., "3-Arylisocoumarin: Synthesis of 3-(4-Methoxyphenyl)Isocoumarin," *J Indian Chem Soc* 53:915-916 (1976).

Schiess et al., "Thermolytic Ring Opening of Acyloxybenzocyclobuteness: An Efficient Route to 3-Substitute Isoquinolines," *Tetrahedron Lett* 26:3959-3962 (1985).

Shapiro et al., "Micro Assay for 3-Hydroxy-3-Methylglutaryl-CoA Reductase in Rat Liver and L-Cell Fibroblasts", *Biochem Biophys Acta* 370:369-377 (1974).

Slowing et al., "Anti-Inflammatory Activity of Leaf Extracts of Eugenia Jambos in Rats", *J Ethnopharmacol* 43:9-11 (1994).

Sun et al., "In Vitro Testing of Drug Absorption for Drug 'Developability' Assessment: Forming an Interface Between in Vitro Preclinical Data and Clinical Outcome," *Curr Opin Drug Discov Devel* 7:75-85 (2004).

Suryadevara et al., "Association of Abnormal Serum Liquids in Elderly Persons with Artherosclerotic Vascular Disease and Demetia. Artheroslerotic Vascular Disease Without Demetia, Demetia Without Artherosclerotic Vascular Disease, and No Dementia or Artherosclerotic Vascular Disease," *J Gerontol Med Sci* 58(9):M859-861 (2003).

Talbert, "Current Recommendations for the Treatment of Dyslipidemia," *Pharm. Ther.* 29:104 (2004).

Tardiff et al., "Probucol and Multivitamins in the Prevention of Restenosis After Coronary Angioplasty," *N Engl J Med* 337:365-367 (1997).

Toth et al., "Therapeutic Interventions Targeted at the Augmentation of Reserve Cholesterol Transport," *Curr Opin Cardiol* 19:374-379 (2004).

Tovar et al., "Pyrylium Salts Via Electrophilic Cyclization: Applications for Novel 3-Arylisoquinoline Syntheses," *J Org Chem* 64:6499-6504 (1999).

Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)," *Biochem Pharmacol* 58:1869-1880 (1999).

Van Der Goot et al., "The Growth-Inhibitory Action of Some 1-Aminoisoquinolines and Related Compounds On Mycoplasma Gallisepticum," *Eur J Med Chem* 10:603-606 (1975).

Varin et al., "Enzymatic Assay for Flavonoid Sulfotransferase," *Anal Biochem* 161:176-180 (1987).

Walle, "Absorption and Metabolism of Flavonoids," *Free Radical Biol Med.* 36(7):829-837 (2004).

English language Derwent abstract for CN 1067070.
English language Derwent abstract for JP 6080656.
English language Derwent abstract for JP 7041442.
English language Derwent abstract for JP 7061942.
English language Derwent abstract for JP 7118241.
English language Derwent abstract for JP 7179380.
English language Derwent abstract for JP 7233109.
English language Derwent abstract for JP 7247289.
English language Derwent abstract for JP 2002/249483.
English language Derwent abstract for JP 2004/307440.

CAPLUS Accession No. 2005:46491, Qin et al., "Synthesis and fungicidal activity of 5,7-dihydroxyldiazinflavanones" [online]. Retrieved from STN on Jan. 31, 2011. Also published in: Huazhong Shifan Daxue Xuebao Zirankexueban38(3):323-325 (2004).

CAPLUS Accession No. 2004:11346, Hu et al., "Synthesis and fungicidal activity of flavanone derivatives containing isopentenyl group" [online]. Retrieved from STN on Jan. 31, 2011. Also published in: Yingyong Huaxue 20(12):1161-1165 (2003).

CAPLUS Acession No. 2003:554477, Qin et al., "Synthesis and fungicidal activity of novel diazaflavanones" [online]. Retrieved from STN on Jan. 31, 2011. Also published in: Nongyaoxue Xuebao 4(4):28-32 (2002).

CAPLUS Accession No. 1991:449453, Liu et al. "Synthesis of 2-aryl-9-bromo-4-oxo-4H-pyrano[3-2-c] quinolines" [online]. Retrieved from STN on Jan. 31, 2011. Also published in: Youji Xuaxue 11(2):191-195 (1991).

Clauson-Kaas et al., "Reactions of 3,4-dihydor-2H-pyrrido[3-2-b]-1-4-oxazines" *Acta Chemica Scandinavica* 25(8):3135-3143 (1971). Retrieved from STN, file HCAPLUS, Accession No. 1972:34186 (Abstact).

Connolly et al., "Synthesis of quinazolinones and quinazolines" *Tetrahedron* 61(43):10153-10202 (2005).

Hisano, T. et al., "Studies on organosulfur compounds. XII. Syntheses and pharmacological activities of 2-heterocyclic substituted 4(3h)-quinazolinones" Chem. Pharm. Bull.23(9):1910-1916 (1975).

Hwang, J. et al., "Syntergistic inhibition of LDL oxidation by phytoestrogene and ascorbic. acid" Free Radical Biology and Medicine 29(1):79-89 (Jul. 1, 2000).

International Searcn Report and Written Opinion issued in International Application No. PCT/IB2010/000159; Date of Mailing: Aug. 5, 2010.

International Search Report and Written Opinion issued in International Application No. PCT/US2009/048457; Date of Mailing: Oct. 16, 2009.

Kalusa et al., "An efficient synthesis of 2,3-diaryl (3H)-quinazolin-4-ones via imidoyl chlorides" Tetrahedron Letters 49(41):5840-5842 (2008).

Martin et al., "Modified Flavinoids As Strong Photoprotecting UV-Absorbers and Antioxidants" Strategies for Safe Food. Eklund, T. et al.,(Eds.) vol. 1, pp. 288-291 (2003).

Nigam et al., "Synthesis and Pharmacological Screening of Some New 2-(Phenyl/Chloromethy)-3-[4 (N, N-Disubstituted Aminocarbonyl) Phenyl]-Substituted-4 (3H)-Quinazolones" Indian Drugs 27(4):238-243 (1990).

Office Action in U.S. Appl. No. 11/254,420, mailed Aug. 5, 2008.
Office Action in U.S. Appl. No. 11/254,420 mailed Sep. 28, 2009.
Office Action in U.S. Appl. No. 11/254,420 mailed Feb. 2, 2010.
Notice of Allowance in U.S. Appl. No. 11/254,420, mailed Jul. 26, 2010.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.
Office Action in U.S. Appl. No. 11 1690,102, mailed Dec. 28, 2010.
Office Action in U.S. Appl. No. 11/670,238: Restriction Requirement, mailed Jul. 20, 2010.
Office Action in U.S. Appl. No. 11/670,238: Restriction Requirement, mailed Mar. 31, 2010.
Office Action in U.S. Appl. No. 11/670,238, mailed Oct. 7, 2010.
Office Action in U.S. Appl. No. 11/070,232, mailed Apr. 19, 2011.

Patani et al., "Bioisosterism: A rational approach in drug design" *Chem Rev.* 96(80:3147-3176 (1996).

Schumutz et al., "synthese von bassaisch substituierten Chromonen" *Helv. Chim. Acta* 620 (1953) (German).

* cited by examiner

FLAVANOIDS AND ISOFLAVANOIDS FOR THE PREVENTION AND TREATMENT OF CARDIOVASCULAR DISEASES

CROSS-REFERENCE TO RELATED APPLICATIONS

This application claims the benefit of U.S. provisional application Ser. No. 60/620,888, filed Oct. 20, 2004; U.S. provisional Ser. No. 60/626,819, filed Nov. 10, 2004; and U.S. provisional application Ser. No. 60/665,859, filed Mar. 29, 2005, each of which is incorporated herein by reference in its entirety.

TECHNICAL FIELD

The present disclosure relates to polyphenol compounds, which are useful for regulating the expression of apolipoprotein A-I (ApoA-I), and their use for treatment and prevention of cardiovascular disease and related disease states, including cholesterol or lipid related disorders, such as, e.g., atherosclerosis.

BACKGROUND

Epidemiologic data demonstrate an inverse relationship between circulating levels of high density lipoprotein cholesterol (HDL-C) and the incidence of clinically significant atherosclerosis. Each 1 mg/dl increment in the HDL-C serum level is associated with a 2-3% decrement in cardiovascular risk; a 1% reduction in LDL-C reduces coronary heart disease (CHD) risk by 2%. Gordon et al., *Am. J. Med.* 62(5):707-14 (1997). Experimental evidence further supports the protective effect of HDL against cardiovascular disease. For example, in subjects with low HDL-C, administration of gemfibrozil results in a 6% increase in the HDL-C level and a corresponding 22% reduction of the CHD risk. Rubins et al., *N. Engl. J. Med.* 341(6):410-8 (1999). Observations in genetic disorders associated with low HDL due to reduced ApoA-I expression, also indicate the link between elevated risk of CHD and low HDL-C.

HDL appears to exert its antiatherogenic effect by mediating reverse cholesterol transport (RCT), in which cholesterol is recruited from peripheral tissues and transported to the liver. In addition, HDL also exerts anti-inflammatory, and-tioxidant effects and promotes fibrinolysis. HDL paticles protect against oxidation of LDL, an important initial step in promoting cholseteol uptake by arterial macrophages. HDL exists in two main forms, one containing both apolipoprotein A-I (ApoA-I) and apolipoprotein A-II (ApoA-II), and the other containing ApoA-I without ApoA-II. Schultz et al., *Nature* 365(6448):762-4 (1993). The cardioprotective effect of HDL is mostly, but not exclusively, attributable to ApoA-I.

Clinical and experimental data suggest that the production of ApoA-I is a critical determinant of circulating HDL. For example, persons with familial hyperalphalipoproteinemia (elevated ApoA-I) appear to be protected from atherosclerosis, while those deficient in ApoA-I (hypoalphalipoproteinemia) show accelerated cardiovascular disease. In addition, various experimental manipulations to increase production of ApoA-I are associated with reduced atherogenicity. For example, human ApoA-I is protective in transgenic animal models (Shah et al., *Circulation* 97(8):780-5 (1998; Rubin et al., *Nature* 353(6341):265-7 (1991), and treatment with ApoA-I$_{Milano}$ prevents atherosclerotic lesions and leads to regression of atherosclerotic plaques in human patients (Nissen et al., *JAMA* 290(17):2292-300 (2003)). Further lines of research supporting an antiatherogenic role of ApoA-I include enhancement of reverse cholesterol transport, attenuation of oxidative stress, increased peroxonase activity, enhanced anticoagulant activity, and anti-inflammatory activity. Accordingly, ApoA-I is an attractive target for therapeutic intervention.

Currently available therapeutic agents that increase the plasma concentration of ApoA-I, for example, recombinant ApoA-I or peptides that mimic ApoA-I, have potential drawbacks related to manufacturing and reproducibility, e.g., stability during storage, delivery of an active product, and in vivo half-life. Therefore, small molecule compounds that upregulate the production of endogenous ApoA-I, such as, e.g., transcriptional upregulators of ApoA-I expression, are very attractive as new therapeutic agents for cardiovascular disease.

One class of compounds that are thought to contribute to the prevention of various diseases, including cancer and cardiovascular diseases, is polyphenols. Polyphenols are common constituents of the human diet, present in most food and beverages of plant origin, and are the most abundant dietary antioxidants. However, polyphenols protective properties are often minimized due to poor bioavailability, lack of clinical significance, and deleterious effects at high concentrations. For example, the most abundant and available source of resveratrol for consumers, red wine, cannot be consumed in therapeutically efficacious quantities on a daily basis due to the numerous well documented deleterious effects of excessive alcohol consumption. The actions of resveratrol may be better or safer in the absence of alcohol.

Several human clinical studies, involving foods or beverages, have yet to demonstrate an unequivocal benefit on primary clinical endpoints, such as oxidative stress, lipemia, and inflammation. For example, out of 12 recent intervention studies with differing polyphenol sources, 6 showed no effect on lipid parameters and the other 6 showed an improvement in the lipid parameters. Manach, *Curr. Opin. Lipidol.* 16(1):77-84 (2005). Such contradictory data has limited the potential use of polyphenols, despite their many beneficial properties.

The use of naturally occurring polyphenols as a potential therapy has also been impeded by the inability to achieve efficacious levels of bioavailability. The bioavailability of polyphenols in humans range from 1% to 26% and has a large inter-individual variability as well as variability between different polyphenols. Polyphenols differ in how they are absorbed, metabolized, and excreted. For example, polyphenol flavonoids, such as quercetin, have been reported to have less than 1% intestinal absorption following oral administration. Gugler et al., *Eur. J. Clin. Pharm.* 9:223 (1975). In addition, metabolites are known to negatively influence the biological activity of the parent compounds. Such metabolites often differ from the parent compound in terms of toxicity, efficacy, and length of residence in the plasma. Another limiting factor may be polyphenols' poor solubility in water which limits the routes of administration. These and other factors have made it difficult to determine appropriate dosages of the naturally occurring polyphenols, naringenin or resveratrol, for use in humans.

Thus, there exists a need for synthetic polyphenols to be developed as therapeutic agents for the treatment and prevention of cardiovascular and related diseases, particularly, cholesterol or lipid related disorders, such as, e.g., atherosclerosis. It is therefore one of the objects of the present invention to provide compounds that upregulate the expression of ApoA-

SUMMARY

The methods of invention include administering to a mammal (e.g., a human) in need thereof a therapeutically effective amount of a flavanoid compound of Formula I:

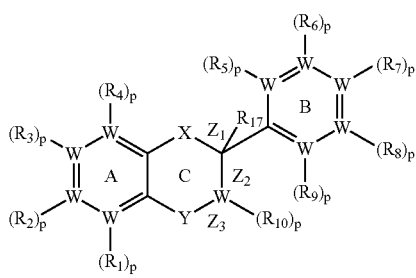

Formula I wherein:

X is selected from $CR_{11}$, $CR_{11}R_{13}$, CO, CS, O, S, SO, $SO_2$, N and $NR_{11}$, wherein $R_{11}$ may be the same or different than $R_{13}$;

Y is selected from $CR_{12}$, $CR_{12}R_{14}$, CO, CS, O, S, SO, $SO_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;

each W is independently selected from C and N, wherein if W is N, then p is 0 and if W is C, then p is 1;

$Z_1$, $Z_2$ and $Z_3$ are each independently selected from a single bond and a double bond;

wherein if Y is O, then X is not CO;

wherein if X is O, the $Z_1$ is a single bond;

wherein if X is O and $Z_2$ is a single bond, then $R_{10}$ is not hydroxyl or ester;

and pharmaceutically acceptable salts and hydrates thereof.

Methods of invention also include administering to a mammal (e.g., a human) in need thereof a therapeutically effective amount of an isoflavanoid compound of Formula IV:

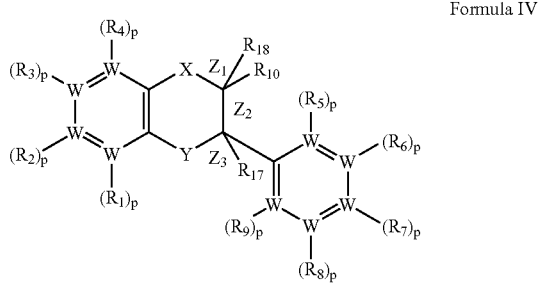

Formula IV wherein:

X is selected from $CR_{11}$, $CR_{11}R_{13}$, CO, CS, O, S, SO, $SO_2$, N and $NR_{11}$, wherein $R_{11}$ may be the same or different than $R_{13}$;

Y is selected from $CR_{12}$, $CR_{12}R_{14}$, CO, CS, O, S, SO, $SO_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{18}$ are connected in a 5 or 6-membered ring to form a bicyclic aryl or bicyclic heteroaryl;

each W is independently selected from C and N, wherein if W is N, then p is 0 and if W is C, then p is 1;

$Z_1$, $Z_2$ and $Z_3$ are each independently selected from a single bond and a double bond;

wherein if Y is O, then X is not CO;

wherein if X is O, Y is CO and $Z_2$ is a double bond, then at least one of $R_5$, $R_6$, $R_8$ and $R_9$ is not hydrogen;

and pharmaceutically acceptable salts and hydrates thereof.

In certain embodiments, the methods and compositions of the invention are useful for treatment of diseases characterized by reduced ApoA-I and/or HDL. The compounds and compositions of the invention can be used to increase expression of ApoA-I. Increasing expression of ApoA-I refers to transcriptionally modulating the expression of the ApoA-I gene thereby affecting the level of the ApoA-I protein expressed, i.e., synthesized and secreted, by the cell. An increase in ApoA-I protein expression leads to an increase in blood levels of HDL. Thus, the methods and compounds of the invention may further be used to reduce plasma cholesterol levels. Accordingly, the methods and compositions of the invention can be used for treatment and prevention of cardiovascular disease and related disease states, particularly, cholesterol or lipid related disorders, such as, atherosclerosis, dyslipidemias, dyslipoproteinemias, hypertension, coronary artery disease, cerebrovascular disease, and the like.

In one aspect, the invention provides a method for prevention of arteriosclerosis lesion development in a mammal, including the development of new arteriosclerotic lesions. In another aspect, the present invention provides a method regressing arteriosclerosis lesions.

The methods and compounds of the invention may further be used to lower blood levels of LDL and triglycerides and/or to increase free radical scavenging. In addition, these methods and compositions may also be used to inhibit HMG-COA reductase, inhibit ACAT, and/or increase ABCA-I activity.

In a further aspect, the invention provides methods and compositions for effecting an increase of HDL in a mammal comprising, wherein the compound is a flavonoid or a isoflavonoid, each derivatized with covalently bonded niacin. In certain embodiments, the covalent bond comprises a reverse ester linkage.

DETAILED DESCRIPTION

Definitions

Figure 1:
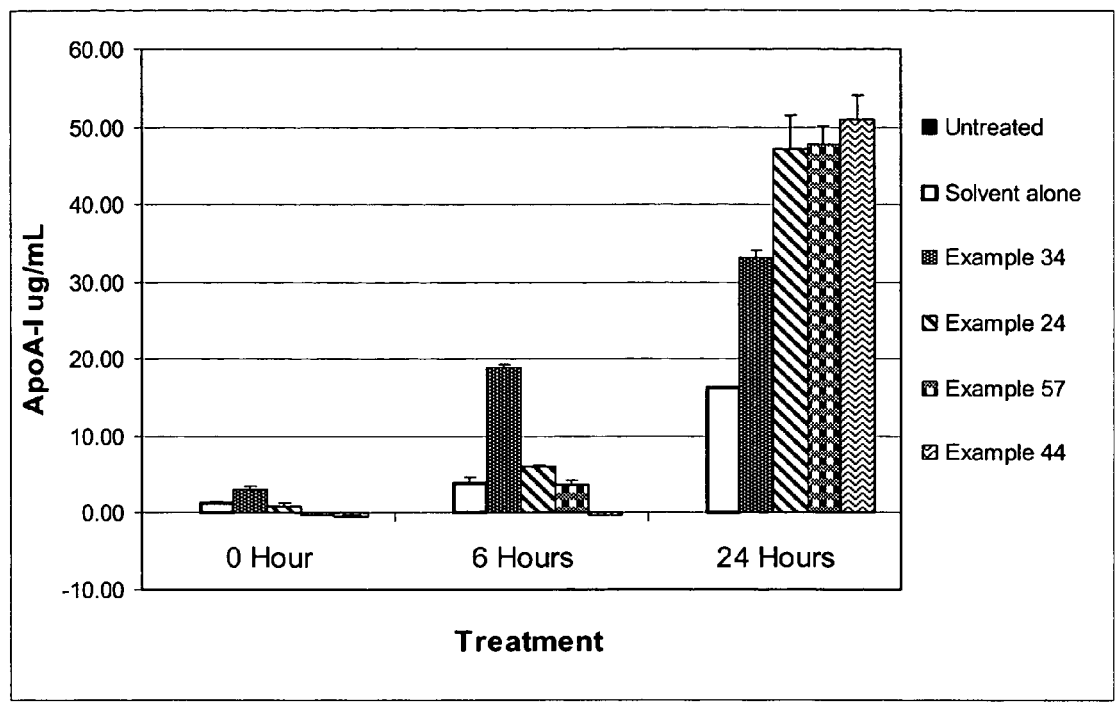
FIG. 1 shows results from an ELISA analysis to measure ApoA-I protein content of conditioned media from: (1) untreated HepG2 cells: (2) HepG2 cells treated with solvent: and (3) HepG2 cells treated with test compound, at 0, 6, and 24 hours after exposure.

The term "aldehyde" or "formyl" as used herein refers to the radical —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as $(C_2-C_{22})$ alkenyl, $(C_2-C_8)$alkenyl, and $(C_2-C_6)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). "Alkoxy" groups also include an alkenyl group attached to an oxygen ("alkenoxy") or an alkynyl group attached to an oxygen ("alkynoxy") groups. Exemplary alkoxy groups include, but are not limited to, groups with an alkyl, alkenyl or alkynyl group of 1-22, 1-8, or 1-6 carbon atoms, referred to herein as $(C_1-C_{22})$alkoxy, $(C_1-C_8)$alkoxy, and $(C_1-C_6)$alkoxy, respectively. Exemplary alkoxy groups include, but are not limited to methoxy, ethoxy, etc.

The term "alkyl" as used herein refers to a saturated straight or branched hydrocarbon, such as a straight or branched group of 1-22, 1-8, or 1-6 carbon atoms, referred to herein as $(C_1-C_{22})$alkyl, $(C_1-C_8)$alkyl, and $(C_1-C_6)$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as $(C_2-C_{22})$ alkynyl, $(C_2-C_8)$alkynyl, and $(C_2-C_6)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" as used herein refers to a radical of the form —$R_aC(O)N(R_b)$—, —$R_aC(O)N(R_b)R_c$—, or —C(O) $NR_bR_c$, wherein $R_b$ and $R_c$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "amide" encompasses groups such as sulfonamide, urea, carbamate, carbamic acid, and cyclic versions thereof. The term "amide" also encompasses an amide group attached to a carboxy group, e.g., -amide-COOH or salts such as -amide-COONa, etc, an amino group attached to a carboxy group, e.g., -amino-COOH or salts such as -amino-COONa, etc.

The term "amine" or "amino" as used herein refers to a radical of the form —$NR_dR_e$, —$N(R_d)R_e$—, or —$R_eN(R_d)$ $R_f$— where $R_d$, $R_e$, and $R_f$ are independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. The amino can be attached to the parent molecular group through the nitrogen, $R_d$, $R_e$ or $R_f$. The amino also may be cyclic, for example any two of $R_a$, $R_b$, and $R_c$ may be joined together or with the N to form a 3- to 12-membered ring, e.g., morpholino or piperidinyl. The term amino also includes the corresponding quaternary ammonium salt of any amino group, e.g., —$[N(R_d)(R_e)(R_f)]^+$. Exemplary amino groups include aminoalkyl groups, wherein at least one of $R_d$, $R_e$, or $R_f$ is an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$) aryl."

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms, referred to herein as "($C_6$) arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "benzyl" as used herein refers to the group —CH$_2$-phenyl.

The term "bicyclic aryl" as used herein refers to an aryl group fused to another aromatic or non-aromatic carbocylic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocylic or heterocyclic ring. Exemplary bicyclic heteroaryls include, but are not limited to, 5,6 or 6,6-fused systems wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, or sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary bicyclic heteroaryl's include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to a radical of the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Exemplary carbamates include, but are not limited to, arylcarbamates or heteroaryl carbamates, e.g. wherein at least one of R$_g$, R$_h$ and R$_i$ are independently selected from aryl or heteroaryl, such as pyridine, pyridazine, pyrimidine, and pyrazine.

The term "carbonyl" as used herein refers to the radical —C(O)—.

The term "carboxy" as used herein refers to the radical —COOH or its corresponding salts, e.g. —COONa, etc. The term carboxy also includes "carboxycarbonyl," e.g. a carboxy group attached to a carbonyl group, e.g., —C(O)—COOH or salts such as —C(O)—COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides, etc., for example, succinic anhydride, succinimide, etc.

The term "ester" refers to a radical having the structure —C(O)O—, —C(O)O—R$_j$—, —R$_k$C(O)O—R$_j$—, or —R$_k$C(O)O—, where O is not bound to hydrogen, and R$_j$ and R$_k$ can independently be selected from alkoxy, aryloxy, alkyl, alkenyl, alkynyl, amide, amino, aryl, arylalkyl, cycloalkyl, ether, formyl, haloalkyl, halogen, heteroaryl, heterocyclyl, ketone, phosphate, sulfide, sulfinyl, sulfonyl, sulfonic acid and thioketone. R$_k$ can be a hydrogen, but R$_j$ cannot be hydrogen. The ester may be cyclic, for example the carbon atom and R$_j$, the oxygen atom and R$_k$, or R$_j$ and R$_k$ may be joined to form a 3- to 12-membered ring. Exemplary esters include, but are not limited to, alkyl esters wherein at least one of Rj or Rk is alkyl, such as -alkyl-C(O)—O—, —C(O)—O-alkyl-, -alkyl-C(O)—O-alkyl-, etc. Exemplary esters also include aryl or heteoaryl esters, e.g. wherein at least one of Rj or Rk is a heteroaryl group such as pyridine, pyridazine, pyrmidine and pyrazine, such as a nicotinate ester. Exemplary esters also include reverse esters having the structure —R$_k$C(O)O—, where the oxygen is bound to the parent molecular group. Exemplary reverse esters include succinate, D-argininate, L-argininate, L-lysinate and D-lysinate. Esters also include carboxylic acid anhydrides and acid halides.

The term "ether" refers to a radical having the structure —R$_l$O—R$_m$—, where R$_l$ and R$_m$ can independently be alkyl, alkenyl, alkynyl, aryl, cycloalkyl, heterocyclyl, or ether. The ether can be attached to the parent molecular group through R$_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1 to 3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "$(C_2-C_5)$heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to the radical —OH.

The term "hydroxyalkyl" as used herein refers to a hydroxy radical attached to an alkyl group.

The term "hydroxyaryl" as used herein refers to a hydroxy radical attached to an aryl group.

The term "ketone" as used herein refers to a radical having the structure —C(O)—Rn (such as acetyl, —C(O)CH$_3$) or —R$_n$—C(O)—R$_o$—. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to the radical —NO$_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluroalkyl groups include, but are not limited to, $C_{1-5}$ perfluoroalkyl, such as trifluoromethyl, etc.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "phosphate" as used herein refers to a radical having the structure —OP(O)O$_2$—, —R$_x$OP(O)O$_2$—, —OP(O)O$_2$R$_y$—, or —R$_x$OP(O)O$_2$R$_y$—, wherein R$_x$ and R$_y$ can be alkyl, alkenyl, alkynyl, alkoxy, amide, amino, aryl, aryloxy, carboxy, cyano, cycloalkyl, ester, ether, halogen, heterocyclyl, hydrogen, hydroxy, ketone, nitro, sulfonate, sulfonyl, and thio.

The term "sulfide" as used herein refers to the radical having the structure R$_z$S—, where R$_z$ can be alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, and ketone. The term "alkylsulfide" as used herein refers to an alkyl group attached to a sulfur atom.

The term "sulfinyl" as used herein refers to a radical having the structure —S(O)O—, —R$_p$S(O)O—, —R$_p$S(O)OR$_q$—, or —S(O)OR$_q$—, wherein R$_p$ and R$_s$ can be alkoxy, aryloxy, alkyl, alkenyl, alkynyl, amide, amino, aryl, arylalkyl, cycloalkyl, ester, ether, formyl, halogen, haloalkyl, heteroaryl, heterocyclyl, hydroxyl, ketone, nitro, phosphate, sulfide, sulfonyl, sulfonic acid, sulfonamide and thioketone. Exemplary sulfinyl groups include, but are not limited to, alkylsulfinyls wherein at least one of R$_p$ or R$_q$ is alkyl, alkenyl or alkynyl.

The term "sulfonamide" as used herein refers to a radical having the structure —(R$_r$)—N—S(O)$_2$—R$_s$— or —R$_t$(R$_r$)—N—S(O)$_2$—R$_s$, where R$_t$, R$_r$, and R$_s$ can be, for example, hydrogen, alkyl, alkenyl, alkynyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonate" as used herein refers to the radical —OSO$_3$$^-$. Sulfonate includes salts such as —OSO$_3$Na, —OSO$_3$K, etc. and the acid —OSO$_3$H The term "sulfonic acid" refers to the radical —SO₃H— and its corresponding salts, e.g. —SO₃K—, —SO₃Na—.

The term "sulfonyl" as used herein refers to a radical having the structure $R_uSO_2$—, where $R_u$ can be alkyl, alkenyl, alkynyl, amino, amide, aryl, cycloalkyl, and heterocyclyl, e.g., alkylsulfonyl. The term "alkylsulfonyl" as used herein refers to an alkyl group attached to a sulfonyl group. "Alkylsulfonyl" groups can optionally contain alkenyl or alkynyl groups.

The term "thioketone" refers to a radical having the structure —$R_v$—C(S)—$R_w$—. The ketone can be attached to another group through $R_v$ or $R_w$. $R_v$ or $R_w$ can be alkyl, alkenyl, alkynyl, cycloalkyl, heterocyclyl or aryl, or $R_v$ or $R_w$ can be joined to form a 3- to 12-membered ring.

"Alkyl," "alkenyl," and "alkynyl" groups, collectively referred to as "saturated and unsaturated hydrocarbons," can be substituted with or interrupted by at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, and N.

As used herein, a "suitable substituent" refers to a group that does not nullify the synthetic or pharmaceutical utility of the compounds of the invention or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N(($C_{1-22}$, $C_{1-8}$, and $C_{1-6}$ alkyl)₂, —NH(($C_6$)aryl), or —N(($C_6$)aryl)₂; formyl; ketones, such as —CO($C_{1-22}$, $C_{1-8}$, and $C_{1-6}$ alkyl), —CO(($C_6$ aryl) esters, such as —CO₂($C_{1-22}$, $C_{1-8}$, and $C_{1-6}$ alkyl) and —CO₂ ($C_6$ aryl). One of skill in art can readily choose a suitable substituent based on the stability and pharmacological and synthetic activity of the compound of the invention.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers. For example, the structure below represents a genus of alkenes in which the double bond is either an "E-double bond" or a "Z-double bond."

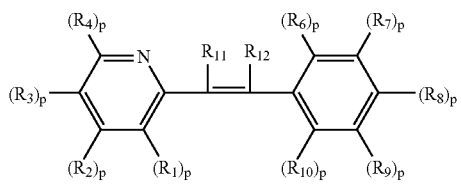

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

EMBODIMENTS OF THE INVENTION

Disclosed herein are methods for increasing expression of ApoA-I in a mammal comprising administering a therapeutically effective amount of a compound of Formula I:

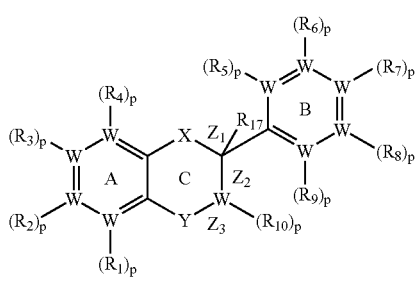

Formula I wherein:
X is selected from $CR_{11}$, $CR_{11}R_{13}$, CO, CS, O, S, SO, $SO_2$, N and $NR_{11}$, wherein $R_{11}$ may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;

each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if X is O, the $Z_1$ is a single bond;
wherein if X is O and $Z_2$ is a single bond, then $R_{10}$ is not hydroxyl or ester;
and pharmaceutically acceptable salts and hydrates thereof.

An alternative embodiment provides flavanoid compounds of Formula 1:

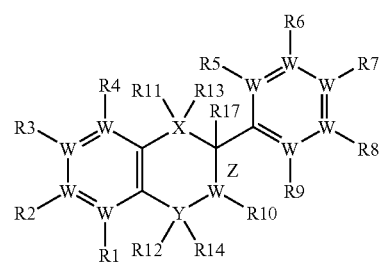

or a pharmaceutically acceptable salt thereof,
wherein
R1, R2, R3, R4, R5, R6, R7, R8, R9, R10, R11, R12, R13, R14, and R17 are independently selected from the group consisting of ($C_1$-$C_{22}$)alkyl, ($C_2$-$C_{22}$)alkenyl, ($C_2$-$C_{22}$) alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein W can be C or N;
wherein when W is an nitrogen atom, the nitrogen atom will only bind to three covalent bonds due to available valence electrons. The structures below demonstrate a nitrogen arrangement of one embodiment of the compounds of Formula 1:

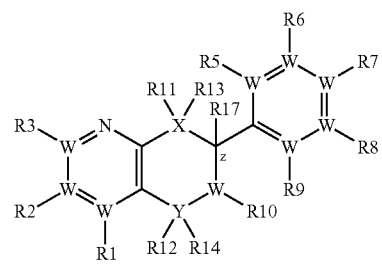

wherein the same applies to any W;

or

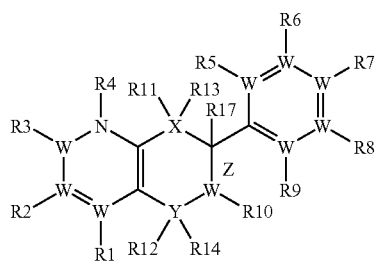

wherein the same applies to any W:

wherein

X can be CH, CH$_2$, CR11, CR13, CHR11, CHR13, CR11R13, CO, CS, O, S, SO, SO$_2$, NH, NR11 with the proviso that X and Y do not exceed the number of valence electrons available as per definitions of X and Y above Y can be CH, CH$_2$, CR12, CR14, CHR12, CHR14, CR11R14, CO, CS, O, S, SO, SO$_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above Wherein

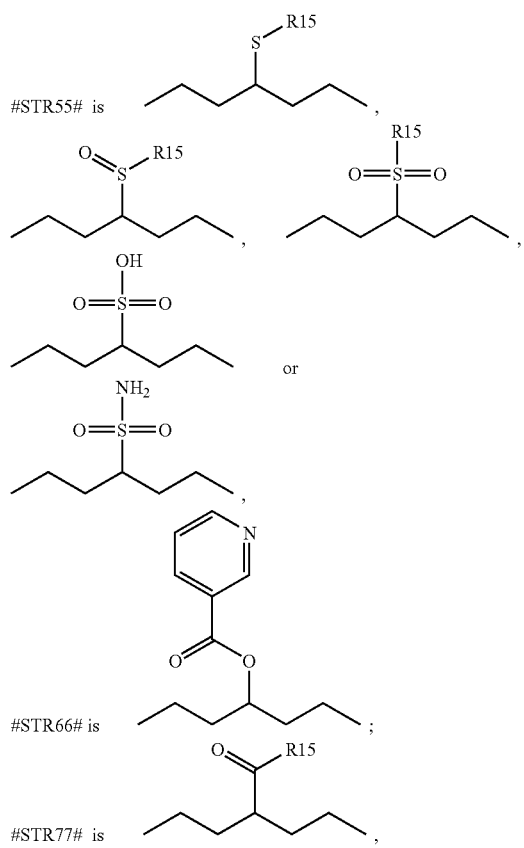

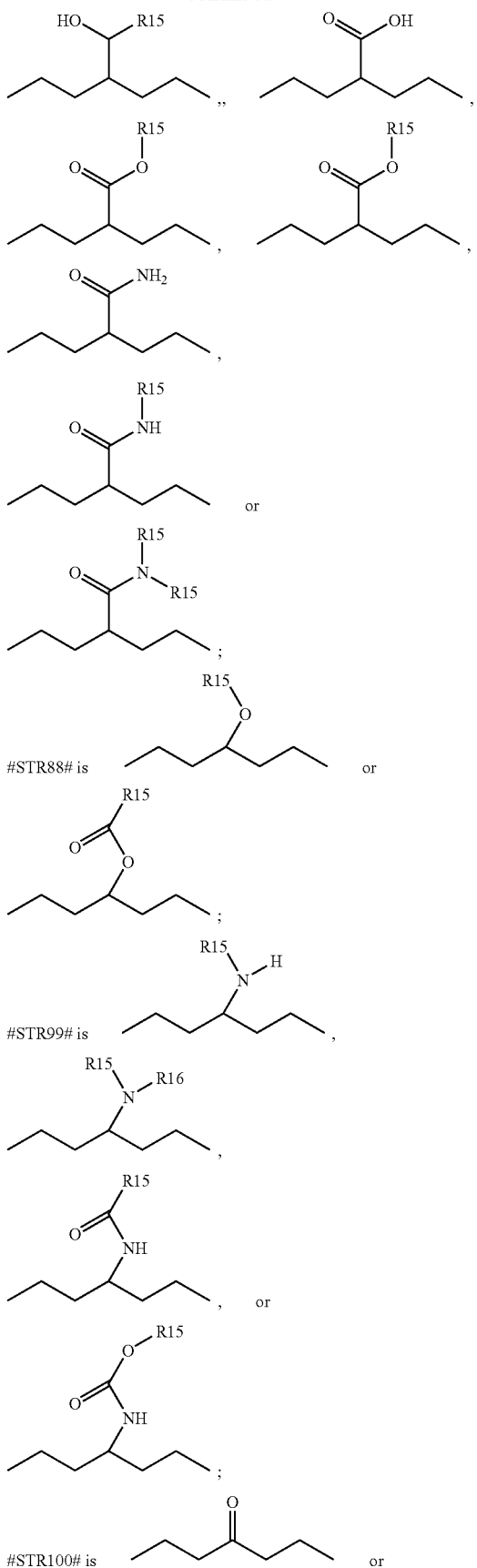

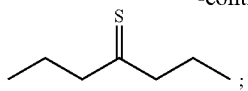

R15 and R16 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein Formula 1 compounds have at least one proviso selected from the following
  a. R7 is a hydroxyl;
  b. at least one W is a N;
  c. at least one of R1-R10 is #STR77#, #STR88# or #STR99#;
  d. at least one of R1-R10 is #STR66#;
  e. one of R1-R10 is a monoester;
  f. one of R1-R10 is a dicarboxylic acid;
  g. one of R1-R10 is succinic acid;
  h. R7 is #STR55#;
  i. R7 and R2 are #STR55#;
  j. R7 and R2 are hydroxyls; and
  k. R7 is #STR66#.

Non-limiting embodiments of Formula 1 include:
  i. R7 is a hydroxyl and at least one W is a N;
  ii. R7 is a hydroxyl and at least one of R1-R6 and R8-R10 is #STR66#;
  iii. R7 is a hydroxyl and at least one of R1-R6 and R8-R10 is #STR77#, #STR88# or #STR99#; and
  iv. R7 is #STR66# and at least one W is a N.

Other alternative embodiments of Formula 1 include

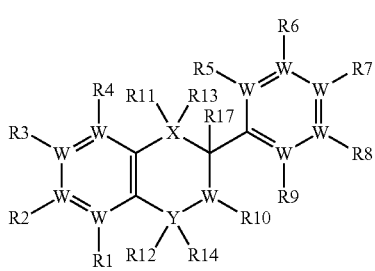
(I)

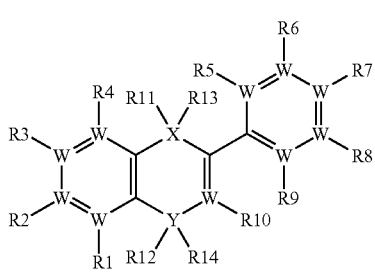
(II)

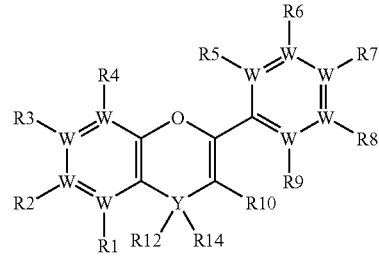
(III)

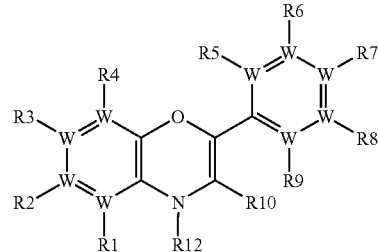
(IV)

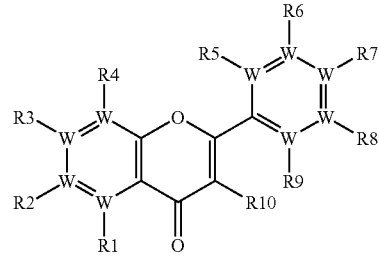
(V)

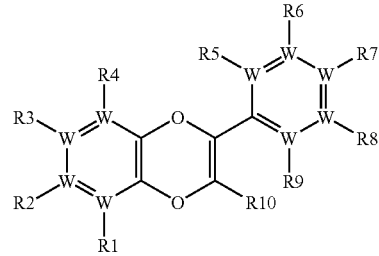
(VI)

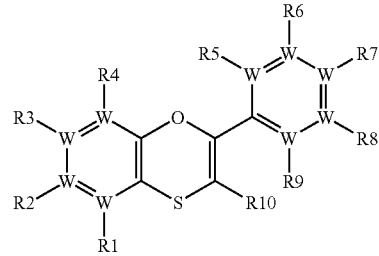
(VII)

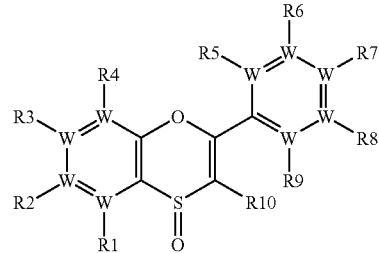
(VIII)

-continued

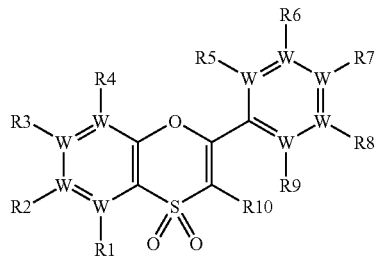
(IX)

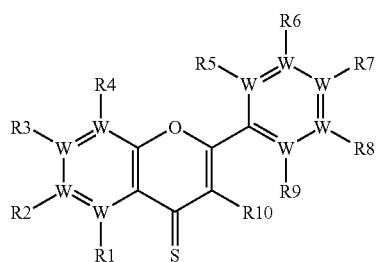
(X)

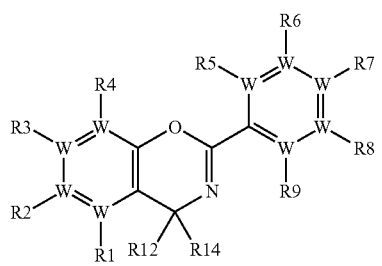
(XI)

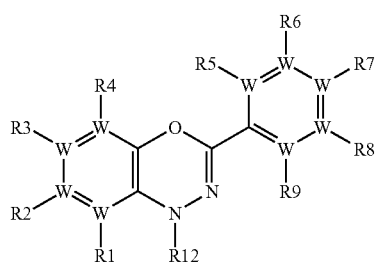
(XII)

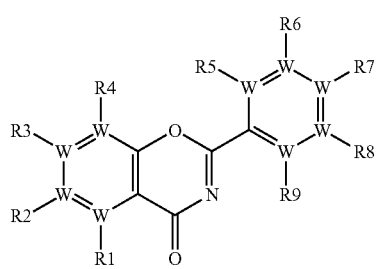
(XIII)

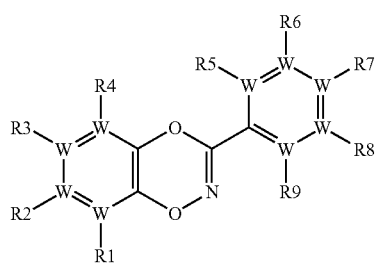
(XIV)

-continued

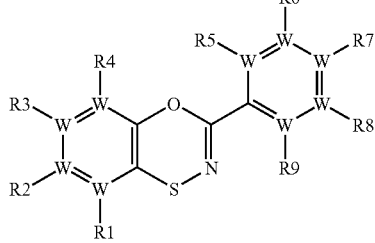
(XV)

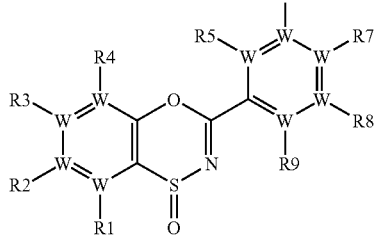
(XVI)

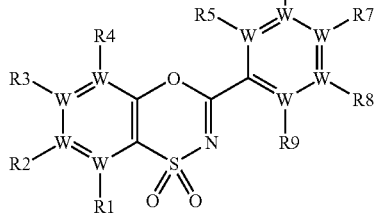
(XVII)

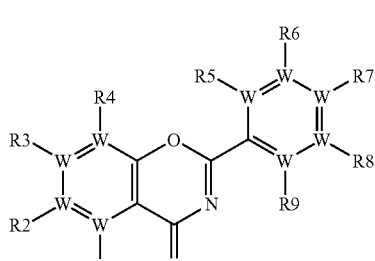
(XVIII)

or a pharmaceutically acceptable salt thereof, wherein

R1, R2, R3, R4, R5, R6, R7, R8, R9, R10, R11, R12, R13, R14, and R17, are independently selected from the group consisting of $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucuronic (AKA glucuronic) acid conjugates], monoesters, dicaboxylic acid, #STR55#, #STR66#, #STR77#, #STR88#, #STR99#, #STR100#, wherein W can be C or N;

wherein when W is an nitrogen atom, the nitrogen atom will only bind to three covalent bonds due to available valence electrons.

The structures below demonstrate a nitrogen arrangement of one embodiment of the compounds of Formula 1:

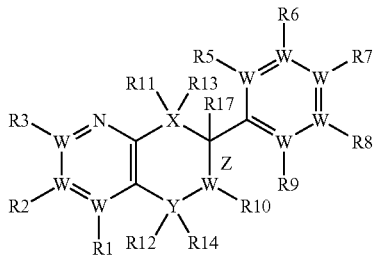

wherein the same applies to any W;
or

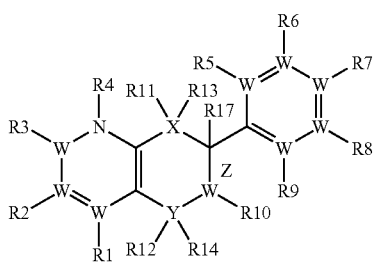

wherein the same applies to any W:

wherein

X can be CH, CH$_2$, CR11, CR13, CHR11, CHR13, CR11R13, CO, CS, O, S, SO, SO$_2$, NH, NR11 with the proviso that X and Y do not exceed the number of valence electrons available as per definitions of X and Y above Y can be CH, CH$_2$, CR12, CR14, CHR12, CHR14, CR11R14, CO, CS, O, S, SO, SO$_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above wherein

STR55# is

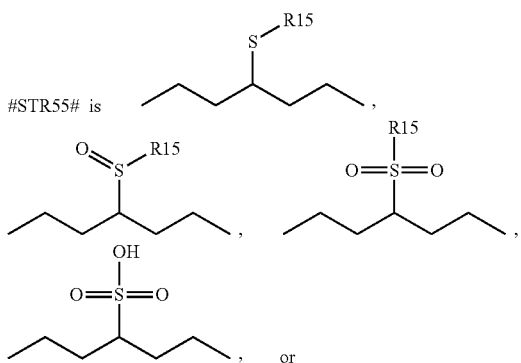

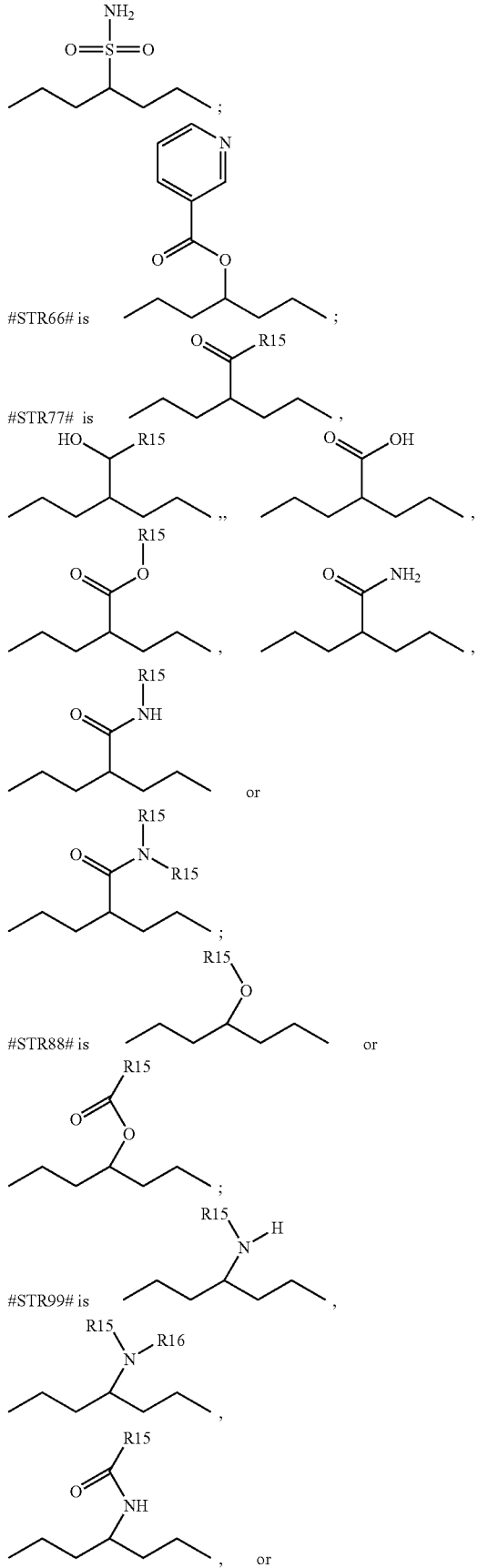

STR66# is

STR77# is

STR88# is

STR99# is

-continued

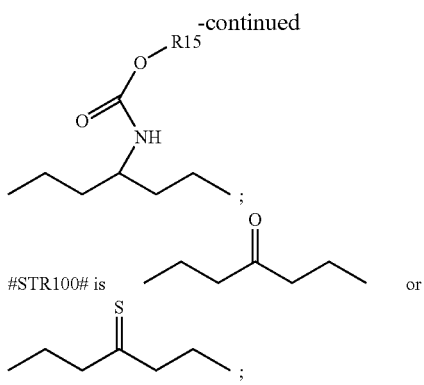

STR100# is

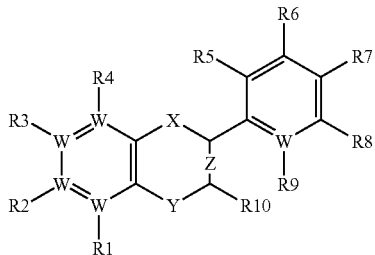

R15 and R16 are substituents independently selected from the group consisting of $(C_1$-$C_{22})$alkyl, $(C_2$-$C_{22})$alkenyl, $(C_1$-$C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein non limiting examples of Formula 1 have at least one proviso selected from the following:

R7 is a hydroxyl;
at least one W is a N;
at least one of R1-R10 is #STR77#, #STR88# or #STR99#;
at least one of R1-R10 is #STR66#;
one of R1-R10 is a monoester;
one of R1-R10 is a dicarboxylic acid;
one of R1-R10 is succinic acid;
R7 is #STR55#;
R7 and R2 are #STR55#;
R7 and R2 are hydroxyls; and
R7 is #STR66#.

Non-limiting examples include compounds of Formula 1 where
R7 is a hydroxyl and at least one W is a N;
R7 is a hydroxyl and at least one of R1-R6 and R8-R10 is #STR66#;
R7 is a hydroxyl and at least one of R1-R6 and R8-R10 is #STR77#, #STR88# or #STR99#; and
R7 is #STR66# and at least one W is a N.

Another embodiment provides flavanoid compounds of Formula 2:

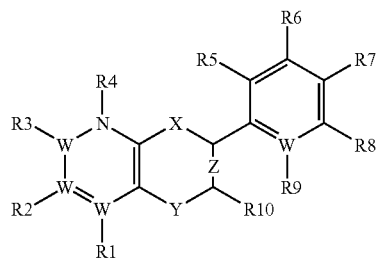

or a pharmaceutically acceptable salt thereof,
wherein
R1, R2, R3, R4, R5, R6, R8, R9, and R10 are independently selected from the group consisting of $(C_1$-$C_{22})$alkyl, $(C_2$-$C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein

W can be C or N;

wherein when W is an nitrogen atom, the nitrogen atom will only bind to three covalent bonds due to available valence electrons. The structures below demonstrate a nitrogen arrangement of one embodiment of the compounds of Formula 2:

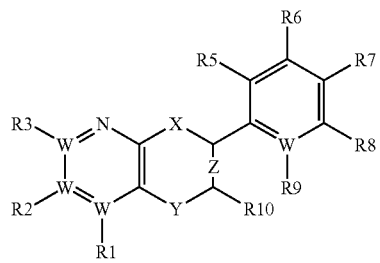

wherein the same applies to any W;
or

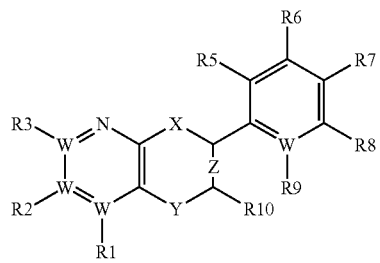

wherein the same applies to any W:
wherein

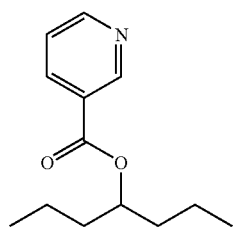

STR66# is wherein

X can be O, S, C, CR13, or NR13;
Y can be O, S, C, CR13, or NR13;
Z can be a single or a double bond
wherein
R13 is #STR77#, #STR88#, #STR99#, or #STR100#, wherein

STR77# means 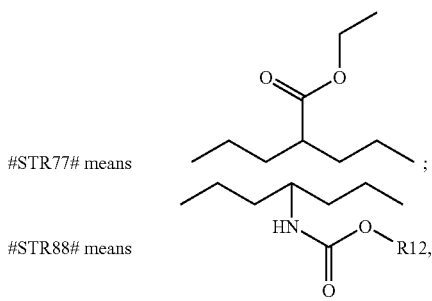;

STR88# means 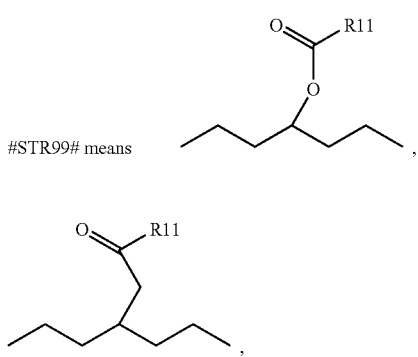, or

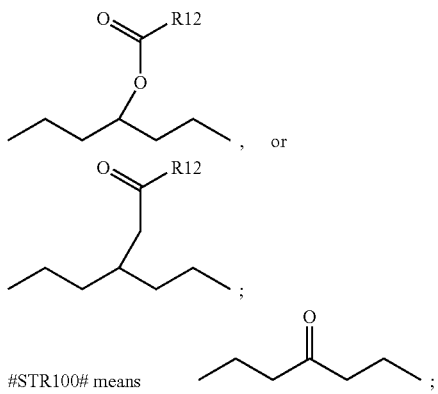

STR99# means 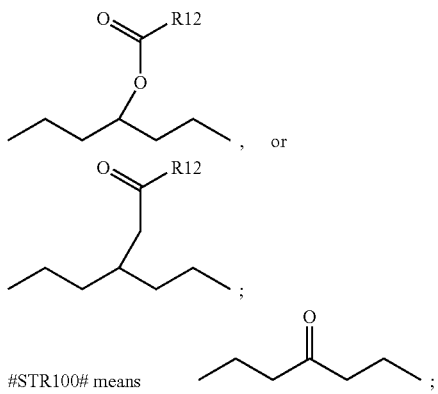,

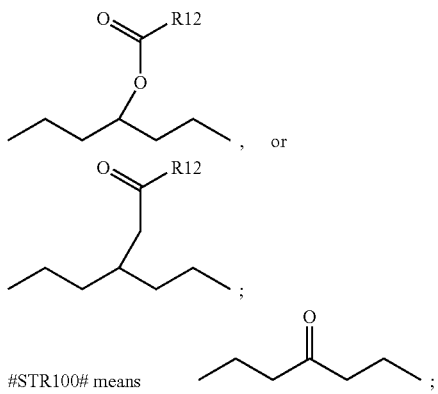,

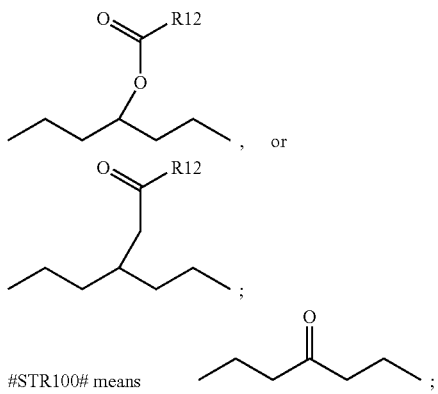, or

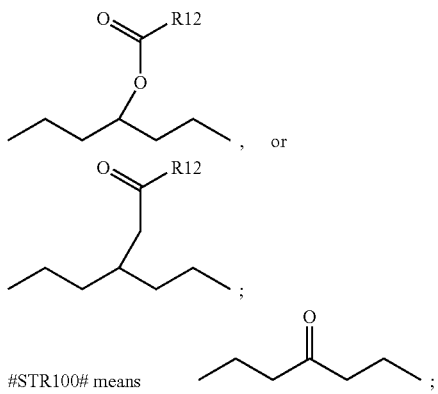;

STR100# means 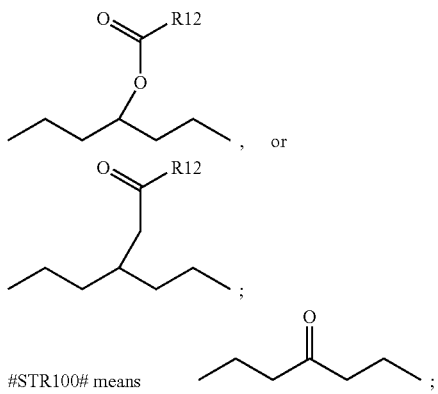;

R11 is pyridine, pyridazine, pyrimidine, pyrazine; and

R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O, with the proviso that;

a) R7 is a hydroxyl; or
b) R7 is a hydroxyl and optionally;
c) at least one W is a N, and/or;
d) at least one of R1-10 is #STR77#, or #STR88#, or #STR99#, and/or;
e) at least one of R1-R10 is #STR66#.

Another embodiment provides compounds comprising the general flavonoid structure of Formula 2:

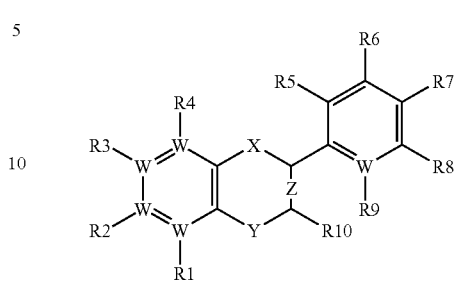

or a pharmaceutically acceptable salt thereof, wherein

R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein

W can be C or N;

wherein when W is an nitrogen atom, the nitrogen atom will only bind to three covalent bonds due to available valence electrons. The structures below demonstrate a nitrogen arrangement of one embodiment of the compounds of Formula 2:

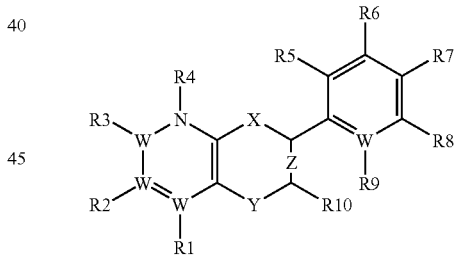

wherein the same applies to any W; or

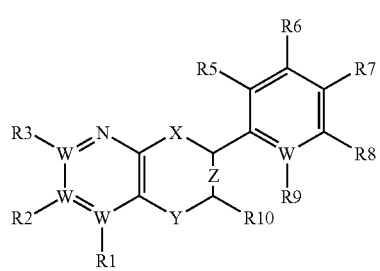

wherein the same applies to any W:

wherein

STR66# is [structure: nicotinate ester of hexan-3-ol]

wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

STR77# means [structure: ethyl 2-propylpentanoate]

STR88# means [structure: HN-C(=O)-O-R12 with dipropyl branching]

[structure: 2-propylpentanoate-O-R12]

STR99# means [structure with R11 ester], [structure with R11 ketone on branched chain], [structure: O-R12 carbonate with branching], or [structure: C(=O)-R12 ketone with branching];

STR100# means [structure: heptan-3-one];

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;

with the proviso that;
a) at least one W is a N and R7 is a hydroxyl; or
b) at least one W is a N and R7 is a hydroxyl, and optionally;
c) at least one of R1-10 is #STR77#, or #STR88#, or #STR99#, and/or;
d) at least one of R1-R10 is #STR66#.

Another embodiment provides compounds comprising the general flavonoid structure of Formula 2:

[Formula 2 structure]

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucuronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 2:

[structure with N at R4 position]

wherein the same applies to any W; or

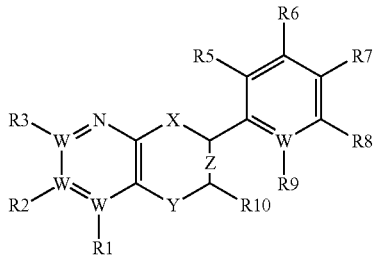

wherein the same applies to any W:
wherein

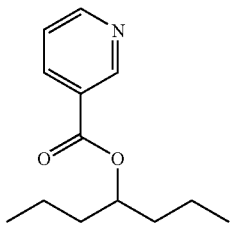

STR66# is wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

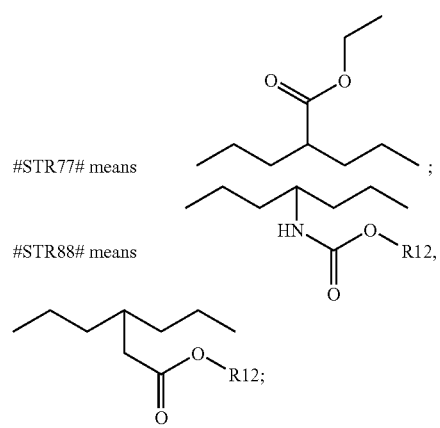

STR77# means

STR88# means

STR99# means

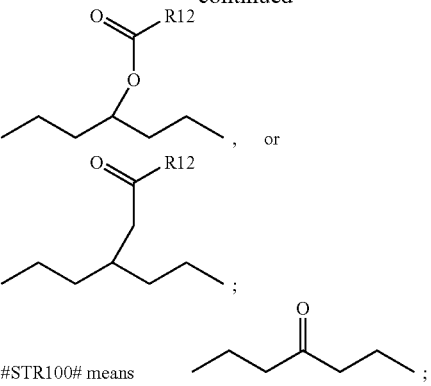

STR100# means

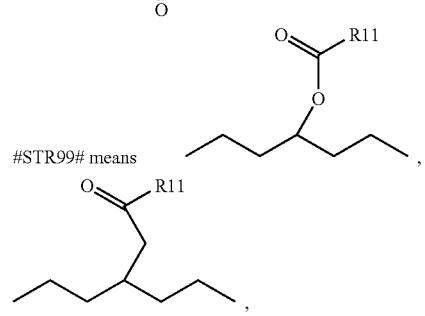

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;

with the proviso that;
a) at least one of R1-10 is selected from #STR77# or #STR88# or #STR99#, and R7 is a hydroxyl; or
b) at least one of R1-10 is selected from #STR77# or #STR88# or #STR99#, and R7 is a hydroxyl, and optionally;
c) at least one W is a N, and/or;
d) at least one of R1-R10 is #STR66#.

Another embodiment provides compounds comprising the general flavonoid structure of Formula 2:

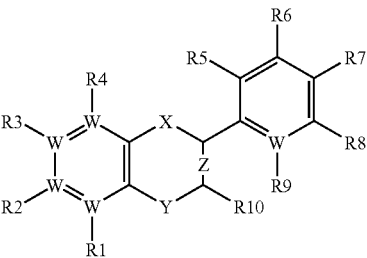

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucuronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 2:

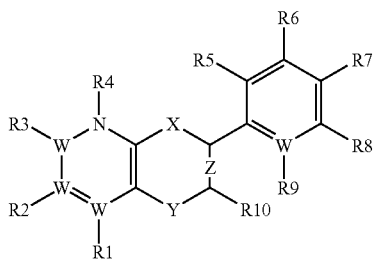

wherein the same applies to any W; or

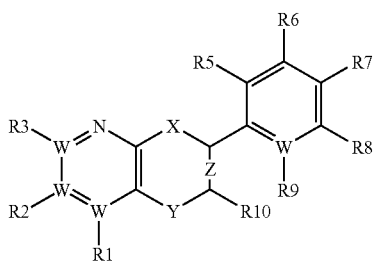

wherein the same applies to any W:
wherein

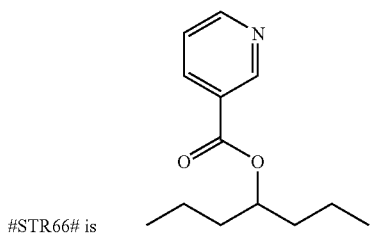

wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

STR77# means 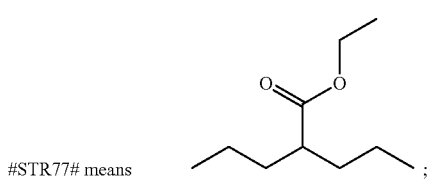;

STR88# means , or

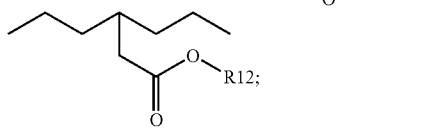;

-continued

STR99# means 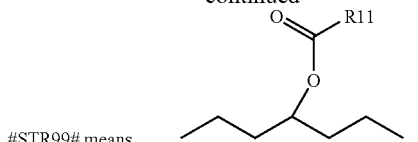,

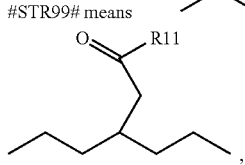,

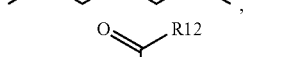, or

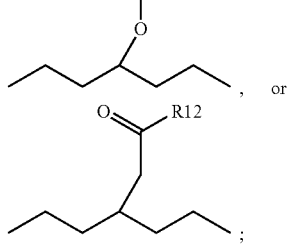;

STR100# means 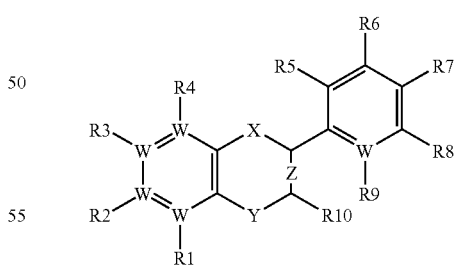;

R11 is pyridine, pyridazine, pyrimidine, pyrazine; and
R12 is $(C_1\text{-}C_{22})$alkyl, $(C_2\text{-}C_{22})$alkenyl, aryl, heteroaryl or a derivative thereof, wherein said derivative is optionally substituted and optionally branched, and may have one or more of the C atoms replaced by S, N or O;
with the proviso that;
a) R7 is a hydroxyl or #STR66# and if R7 is a hydroxyl (R1-R6 and R8-R10) at least one of R1-R10 is #STR66#; or
b) R7 is a hydroxyl or #STR66# and if R7 is a hydroxyl (R1-R6 and R8-R10) at least one of R1-R10 is #STR66# and optionally;
c) at least one W is a N, and/or;
d) at least one of R1-10 is #STR77#, or #STR88#, or #STR99#.

Another embodiment provides compounds comprising the general flavonoid structure of Formula 2:

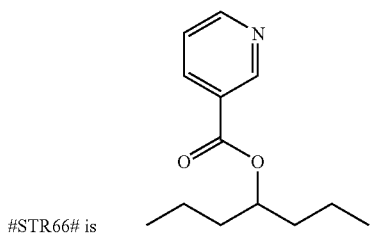

or a pharmaceutically acceptable salt thereof,
wherein
R1, R2, R3, R4, R5, R6, R8, R9, and R10 are independently selected from the group consisting of $(C_1\text{-}C_{22})$alkyl, $(C_2\text{-}C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucuronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 2:

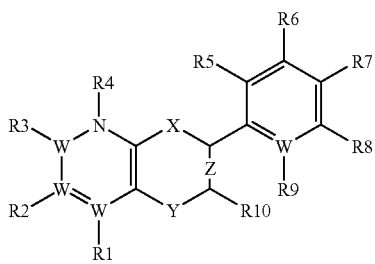

wherein the same applies to any W; or

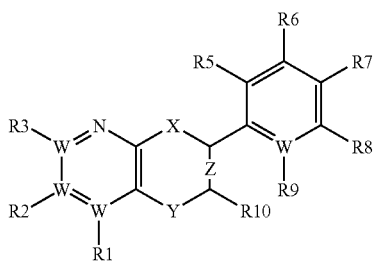

wherein the same applies to any W:
wherein

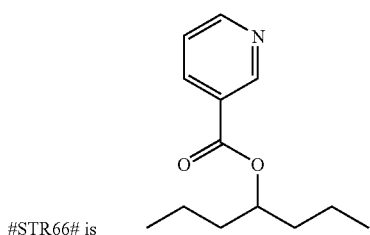

STR66# is wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

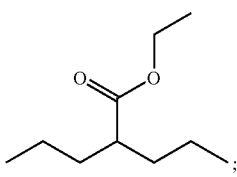

STR77# means

-continued

STR88# means 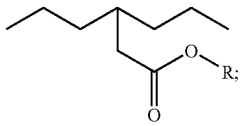

STR99# means 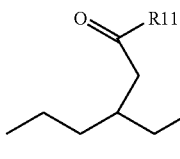

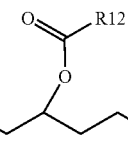

or

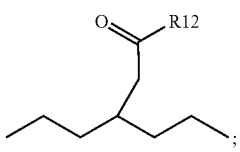

STR100# means 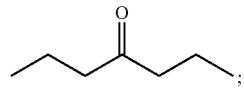 ;

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) R7 is a hydroxyl or #STR66#, and
b) at least one W is a N, and
c) at least one of R1-10 is #STR77#, or #STR88#, or #STR99#, and
d) at least one of R1-R10 is #STR66#.
Non-limiting examples of Formula 2 are provided below:

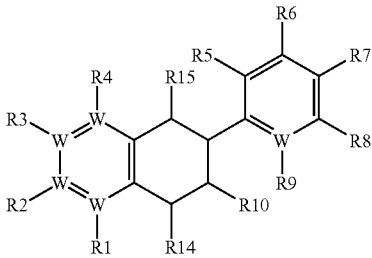

(XIX)

(XX)
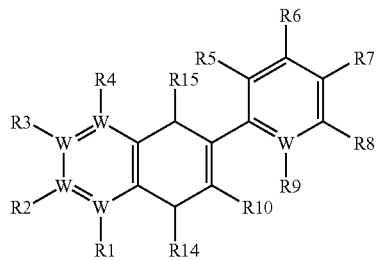

(XXI)
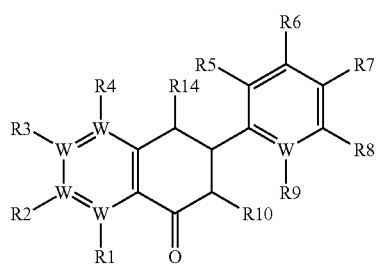

(XXII)
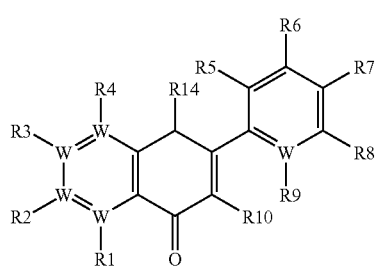

(XXIII)
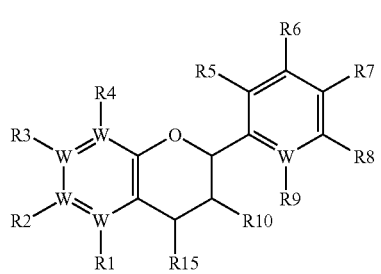

(XXIV)
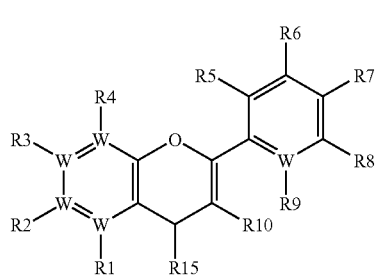

(XXV)
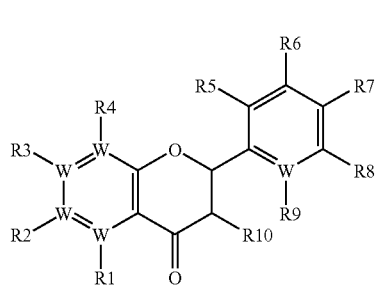

(XXVI)
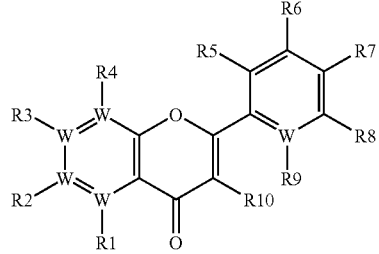

(XXVII)
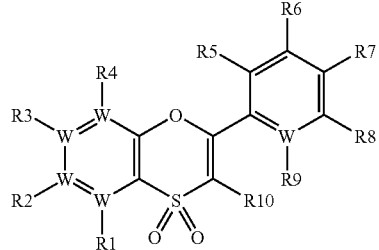

(XXVIII)
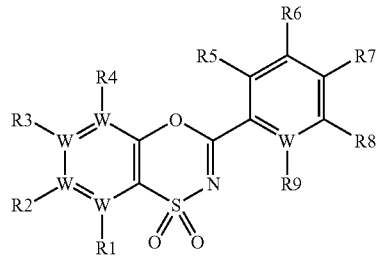

(XXIX)
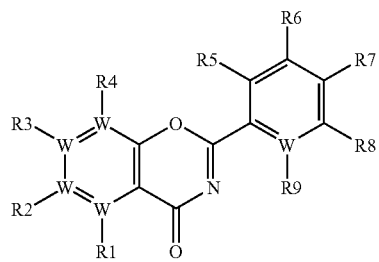

or pharmaceutically acceptable salts thereof, wherein

R1, R2, R3, R4, R5, R6, R8, R9, R10, R14 and R15 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein

W can be C or N;

wherein when W is an nitrogen atom, the nitrogen atom will only bind to three covalent bonds due to available valence electrons. The structures below demonstrate a nitrogen arrangement of one embodiment of the compounds of Formula 2:

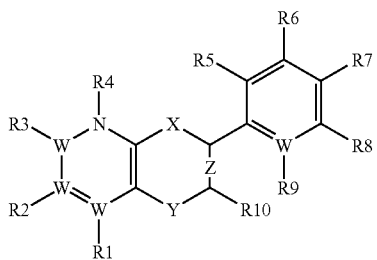

wherein the same applies to any W; or

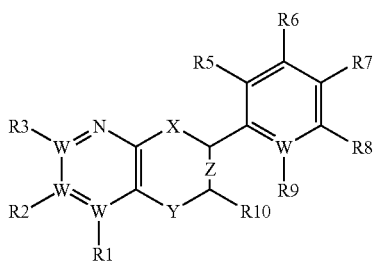

wherein the same applies to any W:
wherein

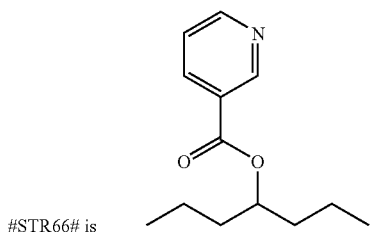

STR66# is wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

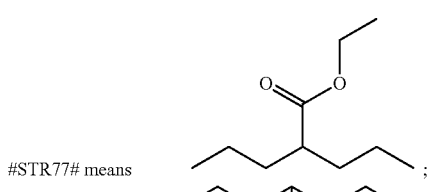

STR77# means

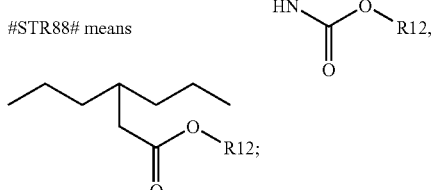

STR88# means

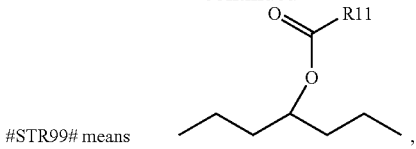

STR99# means

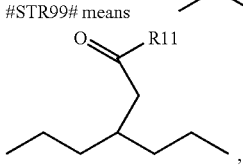

,

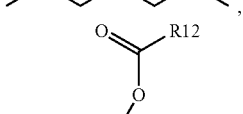

, or

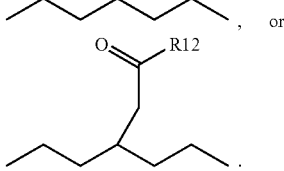

;

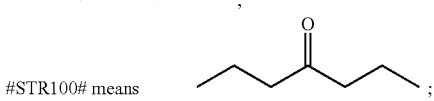

STR100# means

R11 is pyridine, pyridazine, pyrimidine, pyrazine;
R12 is (C$_1$-C$_{22}$)alkyl, (C$_2$C$_{22}$)alkenyl, aryl, heteroaryl or a derivative thereof, wherein said derivative is optionally substituted and optionally branched, and may have one or more of the C atoms replaced by S, N or O;
wherein Formula 2 compounds have at least one of the following groups of provisos:
1) with the proviso that;
 a) R7 is a hydroxyl; or
 b) R7 is a hydroxyl and optionally;
 c) at least one W is a N, and/or;
 d) at least one of R1-10 is #STR77#, or #STR88#, or #STR99#, and/or;
 e) at least one of R1-R10 is #STR66#.
2) with the proviso that;
 a) at least one W is a N and R7 is a hydroxyl; or
 b) at least one W is a N and R7 is a hydroxyl, and optionally;
 c) at least one of R1-10 is #STR77#, or #STR88#, or #STR99#, and/or;
 d) at least one of R1-R10 is #STR66#.
3) with the proviso that;
 a) at least one of R1-10 is selected from #STR77# or #STR88# or #STR99#, and R7 is a hydroxyl; or
 b) at least one of R1-10 is selected from #STR77# or #STR88# or #STR99#, and R7 is a hydroxyl, and optionally;
 c) at least one W is a N, and/or;
 d) at least one of R1-R10 is #STR66#.
4) with the proviso that;
 a) R7 is a hydroxyl or #STR66# and if R7 is a hydroxyl at least one of (R1-R6 and R8-R10) is #STR66#; OR
 b) R7 is a hydroxyl or #STR66# and if R7 is a hydroxyl at least one of (R1-R6 and R8-R10) is #STR66# and optionally;
 c) at least one W is a N, and/or;
 d) at least one of R1-10 is #STR77#, or #STR88#, or #STR99#.

5) with the proviso that;

a) R7 is a hydroxyl or #STR66#, and b) at least one W is a N, and c) at least one of R1-10 is #STR77#, or #STR88#, or #STR99#, and d) at least one of R1-R10 is #STR66#.

Another alternative embodiment provides flavanoid compounds of Formula 3:

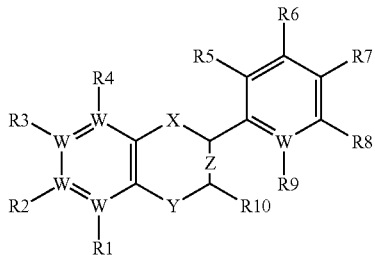

and a pharmaceutically acceptable salt thereof,
wherein

R1, R2, R3, R4, R5, R6, R7, R8, R9, and R10 are independently selected from the group consisting of ($C_1$-$C_{22}$) alkyl, ($C_2$-$C_{22}$)alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], wherein

STR66# is

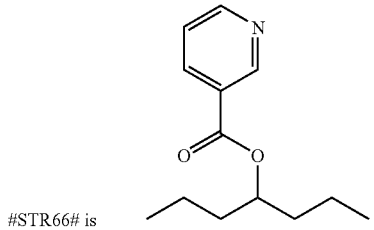

wherein

W can be C or N;

X can be O, S, C, CR13, or NR13;

Y can be O, S, C, CR13, or NR13;

Z can be a single or a double bond

Wherein R13 is #STR100#, #STR77# or #STR99#

Wherein

STR100# means

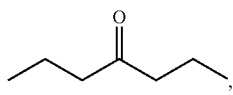

STR77# means

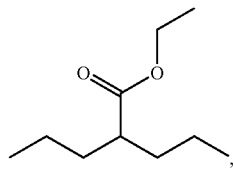

STR99# means

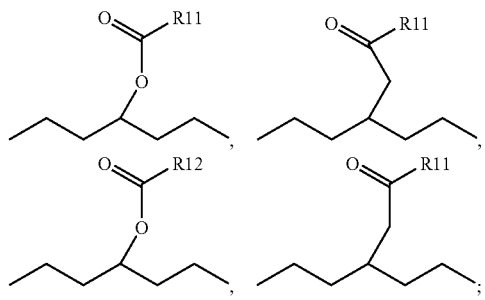

and

R11 is pyridine, pyridazine, pyrimidine, pyrazine;

and R12 is ($C_1$-$C_{22}$)alkyl, ($C_2$-$C_{22}$)alkenyl, aryl, heteroaryl or a derivative thereof, wherein said derivative is optionally substituted and optionally branched, and may have one or more of the C atoms replaced by S, N or O;

with the proviso that;

a) R7 is hydroxyl or #STR66# and at least one W is a N and optionally:

b) at least one of R1-R10 is #STR66#;

The structures below demonstrate a nitrogen arrangement of one embodiment of the compounds of Formula 3:

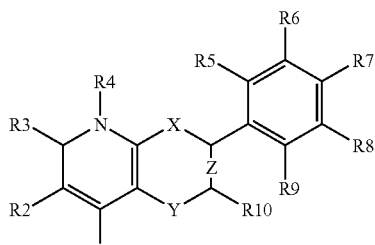

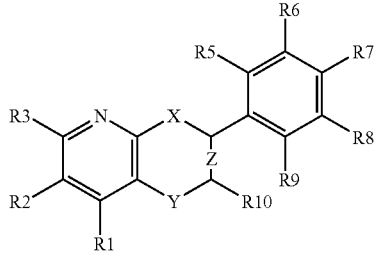

and a pharmaceutically acceptable salt thereof,
wherein

R1, R2, R3, R4, R5, R6, R7, R8, R9, and R10 are independently selected from the group consisting of ($C_1$-$C_{22}$) alkyl, ($C_2$-$C_{22}$)alkenyl, aryl, heteroaryl, hydrogen, hydroxyl [OH], acetyl, hydroxyalkyl, aminoalkyl, Bromide [Br], Iodide [I], methoxy [OCH₃], ethoxy [OCH₂CH₃], fluoride [F], chloride [Cl], CF₃, CCl₃, phosphate, O-sulfate [the sulfate conjugate], O -glucoronidate [the glucoronic (AKA glucuronic) acid conjugates],
wherein

STR66# is 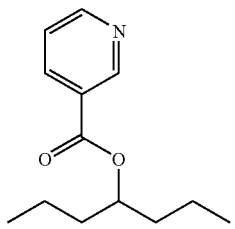

wherein
X can be O, S, C, CR13, or NR13;
Y can be O, S, C, CR13, or NR13;
Z can be a single or a double bond
Wherein R13 is #STR100#, #STR77# or #STR99#
Wherein:
STR100# means

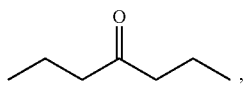,

STR77# means

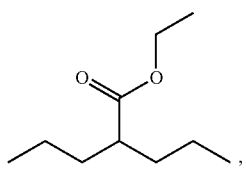,

STR99# means

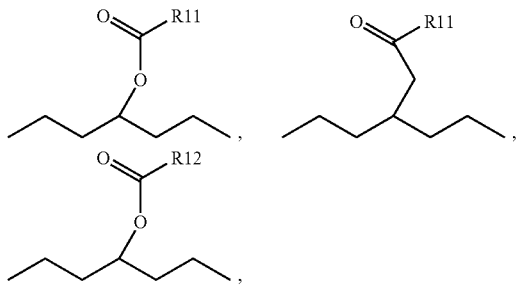

or 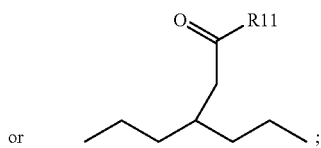;

R11 is pyridine, pyridazine, pyrimidine, pyrazine;

and R12 is (C₁-C₂₂)alkyl, (C₂-C₂₂)alkenyl, aryl, heteroaryl or a derivative thereof, wherein said derivative is optionally substituted and optionally branched, and may have one or more of the C atoms replaced by S, N or O;

with the proviso that a) R7 is a hydroxyl and at least one of R1-10 is #STR66#; and /or b) R7 is #STR66#.

Non-limiting examples of Formula 3 include

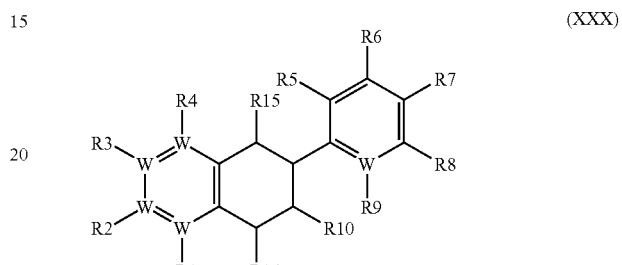 (XXX)

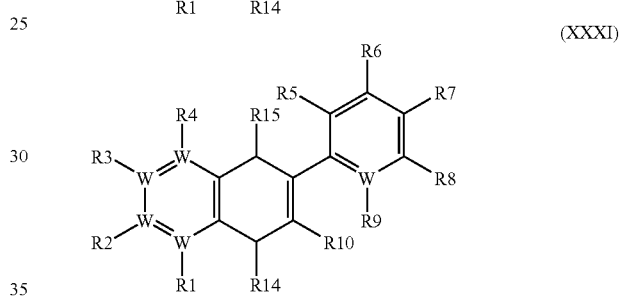 (XXXI)

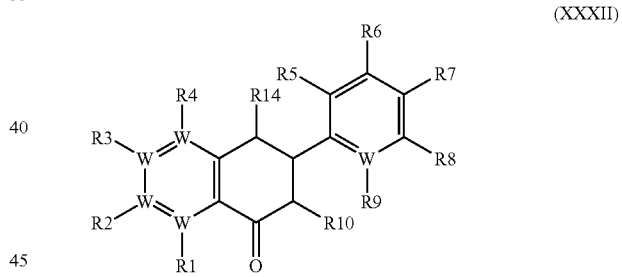 (XXXII)

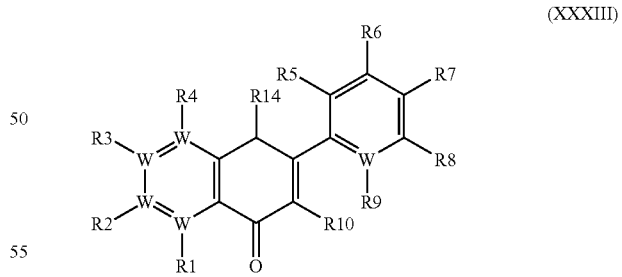 (XXXIII)

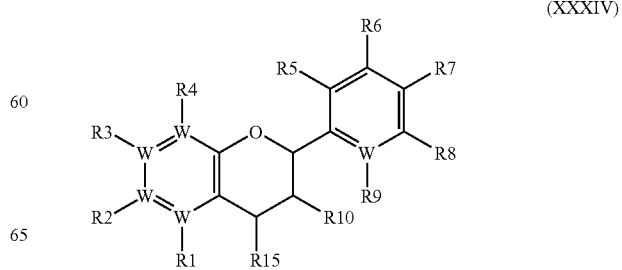 (XXXIV)

-continued

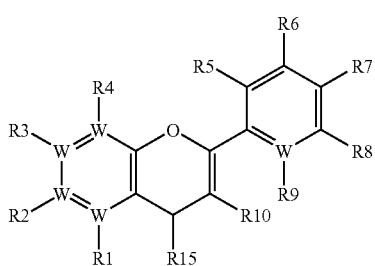
(XXXV)

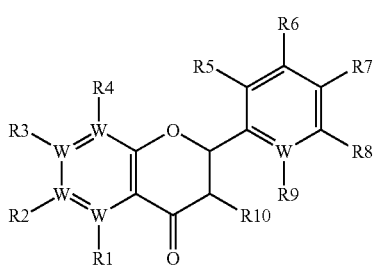
(XXXVI)

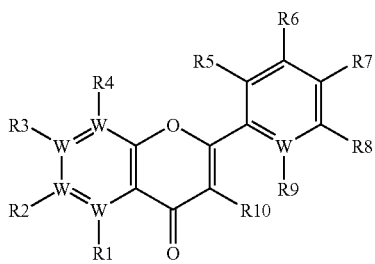
(XXXVII)

and a pharmaceutically acceptable salt thereof,
wherein
R1, R2, R3, R4, R5, R6, R7, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates],
wherein

STR66# means
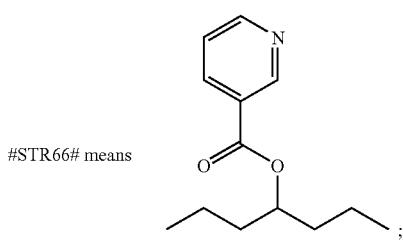
;

wherein
W can be C or N;
X can be O, S, C, CR13, or NR13;
Y can be O, S, C, CR13, or NR13;
Z can be a single or a double bond
Wherein R13 is #STR100#, #STR77# or #STR99#

Wherein
STR100# means

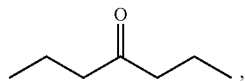,

STR77# means

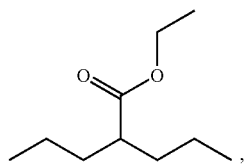,

STR99# means

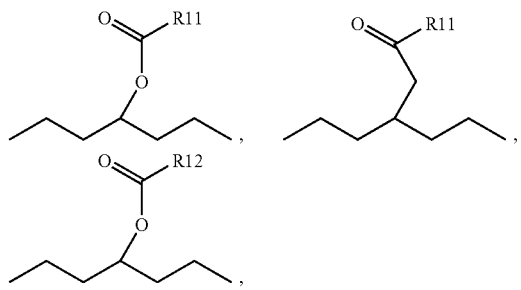

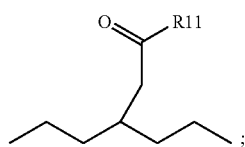;

and
R11 is pyridine, pyridazine, pyrimidine, pyrazine;
and R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) R7 is hydroxyl or #STR66# and at least one W is a N and optionally:
b) at least one of R1-R10 is #STR66#;
The structures below demonstrate a nitrogen arrangement of one embodiment of the compounds of Formula 3:

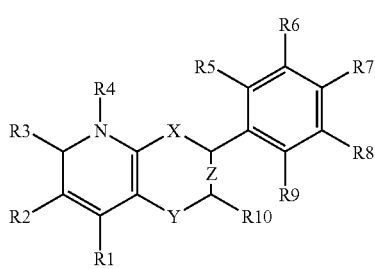

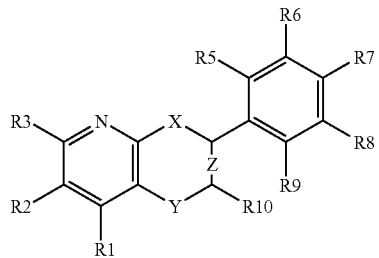
Non-limiting examples of Formula 3 include:
(XXXVIII)
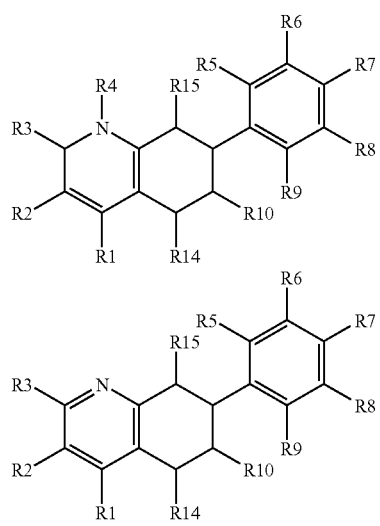
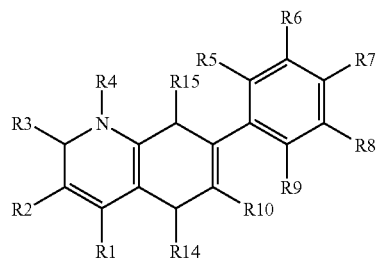
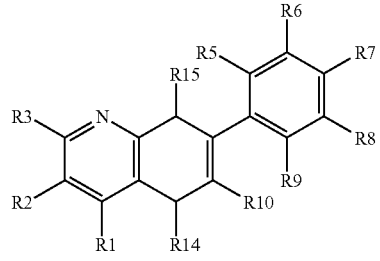
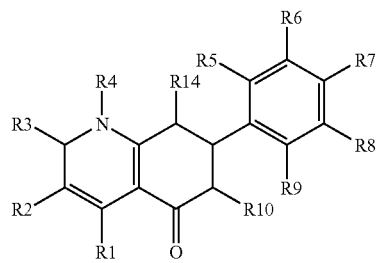
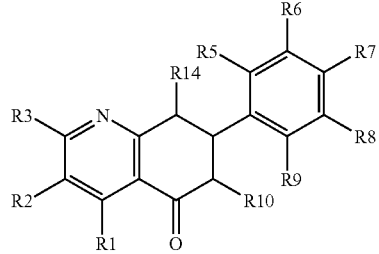
(XLI)
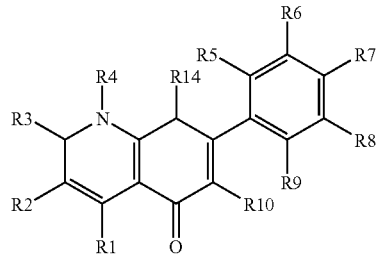
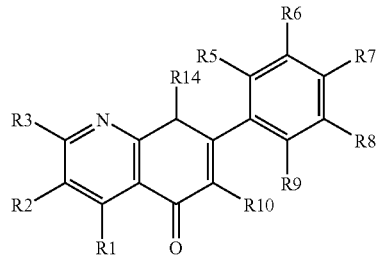
(XLII)
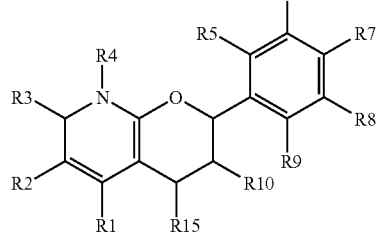
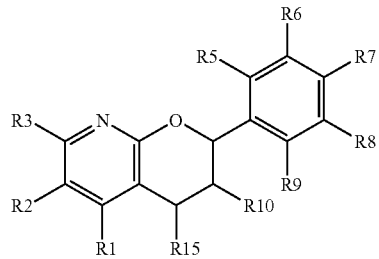
(XLIII)
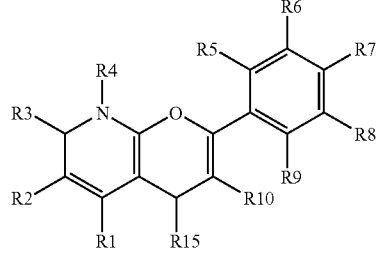

-continued

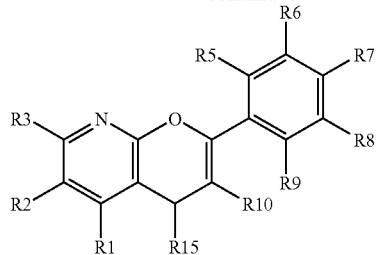

(XLIV)

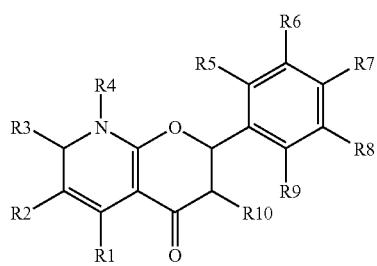

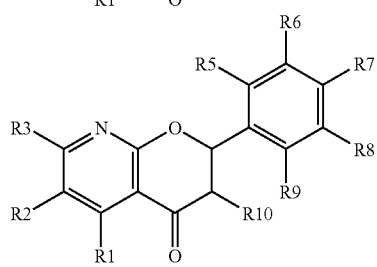

and a pharmaceutically acceptable salt thereof,
wherein
R1, R2, R3, R4, R5, R6, R7, R8, R9, and R10 are independently selected from the group consisting of $(C_1-C_{22})$ alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates],
wherein

STR66# means

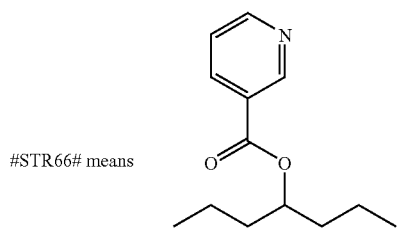

wherein
X can be O, S, C, CR13, or NR13;
Y can be O, S, C, CR13, or NR13;
Z can be a single or a double bond
Wherein R13 is #STR100#, #STR77# or #STR99#

Wherein:
STR100# means

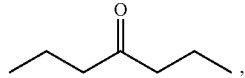

STR77# means

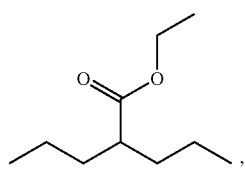

STR99# means

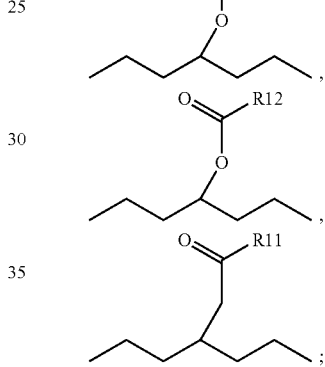

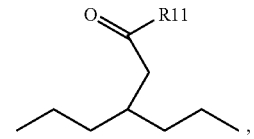

R11 is pyridine, pyridazine, pyrimidine, pyrazine;
and R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that
a) R7 is a hydroxyl and at least one of R1-10 is #STR66#; and/or
b) R7 is #STR66#.

Disclosed herein are methods for increasing expression of ApoA-I in a mammal comprising administering a therapeutically effective amount of a compound of Formula IV:

Formula IV

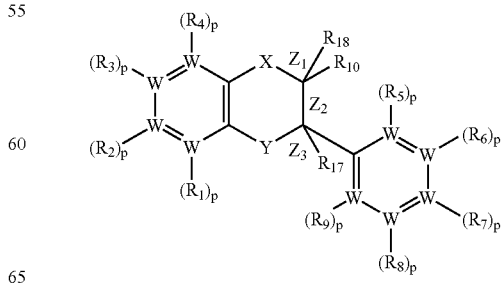

wherein:
- X is selected from $CR_{11}$, $CR_{11}R_{13}$, CO, CS, O, S, SO, $SO_2$, N and $NR_{11}$, wherein $R_{11}$ may be the same or different than $R_{13}$;
- Y is selected from $CR_{12}$, $CR_{12}R_{14}$, CO, CS, O, S, SO, $SO_2$, N and $NR_{12}$, wherein $R_{12}$ may be the same or different than $R_{14}$;
- $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
- two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{18}$ are connected in a 5 or 6-membered ring to form a bicyclic aryl or bicyclic heteroaryl;
- each W is independently selected from C and N, wherein if W is N, then p is 0 and if W is C, then p is 1;
- $Z_1$, $Z_2$ and $Z_3$ are each independently selected from a single bond and a double bond;
- wherein if Y is O, then X is not CO;
- wherein if X is O, Y is CO and $Z_2$ is a double bond, then at least one of $R_5$, $R_6$, $R_8$ and $R_9$ is not hydrogen;
- and pharmaceutically acceptable salts and hydrates thereof.

An alternative embodiment provides isoflavanoid compounds of Formula 4:

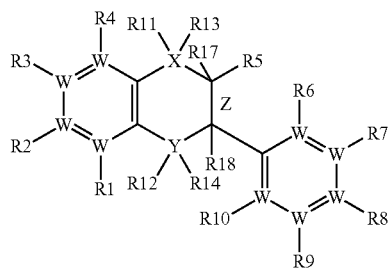

or a pharmaceutically acceptable salt thereof,
wherein
R1, R2, R3, R4, R5, R6, R7, R8, R9, R10, R11, R12, R13, R14, R17 and R18 are independently selected from the group consisting of ($C_1$-$C_{22}$)alkyl, ($C_2$-$C_{22}$)alkenyl, ($C_1$-$C_{22}$)alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 4:

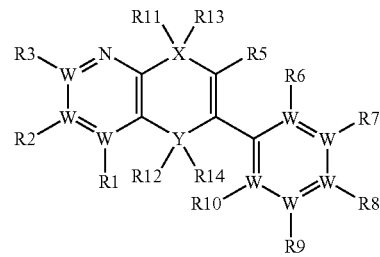

wherein the same applies to any W;
or

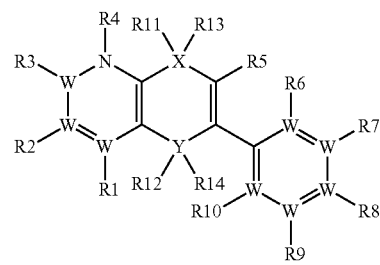

wherein the same applies to any W:
wherein
- X can be CH, $CH_2$, CR11, CR13, CHR11, CHR13, CR11R13, CO, CS, O, S, SO, $SO_2$, NH, NR11 with the proviso that X and Y do not exceed the number of valence electrons available as per definitions of X and Y above
- Y can be CH, $CH_2$, CR12, CR14, CHR12, CHR14, CR11R14, CO, CS, O, S, SO, $SO_2$, NH, NR11 with the proviso that X and Y do not exceed the number of valence electrons available as per definitions of X and Y above
- Z can be a single, double bond or triple bond, with the proviso that X and Y do not exceed the number of valence electrons available as per definitions of X and Y above wherein

STR55# is 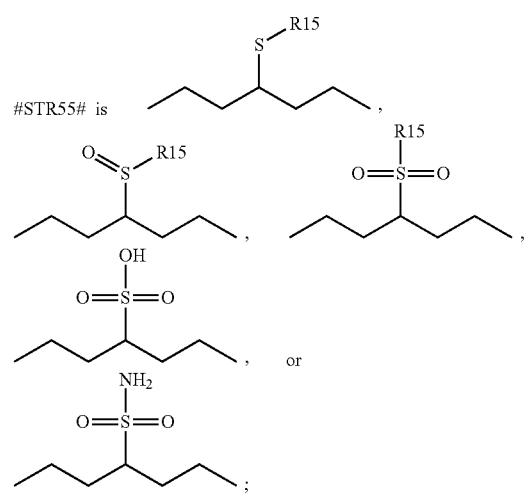

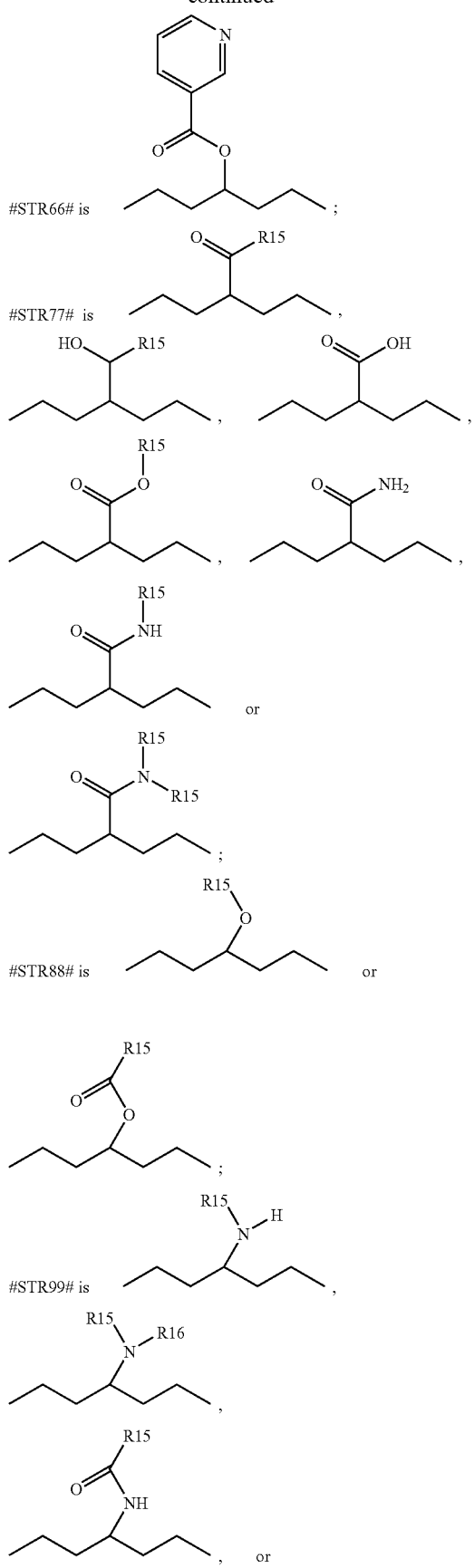
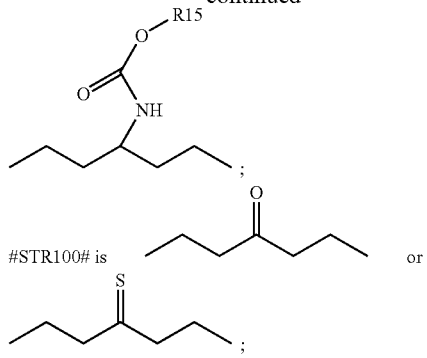

R15 and R16 are substituents independently selected from the group consisting of $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein Formula 4 compounds have at least one proviso selected from the following:

R8 is a hydroxyl;

at least one W is a N;

at least one of R1-R10 is #STR77#, #STR88# or #STR99#;

at least one of R1-R10 is #STR66#;

R8 is #STR66#;

one of R1-R10 is a monoester;

one of R1-R10 is a dicarboxylic acid;

R8 is #STR55#;

R8 and R3 are #STR55#;

R8 and R3 are hydroxyls; and

R8 is #STR66#.

Another embodiment provides for compounds of Formula 4 wherein:

R8 is a hydroxyl and at least one W is a N;

R8 is a hydroxyl and at least one of R1-R7 and R9-R-10 is #STR66#;

R8 is a hydroxyl and at least one of R1-R7 and R9-R10 is #STR77#, #STR88# or #STR99; and R8 is #STR66# and at least one W is a N.

Non-limiting examples of compounds of Formula 4 include:

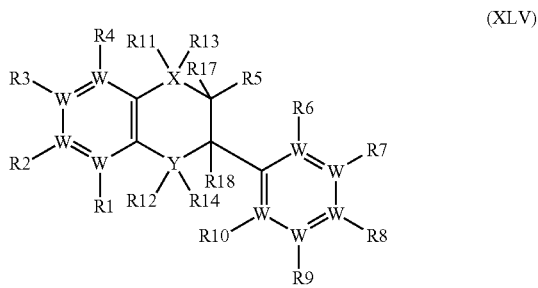

(XLV)

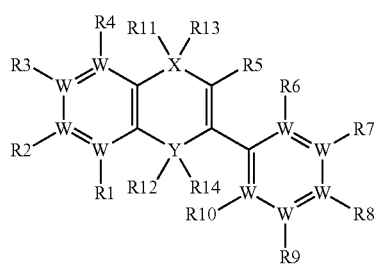 (XLVI)

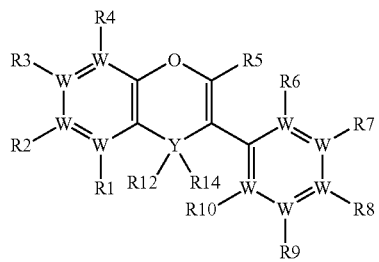 (XLVII)

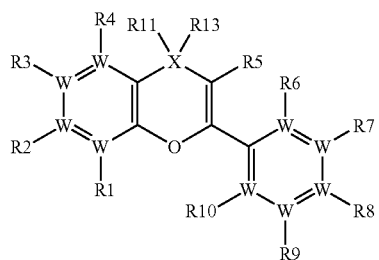 (XLVIII)

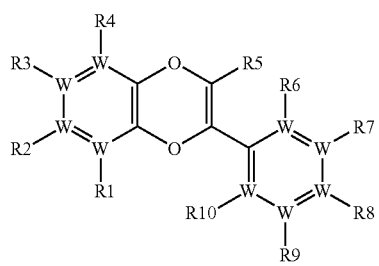 (XLIX)

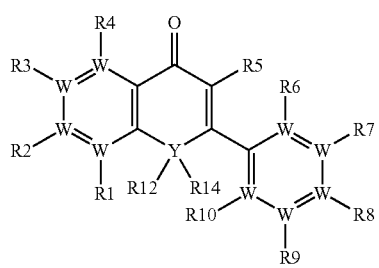 (L)

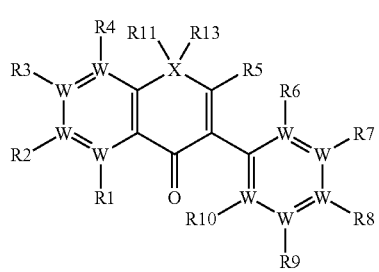 (LI)

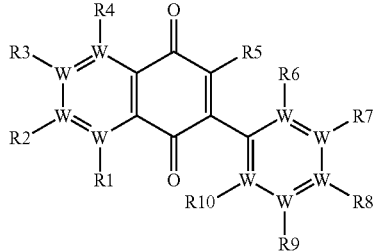 (LII)

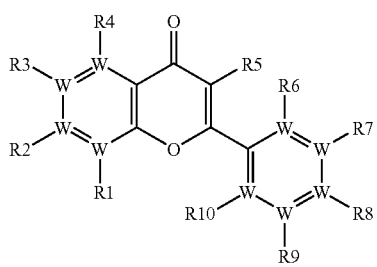 (LIII)

(LIV)

or a pharmaceutically acceptable salt thereof,
wherein
R1, R2, R3, R4, R5, R6, R7, R8, R9, R10, R11, R12, R13, R14, R17 and R18 are independently selected from the group consisting of $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 4:

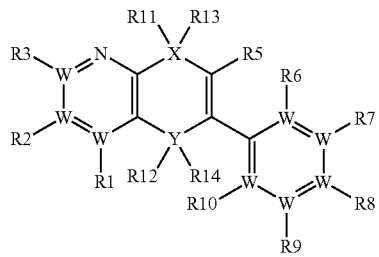

wherein the same applies to any W;
or

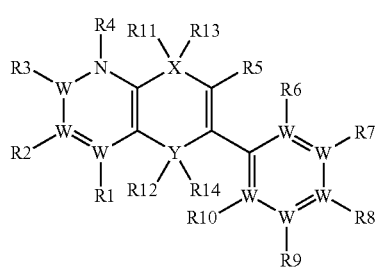

wherein the same applies to any W:

wherein

X can be CH, CH$_2$, CR11, CR13, CHR11, CHR13, CR11R13, CO, CS, O, S, SO, SO$_2$, NH, NR11 with the proviso that X and Y do not exceed the number of valence electrons available as per definitions of X and Y above Y can be CH, CH$_2$, CR12, CR14, CHR12, CHR14, CR11R14, CO, CS, O, S, SO, SO$_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above wherein

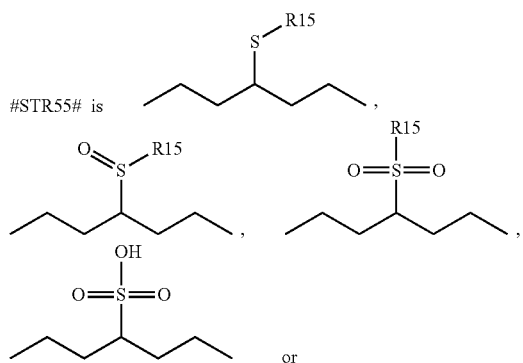

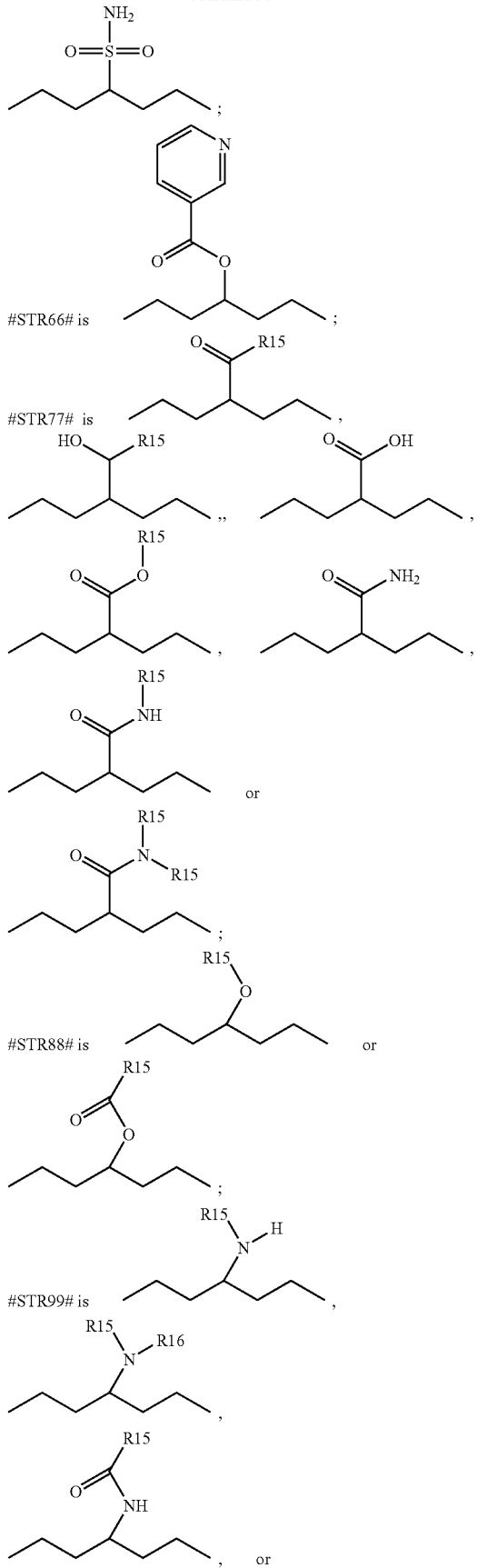

-continued

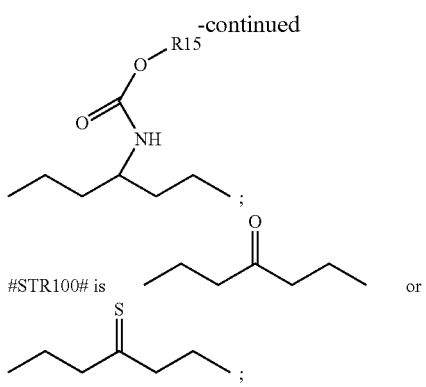

STR100# is

R15 and R16 are substituents independently selected from the group consisting of $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein Formula 4 compounds have at least one proviso selected from the following:

R8 is a hydroxyl;
at least one W is a N;
at least one of R1-R10 is #STR77#, #STR88# or #STR99#;
at least one of R1-R10 is #STR66#;
R8 is #STR66#;
one of R1-R10 is a monoester;
one of R1-R10 is a dicarboxylic acid;
R8 is #STR55#;
R8 and R3 are #STR55#;
R8 and R3 are hydroxyls; and
R8 is #STR66#.

Another embodiment provides for compounds of Formula 4 wherein:

R8 is a hydroxyl and at least one W is a N;
R8 is a hydroxyl and at least one of R1-R7 and R9-R-10 is #STR66#;
R8 is a hydroxyl and at least one of R1-R7 and R9-R10 is #STR77#, #STR88# or #STR99; and
R8 is #STR66# and at least one W is a N.

Another alternative embodiment provides isoflavanoid compounds of Formula 5:

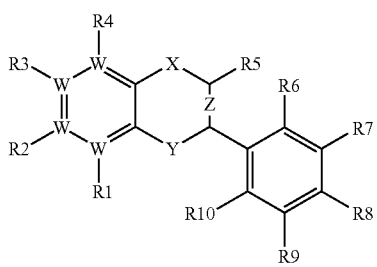

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 5:

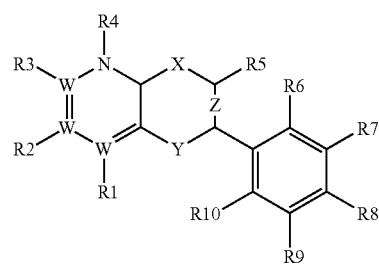

wherein the same applies to any W; or

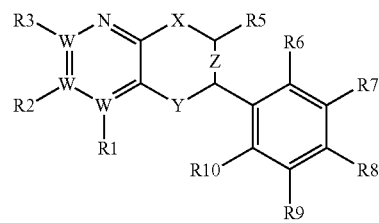

wherein the same applies to any W:
wherein

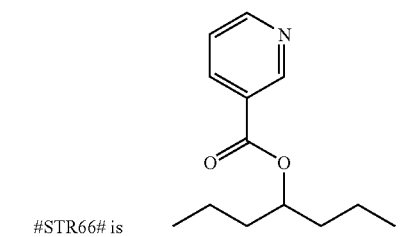

STR66# is wherein
X can be O, S, C, CR13, or NR13;
Y can be O, S, C, CR13, or NR13;
Z can be a single or a double bond
Wherein
R13 is #STR77#, #STR88#, #STR99#, or #STR100#, Wherein

STR77# means 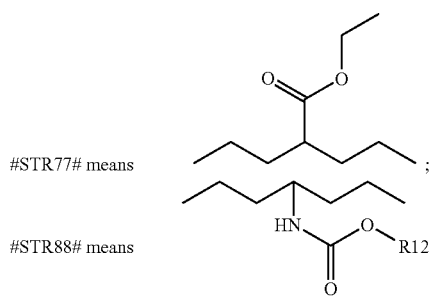;

STR88# means 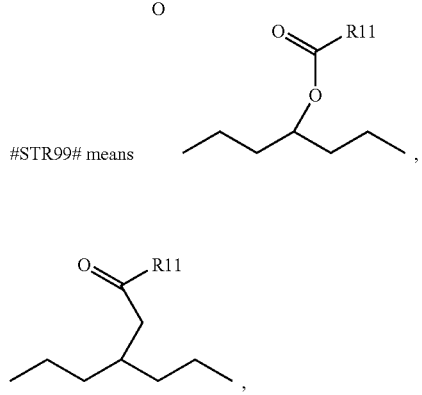, or

STR99# means 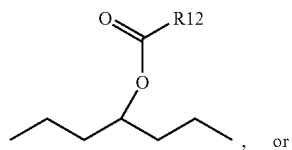,

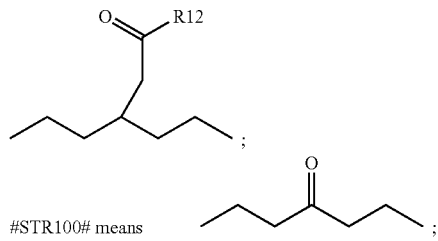, or

STR100# means 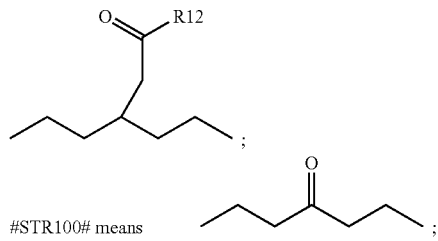;

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;
with the proviso that;
a) R8 is a hydroxyl; or
b) R8 is a hydroxyl, and optionally;
c) at least one W is a N, and/or;
d) at least one of R1-10 is #STR77#, or #STR88#, or #STR99#, and/or;
e) at least one of R1-R10 is #STR66#.

Another alternative embodiment provides compounds comprising the isoflavonoid structure of Formula 5:

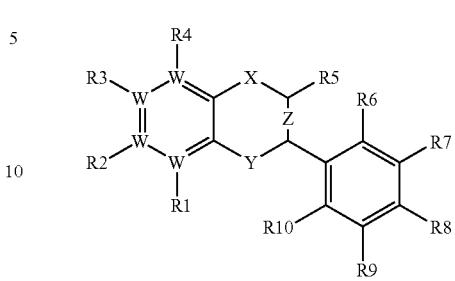

or a pharmaceutically acceptable salt thereof,
wherein

R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein

W can be C or N;

wherein when W is an nitrogen atom, the nitrogen atom will only bind to three covalent bonds due to available valence electrons.

The structures below demonstrate a nitrogen arrangement of one embodiment of the compounds of Formula 5

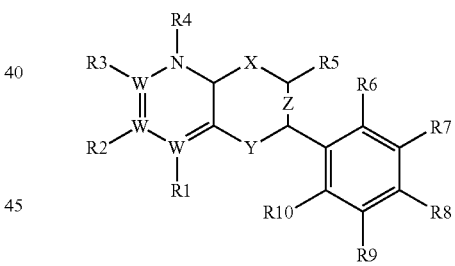

wherein the same applies to any W; or

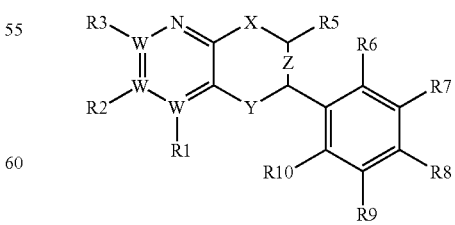

wherein the same applies to any W:

wherein

STR66# is 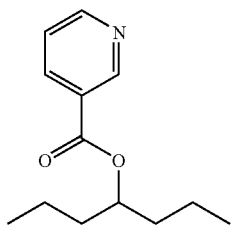

wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

STR77# means 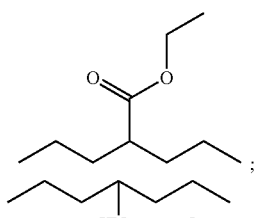 ;

STR88# means 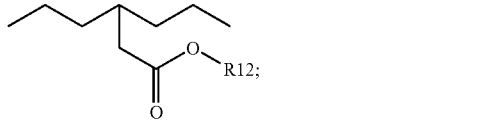 or

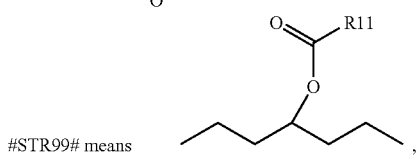 ;

STR99# means  ,

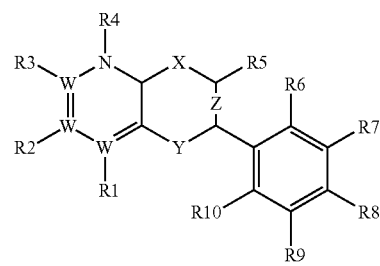, or

STR100# means 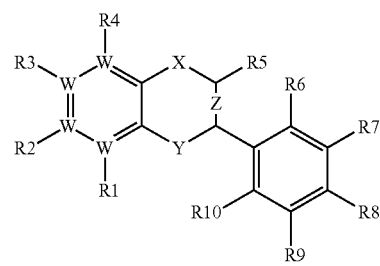 ;

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;

with the proviso that;
a) at least one W is a N and R8 is a hydroxyl; OR
b) at least one W is a N and R8 is a hydroxyl, and optionally;
c) at least one of R1-10 is #STR77#, or #STR88#, or #STR99#, and/or;
d) at least one of R1-R10 is #STR66#.

Another embodiment provides compounds comprising the isoflavonoid structure of Formula 5:

or a pharmaceutically acceptable salt thereof,
wherein
R1, R2, R3, R4, R5, R6, R8, R9, and R10 are independently selected from the group consisting of $(C1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 5 wherein the same applies to any W; or

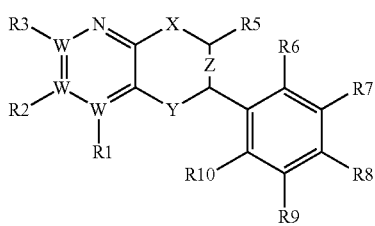

wherein the same applies to any W:
wherein

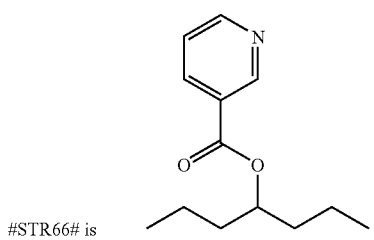

STR66# is wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

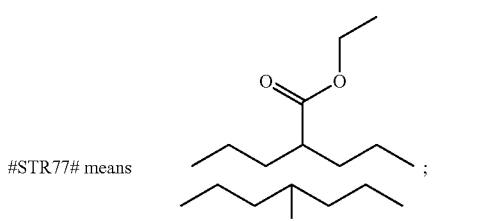

STR77# means

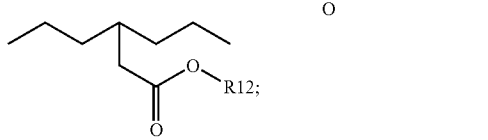

STR88# means

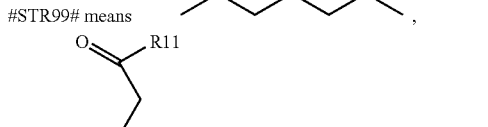

STR99# means

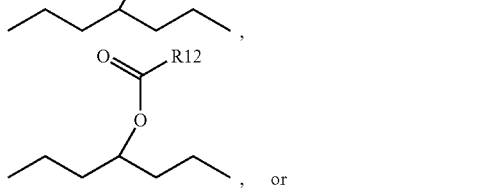

, or

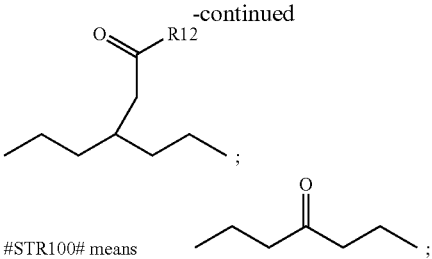

STR100# means 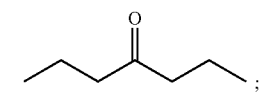 ;

R11 is pyridine, pyridazine, pyrimidine, pyrazine; and

R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;

with the proviso that;

a) at least one of R1-10 is selected from #STR77# or #STR88# or #STR99#, and R8 is a hydroxyl; or b) at least one of R1-10 is selected from #STR77# or #STR88# or #STR99#, and R8 is a hydroxyl, and optionally;

c) at least one W is a N, and/or;

d) at least one of R1-R10 is #STR66#.

Another alternative embodiment provides compounds comprising the general isoflavonoid structure of Formula 5:

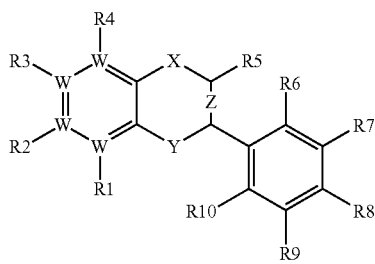

or a pharmaceutically acceptable salt thereof,
wherein

R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein

W can be C or N;

wherein when W is an nitrogen atom, the nitrogen atom will only bind to three covalent bonds due to available valence electrons. The structures below demonstrate a nitrogen arrangement of one embodiment of the compounds of Formula 5.

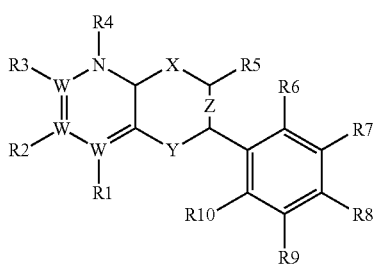

wherein the same applies to any W; or

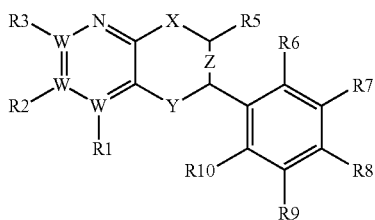

wherein the same applies to any W:
wherein

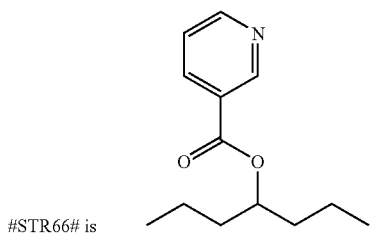

STR66# is wherein
X can be O, S, C, CR13, or NR13;
Y can be O, S, C, CR13, or NR13;
Z can be a single or a double bond
Wherein
R13 is #STR77#, #STR88#, #STR99#, or #STR100#,
Wherein

STR77# means
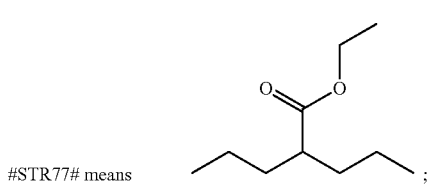
;

STR88# means
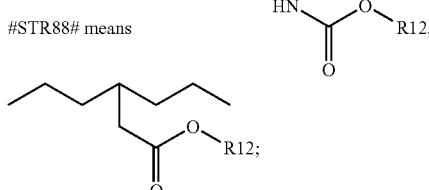
or

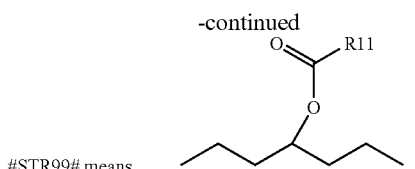
STR99# means
,

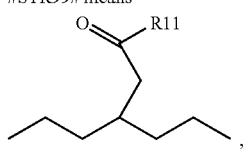
,

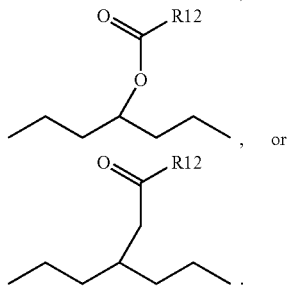
, or
;

STR100# means
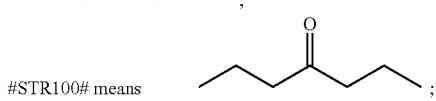
;

R11 is pyridine, pyridazine, pyrimidine, pyrazine; and
R12 is $(C_1-C_{22})$alkyl, $(C_2-C_{22})$alkenyl, aryl, heteroaryl or a derivative thereof, wherein said derivative is optionally substituted and optionally branched, and may have one or more of the C atoms replaced by S, N or O;

with the proviso that;
a) R8 is a hydroxyl or #STR66# and if R8 is a hydroxyl at least one of (R1-R7 and R9-R10) is #STR66#; or
b) R8 is a hydroxyl or #STR66# and if R8 is a hydroxyl at least one of (R1-R7 and R9-R10) is #STR66# and optionally;
c) at least one W is a N, and/or;
d) at least one of R1-10 is #STR77#, or #STR88#, or #STR99#.

Another alternative embodiment provides compounds comprising the general isoflavonoid structure of Formula 5:

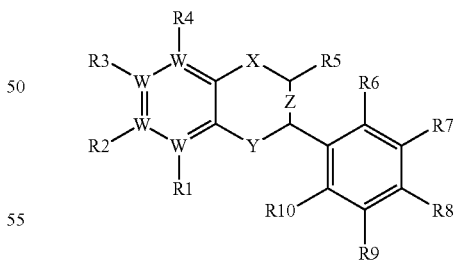

or a pharmaceutically acceptable salt thereof,
wherein
R1, R2, R3, R4, R5, R6, R8, R9, and R10 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [$OCH_3$], ethoxy [$OCH_2CH_3$], fluoride [F], chloride [Cl], $CF_3$, $CCl_3$, phosphate, O-sulfate [the sulfate conjugate], O-glucoronidate [the glucoronic (AKA glucuronic) acid conjugates], #STR66#, #STR77#, #STR88#, #STR99#, #STR100#
wherein
W can be C or N;
wherein when W is an nitrogen atom, the nitrogen atom will only bind to three covalent bonds due to available valence electrons. The structures below demonstrate a nitrogen arrangement of one embodiment of the compounds of Formula 5.

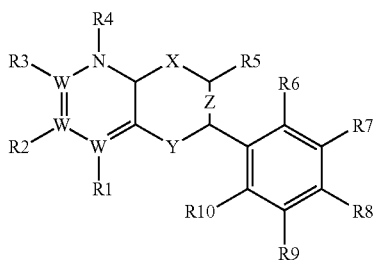

wherein the same applies to any W; or

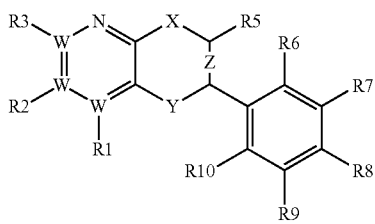

wherein the same applies to any W:
wherein
X can be O, S, C, CR13, or NR13;
Y can be O, S, C, CR13, or NR13;
Z can be a single or a double bond
Wherein
R13 is #STR77#, #STR88#, #STR99#, or #STR100#,
Wherein

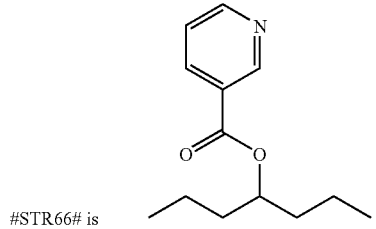

STR66# is

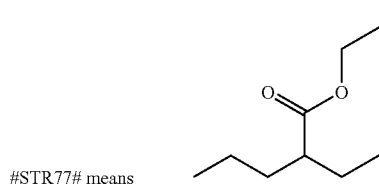

STR77# means

STR88# means 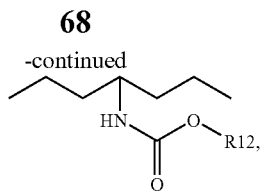

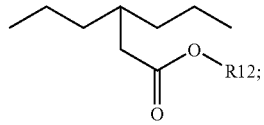

STR99# means 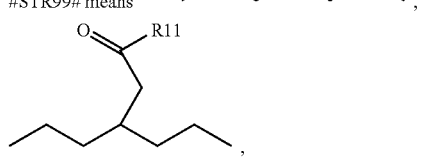

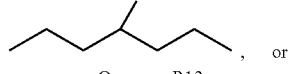

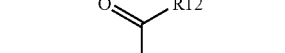, or

STR100# means 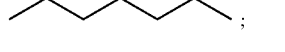

R11 is pyridine, pyridazine, pyrimidine, pyrazine; and
R12 is $(C_1\text{-}C_{22})$alkyl, $(C_2\text{-}C_{22})$alkenyl, aryl, heteroaryl or a derivative thereof, wherein said derivative is optionally substituted and optionally branched, and may have one or more of the C atoms replaced by S, N or O;
with the proviso that;
a) R8 is a hydroxyl or #STR66#, and
b) at least one W is a N, and
c) at least one of R1-10 is #STR77#, or #STR88#, or #STR99#, and
d) at least one of R1-R10 is #STR66#.

Non-limiting examples of compounds of Formula 5 include:

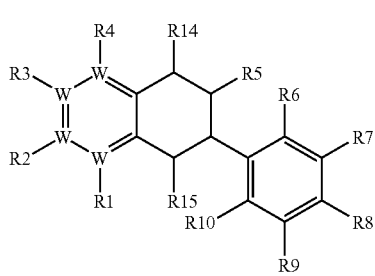

(LV)

-continued (LVI)
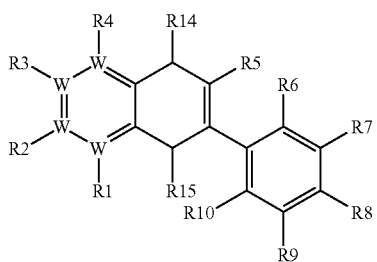

(LVII)
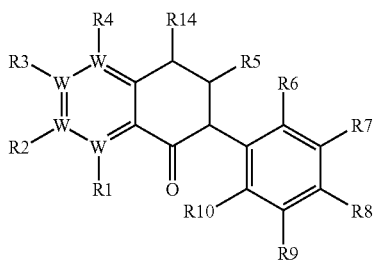

(LVIII)
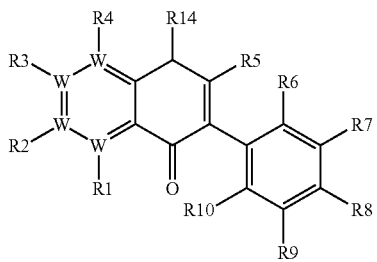

(LIX)
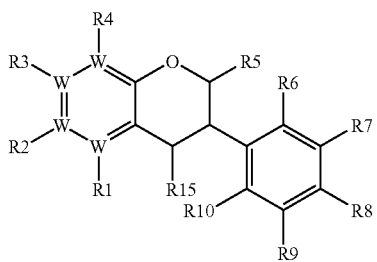

(LX)
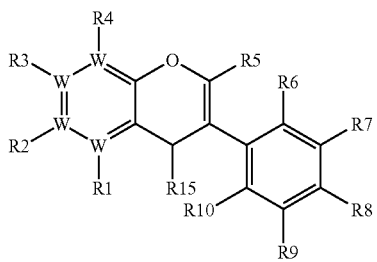

(LXI)
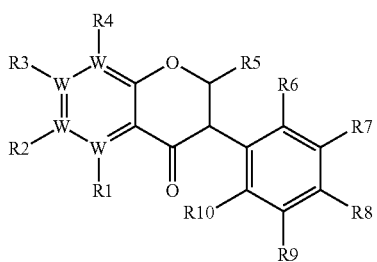

-continued (LXII)
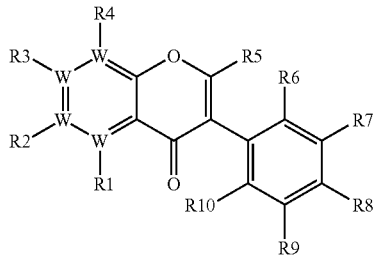

or a pharmaceutically acceptable salts thereof, wherein

R1, R2, R3, R4, R5, R6, R8, R9, R10, R14 and R15 are independently selected from the group consisting of $(C_1-C_{22})$alkyl, $(C_2-C_{22})$alkenyl, aryl, heteroaryl, hydrogen, hydroxyl [OH], acetyl, hydroxyalkyl, aminoalkyl, Bromide [Br], Iodide [I], methoxy [OCH$_3$], ethoxy [OCH$_2$CH$_3$], fluoride [F], chloride [Cl], CF$_3$, CCl$_3$, phosphate, O-sulfate [the sulfate conjugate], O-glucoronidate [the glucoronic (AKA glucuronic) acid conjugates], #STR66#, #STR77#, #STR88#, #STR99#, #STR100# wherein

W can be C or N;

wherein when W is an nitrogen atom, the nitrogen atom will only bind to three covalent bonds due to available valence electrons.

The structures below demonstrate a nitrogen arrangement of one embodiment of the compounds of Formula 5:

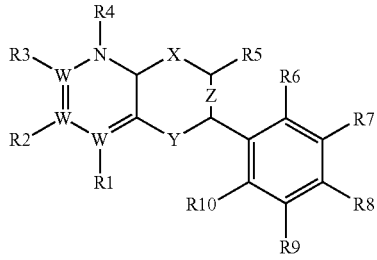

wherein the same applies to any W; or

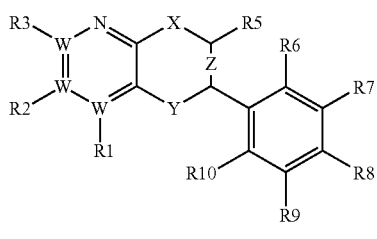

wherein the same applies to any W:

wherein

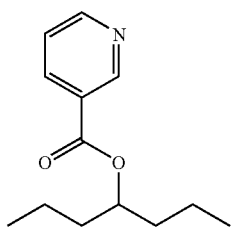

STR66# is wherein
X can be O, S, C, CR13, or NR13;
Y can be O, S, C, CR13, or NR13;
Z can be a single or a double bond
wherein
R13 is #STR77#, #STR88#, #STR99#, or #STR100#,
wherein

STR77# means 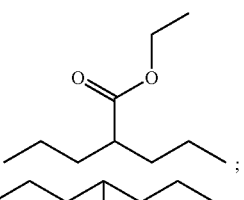;

STR88# means 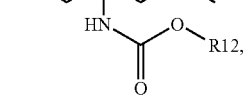, or

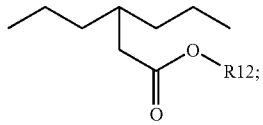;

STR99# means

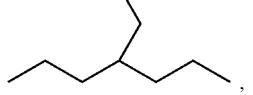,

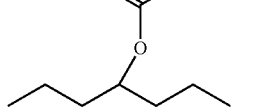, or

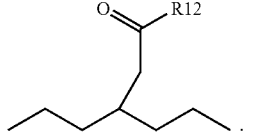;

STR100# means 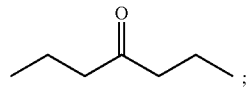;

R11 is pyridine, pyridazine, pyrimidine, pyrazine; and
R12 is $(C_1$-$C_{22})$alkyl, $(C_2$-$C_{22})$alkenyl, aryl, heteroaryl or a derivative thereof, wherein said derivative is optionally substituted and optionally branched, and may have one or more of the C atoms replaced by S, N or O;

wherein Formula 5 compounds have one at least one of the following groups of provisos:
1) with the proviso that;
  a) R8 is a hydroxyl; or
  b) R8 is a hydroxyl, and optionally;
  c) at least one W is a N, and/or;
  d) at least one of R1-10 is #STR77#, or #STR88#, or #STR99#, and/or;
  e) at least one of R1-R10 is #STR66#
2) with the proviso that;
  a) at least one W is a N and R8 is a hydroxyl; or
  b) at least one W is a N and R8 is a hydroxyl, and optionally;
  c) at least one of R1-10 is #STR77#, or #STR88#, or #STR99#, and/or;
  d) at least one of R1-10 is #STR66#
3) with the proviso that;
  a) at least one of R1-10 is selected from #STR77# or #STR88# or #STR99#, and R8 is a hydroxyl; or
  b) at least one of R-10 is selected from #STR77# or #STR88# or #STR99#, and R8 is a hydroxyl, and optionally;
  c) at least one W is a N, and/or;
  d) at least one of R1-R10 is #STR66#.
4) with the proviso that;
  a) R8 is a hydroxyl or #STR66# and if R8 is a hydroxyl at least one of (R1-R7 and R9-R10) is #STR66#; or
  b) R8 is a hydroxyl or #STR66# and if R8 is a hydroxyl at least one of (R1-R7 and R9-R10) is #STR66# and optionally;
  c) at least one W is a N, and/or;
  d) at least one of R-10 is #STR77#, or #STR88#, or #STR99#.
5) with the proviso that;
  a) R8 is a hydroxyl or #STR66#, and
  b) at least one W is a N, and
  c) at least one of R1-10 is #STR77#, or #STR88#, or #STR99#, and
  d) at least one of R1-R10 is #STR66#.

Another alternative embodiment provides polyphenol compounds of Formula 6:

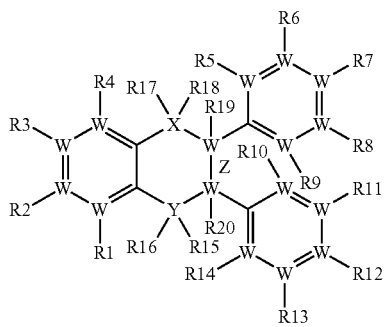

or a pharmaceutically acceptable salt thereof,
wherein
R1, R2, R3, R4, R5, R6, R7, R8, R9, R10, R11, R12, R13, R14, R15, R16, R17, R18, R19 and R20 are independently selected from the group consisting of $(C_1$-$C_{22})$ alkyl, $(C_2$-$C_{22})$alkenyl, $(C_2$-$C_{22})$alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I] fluoride [F], chloride [Cl], CF$_3$, CCl$_3$, sulfonic acid (—SO$_3$H), phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#, wherein W can be C or N;

wherein when W is an nitrogen atom, the nitrogen atom will only bind to three covalent bonds due to available valence electrons.

The structures below demonstrate a nitrogen arrangement of one embodiment of the compounds of Formula 6:

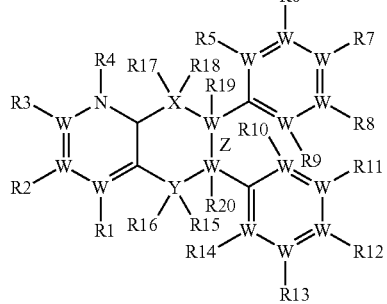

wherein the same applies to any W;
or

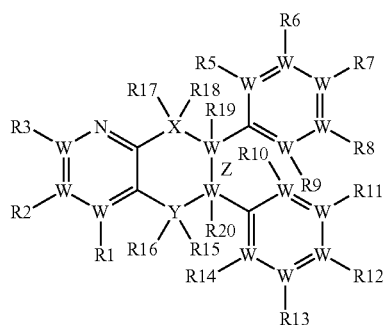

wherein the same applies to any W:

wherein

X can be CH, CH$_2$, CR17, CR18, CHR17, CHR18, CR17R18, CO, CS, O, S, SO, SO$_2$, NH, NR17 with the proviso that X and Y do not exceed the number of valence electrons available as per definitions of X and Y above Y can be CH, CH$_2$, CR15, CR16, CHR15, CHR16, CR15R16, CO, CS, O, S, SO, SO$_2$, NH, NR15 with the proviso that X and Y do not exceed the number of valence electrons available as per definitions of X and Y above Z can be a single or double bond with the proviso that X and Y do not exceed the number of valence electrons available as per definitions of X and Y above wherein

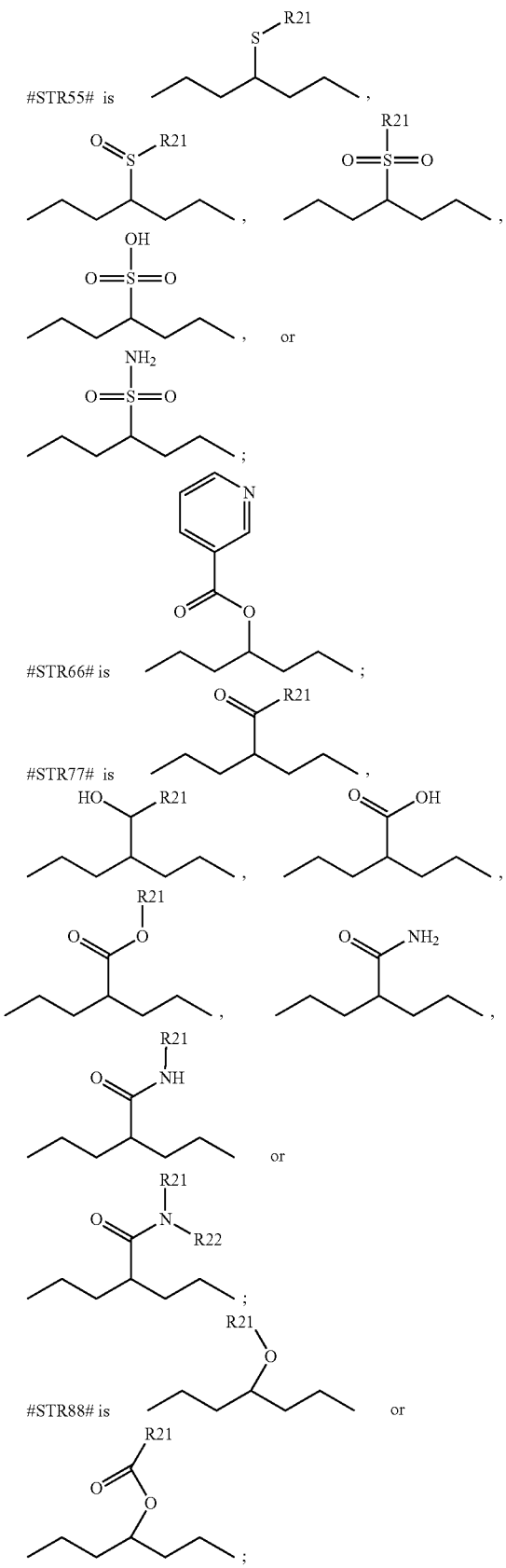

-continued

STR99# is 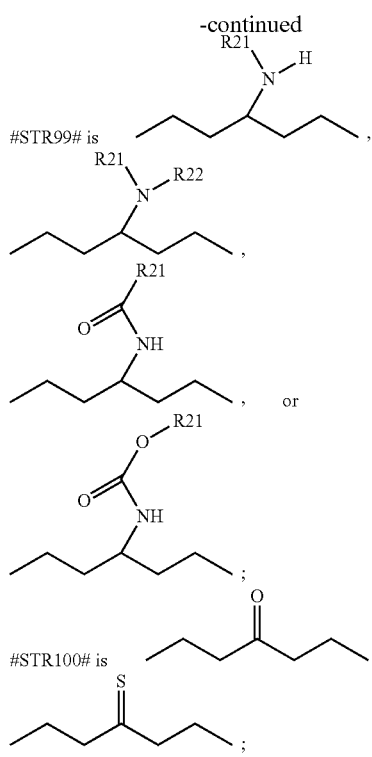,

STR100# is

R21 and R12 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid (—$SO_3H$), phosphate, or a derivative thereof, wherein said derivative is optionally substituted and optionally branched, and may have one or more of the C atoms replaced by S, N or O;

wherein Formula 6 compounds have at least one proviso selected from the following:

R7 and R12 are a hydroxyl;

at least one W is a N;

at least one of R1-R14 is #STR77#, #STR88# or #STR99#;

at least one of R1-R14 is #STR66#;

R7 is #STR66#;

R12 is #STR66#;

one of R1-R14 is a monoester;

one of R1-R14 is a succinic acid;

one of R1-R14 is a dicarboxylic acid;

R7 is #STR55#;

R12 is #STR55#;

R7 and R12 are #STR55#; and

Another embodiment provides for compounds of Formula 6 wherein:

R7 is a hydroxyl and at least one W is a N;

R7 is a hydroxyl and at least one of R1-R6 and R8-R14 is #STR66#;

R7 is a hydroxyl and at least one of R1-R6 and R8-R14 is #STR77#, #STR88# and #STR99#;

R7 is #STR66# and at least one W is a N.

Non-limiting examples of compounds of Formula 6 include:

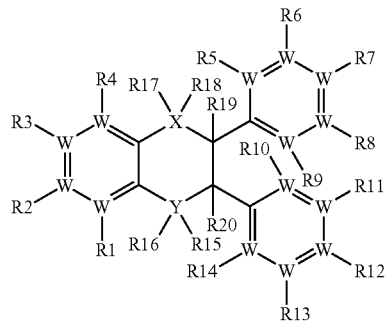

(LXIII)

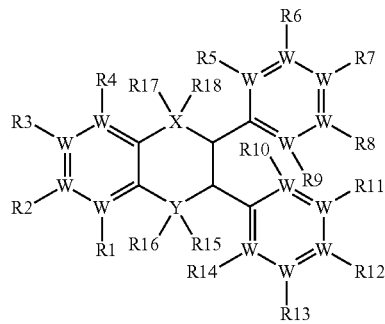

(LXIV)

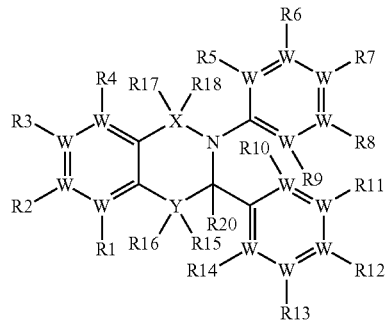

(LXV)

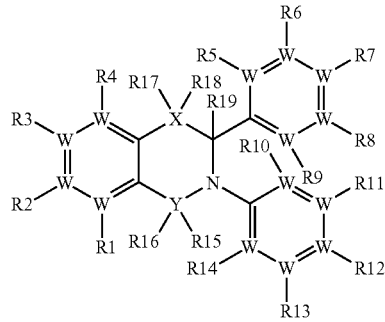

(LXVI)

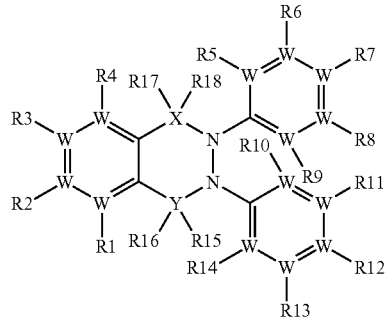

(LXVII)

-continued

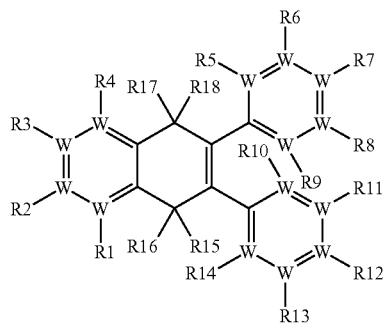
(LXVIII)

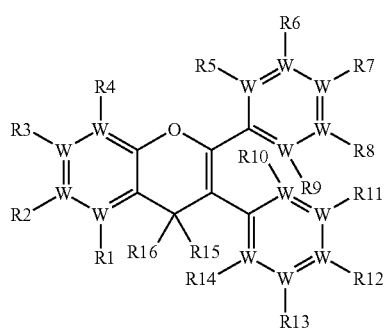
(LXIX)

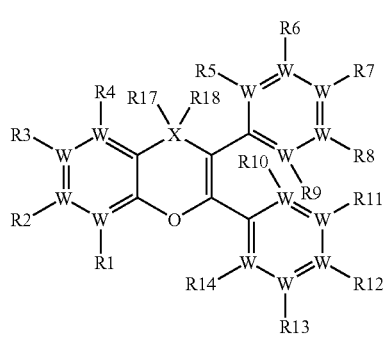
(LXX)

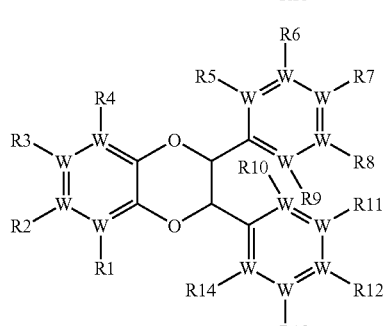
(LXXI)

or a pharmaceutically acceptable salt thereof,
wherein
R1, R2, R3, R4, R5, R6, R7,R8, R9, R10, R11, R12, R13, R14, R15, R16, R17, R18, R19 and R20 are independently selected from the group consisting of ($C_1$-$C_{22}$) alkyl, ($C_2$-$C_{22}$)alkenyl, ($C_2$-$C_{22}$)alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid (—$SO_3H$), phosphate, O-sulfate [the sulfate conjugate], O-glucoronidate [the glucoronic (AKA glucuronic) acid conjugates], monoesters, dicaboxylic acid, #STR55#, #STR66#, #STR77#, #STR88#, #STR99#, #STR100#,
wherein
W can be C or N;
wherein when W is an nitrogen atom, the nitrogen atom will only bind to three covalent bonds due to available valence electrons.

The structures below demonstrate a nitrogen arrangement of one embodiment of the compounds of Formula 6:

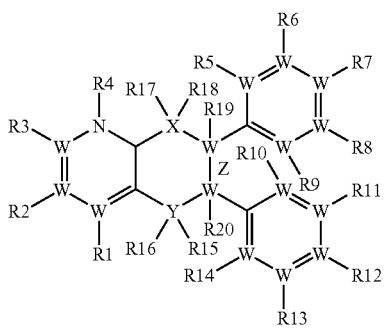

wherein the same applies to any W;
or

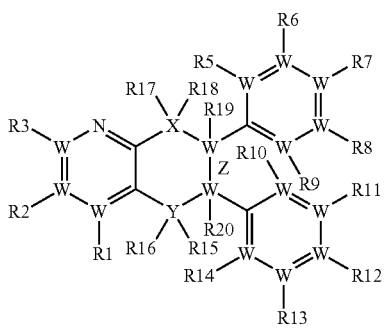

wherein the same applies to any W:
wherein
X can be CH, $CH_2$, CR17, CR18, CHR17, CHR18, CR17R18, CO, CS, O, S, SO, $SO_2$, NH, NR17 with the proviso that X and Y do not exceed the number of valence electrons available as per definitions of X and Y above
Y can be CH, $CH_2$, CR15 CR16, CHR15, CHR16, CR15R16, CO, CS, O, S, SO, $SO_2$, NH, NR15 with the proviso that X and Y do not exceed the number of valence electrons available as per definitions of X and Y above
Z can be a single or double bond with the proviso that X and Y do not exceed the number of valence electrons available as per definitions of X and Y above wherein

STR55# is 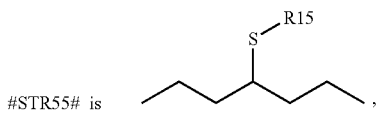,

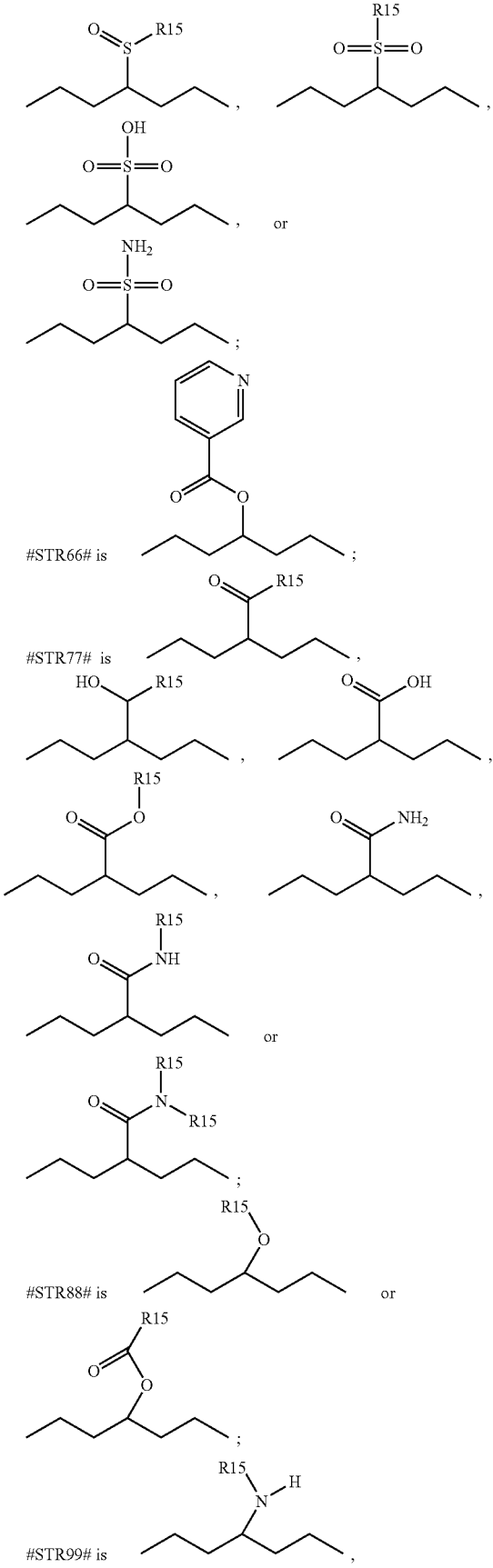
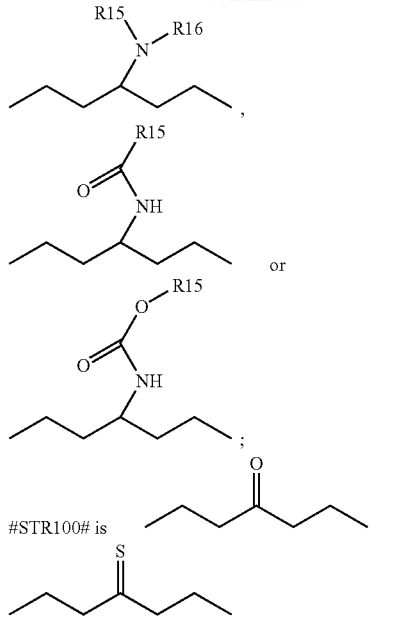

R21 and R12 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, or a derivative thereof, wherein said derivative is optionally substituted and optionally branched, and may have one or more of the C atoms replaced by S, N or O;

wherein compounds have at least one proviso selected from the following:

R7 and R12 are a hydroxyl;

at least one W is a N;

at least one of R1-R14 is #STR77#, #STR88# or #STR99#;

at least one of R1-R14 is #STR66#;

R7 is #STR66#;

R12 is #STR66# one of R1-R14 is a monoester;

one of R1-R14 is a succinic acid;

one of R1-R14 is a dicarboxylic acid;

R7 is #STR55#;

R12 is #STR55#

R7 and R12 are #STR55#; and

Another embodiment provides for compounds of Formula 6 wherein:

R7 is a hydroxyl and at least one W is a N;

R7 is a hydroxyl and at least one of R1-R6 and R8-R14 is #STR66#;

R7 is a hydroxyl and at least one of R1-R6 and R8-R14 is #STR77#, #STR88# and #STR99#;

R7 is #STR66# and at least one W is a N.

The following is a list of specific exemplary embodiments are encompassed by the invention:

1. A method for increasing expression of ApoA-I in a mammal comprising administering a therapeutically effective amount of a compound of Formula I:

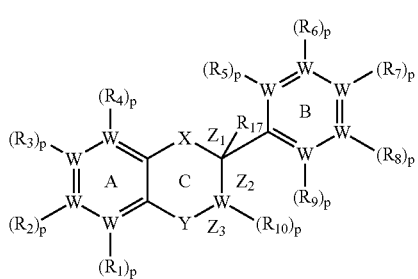

Formula I wherein:
X is selected from $CR_{11}$, $CR_{11}R_{13}$, CO, CS, O, S, SO, $SO_2$, N and $NR_{11}$,
wherein $R_{11}$ may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and R17 are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if X is O, the $Z_1$ is a single bond;
wherein if X is O and $Z_2$ is a single bond, then $R_{10}$ is not hydroxyl or ester;
and pharmaceutically acceptable salts and hydrates thereof.

2. The method of embodiment 1, wherein X is O and Y is CO.
3. The method of embodiment 1, wherein at least one W is N.
4. The method of embodiment 3, wherein X is O and Y is CO.
5. The method of embodiment 1, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ is selected from O-sulfate and O-glucoronidate.
6. The method of embodiment 1, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ is selected from succinate, D-argininate, L-argininate, L-lysinate and D-lysinate.
7. The method of embodiment 1, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ is selected from amide, amino, carbamate, carboxy, ester, ether, formyl, and ketone.
8. The method of embodiment 7, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ is a nicotinate ester.
9. The method of embodiment 1, wherein at least one W in the A ring of Formula I is N.
10. The method of embodiment 1, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate,
subject to the proviso that $R_6$ and $R_8$ are not both simultaneously hydrogen.
11. The method of embodiment 10, wherein X is O and Y is CO.
12. The method of embodiment 10, wherein at least one W is N.
13. The method of embodiment 12, wherein X is O and Y is CO.
14. The method of embodiment 1, wherein $Z_1$ and $Z_3$ are single bonds, and $Z_2$ is a double bond.
15. The method of embodiment 14, wherein X is O and Y is CO.
16. The method of embodiment 14, wherein at least one W is N.
17. The method of embodiment 16, wherein X is O and Y is CO.
18. The method of embodiment 14, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate,
subject to the proviso that $R_6$ and $R_8$ are not both simultaneously hydrogen.
19. The method of embodiment 18, wherein X is O and Y is CO.
20. The method of embodiment 18, wherein at least one W is N.
21. The method of embodiment 20, wherein X is O and Y is CO.
22. The method of embodiment 1, wherein
X is selected from $CR_{11}$, $CR_{11}R_{13}$, CO, CS, and O; and
Y is selected from $CR_{12}$, $CR_{12}R_{14}$, S, SO, $SO_2$, and $NR_{12}$.
23. The method of embodiment 22, wherein at least one W is N.
24. The method of embodiment 22, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate,
subject to the proviso that $R_6$ and $R_8$ are not both simultaneously hydrogen.
25. The method of embodiment 24, wherein at least one W is N.
26. The method of embodiment 22, wherein $Z_1$ and $Z_3$ are single bonds, and $Z_2$ is a double bond.
27. The method of embodiment 26, wherein at least one W is N.
28. The method of embodiment 26, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perluoroalkoxy, O-sulfate, and O-glucoronidate,
subject to the proviso that $R_6$ and $R_8$ are not both simultaneously hydrogen.

29. The method of embodiment 28, wherein at least one W is N.
30. The method of embodiment 1, wherein Formula I has the structure:

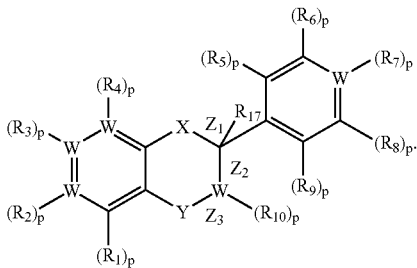

31. The method of embodiment 30, wherein X is O and Y is CO.
32. The method of embodiment 30, wherein at least one W is N.
33. The method of embodiment 32, wherein X is O and Y is CO.
34. The method of embodiment 30, wherein at least one of $R_1, R_2, R_3, R_4, R_5, R_6, R_7, R_8, R_9, R_{10}, R_{11}, R_{12}, R_{13}, R_{14}$ and $R_{17}$ is selected from O-sulfate and O-glucoronidate.
35. The method of embodiment 30, wherein at least one of $R_1, R_2, R_3, R_4, R_5, R_6, R_7, R_8, R_9, R_{10}, R_{11}, R_{12}, R_{13}, R_{14}$ and $R_{17}$ is selected from succinate, D-argininate, L-argininate, L-lysinate and D-lysinate.
36. The method of embodiment 30, wherein at least one of $R_1, R_2, R_3, R_4, R_5, R_6, R_7, R_8, R_9, R_{10}, R_{11}, R_{12}, R_{13}, R_{14}$ and $R_{17}$ is selected from amide, amino, carbamate, carboxy, ester, ether, formyl, and ketone.
37. The method of embodiment 36, wherein at least one of $R_1, R_2, R_3, R_4, R_5, R_6, R_7, R_8, R_9, R_{10}, R_{11}, R_{12}, R_{13}, R_{14}$ and $R_{17}$ is a nicotinate ester.
38. The method of embodiment 30, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen; hydroxyl, hydroxyalkyl, hydroxyaryl, ketone, perfluoroalkyl, perfluorocycloalkyl, perfluoroalkoxy, O-sulfate, and O-glucoronidate,
subject to the proviso that $R_6$ and $R_8$ are not both simultaneously hydrogen.
39. The method of embodiment 38, wherein X is O and Y is CO.
40. The method of embodiment 38, wherein at least one W is N.
41. The method of embodiment 40, wherein X is O and Y is CO.
42. The method of embodiment 30, wherein $Z_1$ and $Z_3$ are single bonds, and $Z_2$ is a double bond.
43. The method of embodiment 42, wherein X is O and Y is CO.
44. The method of embodiment 42, wherein at least one W is N.
45. The method of embodiment 44, wherein X is O and Y is CO.
46. The method of embodiment 42, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate,
subject to the proviso that $R_6$ and $R_8$ are not both simultaneously hydrogen.
47. The method of embodiment 46, wherein X is O and Y is CO.
48. The method of embodiment 46, wherein at least one W is N.
49. The method of embodiment 48, wherein X is O and Y is CO.
50. The method of embodiment 1, wherein Formula I has the structure:

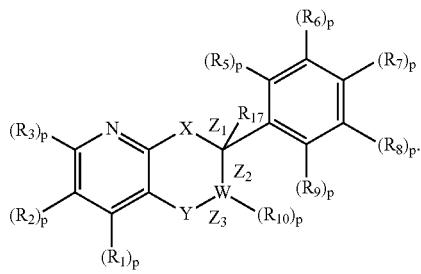

51. The method of embodiment 50, wherein X is O and Y is CO.
52. The method of embodiment 50, wherein at least one W is N.
53. The method of embodiment 52, wherein X is O and Y is CO.
54. The method of embodiment 50, wherein at least one of $R_1, R_2, R_3, R_4, R_5, R_6, R_7, R_8, R_9, R_{10}, R_{11}, R_{12}, R_{13}, R_{14}$ and $R_{17}$ is selected from O-sulfate and O-glucoronidate.
55. The method of embodiment 50, wherein at least one of $R_1, R_2, R_3, R_4, R_5, R_6, R_7, R_8, R_9, R_{10}, R_{11}, R_{12}, R_{13}, R_{14}$ and $R_{17}$ is selected from succinate, D-argininate, L-argininate, L-lysinate and D-lysinate.
56. The method of embodiment 50, wherein at least one of $R_1, R_2, R_3, R_4, R_5, R_6, R_7, R_8, R_9, R_{10}, R_{11}, R_{12}, R_{13}, R_{14}$ and $R_{17}$ is selected from amide, amino, carbamate, carboxy, ester, ether, formyl, and ketone.
57. The method of embodiment 56, wherein at least one of $R_1, R_2, R_3, R_4, R_5, R_6, R_7, R_8, R_9, R_{10}, R_{11}, R_{12}, R_{13}, R_{14}$ and $R_{17}$ is a nicotinate ester.
58. The method of embodiment 50, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate,
subject to the proviso that $R_6$ and $R_8$ are not both simultaneously hydrogen.
59. The method of embodiment 58, wherein X is O and Y is CO.
60. The method of embodiment 58, wherein at least one W is N.
61. The method of embodiment 60, wherein X is O and Y is CO.
62. The method of embodiment 50, wherein $Z_1$ and $Z_3$ are single bonds, and $Z_2$ is a double bond.
63. The method of embodiment 62, wherein X is O and Y is CO.

64. The method of embodiment 62, wherein at least one W is N.

65. The method of embodiment 64, wherein X is O and Y is CO.

66. The method of embodiment 62, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate, glucoronidate, subject to the proviso that $R_6$ and $R_8$ are not both simultaneously hydrogen.

67. The method of embodiment 66, wherein X is O and Y is CO.

68. The method of embodiment 66, wherein at least one W is N.

69. The method of embodiment 68, wherein X is O and Y is CO.

70. The method of embodiment 1, wherein Formula I has the structure:

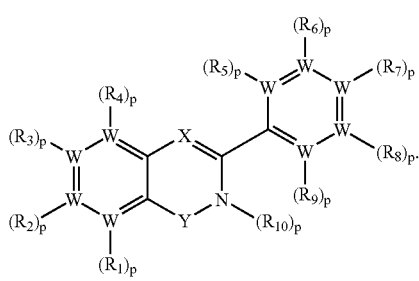

71. The method of embodiment 70, wherein X is $CR_{11}$, $R_{11}$, is hydrogen and Y is CO.

72. The method of embodiment 70, wherein at least one W is N.

73. The method of embodiment 72, wherein X is $CR_{11}$, $R_{11}$ is hydrogen and Y is CO.

74. The method of embodiment 70, wherein at least one of $R_1, R_2, R_3, R_4, R_5, R_6, R_7, R_8, R_9, R_{10}, R_{11}, R_{12}, R_{13}, R_{14}$ and $R_{17}$ is selected from O-sulfate and O-glucoronidate.

75. The method of embodiment 70, wherein at least one of $R_1, R_2, R_3, R_4, R_5, R_6, R_7, R_8, R_9, R_{10}, R_{11}, R_{12}, R_{13}, R_{14}$ and $R_{17}$ is selected from succinate, D-argininate, L-argininate, L-lysinate and D-lysinate.

76. The method of embodiment 70, wherein at least one of $R_1, R_2, R_3, R_4, R_5, R_6, R_7, R_8, R_9, R_{10}, R_{11}, R_{12}, R_{13}, R_{14}$ and $R_{17}$ is selected from amide, amino, carbamate, carboxy, ester, ether, formyl, and ketone.

77. The method of embodiment 76, wherein at least one of $R_1, R_2, R_3, R_4, R_5, R_6, R_7, R_8, R_9, R_{10}, R_{11}, R_{12}, R_{13}, R_{14}$ and $R_{17}$ is a nicotinate ester.

78. The method of embodiment 70, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate, subject to the proviso that $R_6$ and $R_8$ are not both simultaneously hydrogen.

79. The method of embodiment 78, wherein X is $CR_{11}$, $R_{11}$ is hydrogen and Y is CO.

80. The method of embodiment 78, wherein at least one W is N.

81. The method of embodiment 80, wherein X is $CR_{11}$, $R_{11}$ is hydrogen and Y is CO.

82. The method of embodiment 70, wherein $Z_1$ and $Z_3$ are single bonds, and $Z_2$ is a double bond.

83. The method of embodiment 84, wherein X is $CR_{11}$, $R_{11}$ is hydrogen and Y is CO.

84. The method of embodiment 84, wherein at least one W is N.

85. The method of embodiment 86, wherein X is $CR_{11}$, $R_{11}$ is hydrogen and Y is CO.

86. The method of embodiment 82, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate, and O-glucoronidate, subject to the proviso that $R_6$ and $R_8$ are not both simultaneously hydrogen.

87. The method of embodiment 86, wherein X is $CR_{11}$, $R_{11}$ is hydrogen and Y is CO.

88. The method of embodiment 86, wherein at least one W is N.

89. The method of embodiment 88, wherein X is $CR_{11}$, $R_{11}$ is hydrogen and Y is CO.

90. The method of embodiment 70, wherein Formula I is selected from Formulae IA-ID:

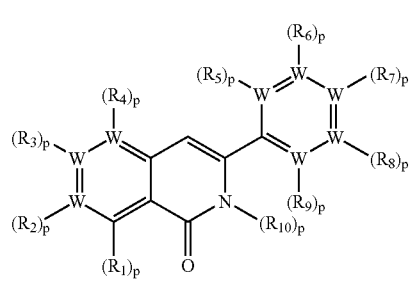

Formula IA

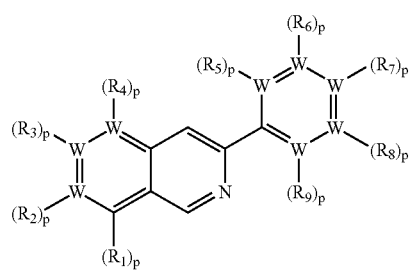

Formula IB

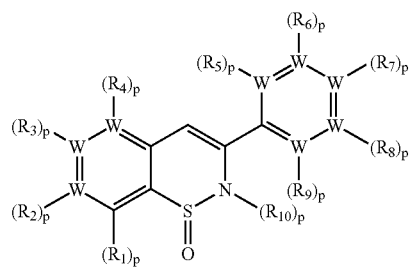

Formula IC

Formula ID

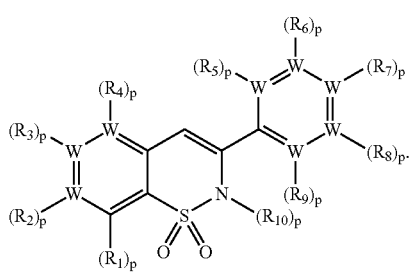

91. The method of embodiment 1, wherein the therapeutically effective amount of the compound of Formula I is administered with a pharmaceutically acceptable carrier in a pharmaceutically acceptable composition.
92. The method of embodiment 1, wherein the therapeutically effective amount of the compound of Formula I is sufficient to establish a concentration ranging from about 0.001 μM to about 100 μM in the mammal.
93. The method of embodiment 92, wherein the concentration ranges from about 1 μM to about 20 μM.
94. The method of embodiment 1, wherein the compound of Formula I is 2-(4-hydroxy-phenyl)-pyrano[2,3-b]pyridin-4-one.
95. The method of embodiment 1, wherein the compound is 3-(4-hydroxyphenyl)-2H-isoquinolin-1-one.
96. The method of embodiment 1, wherein the compound is 4-isoquinolin-3-yl-phenol.
97. A method for increasing expression of ApoA-I in a mammal comprising administering a therapeutically effective amount of a compound of Formula II:

Formula II

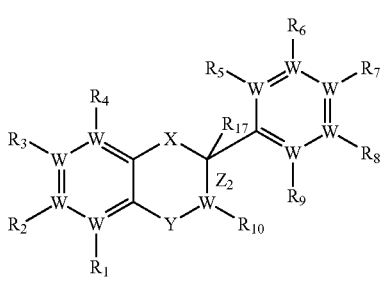

wherein:

X is selected from $CH_2$, $CHR_{11}$, $CHR_{13}$, $CR_{11}R_{13}$, CO, CS, O, S, SO, $SO_2$, NH and $NR_{11}$, wherein $R_{11}$ may be the same or different than $R_{13}$;

Y is selected from $CH_2$, $CHR_{12}$, $CHR_{14}$, $CR_{12}R_{14}$, CO, CS, O, S, SO, $SO_2$, NH and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from ($C_1$-$C_{22}$) alkyl, ($C_2$-$C_{22}$)alkenyl, ($C_2$-$C_{22}$)alkynyl, aryl, heteroaryl, alkoxy, aryloxy, benzyl, phenyl, carbonyl, thioketone, hydrogen, hydroxyl, acetyl, hydroxyalkyl, aminoalkyl, amide, carbamate, halogen, $CF_3$, $CCl_3$, sulfonic acid, phosphate, O-sulfate, O-glucoronidate, monoester, dicarboxylic acid, J, K, L, M, P and Q;

each W is independently selected from C and N;

$Z_2$ is selected from a single bond and a double bond;

J is selected from

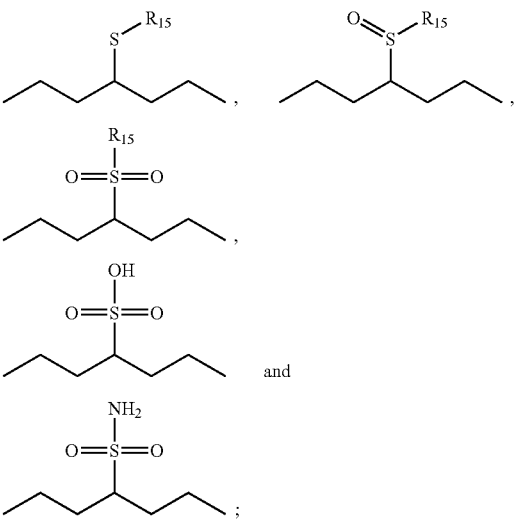

K is

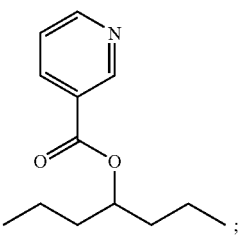

L is selected from

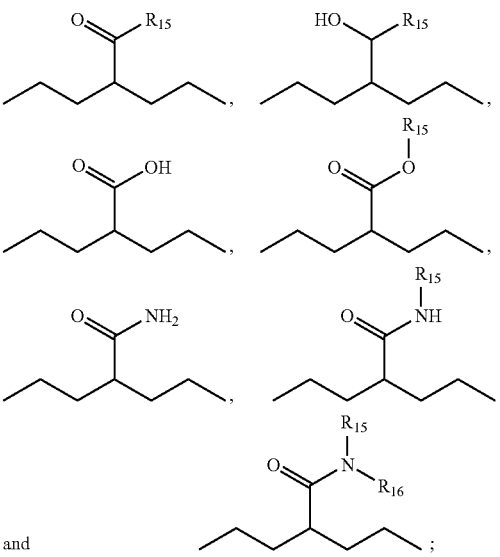

M is selected from

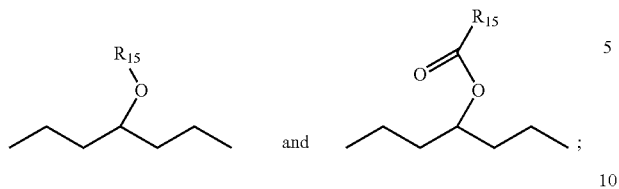

and ;

P is selected from

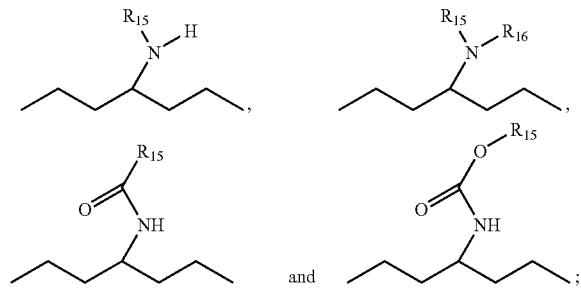

and ;

Q is selected from

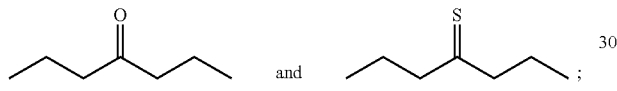

and ;

$R_{15}$ and $R_{16}$ are each independently selected from $(C_1-C_{22})$ alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl, acetyl, hydroxyalkyl, aminoalkyl, amide, carbamate, halogen, $CF_3$, $CCl_3$, sulfonic acid and phosphate;

and pharmaceutically acceptable salts thereof; subject to at least one proviso selected from:

1) $R_7$ is hydroxyl;
2) at least one W is N;
3) at least one of $R_1$-$R_{10}$ is selected from L, M and P;
4) at least one of $R_1$-$R_{10}$ is selected from K;
5) $R_7$ is K;
6) one of $R_1$-$R_{10}$ is a monoester;
7) one of $R_1$-$R_{10}$ is a dicarboxylic acid;
8) one of $R_1$-$R_{10}$ is succinic acid;
9) $R_7$ and $R_2$ are each hydroxyl;
10) $R_7$ is selected from J; and
11) $R_7$ and $R_2$ are each selected from J.

98. The method of embodiment 97, wherein if proviso 1 is selected, a second proviso is selected from provisos 2-4 and 6-9.

99. The method of embodiment 97, wherein $R_7$ is hydroxyl and at least one W is N.

100. The method of embodiment 97, wherein $R_7$ is hydroxyl and at least one of $R_1$-$R_6$ and $R_8$-$R_{10}$ is K.

101. The method of embodiment 97, wherein $R_7$ is hydroxyl and at least one of $R_1$-$R_6$ and $R_8$-$R_{10}$ is selected from L, M and P.

102. The method of embodiment 97, wherein $R_7$ is K and at least one W is N.

103. The method of embodiment 97, wherein Y is selected from $CH_2$, $CHR_{12}$, $CHR_{14}$, $CR_{12}R_{14}$, CO, CS, S, SO, $SO_2$, NH and $NR_{12}$, wherein $R_{12}$ may be the same or different than $R_{14}$.

104. The method of embodiment 97, wherein the compound of Formula II is 2-(4-hydroxy-phenyl)-pyrano[2,3-b]pyridin-4-one.

105. The method of embodiment 97, wherein Formula II is selected from Formulae IIA-IIS:

Formula IIA

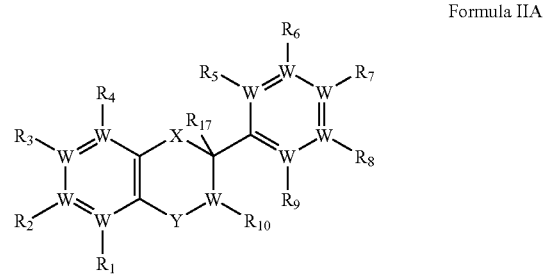

Formula IIB

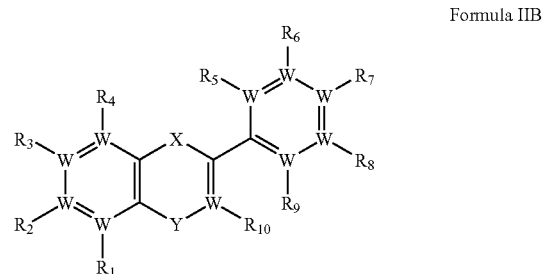

Fourmula IIC

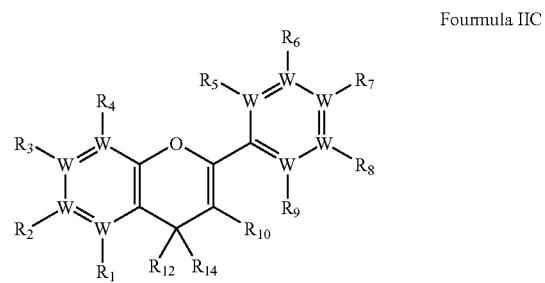

Formula IID

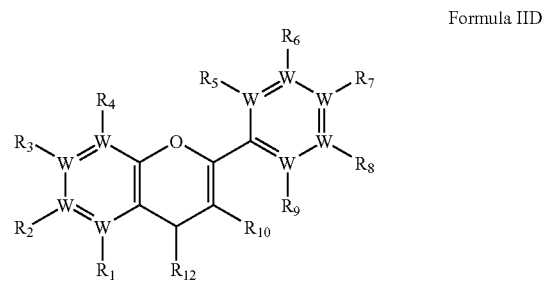

Formula IIE

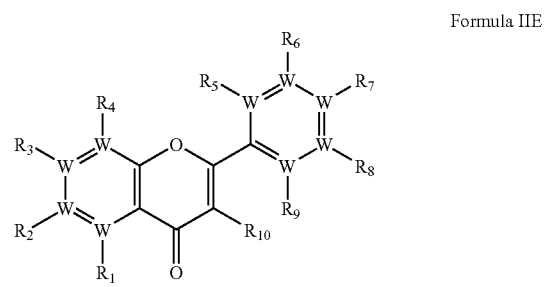

Formula IIF
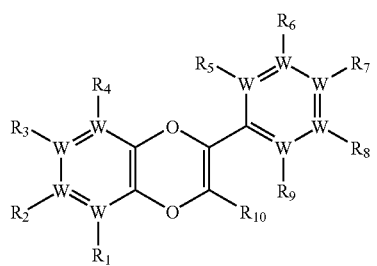
Formula IIG
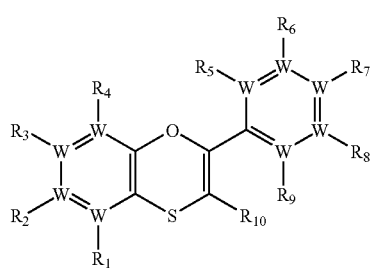
Formula IIH
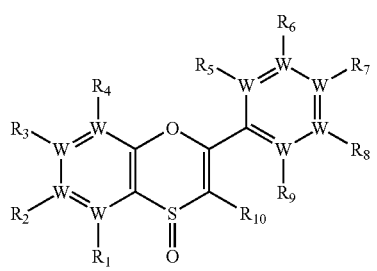
Fourmula IIJ
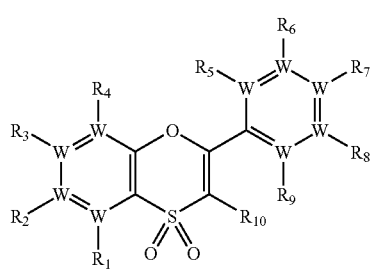
Formula IIK
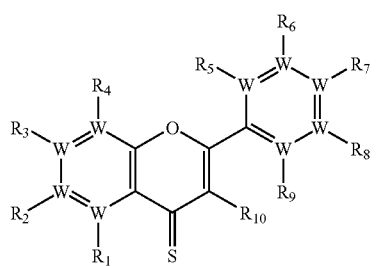
Formula IIL
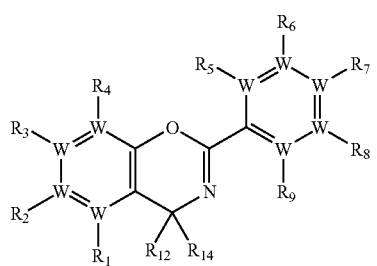
Formula IIM
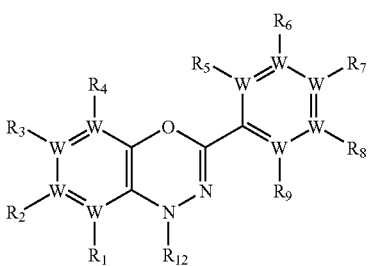
Formula IIN
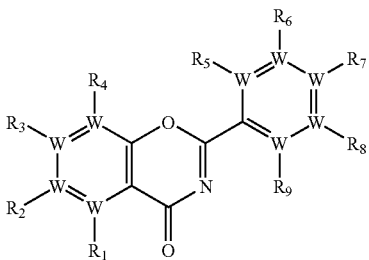
Formula IIO
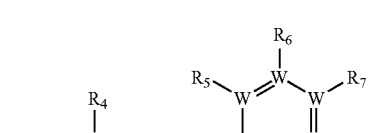
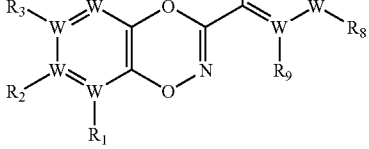
Fourmula IIP
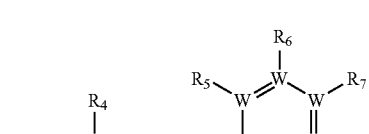
Formula IIQ
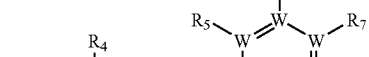
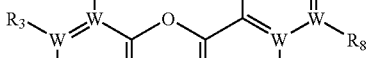
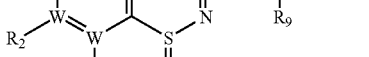
Formula IIR
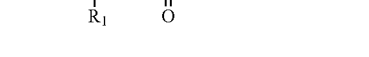
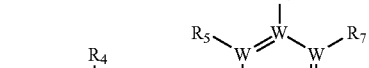
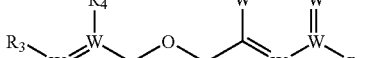

Formula IIS

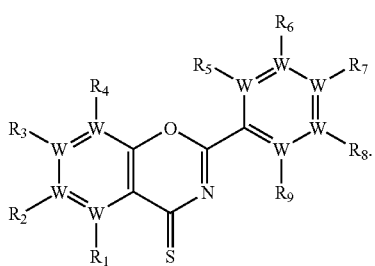

106. A method for increasing expression of ApoA-I in a mammal comprising administering a therapeutically effective amount of a compound selected from Formulae IIT to IIW:

Formula IIT

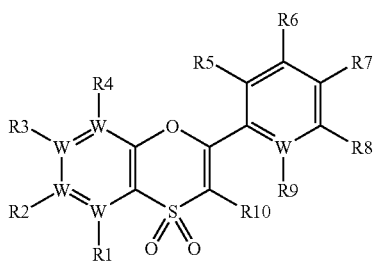

Formula IIU

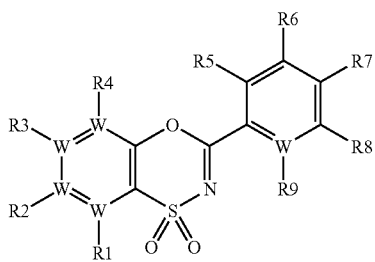

Formula IIW

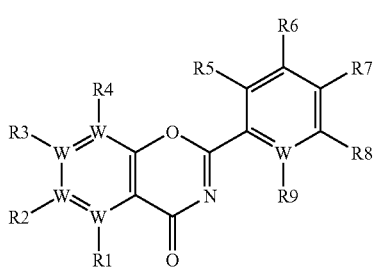

wherein:
$R_1$, $R_2$, $R_3$, $R_4$, $R_5$, $R_6$, $R_8$, $R_9$, and $R_{10}$ are independently selected from ($C_1$-$C_{22}$)alkyl, ($C_2$-$C_{22}$)alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F, and G;
$R_7$ is selected from hydroxyl and K;
each W is independently selected from C and N;

K is

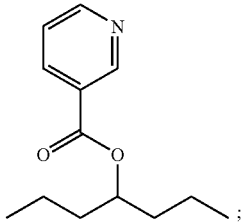

D is

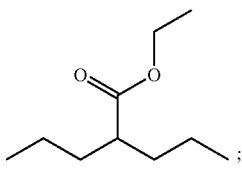

E is selected from

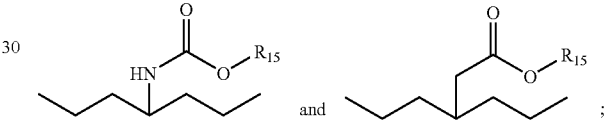

F is selected from

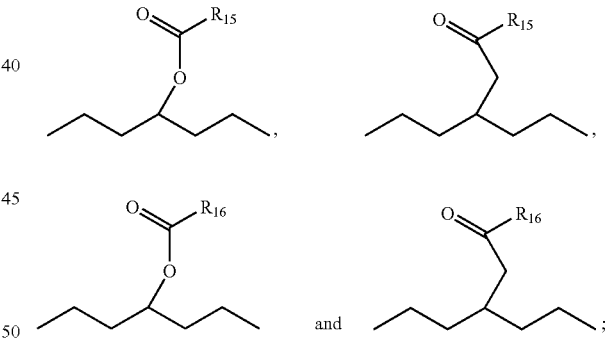

G is

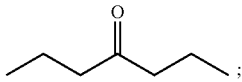

and pharmaceutically acceptable salts thereof;
subject to at least one proviso selected from
1) at least one W is N;
2) at least one of $R_{1-6}$ and $R_{8-10}$ is selected from D, E and F; and
3) at least one of $R_{1-6}$ and $R_{8-10}$ is selected from K.

107. A method for increasing expression of ApoA-I in a mammal comprising administering a therapeutically effective amount of a compound of Formula III:

Formula III

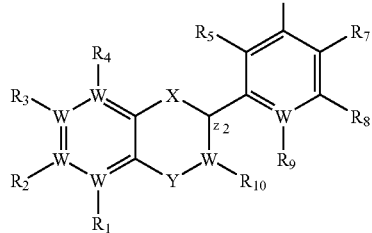

wherein:

$R_1$, $R_2$, $R_3$, $R_4$, $R_5$, $R_6$, $R_8$, $R_9$, and $R_{10}$ are each independently selected from ($C_1$-$C_{22}$)alkyl, ($C_2$-$C_{22}$)alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F and G;

$R_7$ is selected from hydroxyl and K;

each W is independently selected from C and N;

$Z_2$ is selected from a single bond and a double bond;

X is selected from O, S, C, $CR_{11}$ and $NR_{11}$;

Y is selected from O, S, C, $CR_{12}$ and $NR_{12}$;

$R_{11}$ and $R_{12}$ are each independently selected from D, E, F, and G;

K is

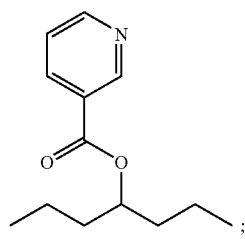

D is

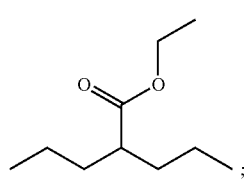

E is selected from

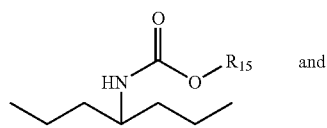 and

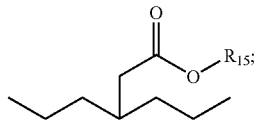

F is selected from

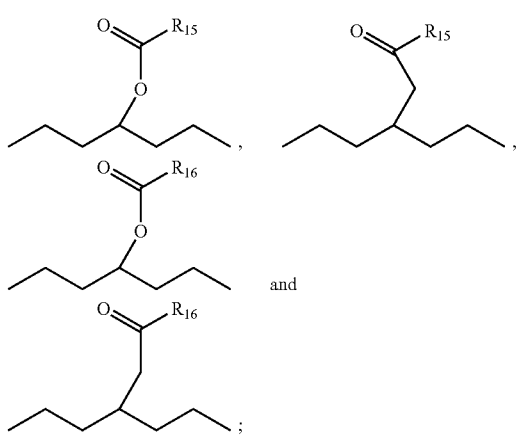 and

G is

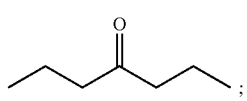

$R_{15}$ is selected from pyridine, pyridazine, pyrimidine, and pyrazine;

$R_{16}$ is selected from ($C_1$-$C_{22}$)alkyl, ($C_2$-$C_{22}$)alkenyl, aryl and heteroaryl;

and pharmaceutically acceptable salts thereof;

subject to at least one proviso selected from 1) at least one W is N;

2) at least one of $R_{1-6}$ and $R_{8-10}$ is selected from D, E, and F; and 3) at least one of $R_{1-6}$ and $R_{8-10}$ is selected from K.

108. The method of embodiment 107, wherein $R_7$ is hydroxyl and at least one of $R_{1-6}$ and $R_{8-10}$ is selected from K.

109. The method of embodiment 108, subject to at least one proviso selected from 1) at least one W is N; and 2) at least one of $R_{1-6}$ and $R_{8-10}$ is selected from D, E and F.

110. The method of embodiment 107, wherein at least one W is N, at least one of $R_{1-6}$ and $R_{8-10}$ is selected from D, E and F, and at least one of $R_{1-6}$ and $R_{8-10}$ is selected from K.

111. The method of embodiment 107, wherein X is O, Y is $CR_{12}$, and $R_{12}$ is G.

112. The method of embodiment 107, wherein the compound of Formula III is 2-(4-hydroxy-phenyl)-pyrano[2,3-b]pyridin-4-one.

113. The method of embodiment 107, wherein Formula III is selected from Formulae IIIA-IIIH:

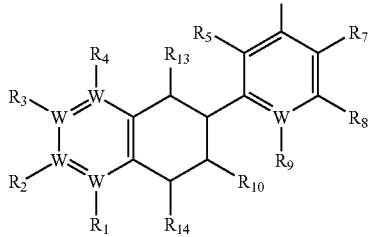
Formula IIIA

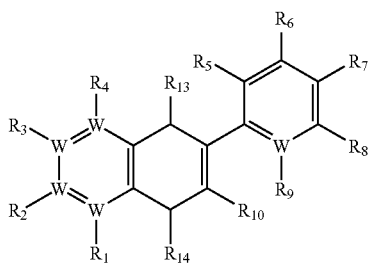
Formula IIIB

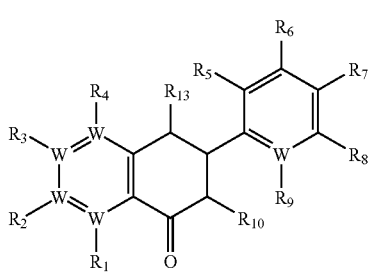
Fourmula IIIC

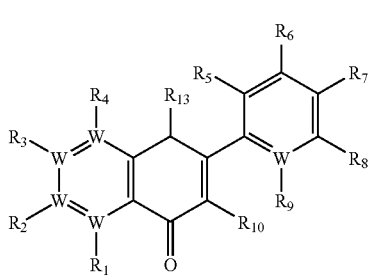
Formula IIID

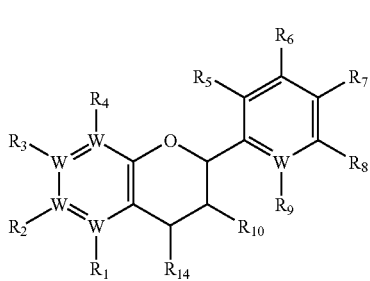
Formula IIIE

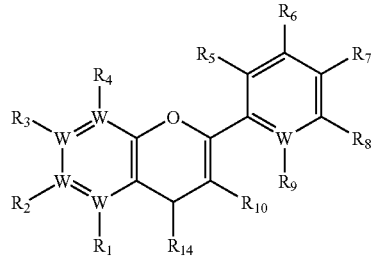
Formula IIIF

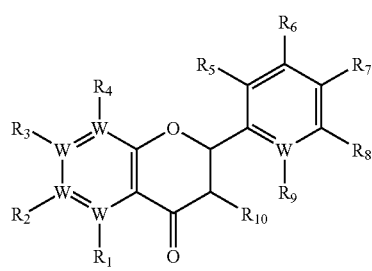
Formula IIIG

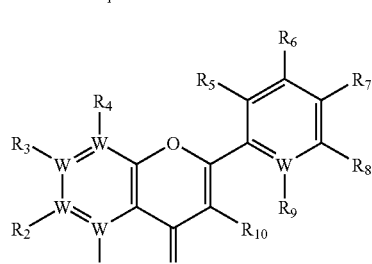
Formula IIIH wherein $R_{13}$ and $R_{14}$ are each independently selected from $(C_1-C_{22})$alkyl, $(C_2-C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F and G.

114. A method for increasing expression of ApoA-I in a mammal comprising administering a therapeutically effective amount of a compound of Formula III:

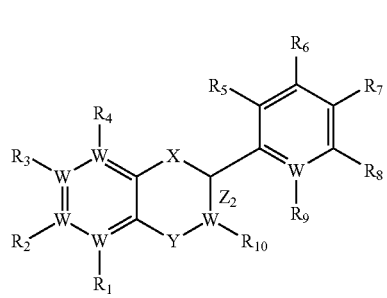
Formula III wherein
$R_1$, $R_2$, $R_3$, $R_4$, $R_5$, $R_6$, $R_8$, $R_9$ and $R_{10}$ are each independently selected from $(C_1-C_{22})$alkyl, $(C_2-C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, and O-glucoronidate;
$R_7$ is selected from hydroxyl and K;
each W is independently selected from C and N;
$Z_2$ is selected from a single bond and a double bond;

X is selected from O, S, C, CR$_{11}$ and NR$_{11}$;
Y is selected from O, S, C, CR$_{12}$ and NR$_{12}$;
R$_{11}$ and R$_{12}$ are each independently selected from D, F and G;
K is

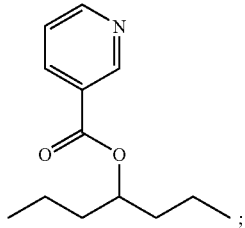

D is

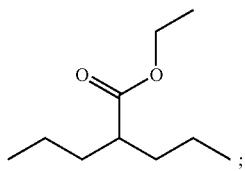

F is selected from

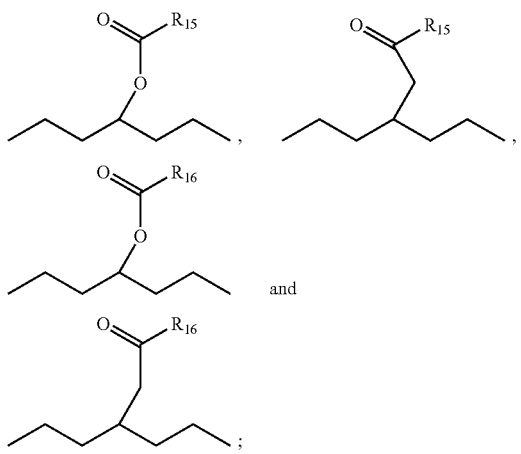

G is

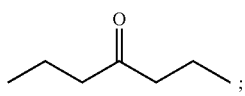

wherein if R$_7$ is hydroxyl, then at least one W is N and at least one of R$_{1-6}$ and R$_{8-10}$ is selected from K, and
wherein if R$_7$ is K, then at least one W is N.

115. The method of embodiment 114, wherein X is O, Y is CR$_{12}$, and R$_{12}$ is G.

116. The method of embodiment 114, wherein Formula III has the structure:

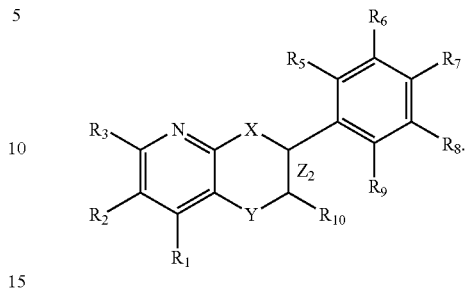

117. The method of embodiment 114, wherein Formula III is selected from Formulae IIIJ to IIIP:

Formula IIIJ

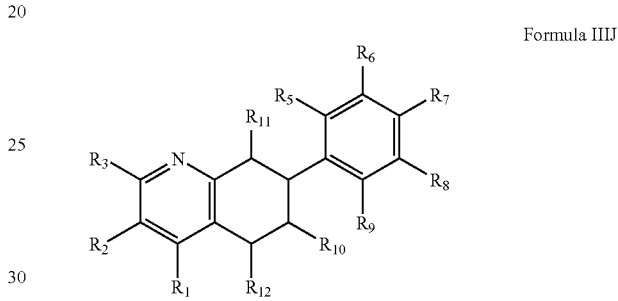

Formula IIIK

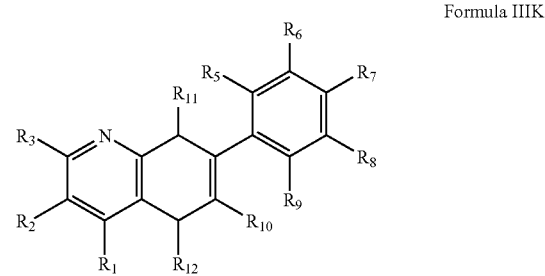

Fourmula IIIL

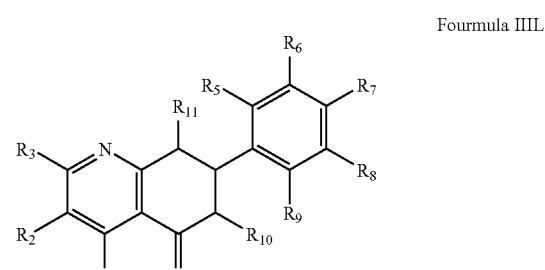

Formula IIIM

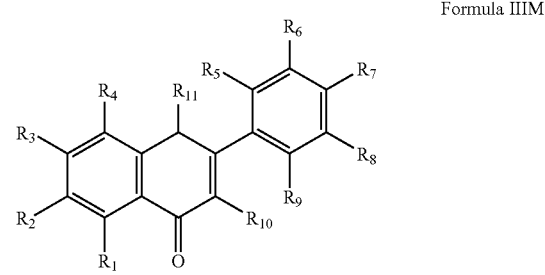

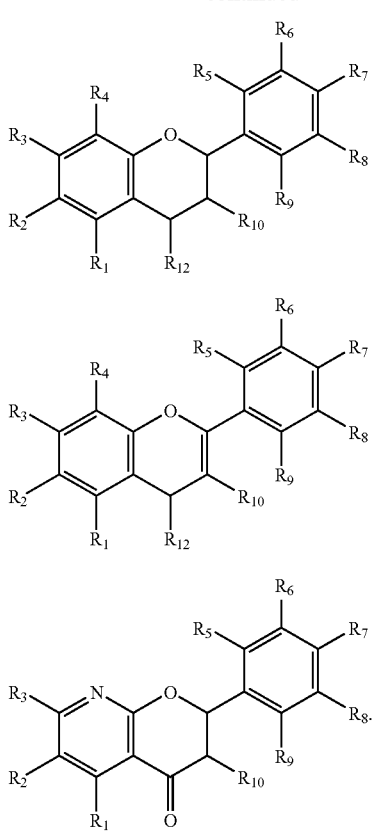

118. The method of embodiment 1, wherein the compound of Formula I is selected from
5,7-Difluoro-2-(4-methoxy-phenyl)-chromen-4-one,
5,7-Difluoro-2-(4-hydroxy-phenyl)-chromen-4-one,
2-(3,5-Difluoro-4-hydroxyphenyl)chromen-4-one,
2-(4-Hydroxy-3,5-dimethylphenyl)chromen-4-one,
2-(5-Methoxy-pyridin-2-yl)-chromen-4-one,
2-(5-Hydroxy-pyridin-2-yl)-chromen-4-one,
2-(6-Hydroxy-pyridin-3-yl)-chromen-4-one,
2-Pyridin-4-yl-chromen-4-one,
2-(4-Methoxy-phenyl)-thiochromen-4-one,
2-(4-Hydroxy-phenyl)-thiochromen-4-one,
2-(4-Hydroxyphenyl)-3-methyl-4H-chromen-4-one,
4-(6-Bromo-4-oxo-4H-chromen-2-yl)-2-fluorophenyl acetate,
1-(2-Nitro-4-methoxy-phenyl)-chromen-4-one,
2-(4-Hydroxy-2-nitrophenyl)chromen-4-one,
2-(2-Amino-4-methoxy-phenyl)-chromen-4-one,
2-(2-Amino-4-hydroxy-phenyl)-chromen-4-one,
N-[5-Hydroxy-2-(4-oxo-4H-chromen-2-yl)-phenyl]acetamide,
6-Hydroxy-2-(4-hydroxymethylphenyl)chromen-4-one,
2-(2-Fluoro-4-hydroxyphenyl)chromen-4-one,
2-(4-Hydroxyphenyl)-8-nitro-4H-chromen-4-one,
2-(4-Hydroxyphenyl)-8-methoxy-4H-chromen-4-one,
2-(4-Hydroxyphenyl)-5,7-dimethoxy-4H-chromen-4-one,
2-(3-Bromo-4-hydroxyphenyl)-4H-chromen-4-one,
2-(4-Hydroxyphenyl)-4-oxo-4H-chromene-6-carbonitrile,
2-(4-Methoxy-phenyl)-chromen-4-one,
2-(3-Fluoro-4-hydroxyphenyl)chromen-4-one,
2-(4-Hydroxyphenyl)-4-oxo-4H-chromene-6-sulfonic acid,
6-Hydroxymethyl-2-(4-hydroxyphenyl)chromen-4-one,
6-((Dimethylamino)methyl)-2-(4-hydrophenyl)-4H-chromen-4-one,
8-Hydroxy-2-(4-hydroxy-phenyl)-chromen-4-one,
2-(4-Hydroxy-phenyl)-chromen-4-one,
7-Hydroxy-2-(4-hydroxy-phenyl)-chromen-4-one,
5-Hydroxy-2-(4-hydroxy-phenyl)-chromen-4-one,
5,7-Dihydroxy-2-(4-hydroxy-phenyl)-chromen-4-one,
5,7-Dihydroxy-2-phenyl-chromen-4-one,
5-Hydroxy-2-phenyl-chromen-4-one,
2-(4-Acetoxy-phenyl)-thiochromen-4-one,
2-(4-Acetoxy-phenyl)-1,1-dioxo-1H-1$\lambda^6$-thiochromen-4-one,
2-(4-Hydroxy-phenyl)-1,1-dioxo-1H-1$\lambda^6$-thiochromen-4-one,
5,7-Dimethoxy-2-(4'-hydroxy-phenyl)-quinolin-4-one,
5,7-Dihydroxy-2-(4-hydroxy-phenyl)-quinolin-4-one,
2-(4-Hydroxy-phenyl)-1H-quinolin-4-one,
2-(4-Hydroxy-phenyl)-pyrano[3,2-b]pyridin-4-one,
2-(4-Methoxyphenyl)-4H-pyrano[2,3-b]pyridine-4-one,
2-(4-Hydroxy-phenyl)-pyrano[2,3-b]pyridin-4-one,
2-(4-(2-Hydroxyethoxy)phenyl)-4H-pyrano[2,3-b]pyridine-4-one,
2-(3-Fluoro-4-hydroxyphenyl)pyrano[2,3-b]pyridine-4-one,
2-(4-Hydroxy-3-methylphenyl)-4H-pyrano[2,3-b]pyridine-4-one,
4-(4-Oxo-4H-pyrano[2,3-b]pyridine-2-yl)benzonitrile,
2-(3-Chloro-4-hydroxyphenyl)-4H-pyrano[2,3-b]pyridine-4-one,
2-(3-Bromo-4-hydroxyphenyl)-4H-pyrano[2,3-b]pyridin-4-one,
2-(4-Hydroxy-3-methoxyphenyl)-4H-pyrano[2,3-b]pyridine-4-one,
2-(4-Hydroxy-phenyl)-pyrano[2,3-c]pyridin-4-one,
2-(4-Hydroxyphenyl)-4-oxo-4H-pyrano[2,3-c]pyridine 7-oxide,
2-(4-Hydroxyphenyl)-4-oxo-4H-pyrano[2,3-b]pyridine 8-oxide,
2-(4-Hydroxy-phenyl)-pyrano[3,2-c]pyridin-4-one,
2-(4-Hydroxyphenyl)-4-oxo-4H-pyrano[3,2-c]pyridine-6-oxide,
3-((Dimethylamino)methyl)-2-(4-hydroxyphenyl)-4H-chromen-4-one,
2-(2-(4-Hydroxyphenyl)-4-oxo-4H-chromen-3-yl)acetonitrile,
3-(Hydroxymethyl)-2-(4-hydroxyphenyl)-4H-chromen-4-one,
2-(4-Hydroxyphenyl)-3-(methoxymethyl)-4H-chromen-4-one,
3-(4-Hydroxyphenyl)-2H-isoquinolin-1-one,
7-(3-Fluoro-4-hydroxyphenyl)-6-methyl-1,6-naphthyridin-5(6H)-one,
3-(3-Fluoro-4-hydroxyphenyl)-5-methoxyisoquinolin-1(2H)-one,
2-Fluoro-4-(5-methoxy-1-(methylamino)isoquinolin-3-yl)phenol,
4-Naphthalen-2-yl-phenol,
6-Naphthalen-2-yl-pyridin-3-ol,
3-(4-Hydroxyphenyl)naphthalene-1-ol,
4-Isoquinolin-3-yl-phenol,
4-(1,6-Naphthyridin-7-yl)phenol,
2-(4-Hydroxy-phenyl)-[1,4]naphthoquinone,
4-(Benzo[b][1,4]dioxin-2-yl)phenyl acetate,
4-(Benzo[b][1,4]dioxin-2-yl)phenol,
4-(4H-Chromen-2-yl)-phenol,
2-(4-Hydroxyphenyl)benzo[e][1,3]oxazin-4-one,
6-Naphthalen-2-yl-pyridin-3-ol, 2-(4-Ethoxycarbonyloxy-phenyl)-4-oxo-4H-quinoline-1-carboxylic acid ethyl ester,
nicotinic acid 4-(4-oxo-4H-chromen-2-yl)-phenyl ester,
Acetic acid 4-(4-oxo-4H-chromen-2-yl)-phenyl ester,
4-(4-Oxo-4H-pyrano[2,3-b]pyridine-2-yl)phenyl acetate,
2-Amino-5-guanidino-pentanoic acid 4-(4-oxo-4H-chromen-2-yl)phenyl ester,
4-(Isoquinolin-3-yl)phenyl 2-amino-5-guanidinopentanoate,
4-(1-Oxo-1,2-dihydroisoquinolin-3-yl)phenyl 2-amino-5-guanidinopentanoate,
2-(4-(Nicotinoyloxy)phenyl)-4-oxochroman-5,7-diyl dinicotinate, and
2-(4-(Nicotinoyloxy)phenyl)-4-oxo-4H-chromene-5,7-diyl dinicotinate.

119. A method of treating or preventing cardiovascular, cholesterol or lipid related disorders comprising administering a therapeutically effective amount of a compound of Formula I:

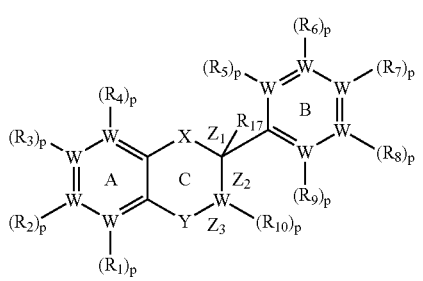

Formula I wherein:
X is selected from $CR_{11}$, $CR_{11}R_{13}$, CO, CS, O, S, SO, $SO_2$, N and $NR_{11}$, wherein $R_{11}$ may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;
each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if X is O, the Z, is a single bond;
wherein if X is O and $Z_2$ is a single bond, then $R_{10}$ is not hydroxyl or ester;
and pharmaceutically acceptable salts and hydrates thereof.

120. The method of embodiment 119, wherein the cardiovascular, cholesterol or lipid related disorder is selected from
acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypertension, hyperlipidemia, intermittent claudication, ischemia, ischemia reperfusion injury, ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.

121. The method of embodiment 118, wherein treating or preventing a cholesterol disorder comprises decreasing blood cholesterol levels.

122. The method of embodiment 118, wherein treating or preventing a cholesterol disorder comprises increasing blood ApoA-I levels.

123. The method of embodiment 118, wherein the therapeutically effective amount of the compound of Formula I is administered with a pharmaceutically acceptable carrier in a pharmaceutically acceptable composition.

124. The method of embodiment 118, wherein the therapeutically effective amount of the compound of Formula I is sufficient to establish a concentration ranging from about 0.001 μM to about 100 μM in the mammal.

125. The method of embodiment 124, wherein the concentration ranges from about 1 μM to about 20 μM.

126. The method of embodiment 118, wherein the compound of Formula I is 2-(4-hydroxy-phenyl)-pyrano[2,3-b]pyridin-4-one.

127. The method of embodiment 118, wherein the compound is 3-(4-hydroxyphenyl)-2H-isoquinolin-1-one.

128. The method of embodiment 118, wherein the compound is 4-isoquinolin-3-yl-phenol.

129. A compound of Formula I:

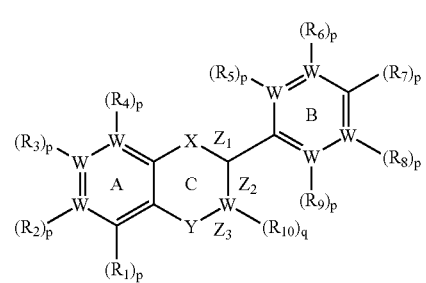

Formula I wherein
X is selected from $CR_{11}$, $CR_{11}R_{13}$, CO, O, N and $NR_{11}$, wherein $R_{11}$ may be the same or different than $R_{13}$;
Y is selected from $CR_{12}$, $CR_{12}R_{14}$, CO, O, N and $NR_{12}$, wherein $R_{12}$ may be the same or different than $R_{14}$;
$R_1$, $R_2$, $R_3$, $R_4$, $R_5$, $R_6$, $R_8$, $R_9$, $R_{10}$, $R_{11}$, $R_{12}$, $R_{13}$, $R_{14}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_8$, $R_9$, $R_{10}$, $R_{11}$, $R_{12}$, $R_{13}$, and $R_{14}$ are connected in a 5 or 6-membered ring to form a bicyclic aryl or bicyclic heteroaryl;

each W is independently selected from C and N, wherein if W is N, then p is 0 and if W is C, then p is 1;

at least one W is N;

$Z_1$, $Z_2$ and $Z_3$ are each independently selected from a single bond and a double bond;

wherein if X is O and $Z_2$ is a single bond, then $R_{10}$ is not hydroxyl or ester;

wherein if a W in the C ring is selected from N and $NR_{10}$, $Z_1$ is a double bond, and $R_5$, $R_6$, $R_8$, and $R_9$ are each hydrogen, then $R_7$ is not hydroxyl or alkoxy;

and pharmaceutically acceptable salts or hydrates thereof.

130. The compound of embodiment 129, wherein $R_7$ is hydroxyl.

131. The compound of embodiment 129, wherein at least one W in the A ring is N.

132. The compound of embodiment 131, wherein X is O, Y is CO and $Z_2$ is a double bond.

133. The compound of embodiment 132, wherein $R_5$, $R_6$, $R_8$, $R_9$ and $R_{10}$ are each hydrogen.

134. The compound of embodiment 129, wherein at least one W in the B ring is N.

135. The compound of embodiment 129, wherein the W in the C ring is selected from N and $NR_{10}$, where $R_{10}$ is selected from hydrogen and methyl.

136. The compound of embodiment 135, wherein $Z_1$ is a double bond.

137. The compound of embodiment 136, wherein $Z_3$ is a double bond and the W in the A ring is N.

138. The compound of embodiment 135, wherein $R_8$ is halogen.

139. The compound of embodiment 129, wherein at least one of $R_1$, $R_2$, $R_3$ and $R_4$ is alkoxy.

140. The compound of embodiment 129, wherein Y is $CR_{12}$ and $R_{12}$ is amino.

141. A pharmaceutical composition comprising a compound of embodiment 129 and a pharmaceutically acceptable carrier.

142. A method of increasing expression of ApoA-I in a mammal comprising administering a therapeutically effective amount of a compound of embodiment 129.

143. A method of treating or preventing cardiovascular, cholesterol or lipid related disorders comprising administering a therapeutically effective amount of a compound of embodiment 129.

144. A method for increasing expression of ApoA-I in a mammal comprising administering a therapeutically effective amount of a compound of Formula IV:

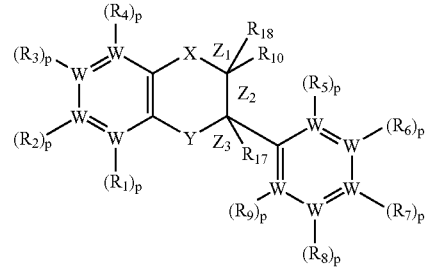

Formula IV wherein:
X is selected from $CR_{11}$, $CR_{11}R_{13}$, CO, CS, O, S, SO, $SO_2$, N and $NR_{11}$, wherein $R_{11}$ may be the same or different than $R_{13}$;

Y is selected from $CR_{12}$, $CR_{12}R_{14}$, CO, CS, O, S, SO, $SO_2$, N and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{18}$ are connected in a 5 or 6-membered ring to form a bicyclic aryl or bicyclic heteroaryl;

each W is independently selected from C and N, wherein if W is N, then p is 0 and if W is C, then p is 1;

$Z_1$, $Z_2$ and $Z_3$ are each independently selected from a single bond and a double bond;

wherein if Y is O, then X is not CO;

wherein if X is O, Y is CO and $Z_2$ is a double bond, then at least one of $R_5$, $R_6$, $R_8$ and $R_9$ is not hydrogen;

and pharmaceutically acceptable salts and hydrates thereof.

145. The method of embodiment 14, wherein X is O and Y is CO.

146. The method of embodiment 14, wherein at least one W is N.

147. The method of embodiment 146, wherein X is O and Y is CO.

148. The method of embodiment 146, wherein at least one W in the A ring of Formula IV is N.

149. The method of embodiment 14, wherein $R_7$ is hydroxyl, and $R_6$ and $R_8$ are independently selected from arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate and O-glucoronidate, subject to the proviso that $R_6$ and $R_8$ are not both simultaneously hydrogen.

150. The method of embodiment 149, wherein X is O and Y is CO.

151. The method of embodiment 149, wherein at least one W is N.
152. The method of embodiment 151, wherein X is O and Y is CO.
153. The method of embodiment 14, wherein $Z_1$ and $Z_3$ are single bonds, and $Z_2$ is a double bond.
154. The method of embodiment 153, wherein X is O and Y is CO.
155. The method of embodiment 153, wherein at least one W is N.
156. The method of embodiment 155, wherein X is O and Y is CO.
157. The method of embodiment 153, wherein $R_7$ is hydroxyl, and $R_6$ and $R_8$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate and O-glucoronidate,
subject to the proviso that $R_6$ and $R_8$ are not both simultaneously hydrogen.
158. The method of embodiment 157, wherein X is O and Y is CO.
159. The method of embodiment 157, wherein at least one W is N.
160. The method of embodiment 159, wherein X is O and Y is CO.
161. The method of embodiment 14, wherein
X is selected from $CR_{11}$, $CR_{11}R_{13}$, CO, CS, and O; and
Y is selected from $CR_{12}$, $CR_{12}R_{14}$, S, SO, $SO_2$, and $NR_{12}$.
162. The method of embodiment 161, wherein at least one W is N.
163. The method of embodiment 161, wherein $R_7$ is hydroxyl, and $R_6$ and $R_8$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate and O-glucoronidate,
subject to the proviso that $R_6$ and $R_8$ are not both simultaneously hydrogen.
164. The method of embodiment 163, wherein at least one W is N.
165. The method of embodiment 161, wherein $Z_1$ and $Z_3$ are single bonds, and $Z_2$ is a double bond.
166. The method of embodiment 165, wherein at least one W is N.
167. The method of embodiment 165, wherein $R_7$ is hydroxyl, and $R_6$ and $R_8$ are independently selected from
arylalkyl, carboxy, cyano, cycloalkyl, ester, formyl, halogen, haloalkyl, heteroaryl, heterocyclyl, hydrogen, hydroxyl, hydroxyalkyl, hydroxyaryl, ketone, perfluoroalkyl, perfluorocycloalkyl, perfluoroalkoxy, O-sulfate and O-glucoronidate,
subject to the proviso that $R_6$ and $R_8$ are not both simultaneously hydrogen.
168. The method of embodiment 167, wherein at least one W is N.
169. The method of embodiment 14, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is selected from O-sulfate and O-glucoronidate.
170. The method of embodiment 14, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is selected from succinate, D-argininate, L-argininate, L-lysinate and D-lysinate.
171. The method of embodiment 14, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is selected from amide, amino, carbamate, carboxy, ester, ether, formyl, and ketone.
172. The method of embodiment 171, wherein at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ is a nicotinate ester.
173. The method of embodiment 14, wherein the therapeutically effective amount of the compound of Formula I is administered with a pharmaceutically acceptable carrier in a pharmaceutically acceptable composition.
174. The method of embodiment 14, wherein the therapeutically effective amount of the compound of Formula IV is sufficient to establish a concentration ranging from about 0.001 μM to about 100 μM in the mammal.
175. The method of embodiment 16, wherein the concentration ranges from about 1 μM to about 20 μM.
176. The method of embodiment 14, wherein the compound of Formula IV is 3-(4-hydroxyphenyl)-4H-pyrano[2,3-b]pyridin-4-one.
177. A method for increasing expression of ApoA-I in a mammal comprising administering a therapeutically effective amount of a compound of Formula V:

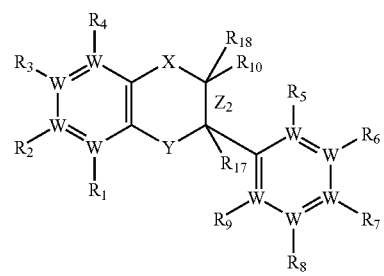

Formula V wherein

X is selected from $CH_2$, $CHR_{11}$, $CHR_{13}$, $CR_{11}R_{13}$, CO, CS, O, S, SO, $SO_2$, NH and $NR_{11}$, wherein $R_{11}$ may be the same or different than $R_{13}$;

Y is selected from $CH_2$, $CHR_{12}$, $CHR_{14}$, $CR_{12}R_{14}$, CO, CS, O, S, SO, $SO_2$, NH and $NR_{12}$, wherein $R_{12}$ may be the same or different than $R_{14}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from ($C_1$-$C_{22}$)alkyl, ($C_2$-$C_{22}$)alkenyl, ($C_2$-$C_{22}$)alkynyl, aryl, heteroaryl, alkoxy, aryloxy, benzyl, phenyl, carbonyl, thioketone, hydrogen, hydroxyl, acetyl, hydroxyalkyl, aminoalkyl, amide, carbamate, halogen, $CF_3$, $CCl_3$, sulfonic acid, phosphate, O-sulfate, O-glucoronidate, monoester, dicarboxylic acid, J, K, L, M, P and Q;

each W is independently selected from C and N;

$Z_2$ is selected from a single bond and a double bond;

J is selected from

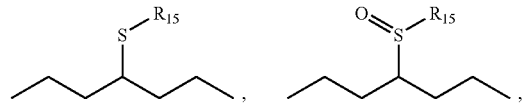

-continued

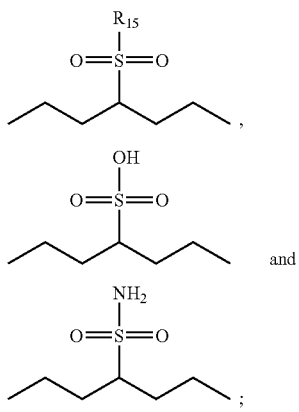

K is

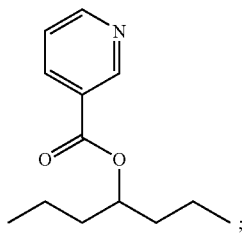

L is selected from

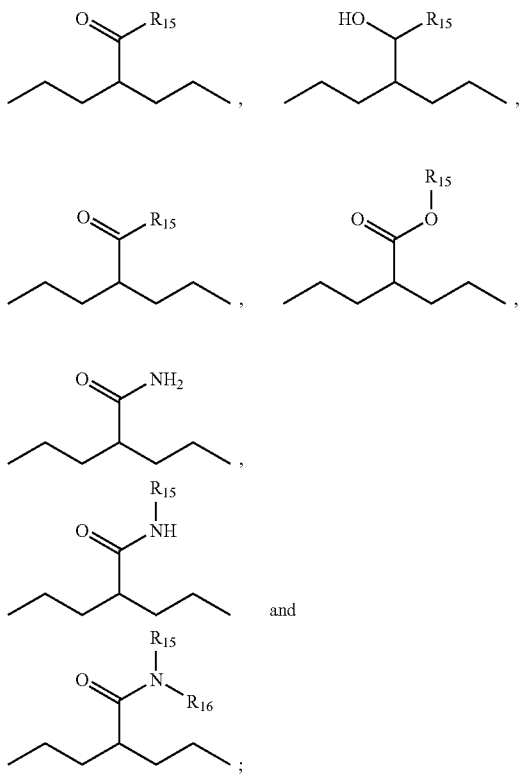

M is selected from

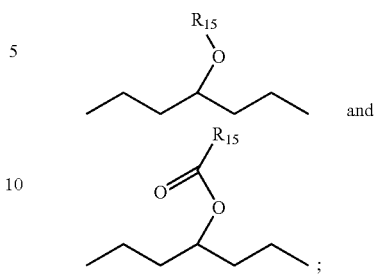

P is selected from

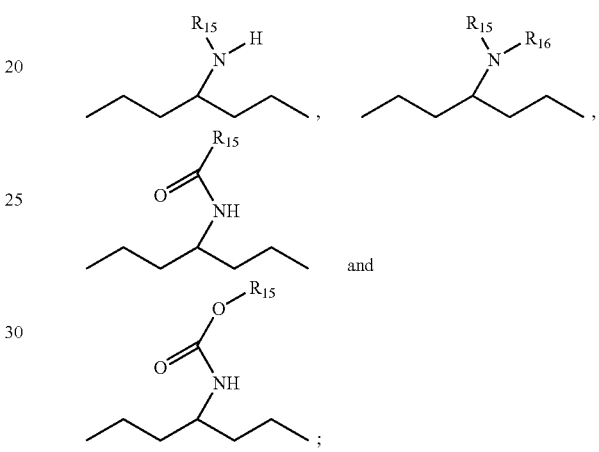

Q is selected from and

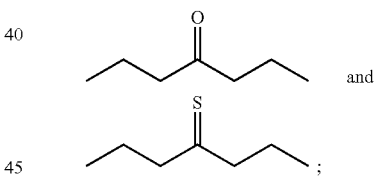

$R_{15}$ and $R_{16}$ are each independently selected from $(C_1-C_{22})$ alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl, acetyl, hydroxyalkyl, aminoalkyl, amide, carbamate, halogen, $CF_3$, $CCl_3$, sulfonic acid and phosphate;

and pharmaceutically acceptable salts thereof;

subject to at least one proviso selected from:
1) $R_7$ is hydroxyl;
2) at least one W is N;
3) at least one of $R_1-R_{10}$ is selected from L, M and P;
4) at least one of $R_1-R_{10}$ is selected from K;
5) $R_7$ is K;
6) one of $R_1-R_{10}$ is a monoester;
7) one of $R_1-R_{10}$ is a dicarboxylic acid;
8) one of $R_1-R_{10}$ is succinic acid;
9) $R_7$ and $R_2$ are each hydroxyl; and
10) $R_7$ is selected from J.

178. The method of embodiment 177, wherein if proviso 1 is selected, a second proviso is selected from provisos 2-4 and 6-9.

179. The method of embodiment 177, wherein $R_7$ is hydroxyl and at least one W is N.
180. The method of embodiment 177, wherein $R_7$ is hydroxyl and at least one of $R_1$-$R_6$ and $R_8$-$R_{10}$ is K.
181. The method of embodiment 177, wherein $R_7$ is hydroxyl and at least one of $R_1$-$R_6$ and $R_8$-$R_{10}$ is selected from L, M and P.
182. The method of embodiment 177, wherein $R_7$ is K and at least one W is N.
183. The method of embodiment 177, wherein Y is selected from $CH_2$, $CHR_{12}$, $CHR_{14}$, $CR_{12}R_{14}$, CO, CS, S, SO, $SO_2$, NH and $NR_{12}$, wherein $R_{12}$ may be the same or different than $R_{14}$.
184. The method of embodiment 177, wherein Formula V is selected from Formulae VA to VK:

Formula VA
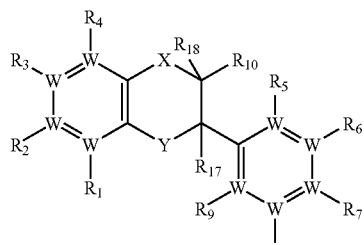

Formula VB
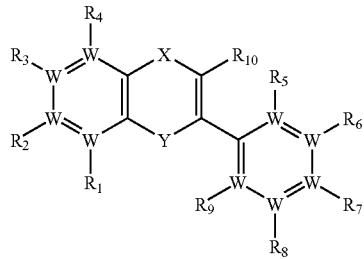

Formula VC
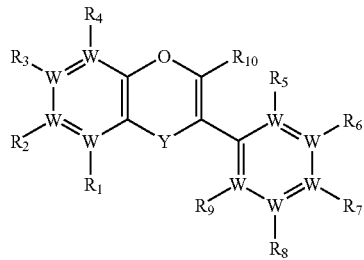

Formula VD
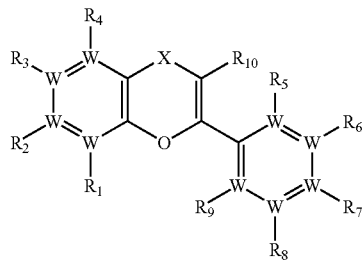

Formula VE
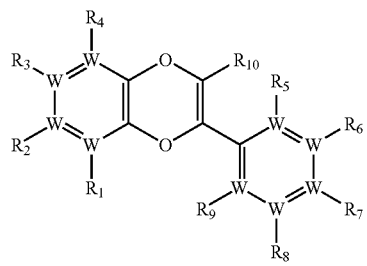

Formula VF
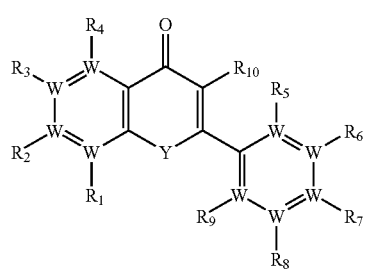

Formula VG
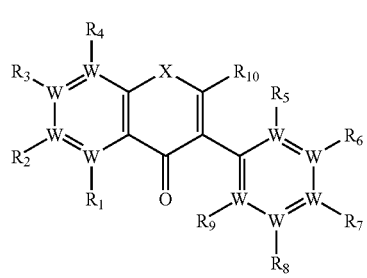

Formula VH
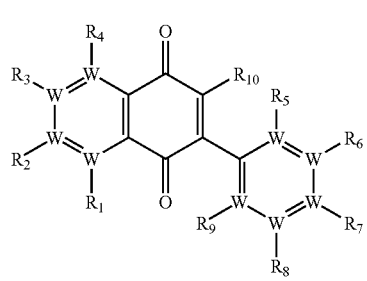

Formula VJ
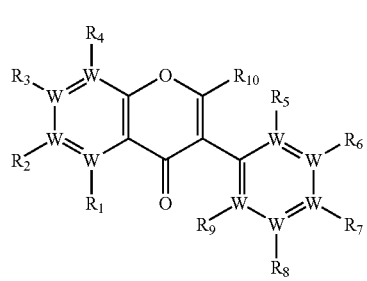

Formula VK
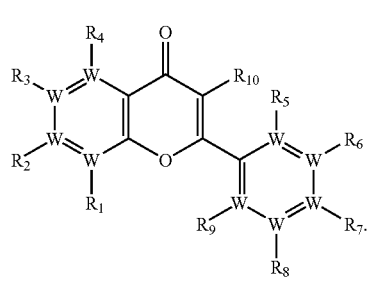

185. A method for increasing expression of ApoA-I in a mammal comprising administering a therapeutically effective amount of a compound of Formula VI:

Formula VI

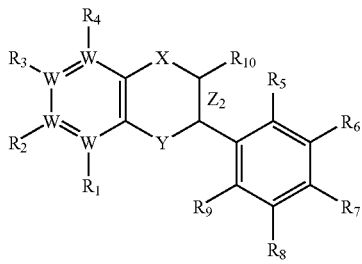

wherein:

$R_1$, $R_2$, $R_3$, $R_4$, $R_5$, $R_6$, $R_8$, $R_9$, and $R_{10}$ are independently selected from $(C_1$-$C_{22})$alkyl, $(C_2$-$C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F, and G;

$R_7$ is selected from hydroxyl and K;

each W is independently selected from C and N;

X is selected from O, S, C, $CR_{11}$ and $NR_{11}$;

Y is selected from O, S, C, $CR_{12}$ and $NR_{12}$;

$R_{11}$ and $R_{12}$ are each independently selected from D, E, F, and G;

K is

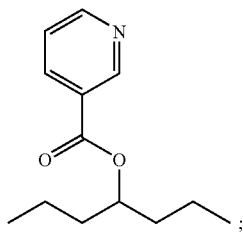

D is

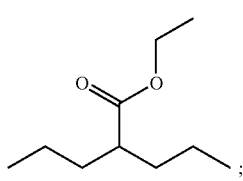

E is selected from

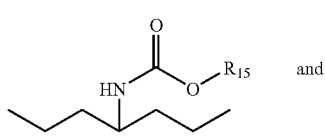

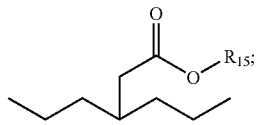

F is selected from

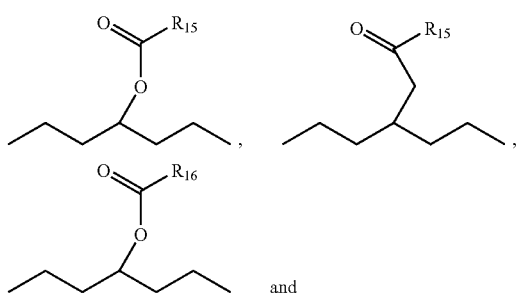

G is

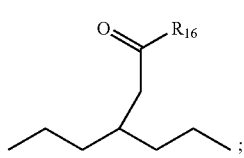

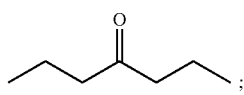

$R_{15}$ is selected from pyridine, pyridazine, pyrimidine, and pyrazine;

$R_{16}$ is selected from $(C_1$-$C_{22})$alkyl, $(C_2$-$C_{22})$alkenyl, aryl and heteroaryl;

and pharmaceutically acceptable salts thereof;

subject to at least one proviso selected from 1) at least one W is N;

2) at least one of $R_{1-6}$ and $R_{8-10}$ is selected from D, E and F; and 3) at least one of $R_{1-6}$ and $R_{8-10}$ is selected from K.

186. The method of embodiment 185, wherein $R_7$ is hydroxyl and at least one of $R_{1-6}$ and $R_{8-10}$ is selected from K.

187. The method of embodiment 186, subject to at least one proviso selected from 1) at least one W is N; and 2) at least one of $R_{1-6}$ and $R_{8-10}$ is selected from D, E and F.

188. The method of embodiment 185, wherein at least one W is N, at least one of $R_{1-6}$ and $R_{8-10}$ is selected from D, E and F, and at least one of $R_{1-6}$ and $R_{8-10}$ is selected from K.

189. The method of embodiment 185, wherein X is O, Y is $CR_{12}$, and $R_{12}$ is G.

190. The method of embodiment 185, wherein Formula VI is selected from Formulae VIA-VIH:

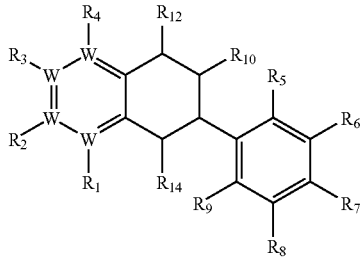

Formula VIA

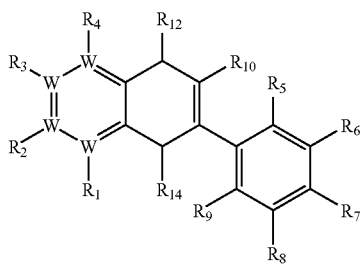

Formula VIB

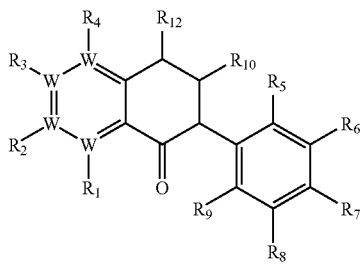

Formula VIC

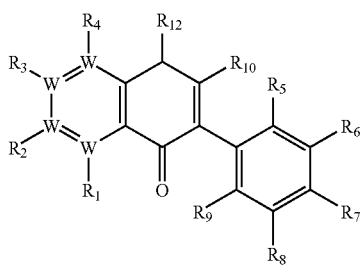

Formula VID

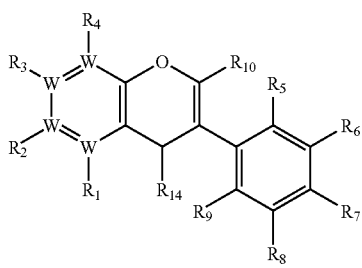

Formula VIE

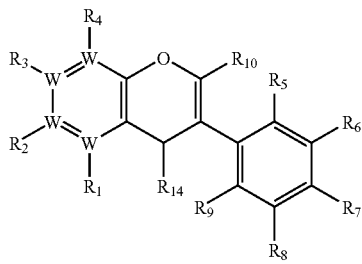

Formula VIF

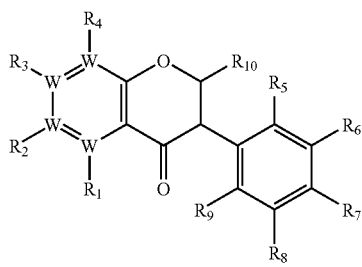

Formula VIG

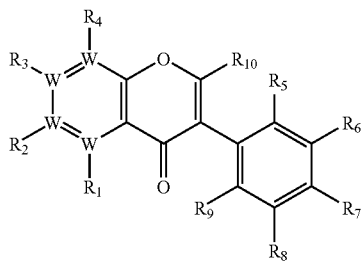

Formula VIH wherein $R_{13}$ and $R_{14}$ are each independently selected from $(C_1-C_{22})$alkyl, $(C_2-C_{22})$alkenyl, aryl, heteroaryl, hydrogen, hydroxyl, acetyl, hydroxyalkyl, aminoalkyl, bromide, iodide, methoxy, ethoxy, fluoride, chloride, $CF_3$, $CCl_3$, phosphate, O-sulfate, O-glucoronidate, K, D, E, F and G 191. A method of treating or preventing cardiovascular, cholesterol or lipid related disorders comprising administering a therapeutically effective amount of a compound of Formula IV:

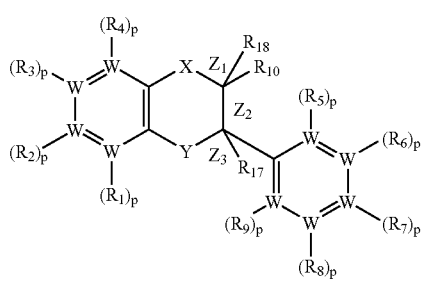

Formula IV wherein:
X is selected from $CR_{11}$, $CR_{11}R_{13}$, CO, CS, O, S, SO, $SO_2$, N and $NR_{11}$, wherein $R_{11}$ may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{17}$ and $R_{18}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{18}$ are connected in a 5 or 6-membered ring to form a bicyclic aryl or bicyclic heteroaryl;

each W is independently selected from C and N, wherein if W is N, then p is 0 and if W is C, then p is 1;

$Z_1$, $Z_2$ and $Z_3$ are each independently selected from a single bond and a double bond;

wherein if Y is O, X is not CO;

wherein if X is O, Y is CO and $Z_2$ is a double bond, then at least one of $R_5$, $R_6$, $R_8$ and $R_9$ is not hydrogen;

and pharmaceutically acceptable salts and hydrates thereof.

192. The method of embodiment 191, wherein the cardiovascular, cholesterol or lipid related disorder is selected from acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypertension, hyperlipidemia, intermittent claudication, ischemia, ischemia reperfusion injury, ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.

193. The method of embodiment 191, wherein treating or preventing a cholesterol disorder comprises decreasing blood cholesterol levels.

194. The method of embodiment 191, wherein treating or preventing a cholesterol disorder comprises increasing blood ApoA-I levels.

195. The method of embodiment 191, wherein the therapeutically effective amount of the compound of Formula IV is administered with a pharmaceutically acceptable carrier in a pharmaceutically acceptable composition.

196. The method of embodiment 191, wherein the therapeutically effective amount of the compound of Formula IV is sufficient to establish a concentration ranging from about 0.001 μM to about 100 μM in the mammal.

197. The method of embodiment 196, wherein the concentration ranges from about 1 μM to about 20 μM.

198. The method of embodiment 191, where in the therapeutically effective amount of compound of Formula IV is sufficient to establish a concentration range from about 1 mg/kg to 30 mg/kg in the mammal.

199. The method of embodiment 191, wherein the compound of Formula IV is 3-(4-hydroxyphenyl)-4H-pyrano[2,3-b]pyridin-4-one.

Pharmaceutical Formulations and Methods of Treatment

The present disclosure also provides pharmaceutical compositions comprising compounds as disclosed herein formulated together with one or more pharmaceutically acceptable carriers. These formulations include those suitable for oral, rectal, topical, buccal and parenteral (e.g. subcutaneous, intramuscular, intradermal, or intravenous) administration, although the most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of the compound as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with the compound as a unit-dose formulation, for example, a tablet, which may contain from 0.05% to 95% by weight of the active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, .lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the active compound with a liquid or finely divided solid carrier, or both, and then, if necessary, shaping the product. For example, a tablet may be prepared by compressing or molding a powder or granules of the compound, optionally with one or more assessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Molded tablets may be made by molding, in a suitable machine, the powdered compound moistened with an inert liquid diluent.

Formulations suitable for buccal (sub-lingual) administration include lozenges comprising a compound in a flavored base, usually sucrose and acacia or tragacanth, and pastilles comprising the compound in an inert base such as gelatin and glycerin or sucrose and acacia.

Formulations of the present invention suitable for parenteral administration comprise sterile aqueous preparations of the compounds, which are approximately isotonic with the blood of the intended recipient. These preparations are administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention may contain from 0.1 to 5% w/w of the active compound.

Formulations suitable for rectal administration are presented as unit-dose suppositories. These may be prepared by admixing the compound with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. Compounds of the invention may be administered in a dose of about 1 µg/kg to about 200 mg/kg daily; such as from about 1 µg/kg to about 150 mg/kg, from about 1 mg/kg to about 200 mg/kg, from about 1 µg/kg to about 100 mg/kg, from about 1 µg/kg to about 1 mg/kg, from about 50 µg/kg to about 200 mg/kg, from about 10 µg/kg to about 1 mg/kg, from about 10 µg/kg to about 100 µg/kg, from about 100 µg to about 10 mg/kg, and from about 500 µg/kg to about 50 mg/kg. The dosages, however, may be varied depending upon the requirements of the patient, the severity of the condition being treated, and the compound being used. In one embodiment, the therapeutically effective amount of a disclosed compound is sufficient to establish a maximal plasma concentration ranging from about 0.001 µM to about 100 µM, e.g., from about 1 µM to about 20 µM. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture assays or animal models. Levels in plasma may be measured, for example, by high performance liquid chromatography. The effects of any particular dosage can be monitored by a suitable bioassay. Examples of dosages are: about $0.1 \times IC_{50}$, about $0.5 \times IC_{50}$, about $1 \times IC_{50}$, about $5 \times IC_{50}$, $10 \times IC_{50}$, about $50 \times IC_{50}$, and about $100 \times IC_{50}$.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4): 219-244 (1966) and Table 1 for Equivalent Surface Area Dosage Factors).

TABLE 1

| From: | To: | | | | |
| --- | --- | --- | --- | --- | --- |
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and sex, as well as the severity of the medical condition in the subject. The dosage may be determined by a physician and adjusted, as necessary, to suit observed effects of the treatment.

In one embodiment, a compound as disclosed herein, or a pharmaceutically acceptable salt or hydrate thereof, is administered in combination with another therapeutic agent. The other therapeutic agent can provide additive or synergistic value relative to the administration of a flavanoid or isoflavanoid compound alone. The therapeutic agent can be, for example, a statin; a PPAR agonist, e.g., a thiazolidinedione or fibrate; a bile-acid-binding-resin; a niacin; a RXR agonist; an anti-obesity drug; a hormone; a tyrophostine; a sulfonylurea-based drug; a biguanide; an alpha-glucosidase inhibitor; apolipoprotein E; a cardiovascular drug; an HDL-raising drug; an HDL enhancer; or a regulator of the apolipoprotein A-IV and/or apolipoprotein genes.

In one embodiment, a method of treating or preventing cardiovascular, cholesterol or lipid related disorders comprises administering a therapeutically effective amount of a disclosed compound. The disclosed compound may be administered as a pharmaceutically acceptable composition, comprising a disclosed compound and a pharmaceutically acceptable carrier. Another embodiment provides methods for the prevention of a cardiovascular, cholesterol or lipid related disorder, comprising administering to a mammal a therapeutically effective amount of a presently disclosed compound or composition.

Exemplary cardiovascular, cholesterol or lipid related disorders include, but are not limited to acute coronary syndrome, angina pectoris, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypertension, hyperlipidemia, intermittent claudication, ischemia, ischemia reperfusion injury, ischemic heart diseases, multi-infarct dementia, myocardial infarction, peripheral vascular disease, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X and impotence.

As used herein, the term "cardiovascular disease" refers to diseases and disorders of the heart and circulatory system. These diseases are often associated with dyslipoproteinemias and/or dyslipidemias. "Endothelium dysfunction(s)" include, but are not limited to, dysfunctions affecting blood vessel elasticity; peripheral vascular disease; coronary heart disease; myocardial infarcation; cerebral infarction and restenosis. "Syndrome X" or "Metabolic Syndrome(s)" include, but are not limited to hypertension and dyslipidemia/dyslipoproteinemia.

In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

One embodiment provides a compound for administration to a patient, such as a human, as a preventative measure against cardiovascular, cholesterol or lipid related disorder. As used herein, "prevention" or "preventing" refers to a reduction of the risk of acquiring a given disease or disorder. In another embodiment, the present compositions are administered as a preventative measure to a patient, such as a human having a genetic predisposition to, for example, a cardiovascular disease, a dyslipidemia, a dyslipoproteinemia, Alzheimer's Disease, hypertension, atherosclerosis, or inflammation.

In another embodiment, the compositions of the invention are administered as a preventative measure to a patient having a non-genetic predisposition to, for example, cardiovascular disease, a dyslipidemia, a dyslipoproteinemia, Alzheimer's Disease, hypertension, atherosclerosis, or inflammation. Examples of such non-genetic predispositions include, but are not limited to, cardiac bypass surgery and percutaneous transluminal coronary angioplasty, which often leads to restenosis, an accelerated form of atherosclerosis; diabetes in women, which often leads to polycystic ovarian disease; and cardiovascular disease, which often leads to impotence. Accordingly, the present compositions may be used for the prevention of one disease or disorder and concurrently treating another (e.g., prevention of polycystic ovarian disease while treating diabetes; prevention of impotence while treating a cardiovascular disease).

Angioplasty and open heart surgery, such as coronary bypass surgery, may be required to treat cardivascular diseases, such as atherosclerosis. These surgical procedures entail using invasive surgical devices and/or implants, and are associated with a high risk of restenosis and thrombosis. Accordingly, the compounds of the invention may be used as coatings on surgical devices (e.g., catheters) and implants (e.g., stents) to reduce the risk of restenosis and thrombosis associated with invasive procedures used in the treatment of cardiovascular diseases.

The present invention provides methods for the treatment or prevention of a dyslipidemia comprising administering to a patient a therapeutically effective amount of a presently disclosed compound. In one embodiment, the compound is administered as a pharmaceutically acceptable composition. As used herein, the term "dyslipidemias" refers to disorders that lead to or are manifested by aberrant levels of circulating lipids. To the extent that levels of lipids in the blood are too high, the disclosed compounds or compositions may be administered to a patient to restore normal levels. Normal levels of lipids are reported in medical treatises known to those of skill in the art.

Dyslipidemias which the disclosed compounds or compositions are useful for preventing or treating include but are not limited to hyperlipidemia and low blood levels of high density lipoprotein (HDL) cholesterol. Hyperlipidemia includes, but is not limited to, familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g., beta-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

One embodiment provides methods for altering lipid metabolism in a patient, e.g., increasing the ratio of HDL to LDL in the blood of a patient, comprising administering to the patient a composition of the invention in an amount effective alter lipid metabolism.

Another embodiment provides methods for the treatment or prevention of a dyslipoproteinemia comprising administering to a patient a therapeutically effective amount of a disclosed compound or composition. As used herein, the term "dyslipoproteinemias" refers to disorders that lead to or are manifested by aberrant levels of circulating lipoproteins. To the extent that levels of lipoproteins in the blood are too high, the disclosed compounds or compositions are administered to a patient to restore normal levels. Conversely, to the extent that levels of lipoproteins in the blood are too low, the disclosed compounds or compositions are administered to a patient to restore normal levels. Normal levels of lipoproteins are reported in medical treatises known to those of skill in the art.

Dyslipoproteinemias which the disclosed compounds or compositions are useful for preventing or treating include, but are not limited to, high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes mellitus; lipoprotein abnormalities associated with obesity; lipoprotein abnormalities associated with Alzheimer's Disease; and familial combined hyperlipidemia.

One embodiment provides methods for elevating the levels of HDL associated proteins, such as ApoA-I, in the blood of a mammal, comprising administering to the mammal a composition comprising a disclosed compound or composition in an amount effective to elevate levels of HDL associated proteins in the mammal.

Another embodiment provides methods for the treatment or prevention of Alzheimer's Disease, hypertension, and/or atherosclerosis, comprising administering to a mammal a therapeutically effective amount of a disclosed compound or composition. As used herein, "treatment or prevention of Alzheimer's Disease" encompasses treatment or prevention of lipoprotein abnormalities associated with Alzheimer's Disease.

"Diseases and conditions associated with diabetes mellitus" as defined herein comprise, but are not restricted to, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, skin and connective tissue disorders, foot ulcerations, metabolic acidosis, arthritis, osteoporosis and impaired glucose tolerance.

PREPARATION OF COMPOUNDS

Flavanoid compounds may be represented by the general structure of Formula A.

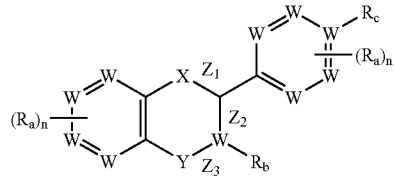

A $R_a$ may be selected from groups including, but not limited to, alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. $R_b$ may be selected from groups including, but not limited to, alkyl, amino, cyano, halogen and hydrogen. $R_c$ represents substituents such as alkyl, alkoxy, halogen, hydroxyl and hydrogen. It should be appreciated that these designations are non-limiting examples of the flavanoid compounds disclosed herein.

One of ordinary skill will appreciate that flavanoid compounds as disclosed herein may be synthesized from readily available starting materials as outlined below.

Formula B represents a general formula for flavanoid compounds comprising a phenyl-chromene:

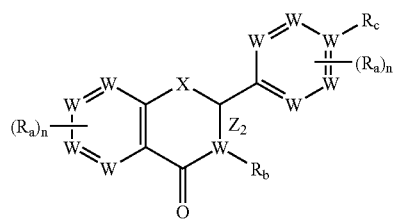

B

Flavanoids of Formula B can be synthesized by the procedure of Scheme 1:

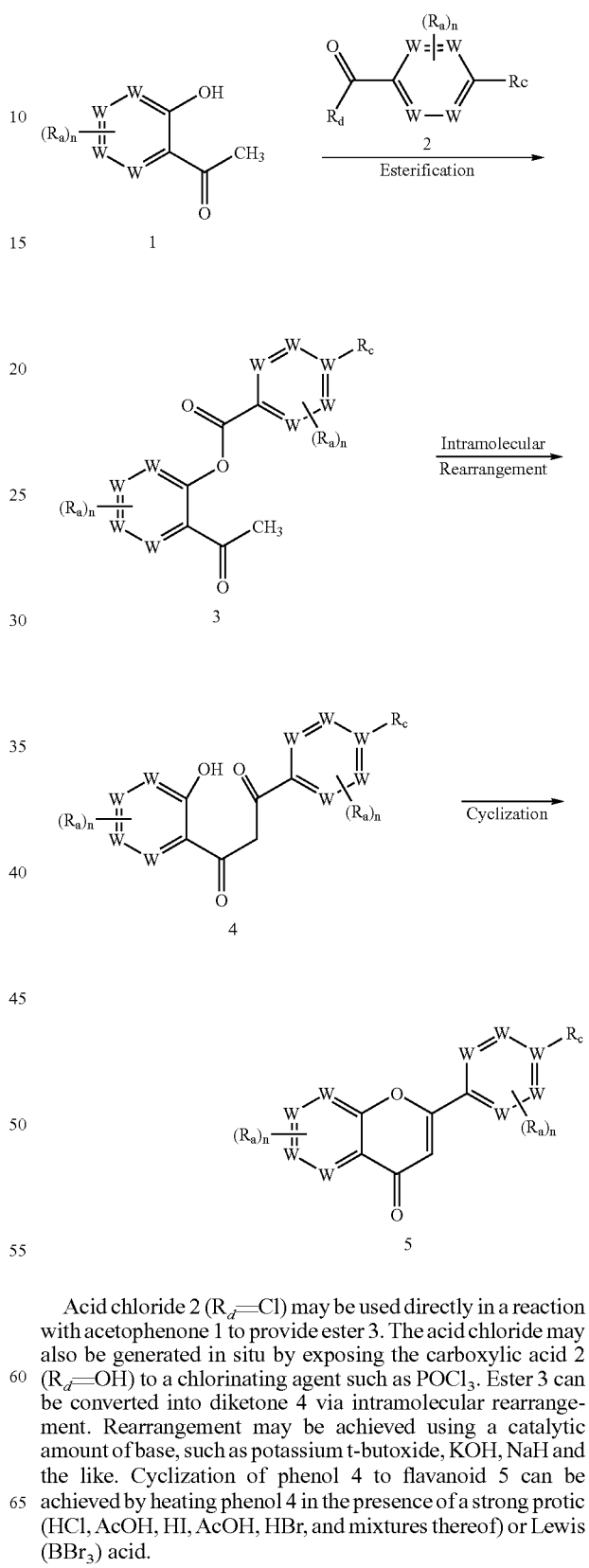

Acid chloride 2 ($R_d$=Cl) may be used directly in a reaction with acetophenone 1 to provide ester 3. The acid chloride may also be generated in situ by exposing the carboxylic acid 2 ($R_d$=OH) to a chlorinating agent such as $POCl_3$. Ester 3 can be converted into diketone 4 via intramolecular rearrangement. Rearrangement may be achieved using a catalytic amount of base, such as potassium t-butoxide, KOH, NaH and the like. Cyclization of phenol 4 to flavanoid 5 can be achieved by heating phenol 4 in the presence of a strong protic (HCl, AcOH, HI, AcOH, HBr, and mixtures thereof) or Lewis ($BBr_3$) acid.

Flavanoid compounds can be synthesized following the procedure of Scheme 2:

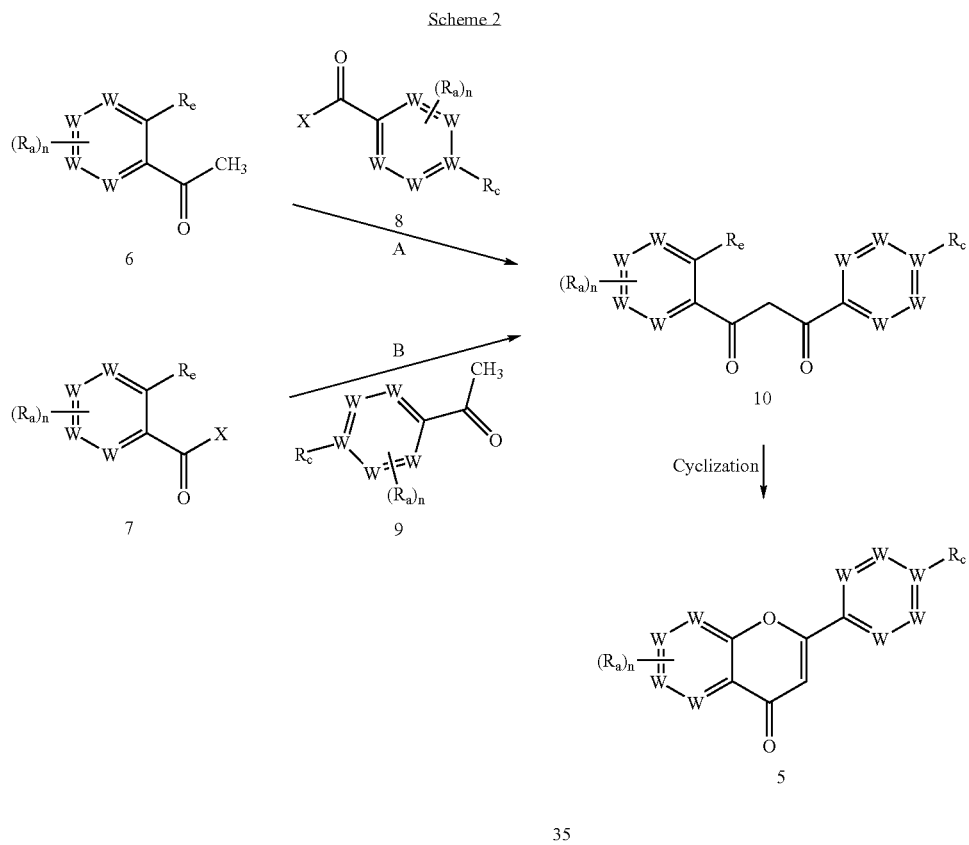

Diketone 10 may be prepared by first exposing methyl ketones 6 or 9 to basic conditions, such as potassium t-butoxide, KOH, NaH and the like, to form the corresponding enolate. Then, reaction with acyl halide 8 or 7 (X=Hal), respectively, affords diketone 10. Cyclization of diketone 10 to flavanoid 5 may likewise be accomplished by a number of methods. When $R_e$=F, exposure of 10 to heat and a polar solvent results in ring closure via nucleophilic aromatic substitution. Alternatively, strong protic or Lewis acids may be used when $R_e$=alkoxy, SH, or $NH_2$. Exemplary acids include HCl, AcOH, HI, AcOH, HBr, $BBr_3$, and mixtures thereof.

Formula C represents flavanoid compounds comprising a naphthyl:

Flavanoids of Formula C can be prepared via the procedure of Scheme 3.

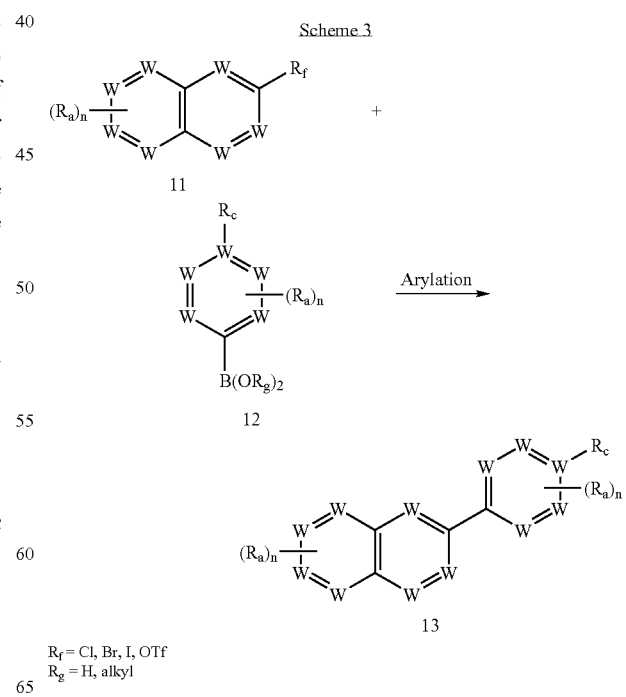

$R_f$ = Cl, Br, I, OTf
$R_g$ = H, alkyl

Arylation of naphthalene analog 11 with boronic acid (or boronic ester) 12 occurs by a Pd-catalyzed Suzuki coupling. Suitable Pd catalysts include $Pd(Ph_3)_4$ along with non-phosphine Pd catalysts, such palladium acetate. Other coupling procedures that may be used in the synthesis of flavanoid 13 include Stille coupling.

Formula D represents a general formula for isoflavanoid compounds:

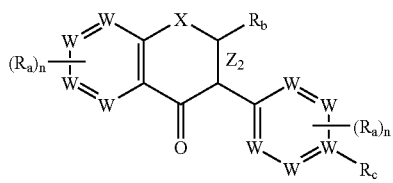

D

Scheme 4 illustrates a general synthesis of compounds of Formula D.

Scheme 4

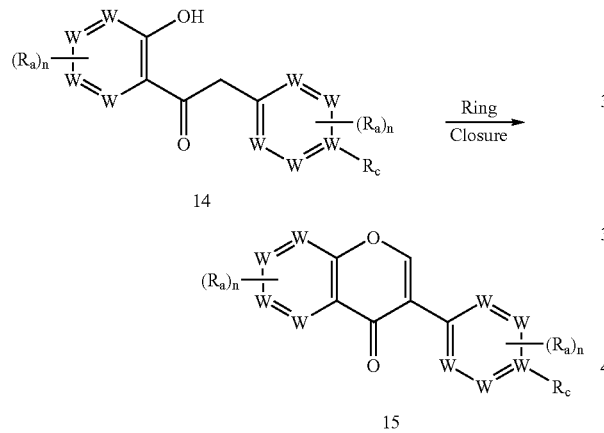

Treatment of phenol 14 with boron trifluoride etherate and methane sulfonylchloride gives isoflavanoid 15. Variations of the Scheme 4 procedure include the method described by Fokialakis et al., *Chemistry & Biology* 11: 397-406 (2004).

Prodrugs of flavanoid compounds can be prepared according to Scheme 5:

Scheme 5

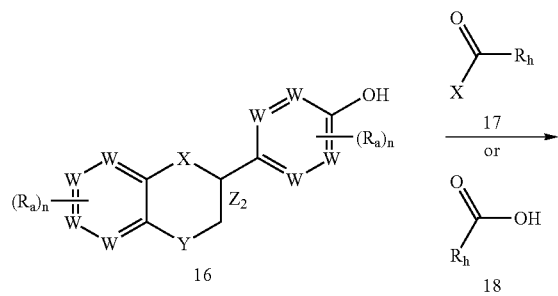

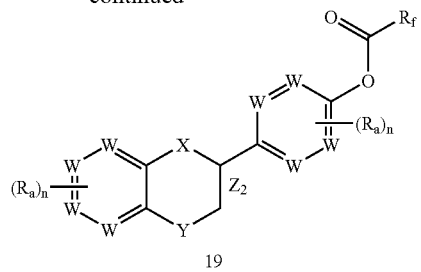

Prodrug esters 19 can be synthesized by treating phenol 16 with acid halide 17. Suitable acid halides include acid chlorides and bromides. Alternatively, esterification of phenol 16 with acid 18 in the presence of a carbodiimide, such as EDCI, affords ester 19.

EXAMPLES

Examples of flavanoid compounds of Formula I include, but are not limited to, the following compounds:

a) 2-(4-Hydroxy-phenyl)-1H-quinolin-4-one

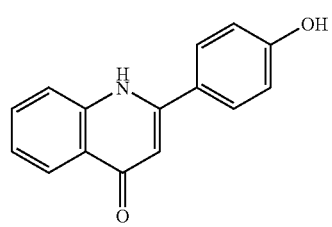

and its derivatives, including, but not limited to:
2-(2,4-Dihydroxy-phenyl)-1H-quinolin-4-one
2-(3,4-Dihydroxy-phenyl)-1H-quinolin-4-one
5-Hydroxy-2-(4-hydroxy-phenyl)-1H-quinolin-4-one
6-Hydroxy-2-(4-hydroxy-phenyl)-1H-quinolin-4-one
7-Hydroxy-2-(4-hydroxy-phenyl)-1H-quinolin-4-one
8-Hydroxy-2-(4-hydroxy-phenyl)-1H-quinolin-4-one
5,7-Dihydroxy-2-(4-hydroxy-phenyl)-1H-quinolin-4-one
6,7- Dihydroxy -2-(4-hydroxy-phenyl)-1H-quinolin-4-one
7,8- Dihydroxy -2-(4-hydroxy-phenyl)-1H-quinolin-4-one
2-(2,4-Dihydroxy-phenyl)-7-hydroxy-1H-quinolin-4-one
2-(3,4-Dihydroxy-phenyl)-7-hydroxy-1H-quinolin-4-one
5,6-Dihydroxy-2-(4-hydroxy-phenyl)-1H-quinolin-4-one
5,8-Dihydroxy-2-(4-hydroxy-phenyl)-1H-quinolin-4-one
2-(2,4-Dihydroxy-phenyl)-5-hydroxy-1H-quinolin-4-one
2-(3,4-Dihydroxy-phenyl)-5-hydroxy-1H-quinolin-4-one
2-(2-Fluoro-4-hydroxy-phenyl)-1H-quinolin-4-one
2-(3-Fluoro-4-hydroxy-phenyl)-1H-quinolin-4-one
5-Fluoro-2-(4-hydroxy-phenyl)-1H-quinolin-4-one
6-Fluoro-2-(4-hydroxy-phenyl)-1H-quinolin-4-one
7-Fluoro-2-(4-hydroxy-phenyl)-1H-quinolin-4-one
8-Fluoro-2-(4-hydroxy-phenyl)-1H-quinolin-4-one
5,7-Difluoro-2-(4-hydroxy-phenyl)-1H-quinolin-4-one
6,7-Difluoro-2-(4-hydroxy-phenyl)-1H-quinolin-4-one
7,8-Difluoro-2-(4-hydroxy-phenyl)-1H-quinolin-4-one
7-Fluoro-2-(2-fluoro-4-hydroxy-phenyl)-1H-quinolin-one
7-Fluoro-2-(3-fluoro-4-hydroxy-phenyl)-1H-quinolin-4-one
5,6-Difluoro-2-(4-hydroxy-phenyl)-1H-quinolin-4-one
5,8-Difluoro-2-(4-hydroxy-phenyl)-1H-quinolin-4-one
5-Fluoro-2-(2-fluoro-4-hydroxy-phenyl)-1H-quinolin-4-one 5-Fluoro-2-(3-fluoro-4-hydroxy-phenyl)-1H-quinolin-4-one
Nicotinic acid 5-hydroxy-2-(4-oxo-1,4-dihydro-quinolin-2-yl)-phenyl ester
Nicotinic acid 2-hydroxy-5-(4-oxo-1,4-dihydro-quinolin-2-yl)-phenyl ester
Nicotinic acid 4-(4-oxo-1,4-dihydro-quinolin-2-yl)-phenyl ester
Nicotinic acid 2-(4-hydroxy-phenyl)-4-oxo-1,4-dihydro-quinolin-5-yl ester
Nicotinic acid 2-(4-hydroxy-phenyl)-4-oxo-1,4-dihydro-quinolin-6-yl ester
Nicotinic acid 2-(4-hydroxy-phenyl)-4-oxo-1,4-dihydro-quinolin-7-yl ester
Nicotinic acid 2-(4-hydroxy-phenyl)-4-oxo-1,4-dihydro-quinolin-8-yl ester b) Nicotinic acid 4-(4-oxo-1,4-dihydro-quinolin-2-yl)-phenyl ester

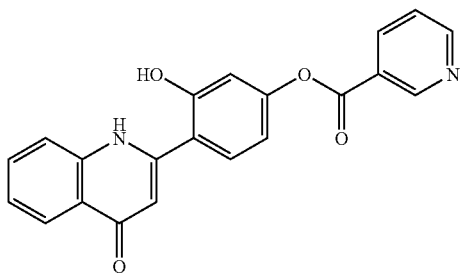

and its derivatives, including, but not limited to:
Nicotinic acid 3-hydroxy-4-(4-oxo-1,4-dihydro-quinolin-2-yl)-phenyl ester
Nicotinic acid 2-hydroxy-4-(4-oxo-1,4-dihydro-quinolin-2-yl)-phenyl ester
Nicotinic acid 4-(5-hydroxy-4-oxo-1,4-dihydro-quinolin-2-yl)-phenyl ester
Nicotinic acid 4-(6-hydroxy-4-oxo-1,4-dihydro-quinolin-2-yl)-phenyl ester
Nicotinic acid 4-(7-hydroxy-4-oxo-1,4-dihydro-quinolin-2-yl)-phenyl ester
Nicotinic acid 4-(8-hydroxy-4-oxo-1,4-dihydro-quinolin-2-yl)-phenyl ester
Nicotinic acid 3-hydroxy-4-(7-hydroxy-4-oxo-1,4-dihydro-quinolin-2-yl)-phenyl ester
Nicotinic acid 2-hydroxy-4-(7-hydroxy-4-oxo-1,4-dihydro-quinolin-2-yl)-phenyl ester
Nicotinic acid 4-(5,7-dihydroxy-4-oxo-1,4-dihydro-quinolin-2-yl)-phenyl ester
Nicotinic acid 4-(6,7-dihydroxy-4-oxo-1,4-dihydro-quinolin-2-yl)-phenyl ester
Nicotinic acid 4-(7,8-dihydroxy-4-oxo-1,4-dihydro-quinolin-2-yl)-phenyl ester
Nicotinic acid 3-hydroxy-4-(5-hydroxy-4-oxo-1,4-dihydro-quinolin-2-yl)-phenyl ester
Nicotinic acid 3-hydroxy-4-(5-hydroxy-4-oxo-1,4-dihydro-quinolin-2-yl)-phenyl ester
Nicotinic acid 4-(5,6-dihydroxy-4-oxo-1,4-dihydro-quinolin-2-yl)-phenyl ester
Nicotinic acid 4-(5,8-dihydroxy-4-oxo-1,4-dihydro-quinolin-2-yl)-phenyl ester
Nicotinic acid 3-fluoro-4-(4-oxo-1,4-dihydro-quinolin-2-yl)-phenyl ester
Nicotinic acid 2-fluoro-4-(4-oxo-1,4-dihydro-quinolin-2-yl)-phenyl ester
Nicotinic acid 4-(8-hydroxy-4-oxo-1,4-dihydro-quinolin-2-yl)-phenyl ester
Nicotinic acid 4-(5-fluoro-4-oxo-1,4-dihydro-quinolin-2-yl)-phenyl ester
Nicotinic acid 4-(7-fluoro-4-oxo-1,4-dihydro-quinolin-2-yl)-phenyl ester
Nicotinic acid 4-(8-fluoro-4-oxo-1,4-dihydro-quinolin-2-yl)-phenyl ester
Nicotinic acid 3-fluoro-4-(7-fluoro-4-oxo-1,4-dihydro-quinolin-2-yl)-phenyl ester
Nicotinic acid 2-fluoro-4-(7-fluoro-4-oxo-1,4-dihydro-quinolin-2-yl)-phenyl ester
Nicotinic acid 4-(5,7-difluoro-4-oxo-1,4-dihydro-quinolin-2-yl)-phenyl ester
Nicotinic acid 4-(6,7-difluoro-4-oxo-1,4-dihydro-quinolin-2-yl)-phenyl ester
Nicotinic acid 4-(7,8-difluoro-4-oxo-1,4-dihydro-quinolin-2-yl)-phenyl ester
Nicotinic acid 3-fluoro-4-(5-fluoro-4-oxo-1,4-dihydro-quinolin-2-yl)-phenyl ester
Nicotinic acid 2-fluoro-4-(5-fluoro-4-oxo-1,4-dihydro-quinolin-2-yl)-phenyl ester
Nicotinic acid 4-(5,6-difluoro-4-oxo-1,4-dihydro-quinolin-2-yl)-phenyl ester
Nicotinic acid 4-(5,7-difluoro-4-oxo-1,4-dihydro-quinolin-2-yl)-phenyl ester
Nicotinic acid 4-(5,8-difluoro-4-oxo-1,4-dihydro-quinolin-2-yl)-phenyl ester c) 2-(4-Hydroxy-phenyl)-4-oxo-4H-quinoline-1-carboxylic acid ethyl ester

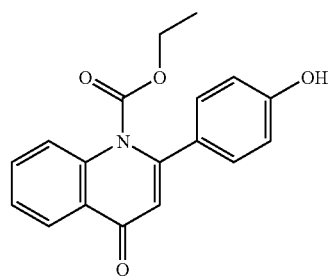

and its derivatives, including, but not limited to:
2-(3,4-Dihydroxy-phenyl)-4-oxo-4H-quinoline-1-carboxylic acid ethyl ester
5-Hydroxy-2-(4-hydroxy-phenyl)-4-oxo-4H-quinoline-1-carboxylic acid ethyl ester
6-Hydroxy-2-(4-hydroxy-phenyl)-4-oxo-4H-quinoline-1-carboxylic acid ethyl ester
7-Hydroxy-2-(4-hydroxy-phenyl)-4-oxo-4H-quinoline-1-carboxylic acid ethyl ester
8-Hydroxy-2-(4-hydroxy-phenyl)-4-oxo-4H-quinoline-1-carboxylic acid ethyl ester
5,7-Dihydroxy-2-(4-hydroxy-phenyl)-4-oxo-4H-quinoline-1-carboxylic acid ethyl ester
6,7-Dihydroxy-2-(4-hydroxy-phenyl)-4-oxo-4H-quinoline-1-carboxylic acid ethyl ester
7,8-Dihydroxy-2-(4-hydroxy-phenyl)-4-oxo-4H-quinoline-1-carboxylic acid ethyl ester
2-(3,4-Dihydroxy-phenyl)-7-hydroxy-4-oxo-4H-quinoline-1-carboxylic acid ethyl ester 5,6-Dihydroxy-2-(4-hydroxy-phenyl)-4-oxo-4H-quinoline-1-carboxylic acid ethyl ester
5,8-Dihydroxy-2-(4-hydroxy-phenyl)-4-oxo-4H-quinoline-1-carboxylic acid ethyl ester
2-(3,4-Dihydroxy-phenyl)-5-hydroxy-4-oxo-4H-quinoline-1-carboxylic acid ethyl ester
2-(3-Fluoro-4-hydroxy-phenyl)-4-oxo-4H-quinoline-1-carboxylic acid ethyl ester
5-Fluoro-2-(4-hydroxy-phenyl)-4-oxo-4H-quinoline-1-carboxylic acid ethyl ester
6-Fluoro-2-(4-hydroxy-phenyl)-4-oxo-4H-quinoline-1-carboxylic acid ethyl ester
7-Fluoro-2-(4-hydroxy-phenyl)-4-oxo-4H-quinoline-1-carboxylic acid ethyl ester
8-Fluoro-2-(4-hydroxy-phenyl)-4-oxo-4H-quinoline-1-carboxylic acid ethyl ester
5,7-Difluoro-2-(4-hydroxy-phenyl)-4-oxo-4H-quinoline-1-carboxylic acid ethyl ester
6,7-Difluoro-2-(4-hydroxy-phenyl)-4-oxo-4H-quinoline-1-carboxylic acid ethyl ester
7,8-Difluoro-2-(4-hydroxy-phenyl)-4-oxo-4H-quinoline-1-carboxylic acid ethyl ester
7-Fluoro-2-(3-fluoro-4-hydroxy-phenyl)-4-oxo-4H-quinoline-1-carboxylic acid ethyl ester
5,6-Difluoro-2-(4-hydroxy-phenyl)-4-oxo-4H-quinoline-1-carboxylic acid ethyl ester
5.8-Difluoro-2-(4-hydroxy-phenyl)-4-oxo-4H-quinoline-1-carboxylic acid ethyl ester
5-Fluoro-2-(3-fluoro-4-hydroxy-phenyl)-4-oxo-4H-quinoline-1-carboxylic acid ethyl ester d) 4-Oxo-2-[4-(pyridine-3-carbonyloxy)-phenyl]-4H-quinoline-1-carboxylic acid ethyl ester

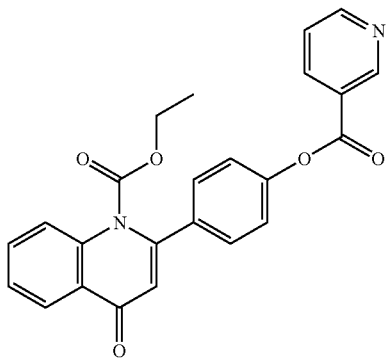

and its derivatives, including but not limited to:
2-[3-Hydroxy-4-(pyridine-3-carbonyloxy)-phenyl]-4-oxo-4H-quinoline-1-carboxylic acid ethyl ester
5-Hydroxy-4-oxo-2-[4-(pyridine-3-carbonyloxy)-phenyl]-4H-quinoline-1-carboxylic acid ethyl ester
6-Hydroxy-4-oxo-2-[4-(pyridine-3-carbonyloxy)-phenyl]-4H-quinoline-1-carboxylic acid ethyl ester
7-Hydroxy-4-oxo-2-[4-(pyridine-3-carbonyloxy)-phenyl]-4H-quinoline-1-carboxylic acid ethyl ester
8-Hydroxy-4-oxo-2-[4-(pyridine-3-carbonyloxy)-phenyl]-4H-quinoline-1-carboxylic acid ethyl ester
7-Hydroxy-2-[3-hydroxy-4-(pyridine-3-carbonyloxy)-phenyl]-4-oxo-4H-quinoline-1-carboxylic acid ethyl ester
5,7-Dihydroxy-4-oxo-2-[4-(pyridine-3-carbonyloxy)-phenyl]-4H-quinoline-1-carboxylic acid ethyl ester
6,7-Dihydroxy-4-oxo-2-[4-(pyridine-3-carbonyloxy)-phenyl]-4H-quinoline-1-carboxylic acid ethyl ester
7,8-Dihydroxy-4-oxo-2-[4-(pyridine-3-carbonyloxy)-phenyl]-4H-quinoline-1-carboxylic acid ethyl ester
5-Hydroxy-2-[3-hydroxy-4-(pyridine-3-carbonyloxy)-phenyl]-4-oxo-4H-quinoline-1-carboxylic acid ethyl ester
5,6-Dihydroxy-4-oxo-2-[4-(pyridine-3-carbonyloxy)-phenyl]-4H-quinoline-1-carboxylic acid ethyl ester
5,8-Dihydroxy-4-oxo-2-[4-(pyridine-3-carbonyloxy)-phenyl]-4H-quinoline-1-carboxylic acid ethyl ester
2-[3-Fluoro-4-(pyridine-3-carbonyloxy)-phenyl]-4-oxo-4H-quinoline-1-carboxylic acid ethyl ester
5-Fluoro-4-oxo-2-[4-(pyridine-3-carbonyloxy)-phenyl]-4H-quinoline-1-carboxylic acid ethyl ester
6-Fluoro-4-oxo-2-[4-(pyridine-3-carbonyloxy)-phenyl]-4H-quinoline-1-carboxylic acid ethyl ester
7-Fluoro-4-oxo-2-[4-(pyridine-3-carbonyloxy)-phenyl]-4H-quinoline-1-carboxylic acid ethyl ester
8-Fluoro-4-oxo-2-[4-(pyridine-3-carbonyloxy)-phenyl]-4H-quinoline-1-carboxylic acid ethyl ester
7-Fluoro-2-[3-fluoro-4-(pyridine-3-carbonyloxy)-phenyl]-4-oxo-4H-quinoline-1-carboxylic acid ethyl ester
5,7-Difluoro-4-oxo-2-[4-(pyridine-3-carbonyloxy)-phenyl]-4H-quinoline-1-carboxylic acid ethyl ester
6,7-Difluoro-4-oxo-2-[4-(pyridine-3-carbonyloxy)-phenyl]-4H-quinoline-1-carboxylic acid ethyl ester
7,8-Difluoro-4-oxo-2-[4-(pyridine-3-carbonyloxy)-phenyl]-4H-quinoline-1-carboxylic acid ethyl ester
5-Fluoro-2-[3-fluoro-4-(pyridine-3-carbonyloxy)-phenyl]-4-oxo-4H-quinoline-1-carboxylic acid ethyl ester
5,6-Difluoro-4-oxo-2-[4-(pyridine-3-carbonyloxy)-phenyl]-4H-quinoline-1-carboxylic acid ethyl ester
5,8-Difluoro-4-oxo-2-[4-(pyridine-3-carbonyloxy)-phenyl]-4H-quinoline-1-carboxylic acid ethyl ester e) [5-Hydroxy-2-(4-oxo-1,4-dihydro-quinolin-2-yl)-phenyl]-carbamic acid ethyl ester

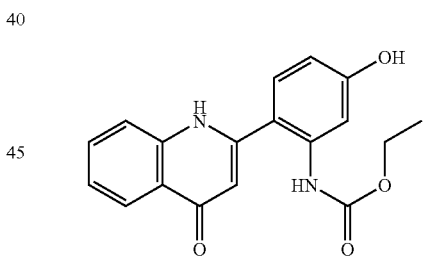

and its derivatives, including but not limited to:
[3,5-Dihydroxy-2-(4-oxo-1,4-dihydro-quinolin-2-yl)-phenyl]-carbamic acid ethyl ester
[4,5-Dihydroxy-2-(4-oxo-1,4-dihydro-quinolin-2-yl)-phenyl]-carbamic acid ethyl ester
[5-Hydroxy-2-(5-hydroxy-4-oxo-1,4-dihydro-quinolin-2-yl)-phenyl]-carbamic acid ethyl ester
[5-Hydroxy-2-(6-hydroxy-4-oxo-1,4-dihydro-quinolin-2-yl)-phenyl]-carbamic acid ethyl ester
[5-Hydroxy-2-(7-hydroxy-4-oxo-1,4-dihydro-quinolin-2-yl)-phenyl]-carbamic acid ethyl ester
[5-Hydroxy-2-(8-hydroxy-4-oxo-1,4-dihydro-quinolin-2-yl)-phenyl]-carbamic acid ethyl ester
[2-(5,7-Dihydroxy-4-oxo-1,4-dihydro-quinolin-2-yl)-5-hydroxy-phenyl]-carbamic acid ethyl ester
[2-(6,7-Dihydroxy-4-oxo-1,4-dihydro-quinolin-2-yl)-5-hydroxy-phenyl]-carbamic acid ethyl ester

[2-(7,8-Dihydroxy-4-oxo-1,4-dihydro-quinolin-2-yl)-5-hydroxy-phenyl]-carbamic acid ethyl ester
[3,5-Dihydroxy-2-(7-hydroxy-4-oxo-1,4-dihydro-quinolin-2-yl)-phenyl]-carbamic acid ethyl ester
[4,5-Dihydroxy-2-(7-hydroxy-4-oxo-1,4-dihydro-quinolin-2-yl)-phenyl]-carbamic acid ethyl ester
[2-(5,6-Dihydroxy-4-oxo-1,4-dihydro-quinolin-2-yl)-5-hydroxy-phenyl]-carbamic acid ethyl ester
[2-(5,8-Dihydroxy-4-oxo-1,4-dihydro-quinolin-2-yl)-5-hydroxy-phenyl]-carbamic acid ethyl ester
[3,5-Dihydroxy-2-(5-hydroxy-4-oxo-1,4-dihydro-quinolin-2-yl)-phenyl]-carbamic acid ethyl ester
[4,5-Dihydroxy-2-(5-hydroxy-4-oxo-1,4-dihydro-quinolin-2-yl)-phenyl]-carbamic acid ethyl ester
[3-Fluoro-5-hydroxy-2-(4-oxo-1,4-dihydro-quinolin-2-yl)-phenyl]-carbamic acid ethyl ester
[4-Fluoro-5-hydroxy-2-(4-oxo-1,4-dihydro-quinolin-2-yl)-phenyl]-carbamic acid ethyl ester
[2-(5-Fluoro-4-oxo-1,4-dihydro-quinolin-2-yl)-5-hydroxy-phenyl]-carbamic acid ethyl ester
[2-(6-Fluoro-4-oxo-1,4-dihydro-quinolin-2-yl)-5-hydroxy-phenyl]-carbamic acid ethyl ester
[2-(7-Fluoro-4-oxo-1,4-dihydro-quinolin-2-yl)-5-hydroxy-phenyl]-carbamic acid ethyl ester
[2-(8-Fluoro-4-oxo-1,4-dihydro-quinolin-2-yl)-5-hydroxy-phenyl]-carbamic acid ethyl ester
[2-(5,7-Difluoro-4-oxo-1,4-dihydro-quinolin-2-yl)-5-hydroxy-phenyl]-carbamic acid ethyl ester
[2-(6,7-Difluoro-4-oxo-1,4-dihydro-quinolin-2-yl)-5-hydroxy-phenyl]-carbamic acid ethyl ester
[2-(7,8-Difluoro-4-oxo-1,4-dihydro-quinolin-2-yl)-5-hydroxy-phenyl]-carbamic acid ethyl ester
[3-Fluoro-2-(7-fluoro-4-oxo-1,4-dihydro-quinolin-2-yl)-5-hydroxy-phenyl]-carbamic acid ethyl ester
[4-Fluoro-2-(7-fluoro-4-oxo-1,4-dihydro-quinolin-2-yl)-5-hydroxy-phenyl]-carbamic acid ethyl ester
[2-(5,6-Difluoro-4-oxo-1,4-dihydro-quinolin-2-yl)-5-hydroxy-phenyl]-carbamic acid ethyl ester
[2-(5,8-Difluoro-4-oxo-1,4-dihydro-quinolin-2-yl)-5-hydroxy-phenyl]-carbamic acid ethyl ester
[4-Fluoro-2-(7-fluoro-4-oxo-1,4-dihydro-quinolin-2-yl)-5-hydroxy-phenyl]-carbamic acid ethyl ester
[4-Fluoro-2-(5-fluoro-4-oxo-1,4-dihydro-quinolin-2-yl)-5-hydroxy-phenyl]-carbamic acid ethyl ester f) Nicotinic acid 3-ethoxycarbonylamino-4-(4-oxo-1,4-dihydro-quinolin-2-yl)-phenyl ester

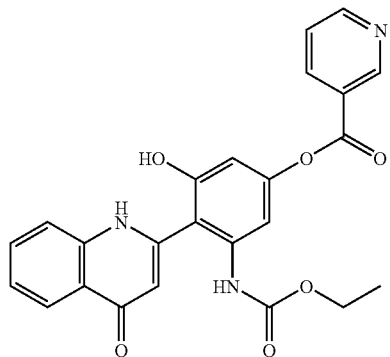

and its derivatives, including but not limited to:

Nicotinic acid 3-ethoxycarbonylamino-5-hydroxy-4-(4-oxo-1,4-dihydro-quinolin-2-yl)-phenyl ester
Nicotinic acid 5-ethoxycarbonylamino-2-hydroxy-4-(4-oxo-1,4-dihydro-quinolin-2-yl)-phenyl ester
Nicotinic acid 3-ethoxycarbonylamino-4-(5-hydroxy-4-oxo-1,4-dihydro-quinolin-2-yl)-phenyl ester
Nicotinic acid 3-ethoxycarbonylamino-4-(6-hydroxy-4-oxo-1,4-dihydro-quinolin-2-yl)-phenyl ester
Nicotinic acid 3-ethoxycarbonylamino-4-(7-hydroxy-4-oxo-1,4-dihydro-quinolin-2-yl)-phenyl ester
Nicotinic acid 3-ethoxycarbonylamino-4-(8-hydroxy-4-oxo-1,4-dihydro-quinolin-2-yl)-phenyl ester
Nicotinic acid 3-ethoxycarbonylamino-5-hydroxy-4-(7-hydroxy-4-oxo-1,4-dihydro-quinolin-2-yl)-phenyl ester
Nicotinic acid 5-ethoxycarbonylamino-2-hydroxy-4-(7-hydroxy-4-oxo-1,4-dihydro-quinolin-2-yl)-phenyl ester
Nicotinic acid 4-(5,7-dihydroxy-4-oxo-1,4-dihydro-quinolin-2-yl)-3-ethoxycarbonylamino-phenyl ester
Nicotinic acid 4-(6,7-dihydroxy-4-oxo-1,4-dihydro-quinolin-2-yl)-3-ethoxycarbonylamino-phenyl ester
Nicotinic acid 4-(7,8-dihydroxy-4-oxo-1,4-dihydro-quinolin-2-yl)-3-ethoxycarbonylamino-phenyl ester
Nicotinic acid 3-ethoxycarbonylamino-5-hydroxy-4-(5-hydroxy-4-oxo-1,4-dihydro-quinolin-2-yl)-phenyl ester
Nicotinic acid 5-ethoxycarbonylamino-2-hydroxy-4-(5-hydroxy-4-oxo-1,4-dihydro-quinolin-2-yl)-phenyl ester
Nicotinic acid 4-(5,6-dihydroxy-4-oxo-1,4-dihydro-quinolin-2-yl)-3-ethoxycarbonylamino-phenyl ester
Nicotinic acid 4-(5,8-dihydroxy-4-oxo-1,4-dihydro-quinolin-2-yl)-3-ethoxycarbonylamino-phenyl ester
Nicotinic acid 3-ethoxycarbonylamino-5-fluoro-4-(4-oxo-1,4-dihydro-quinolin-2-yl)-phenyl ester
Nicotinic acid 5-ethoxycarbonylamino-2-fluoro-4-(4-oxo-1,4-dihydro-quinolin-2-yl)-phenyl ester
Nicotinic acid 3-ethoxycarbonylamino-4-(5-fluoro-4-oxo-1,4-dihydro-quinolin-2-yl)-phenyl ester
Nicotinic acid 3-ethoxycarbonylamino-4-(6-fluoro-4-oxo-1,4-dihydro-quinolin-2-yl)-phenyl ester
Nicotinic acid 3-ethoxycarbonylamino-4-(7-fluoro-4-oxo-1,4-dihydro-quinolin-2-yl)-phenyl ester
Nicotinic acid 3-ethoxycarbonylamino-4-(8-fluoro-4-oxo-1,4-dihydro-quinolin-2-yl)-phenyl ester
Nicotinic acid 3-ethoxycarbonylamino-5-fluoro-4-(7-fluoro-4-oxo-1,4-dihydro-quinolin-2-yl)-phenyl ester
Nicotinic acid 5-ethoxycarbonylamino-2-fluoro-4-(7-fluoro-4-oxo-1,4-dihydro-quinolin-2-yl)-phenyl ester
Nicotinic acid 4-(5,7-difluoro-4-oxo-1,4-dihydro-quinolin-2-yl)-3-ethoxycarbonylamino-phenyl ester
Nicotinic acid 4-(6,7-difluoro-4-oxo-1,4-dihydro-quinolin-2-yl)-3-ethoxycarbonylamino-phenyl ester
Nicotinic acid 4-(7,8-difluoro-4-oxo-1,4-dihydro-quinolin-2-yl)-3-ethoxycarbonylamino-phenyl ester
Nicotinic acid 3-ethoxycarbonylamino-5-fluoro-4-(5-fluoro-4-oxo-1,4-dihydro-quinolin-2-yl)-phenyl ester
Nicotinic acid 5-ethoxycarbonylamino-2-fluoro-4-(5-fluoro-4-oxo-1,4-dihydro-quinolin-2-yl)-phenyl ester
Nicotinic acid 4-(5,6-difluoro-4-oxo-1,4-dihydro-quinolin-2-yl)-3-ethoxycarbonylamino-phenyl ester Nicotinic acid 4-(5,8-difluoro-4-oxo-1,4-dihydro-quinolin-2-yl)-3-ethoxycarbonylamino-phenyl ester g) 2-(2-Ethoxycarbonylamino-4-hydroxy-phenyl)-4-oxo-4H-quinoline-1-carboxylic acid ethyl ester

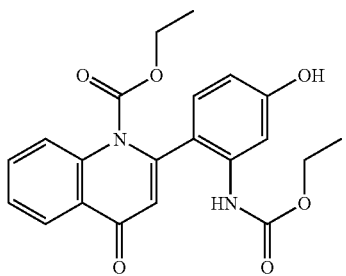

and its derivatives, including but not limited to:
2-(2-Ethoxycarbonylamino-4,5-dihydroxy-phenyl)-4-oxo-4H-quinoline-1-carboxylic acid ethyl ester
2-(2-Ethoxycarbonylamino-4-hydroxy-phenyl)-5-hydroxy-4-oxo-4H-quinoline-1-carboxylic acid ethyl ester
2-(2-Ethoxycarbonylamino-4-hydroxy-phenyl)-6-hydroxy-4-oxo-4H-quinoline-1-carboxylic acid ethyl ester
2-(2-Ethoxycarbonylamino-4-hydroxy-phenyl)-7-hydroxy-4-oxo-4H-quinoline-1-carboxylic acid ethyl ester
2-(2-Ethoxycarbonylamino-5-fluoro-4-hydroxy-phenyl)-4-oxo-4H-quinoline-1-carboxylic acid ethyl ester
2-(2-Ethoxycarbonylamino-4-hydroxy-phenyl)-5-fluoro-4-oxo-4H-quinoline-1-carboxylic acid ethyl ester
2-(2-Ethoxycarbonylamino-4-hydroxy-phenyl)-6-fluoro-4-oxo-4H-quinoline-1-carboxylic acid ethyl ester
2-(2-Ethoxycarbonylamino-4-hydroxy-phenyl)-7-fluoro-4-oxo-4H-quinoline-1-carboxylic acid ethyl ester
2-(2-Ethoxycarbonylamino-4-hydroxy-phenyl)-7-fluoro-4-oxo-4H-quinoline-1-carboxylic acid ethyl ester h) 2-[2-Ethoxycarbonylamino-4-(pyridine-3-carbonyloxy)-phenyl]-4-oxo-4H-quinoline-1-carboxylic acid ethyl ester

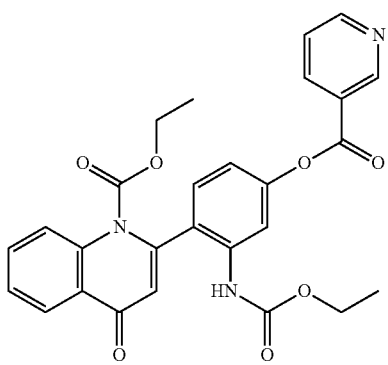

and its derivatives:
2-[2-Ethoxycarbonylamino-5-hydroxy-4-(pyridine-3-carbonyloxy)-phenyl]-4-oxo-4H-quinoline-1-carboxylic acid ethyl ester
2-[2-Ethoxycarbonylamino-4-(pyridine-3-carbonyloxy)-phenyl]-5-hydroxy-4-oxo-4H-quinoline-1-carboxylic acid ethyl ester
2-[2-Ethoxycarbonylamino-4-(pyridine-3-carbonyloxy)-phenyl]-6-hydroxy-4-oxo-4H-quinoline-1-carboxylic acid ethyl ester
2-[2-Ethoxycarbonylamino-4-(pyridine-3-carbonyloxy)-phenyl]-7-hydroxy-4-oxo-4H-quinoline-1-carboxylic acid ethyl ester
2-[2-Ethoxycarbonylamino-4-(pyridine-3-carbonyloxy)-phenyl]-8-hydroxy-4-oxo-4H-quinoline-1-carboxylic acid ethyl ester
2-[2-Ethoxycarbonylamino-5-hydroxy-4-(pyridine-3-carbonyloxy)-phenyl]-7-hydroxy-4-oxo-4H-quinoline-1-carboxylic acid ethyl ester
2-[2-Ethoxycarbonylamino-4-(pyridine-3-carbonyloxy)-phenyl]-5,7-dihydroxy-4-oxo-4H-quinoline-1-carboxylic acid ethyl ester
2-[2-Ethoxycarbonylamino-4-(pyridine-3-carbonyloxy)-phenyl]-6,7-dihydroxy-4-oxo-4H-quinoline-1-carboxylic acid ethyl ester
2-[2-Ethoxycarbonylamino-4-(pyridine-3-carbonyloxy)-phenyl]-7,8-dihydroxy-4-oxo-4H-quinoline-1-carboxylic acid ethyl ester
2-[2-Ethoxycarbonylamino-5-hydroxy-4-(pyridine-3-carbonyloxy)-phenyl]-5-hydroxy-4-oxo-4H-quinoline-1-carboxylic acid ethyl ester
2-[2-Ethoxycarbonylamino-4-(pyridine-3-carbonyloxy)-phenyl]-5,6-dihydroxy-4-oxo-4H-quinoline-1-carboxylic acid ethyl ester
2-[2-Ethoxycarbonylamino-4-(pyridine-3-carbonyloxy)-phenyl]-5,8-dihydroxy-4-oxo-4H-quinoline-1-carboxylic acid ethyl ester
2-[2-Ethoxycarbonylamino-5-fluoro-4-(pyridine-3-carbonyloxy)-phenyl]-4-oxo-4H-quinoline-1-carboxylic acid ethyl ester
2-[2-Ethoxycarbonylamino-4-(pyridine-3-carbonyloxy)-phenyl]-5-fluoro-4-oxo-4H-quinoline-1-carboxylic acid ethyl ester
2-[2-Ethoxycarbonylamino-4-(pyridine-3-carbonyloxy)-phenyl]-6-fluoro-4-oxo-4H-quinoline-1-carboxylic acid ethyl ester
2-[2-Ethoxycarbonylamino-4-(pyridine-3-carbonyloxy)-phenyl]-7-fluoro-4-oxo-4H-quinoline-1-carboxylic acid ethyl ester
2-[2-Ethoxycarbonylamino-4-(pyridine-3-carbonyloxy)-phenyl]-8-fluoro-4-oxo-4H-quinoline-1-carboxylic acid ethyl ester
2-[2-Ethoxycarbonylamino-5-fluoro-4-(pyridine-3-carbonyloxy)-phenyl]-7-fluoro-4-oxo-4H-quinoline-1-carboxylic acid ethyl ester
2-[2-Ethoxycarbonylamino-4-(pyridine-3-carbonyloxy)-phenyl]-5,7-difluoro-4-oxo-4H-quinoline-1-carboxylic acid ethyl ester
2-[2-Ethoxycarbonylamino-4-(pyridine-3-carbonyloxy)-phenyl]-6,7-difluoro-4-oxo-4H-quinoline-1-carboxylic acid ethyl ester
2-[2-Ethoxycarbonylamino-4-(pyridine-3-carbonyloxy)-phenyl]-7,8-difluoro-4-oxo-4H-quinoline-1-carboxylic acid ethyl ester
2-[2-Ethoxycarbonylamino-5-fluoro-4-(pyridine-3-carbonyloxy)-phenyl]-5-fluoro-4-oxo-4H-quinoline-1-carboxylic acid ethyl ester
2-[2-Ethoxycarbonylamino-4-(pyridine-3-carbonyloxy)-phenyl]-5,6-difluoro-4-oxo-4H-quinoline-1-carboxylic acid ethyl ester 2-[2-Ethoxycarbonylamino-4-(pyridine-3-carbonyloxy)-phenyl]-5,8-difluoro-4-oxo-4H-quinoline-1-carboxylic acid ethyl ester i) 2-(4-Hydroxy-phenyl)-pyrano[2,3-b]pyridin-4-one

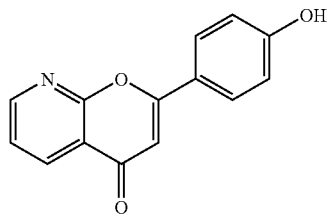

and its derivatives, including but not limited to:

2-(2,4-Dihydroxy-phenyl)-pyrano[2,3-b]pyridin-4-one
2-(3,4-Dihydroxy-phenyl)-pyrano[2,3-b]pyridin-4-one
5-Hydroxy-2-(4-hydroxy-phenyl)-pyrano[2,3-b]pyridin-4-one
6-Hydroxy-2-(4-hydroxy-phenyl)-pyrano[2,3-b]pyridin-4-one
7-Hydroxy-2-(4-hydroxy-phenyl)-pyrano[2,3-b]pyridin-4-one
Nicotinic acid 4-(4-oxo-4H-pyrano[2,3-b]pyridin-2-yl)-phenyl ester
Nicotinic acid 3-hydroxy-4-(4-oxo-4H-pyrano[2,3-b]pyridin-2-yl)-phenyl ester
Nicotinic acid 2-hydroxy-4-(4-oxo-4H-pyrano[2,3-b]pyridin-2-yl)-phenyl ester
Nicotinic acid 4-(5-hydroxy-4-oxo-4H-pyrano[2,3-b]pyridin-2-yl)-phenyl ester
Nicotinic acid 4-(6-hydroxy-4-oxo-4H-pyrano[2,3-b]pyridin-2-yl)-phenyl ester
Nicotinic acid 4-(7-hydroxy-4-oxo-4H-pyrano[2,3-b]pyridin-2-yl)-phenyl ester
[5-Hydroxy-2-(4-oxo-4H-pyrano[2,3-b]pyridin-2-yl)-phenyl]-carbamic acid ethyl ester
[3,5-Dihydroxy-2-(4-oxo-4H-pyrano[2,3-b]pyridin-2-yl)-phenyl]-carbamic acid ethyl ester
[4,5-Dihydroxy-2-(4-oxo-4H-pyrano[2,3-b]pyridin-2-yl)-phenyl]-carbamic acid ethyl ester
[5-Hydroxy-2-(5-hydroxy-4-oxo-4H-pyrano[2,3-b]pyridin-2-yl)-phenyl]-carbamic acid ethyl ester
[5-Hydroxy-2-(6-hydroxy-4-oxo-4H-pyrano[2,3-b]pyridin-2-yl)-phenyl]-carbamic acid ethyl ester
[5-Hydroxy-2-(7-hydroxy-4-oxo-4H-pyrano[2,3-b]pyridin-2-yl)-phenyl]-carbamic acid ethyl ester
Nicotinic acid 3-ethoxycarbonylamino-4-(4-oxo-4H-pyrano[2,3-b]pyridin-2-yl)-phenyl ester
Nicotinic acid 3-ethoxycarbonylamino-5-hydroxy-4-(4-oxo-4H-pyrano[2,3-b]pyridin-2-yl)-phenyl ester
Nicotinic acid 5-ethoxycarbonylamino-2-hydroxy-4-(4-oxo-4H-pyrano[2,3-b]pyridin-2-yl)-phenyl ester
Nicotinic acid 3-ethoxycarbonylamino-4-(5-hydroxy-4-oxo-4H-pyrano[2,3-b]pyridin-2-yl)-phenyl ester
Nicotinic acid 3-ethoxycarbonylamino-4-(6-hydroxy-4-oxo-4H-pyrano[2,3-b]pyridin-2-yl)-phenyl ester Nicotinic acid 3-ethoxycarbonylamino-4-(7-hydroxy-4-oxo-4H-pyrano[2,3-b]pyridin-2-yl)-phenyl ester j) 2-(4-Hydroxy-phenyl)-pyrano[2,3-c]pyridin-4-one

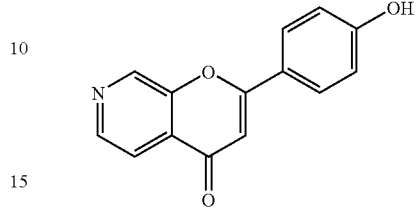

and its derivatives, including but not limited to:

2-(2,4-Dihydroxy-phenyl)-pyrano[2,3-c]pyridin-4-one
2-(3,4-Dihydroxy-phenyl)-pyrano[2,3-c]pyridin-4-one
5-Hydroxy-2-(4-hydroxy-phenyl)-pyrano[2,3-c]pyridin-4-one
6-Hydroxy-2-(4-hydroxy-phenyl)-pyrano[2,3-c]pyridin-4-one
8-Hydroxy-2-(4-hydroxy-phenyl)-pyrano[2,3-c]pyridin-4-one
Nicotinic acid 4-(4-oxo-4H-pyrano[2,3-c]pyridin-2-yl)-phenyl ester
Nicotinic acid 3-hydroxy-4-(4-oxo-4H-pyrano[2,3-c]pyridin-2-yl)-phenyl ester
Nicotinic acid 2-hydroxy-4-(4-oxo-4H-pyrano[2,3-c]pyridin-2-yl)-phenyl ester
Nicotinic acid 4-(5-hydroxy-4-oxo-4H-pyrano[2,3-c]pyridin-2-yl)-phenyl ester
Nicotinic acid 4-(6-hydroxy-4-oxo-4H-pyrano[2,3-c]pyridin-2-yl)-phenyl ester
Nicotinic acid 4-(8-hydroxy-4-oxo-4H-pyrano[2,3-c]pyridin-2-yl)-phenyl ester
[5-Hydroxy-2-(4-oxo-4H-pyrano[2,3-c]pyridin-2-yl)-phenyl]-carbamic acid ethyl ester
[3,5-Dihydroxy-2-(4-oxo-4H-pyrano[2,3-c]pyridin-2-yl)-phenyl]-carbamic acid ethyl ester
[4,5-Dihydroxy-2-(4-oxo-4H-pyrano[2,3-c]pyridin-2-yl)-phenyl]-carbamic acid ethyl ester
[5-Hydroxy-2-(5-hydroxy-4-oxo-4H-pyrano[2,3-c]pyridin-2-yl)-phenyl]-carbamic acid ethyl ester
[5-Hydroxy-2-(6-hydroxy-4-oxo-4H-pyrano[2,3-c]pyridin-2-yl)-phenyl]-carbamic acid ethyl ester
[5-Hydroxy-2-(8-hydroxy-4-oxo-4H-pyrano[2,3-c]pyridin-2-yl)-phenyl]-carbamic acid ethyl ester
Nicotinic acid 3-ethoxycarbonylamino-4-(4-oxo-4H-pyrano[2,3-c]pyridin-2-yl)-phenyl ester
Nicotinic acid 3-ethoxycarbonylamino-5-hydroxy-4-(4-oxo-4H-pyrano[2,3-c]pyridin-2-yl)-phenyl ester
Nicotinic acid 5-ethoxycarbonylamino-2-hydroxy-4-(4-oxo-4H-pyrano[2,3-c]pyridin-2-yl)-phenyl ester
Nicotinic acid 3-ethoxycarbonylamino-4-(5-hydroxy-4-oxo-4H-pyrano[2,3-c]pyridin-2-yl)-phenyl ester
Nicotinic acid 3-ethoxycarbonylamino-4-(6-hydroxy-4-oxo-4H-pyrano[2,3-c]pyridin-2-yl)-phenyl ester Nicotinic acid 3-ethoxycarbonylamino-4-(8-hydroxy-4-oxo-4H-pyrano[2,3-c]pyridin-2-yl)-phenyl ester k) 2-(4-Hydroxy-phenyl)-pyrano[3,2-c]pyridin-4-one

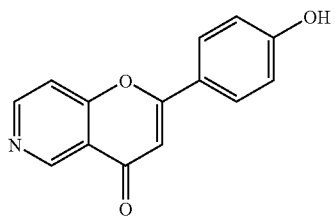

and its derivatives, including but not limited to:

2-(2,4-Dihydroxy-phenyl)-pyrano[3,2-c]pyridin-4-one
2-(3,4-Dihydroxy-phenyl)-pyrano[3,2-c]pyridin-4-one
5-Hydroxy-2-(4-hydroxy-phenyl)-pyrano[3,2-c]pyridin-4-one
7-Hydroxy-2-(4-hydroxy-phenyl)-pyrano[3,2-c]pyridin-4-one
8-Hydroxy-2-(4-hydroxy-phenyl)-pyrano[3,2-c]pyridin-4-one
Nicotinic acid 4-(4-oxo-4H-pyrano[3,2-c]pyridin-2-yl)-phenyl ester
Nicotinic acid 3-hydroxy-4-(4-oxo-4H-pyrano[3,2-c]pyridin-2-yl)-phenyl ester
Nicotinic acid 2-hydroxy-4-(4-oxo-4H-pyrano[3,2-c]pyridin-2-yl)-phenyl ester
Nicotinic acid 4-(5-hydroxy-4-oxo-4H-pyrano[3,2-c]pyridin-2-yl)-phenyl ester
Nicotinic acid 4-(7-hydroxy-4-oxo-4H-pyrano[3,2-c]pyridin-2-yl)-phenyl ester
Nicotinic acid 4-(8-hydroxy-4-oxo-4H-pyrano[3,2-c]pyridin-2-yl)-phenyl ester
[5-Hydroxy-2-(4-oxo-4H-pyrano[3,2-c]pyridin-2-yl)-phenyl]-carbamic acid ethyl ester
[3,5-Dihydroxy-2-(4-oxo-4H-pyrano[3,2-c]pyridin-2-yl)-phenyl]-carbamic acid ethyl ester
[4,5-Dihydroxy-2-(4-oxo-4H-pyrano[3,2-c]pyridin-2-yl)-phenyl]-carbamic acid ethyl ester
[5-Hydroxy-2-(5-hydroxy-4-oxo-4H-pyrano3,2-c]pyridin-2-yl)-phenyl]-carbamic acid ethyl ester
[5-Hydroxy-2-(7-hydroxy-4-oxo-4H-pyrano[3,2-c]pyridin-2-yl)-phenyl]-carbamic acid ethyl ester
[5-Hydroxy-2-(8-hydroxy-4-oxo-4H-pyrano[3,2-c]pyridin-2-yl)-phenyl]-carbamic acid ethyl ester
Nicotinic acid 3-ethoxycarbonylamino-4-(4-oxo-4H-pyrano[3,2-c]pyridin-2-yl)-phenyl ester
Nicotinic acid 3-ethoxycarbonylamino-5-hydroxy-4-(4-oxo-4H-pyrano[3,2-c]pyridin-2-yl)-phenyl ester
Nicotinic acid 5-ethoxycarbonylamino-2-hydroxy-4-(4-oxo-4H-pyrano3,2-c]pyridin-2-yl)-phenyl ester
Nicotinic acid 3-ethoxycarbonylamino-4-(5-hydroxy-4-oxo-4H-pyrano[3,2-c]pyridin-2-yl)-phenyl ester
Nicotinic acid 3-ethoxycarbonylamino-4-(7-hydroxy-4-oxo-4H-pyrano[3,2-c]pyridin-2-yl)-phenyl ester Nicotinic acid 3-ethoxycarbonylamino-4-(8-hydroxy-4-oxo-4H-pyrano[3,2-c]pyridin-2-yl)-phenyl ester l) 2-(4-Hydroxy-phenyl)-pyrano[3,2-b]pyridin-4-one

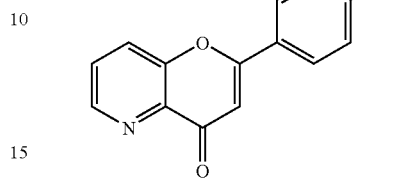

and its derivatives, inclduing but not limited to:

2-(2,4-Dihydroxy-phenyl)-pyrano[3,2-b]pyridin-4-one
2-(3,4-Dihydroxy-phenyl)-pyrano[3,2-b]pyridin-4-one
6-Hydroxy-2-(4-hydroxy-phenyl)-pyrano[3,2-b]pyridin-4-one
7-Hydroxy-2-(4-hydroxy-phenyl)-pyrano[3,2-b]pyridin-4-one
8-Hydroxy-2-(4-hydroxy-phenyl)-pyrano[3,2-b]pyridin-4-one
Nicotinic acid 4-(4-oxo-4H-pyrano[3,2-b]pyridin-2-yl)-phenyl ester
Nicotinic acid 3-hydroxy-4-(4-oxo-4H-pyrano[3,2-b]pyridin-2-yl)-phenyl ester
Nicotinic acid 2-hydroxy-4-(4-oxo-4H-pyrano[3,2-b]pyridin-2-yl)-phenyl ester
Nicotinic acid 4-(6-hydroxy-4-oxo-4H-pyrano[3,2-b]pyridin-2-yl)-phenyl ester
Nicotinic acid 4-(7-hydroxy-4-oxo-4H-pyrano[3,2-b]pyridin-2-yl)-phenyl ester
Nicotinic acid 4-(8-hydroxy-4-oxo-4H-pyrano[3,2-b]pyridin-2-yl)-phenyl ester
[5-Hydroxy-2-(4-oxo-4H-pyrano[3,2-b]pyridin-2-yl)-phenyl]-carbamic acid ethyl ester
[3,5-Dihydroxy-2-(4-oxo-4H-pyrano[3,2-b]pyridin-2-yl)-phenyl]-carbamic acid ethyl ester
[4,5-Dihydroxy-2-(4-oxo-4H-pyrano[3,2-b]pyridin-2-yl)-phenyl]-carbamic acid ethyl ester
[5-Hydroxy-2-(6-hydroxy-4-oxo-4H-pyrano[3,2-b]pyridin-2-yl)-phenyl]-carbamic acid ethyl ester
[5-Hydroxy-2-(7-hydroxy-4-oxo-4H-pyrano[3,2-b]pyridin-2-yl)-phenyl]-carbamic acid ethyl ester
[5-Hydroxy-2-(8-hydroxy-4-oxo-4H-pyrano[3,2-b]pyridin-2-yl)-phenyl]-carbamic acid ethyl ester
Nicotinic acid 3-ethoxycarbonylamino-4-(4-oxo-4H-pyrano[3,2-b]pyridin-2-yl)-phenyl ester
Nicotinic acid 3-ethoxycarbonylamino-5-hydroxy-4-(4-oxo-4H-pyrano[3,2-b]pyridin-2-yl)-phenyl ester
Nicotinic acid 5-ethoxycarbonylamino-2-hydroxy-4-(4-oxo-4H-pyrano[3,2-b]pyridin-2-yl)-phenyl ester
Nicotinic acid 3-ethoxycarbonylamino-4-(6-hydroxy-4-oxo-4H-pyrano[3,2-b]pyridin-2-yl)-phenyl ester
Nicotinic acid 3-ethoxycarbonylamino-4-(7-hydroxy-4-oxo-4H-pyrano[3,2-b]pyridin-2-yl)-phenyl ester Nicotinic acid 3-ethoxycarbonylamino-4-(8-hydroxy-4-oxo-4H-pyrano[3,2-b]pyridin-2-yl)-phenyl ester m) 2-(5-Hydroxy-pyridin-2-yl)-chromen-4-one

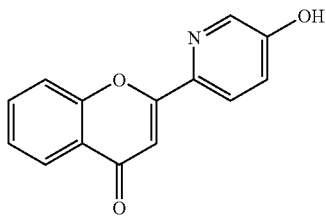

and its derivatives, including but not limited to:
2-(5,6-Dihydroxy-pyridin-2-yl)-chromen-4-one
2-(3,5-Dihydroxy-pyridin-2-yl)-chromen-4-one
2-(4,5-Dihydroxy-pyridin-2-yl)-5-hydroxy-chromen-4-one
5-Hydroxy-2-(5-hydroxy-pyridin-2-yl)-chromen-4-one
6-Hydroxy-2-(5-hydroxy-pyridin-2-yl)-chromen-4-one
7-Hydroxy-2-(5-hydroxy-pyridin-2-yl)-chromen-4-one
8-Hydroxy-2-(5-hydroxy-pyridin-2-yl)-chromen-4-one
Nicotinic acid 6-(4-oxo-4H-chromen-2-yl)-pyridin-3-yl ester
Nicotinic acid 2-hydroxy-6-(4-oxo-4H-chromen-2-yl)-pyridin-3-yl ester
Nicotinic acid 5-hydroxy-6-(4-oxo-4H-chromen-2-yl)-pyridin-3-yl ester
Nicotinic acid 4-hydroxy-6-(4-oxo-4H-chromen-2-yl)-pyridin-3-yl ester
Nicotinic acid 6-(5-hydroxy-4-oxo-4H-chromen-2-yl)-pyridin-3-yl ester
Nicotinic acid 6-(6-hydroxy-4-oxo-4H-chromen-2-yl)-pyridin-3-yl ester
Nicotinic acid 6-(7-hydroxy-4-oxo-4H-chromen-2-yl)-pyridin-3-yl ester
Nicotinic acid 6-(8-hydroxy-4-oxo-4H-chromen-2-yl)-pyridin-3-yl ester
[5-Hydroxy-2-(4-oxo-4H-chromen-2-yl)-pyridin-3-yl]-carbamic acid ethyl ester
[5,6-Dihydroxy-2-(4-oxo-4H-chromen-2-yl)-pyridin-3-yl]-carbamic acid ethyl ester
[5-Hydroxy-2-(5-hydroxy-4-oxo-4H-chromen-2-yl)-pyridin-3-yl]-carbamic acid ethyl ester
[5-Hydroxy-2-(6-hydroxy-4-oxo-4H-chromen-2-yl)-pyridin-3-yl]-carbamic acid ethyl ester
[5-Hydroxy-2-(7-hydroxy-4-oxo-4H-chromen-2-yl)-pyridin-3-yl]-carbamic acid ethyl ester
[5-Hydroxy-2-(8-hydroxy-4-oxo-4H-chromen-2-yl)-pyridin-3-yl]-carbamic acid ethyl ester
Nicotinic acid 5-ethoxycarbonylamino-6-(4-oxo-4H-chromen-2-yl)-pyridin-3-yl ester
Nicotinic acid 5-ethoxycarbonylamino-2-hydroxy-6-(4-oxo-4H-chromen-2-yl)-pyridin-3-yl ester
Nicotinic acid 5-ethoxycarbonylamino-6-(5-hydroxy-4-oxo-4H-chromen-2-yl)-pyridin-3-yl ester
Nicotinic acid 5-ethoxycarbonylamino-6-(6-hydroxy-4-oxo-4H-chromen-2-yl)-pyridin-3-yl ester
Nicotinic acid 5-ethoxycarbonylamino-6-(7-hydroxy-4-oxo-4H-chromen-2-yl)-pyridin-3-yl ester Nicotinic acid 5-ethoxycarbonylamino-6-(8-hydroxy-4-oxo-4H-chromen-2-yl)-pyridin-3-yl ester n) 2-(6-Hydroxy-pyridin-3-yl)-chromen-4-one

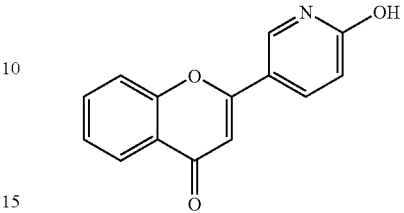

and its derivatives, including but not limited to:
2-(2,6-Dihydroxy-pyridin-3-yl)-chromen-4-one
5-Hydroxy-2-(6-hydroxy-pyridin-3-yl)-chromen-4-one
6-Hydroxy-2-(6-hydroxy-pyridin-3-yl)-chromen-4-one
7-Hydroxy-2-(6-hydroxy-pyridin-3-yl)-chromen-4-one
8-Hydroxy-2-(6-hydroxy-pyridin-3-yl)-chromen-4-one
Nicotinic acid 5-(4-oxo-4H-chromen-2-yl)-pyridin-2-yl ester
Nicotinic acid 4-hydroxy-5-(4-oxo-4H-chromen-2-yl)-pyridin-2-yl ester
Nicotinic acid 6-hydroxy-5-(4-oxo-4H-chromen-2-yl)-pyridin-2-yl ester
Nicotinic acid 5-(5-hydroxy-4-oxo-4H-chromen-2-yl)-pyridin-2-yl ester
Nicotinic acid 5-(6-hydroxy-4-oxo-4H-chromen-2-yl)-pyridin-2-yl ester
Nicotinic acid 5-(7-hydroxy-4-oxo-4H-chromen-2-yl)-pyridin-2-yl ester
Nicotinic acid 5-(8-hydroxy-4-oxo-4H-chromen-2-yl)-pyridin-2-yl ester
[6-Hydroxy-3-(4-oxo-4H-chromen-2-yl)-pyridin-2-yl]-carbamic acid ethyl ester
[4,6-Dihydroxy-3-(4-oxo-4H-chromen-2-yl)-pyridin-2-yl]-carbamic acid ethyl ester
[6-Hydroxy-3-(5-hydroxy-4-oxo-4H-chromen-2-yl)-pyridin-2-yl]-carbamic acid ethyl ester
[6-Hydroxy-3-(6-hydroxy-4-oxo-4H-chromen-2-yl)-pyridin-2-yl]-carbamic acid ethyl ester
[6-Hydroxy-3-(7-hydroxy-4-oxo-4H-chromen-2-yl)-pyridin-2-yl]-carbamic acid ethyl ester
[6-Hydroxy-3-(8-hydroxy-4-oxo-4H-chromen-2-yl)-pyridin-2-yl]-carbamic acid ethyl ester
[2-Hydroxy-5-(4-oxo-4H-chromen-2-yl)-pyridin-4-yl]-carbamic acid ethyl ester
[2,6-Dihydroxy-3-(4-oxo-4H-chromen-2-yl)-pyridin-4-yl]-carbamic acid ethyl ester
[2-Hydroxy-5-(5-hydroxy-4-oxo-4H-chromen-2-yl)-pyridin-4-yl]-carbamic acid ethyl ester
[2-Hydroxy-5-(6-hydroxy-4-oxo-4H-chromen-2-yl)-pyridin-4-yl]-carbamic acid ethyl ester
[2-Hydroxy-5-(7-hydroxy-4-oxo-4H-chromen-2-yl)-pyridin-4-yl]-carbamic acid ethyl ester
[2-Hydroxy-5-(8-hydroxy-4-oxo-4H-chromen-2-yl)-pyridin-4-yl]-carbamic acid ethyl ester
Nicotinic acid 4-ethoxycarbonylamino-5-(4-oxo-4H-chromen-2-yl)-pyridin-2-yl ester
Nicotinic acid 4-ethoxycarbonylamino-6-hydroxy-5-(4-oxo-4H-chromen-2-yl)-pyridin-2-yl ester
Nicotinic acid 4-ethoxycarbonylamino-5-(5-hydroxy-4-oxo-4H-chromen-2-yl)-pyridin-2-yl ester Nicotinic acid 4-ethoxycarbonylamino-5-(6-hydroxy-4-oxo-4H-chromen-2-yl)-pyridin-2-yl ester
Nicotinic acid 4-ethoxycarbonylamino-5-(7-hydroxy-4-oxo-4H-chromen-2-yl)-pyridin-2-yl ester
Nicotinic acid 4-ethoxycarbonylamino-5-(8-hydroxy-4-oxo-4H-chromen-2-yl)-pyridin-2-yl ester
Nicotinic acid 6-ethoxycarbonylamino-5-(4-oxo-4H-chromen-2-yl)-pyridin-2-yl ester
Nicotinic acid 6-ethoxycarbonylamino-4-hydroxy-5-(4-oxo-4H-chromen-2-yl)-pyridin-2-yl ester
Nicotinic acid 6-ethoxycarbonylamino-5-(5-hydroxy-4-oxo-4H-chromen-2-yl)-pyridin-2-yl ester
Nicotinic acid 6-ethoxycarbonylamino-5-(6-hydroxy-4-oxo-4H-chromen-2-yl)-pyridin-2-yl ester
Nicotinic acid 6-ethoxycarbonylamino-5-(7-hydroxy-4-oxo-4H-chromen-2-yl)-pyridin-2-yl ester
Nicotinic acid 6-ethoxycarbonylamino-5-(8-hydroxy-4-oxo-4H-chromen-2-yl)-pyridin-2-yl ester o) 2-(4-Hydroxy-phenyl)-benzo[e][1,3]oxazin-4-one

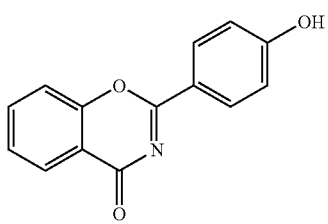

and its derivatives, including but limited to:
2-(2,4-Dihydroxy-phenyl)-benzo[e][1,3]oxazin-4-one
2-(3,4-Dihydroxy-phenyl)-benzo[e][1,3]oxazin-4-one
5-Hydroxy-2-(4-hydroxy-phenyl)-benzo[e][1,3]oxazin-4-one
6-Hydroxy-2-(4-hydroxy-phenyl)-benzo[e][1,3]oxazin-4-one
7-Hydroxy-2-(4-hydroxy-phenyl)-benzo[e][1,3]oxazin-4-one
8-Hydroxy-2-(4-hydroxy-phenyl)-benzo[e][1,3]oxazin-4-one
Nicotinic acid 4-(4-oxo-4H-benzo[e][1,3]oxazin-2-yl)-phenyl ester
Nicotinic acid 3-hydroxy-4-(4-oxo-4H-benzo[e][1,3]oxazin-2-yl)-phenyl ester
Nicotinic acid 2-hydroxy-4-(4-oxo-4H-benzo[e][1,3]oxazin-2-yl)-phenyl ester
Nicotinic acid 4-(5-hydroxy-4-oxo-4H-benzo[e][1,3]oxazin-2-yl)-phenyl ester
Nicotinic acid 4-(6-hydroxy-4-oxo-4H-benzo[e][1,3]oxazin-2-yl)-phenyl ester
Nicotinic acid 4-(7-hydroxy-4-oxo-4H-benzo[e][1,3]oxazin-2-yl)-phenyl ester
Nicotinic acid 4-(8-hydroxy-4-oxo-4H-benzo[e][1,3]oxazin-2-yl)-phenyl ester
[5-Hydroxy-2-(4-oxo-4H-benzo[e][1,3]oxazin-2-yl)-phenyl]-carbamic acid ethyl ester
[3,5-Dihydroxy-2-(4-oxo-4H-benzo[e][1,3]oxazin-2-yl)-phenyl]-carbamic acid ethyl ester
[4,5-Dihydroxy-2-(4-oxo-4H-benzo[e][1,3]oxazin-2-yl)-phenyl]-carbamic acid ethyl ester
[5-Hydroxy-2-(5-hydroxy-4-oxo-4H-benzo[e][1,3]oxazin-2-yl)-phenyl]-carbamic acid ethyl ester
[5-Hydroxy-2-(6-hydroxy-4-oxo-4H-benzo[e][1,3]oxazin-2-yl)-phenyl]-carbamic acid ethyl ester
[5-Hydroxy-2-(7-hydroxy-4-oxo-4H-benzo[e][1,3]oxazin-2-yl)-phenyl]-carbamic acid ethyl ester
[5-Hydroxy-2-(8-hydroxy-4-oxo-4H-benzo[e][1,3]oxazin-2-yl)-phenyl]-carbamic acid ethyl ester
Nicotinic acid 3-ethoxycarbonylamino-4-(4-oxo-4H-benzo[e][1,3]oxazin-2-yl)-phenyl ester
Nicotinic acid 3-ethoxycarbonylamino-4-(4-oxo-4H-benzo[e][1,3]oxazin-2-yl)-phenyl ester
Nicotinic acid 5-ethoxycarbonylamino-2-hydroxy-4-(4-oxo-4H-benzo[e][1,3]oxazin-2-yl)-phenyl ester
Nicotinic acid 3-ethoxycarbonylamino-4-(5-hydroxy-4-oxo-4H-benzo[e][1,3]oxazin-2-yl)-phenyl ester
Nicotinic acid 3-ethoxycarbonylamino-4-(6-hydroxy-4-oxo-4H-benzo[e][1,3]oxazin-2-yl)-phenyl ester
Nicotinic acid 3-ethoxycarbonylamino-4-(7-hydroxy-4-oxo-4H-benzo[e][1,3]oxazin-2-yl)-phenyl ester
Nicotinic acid 3-ethoxycarbonylamino-4-(8-hydroxy-4-oxo-4H-benzo[e][1,3]oxazin-2-yl)-phenyl ester p) 7-(4-Hydroxy-phenyl)-pyrano[2,3-d]pyrimidin-5-one

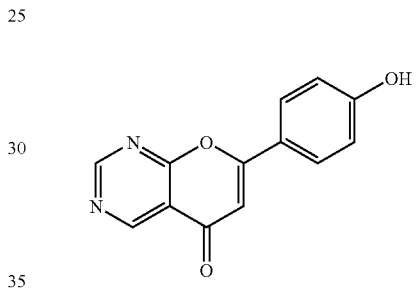

and its derivatives, including but not limited to:
7-(2,4-Dihydroxy-phenyl)-pyrano[2,3-d]pyrimidin-5-one
7-(3,4-Dihydroxy-phenyl)-pyrano[2,3-d]pyrimidin-5-one
4-Hydroxy-7-(4-hydroxy-phenyl)-pyrano[2,3-d]pyrimidin-5-one
2-Hydroxy-7-(4-hydroxy-phenyl)-pyrano[2,3-d]pyrimidin-5-one
Nicotinic acid 4-(5-oxo-5H-pyrano[2,3-d]pyrimidin-7-yl)-phenyl ester
Nicotinic acid 3-hydroxy-4-(5-oxo-5H-pyrano[2,3-d]pyrimidin-7-yl)-phenyl ester
Nicotinic acid 2-hydroxy-4-(5-oxo-5H-pyrano[2,3-d]pyrimidin-7-yl)-phenyl ester
Nicotinic acid 4-(4-hydroxy-5-oxo-5H-pyrano[2,3-d]pyrimidin-7-yl)-phenyl ester
Nicotinic acid 4-(2-hydroxy-5-oxo-5H-pyrano[2,3-d]pyrimidin-7-yl)-phenyl ester
[5-Hydroxy-2-(5-oxo-5H-pyrano[2,3-d]pyrimidin-7-yl)-phenyl]-carbamic acid ethyl ester
[3,5-Dihydroxy-2-(5-oxo-5H-pyrano[2,3-d]pyrimidin-7-yl)-phenyl]-carbamic acid ethyl ester
[4,5-Dihydroxy-2-(5-oxo-5H-pyrano[2,3-d]pyrimidin-7-yl)-phenyl]-carbamic acid ethyl ester
[5-Hydroxy-2-(4-hydroxy-5-oxo-5H-pyrano[2,3-d]pyrimidin-7-yl)-phenyl]-carbamic acid ethyl ester
[5-Hydroxy-2-(2-hydroxy-5-oxo-5H-pyrano[2,3-d]pyrimidin-7-yl)-phenyl]-carbamic acid ethyl ester
Nicotinic acid 3-ethoxycarbonylamino-4-(5-oxo-5H-pyrano[2,3-d]pyrimidin-7-yl)-phenyl ester
Nicotinic acid 3-ethoxycarbonylamino-5-hydroxy-4-(5-oxo-5H-pyrano[2,3-d]pyrimidin-7-yl)-phenyl ester Nicotinic acid 5-ethoxycarbonylamino-2-hydroxy-4-(5-oxo-5H-pyrano[2,3-d]pyrimidin-7-yl)-phenyl ester Nicotinic acid 3-ethoxycarbonylamino-4-(4-hydroxy-5-oxo-5H-pyrano[2,3-d]pyrimidin-7-yl)-phenyl ester Nicotinic acid 3-ethoxycarbonylamino-4-(2-hydroxy-5-oxo-5H-pyrano[2,3-d]pyrimidin-7-yl)-phenyl ester q) 6-(4-Hydroxy-phenyl)-pyrano[3,2-d]pyrimidin-8-one and its derivatives, including but not limited to:

6-(2,4-Dihydroxy-phenyl)-pyrano[3,2-d]pyrimidin-8-one 6-(3,4-Dihydroxy-phenyl)-pyrano[3,2-d]pyrimidin-8-one 2-Hydroxy-6-(4-hydroxy-phenyl)-pyrano[3,2-d]pyrimidin-8-one 4-Hydroxy-6-(4-hydroxy-phenyl)-pyrano[3,2-d]pyrimidin-8-one Nicotinic acid 4-(8-oxo-8H-pyrano[3,2-d]pyrimidin-6-yl)-phenyl ester Nicotinic acid 3-hydroxy-4-(8-oxo-8H-pyrano[3,2-d]pyrimidin-6-yl)-phenyl ester Nicotinic acid 2-hydroxy-4-(8-oxo-8H-pyrano[3,2-d]pyrimidin-6-yl)-phenyl ester Nicotinic acid 4-(2-hydroxy-8-oxo-8H-pyrano[3,2-d]pyrimidin-6-yl)-phenyl ester Nicotinic acid 4-(2-hydroxy-8-oxo-8H-pyrano[3,2-d]pyrimidin-6-yl)-phenyl ester

[5-Hydroxy-2-(8-oxo-8H-pyrano[3,2-d]pyrimidin-6-yl)-phenyl]-carbamic acid ethyl ester

[3,5-Dihydroxy-2-(8-oxo-8H-pyrano[3,2-d]pyrimidin-6-yl)-phenyl]-carbamic acid ethyl ester

[4,5-Dihydroxy-2-(8-oxo-8H-pyrano[3,2-d]pyrimidin-6-yl)-phenyl]-carbamic acid ethyl ester

[5-Hydroxy-2-(2-hydroxy-8-oxo-8H-pyrano[3,2-d]pyrimidin-6-yl)-phenyl]-carbamic acid ethyl ester

[5-Hydroxy-2-(4-hydroxy-8-oxo-8H-pyrano[3,2-d]pyrimidin-6-yl)-phenyl]-carbamic acid ethyl ester Nicotinic acid 3-ethoxycarbonylamino-4-(8-oxo-8H-pyrano[3,2-d]pyrimidin-6-yl)-phenyl ester Nicotinic acid 3-ethoxycarbonylamino-5-hydroxy-4-(8-oxo-8H-pyrano[3,2-d]pyrimidin-6-yl)-phenyl ester Nicotinic acid 5-ethoxycarbonylamino-2-hydroxy-4-(8-oxo-8H-pyrano[3,2-d]pyrimidin-6-yl)-phenyl ester Nicotinic acid 3-ethoxycarbonylamino-4-(2-hydroxy-8-oxo-8H-pyrano[3,2-d]pyrimidin-6-yl)-phenyl ester Nicotinic acid 3-ethoxycarbonylamino-4-(4-hydroxy-8-oxo-8H-pyrano[3,2-d]pyrimidin-6-yl)-phenyl ester r) 6-(4-Hydroxy-phenyl)-pyrano[2,3-b]pyrazin-8-one and its derivatives, including, but not limited to:

6-(2,4-Dihydroxy-phenyl)-pyrano[2,3-b]pyrazin-8-one 6-(3,4-Dihydroxy-phenyl)-pyrano[2,3-b]pyrazin-8-one 2-Hydroxy-6-(4-hydroxy-phenyl)-pyrano[2,3-b]pyrazin-8-one 3-Hydroxy-6-(4-hydroxy-phenyl)-pyrano[2,3-b]pyrazin-8-one Nicotinic acid 4-(8-oxo-8H-pyrano[2,3-b]pyrazin-6-yl)-phenyl ester Nicotinic acid 3-hydroxy-4-(8-oxo-8H-pyrano[2,3-b]pyrazin-6-yl)-phenyl ester Nicotinic acid 2-hydroxy-4-(8-oxo-8H-pyrano[2,3-b]pyrazin-6-yl)-phenyl ester Nicotinic acid 4-(2-hydroxy-8-oxo-8H-pyrano[2,3-b]pyrazin-6-yl)-phenyl ester Nicotinic acid 4-(3-hydroxy-8-oxo-8H-pyrano[2,3-b]pyrazin-6-yl)-phenyl ester

[5-Hydroxy-2-(8-oxo-8H-pyrano[2,3-b]pyrazin-6-yl)-phenyl]-carbamic acid ethyl ester

[3,5-Dihydroxy-2-(8-oxo-8H-pyrano[2,3-b]pyrazin-6-yl)-phenyl]-carbamic acid ethyl ester

[4,5-Dihydroxy-2-(8-oxo-8H-pyrano[2,3-b]pyrazin-6-yl)-phenyl]-carbamic acid ethyl ester

[5-Hydroxy-2-(2-hydroxy-8-oxo-8H-pyrano[2,3-b]pyrazin-6-yl)-phenyl]-carbamic acid ethyl ester

[5-Hydroxy-2-(3-hydroxy-8-oxo-8H-pyrano[2,3-b]pyrazin-6-yl)-phenyl]-carbamic acid ethyl ester Nicotinic acid 3-ethoxycarbonylamino-4-(8-oxo-8H-pyrano[2,3-b]pyrazin-6-yl)-phenyl ester Nicotinic acid 3-ethoxycarbonylamino-5-hydroxy-4-(8-oxo-8H-pyrano[2,3-b]pyrazin-6-yl)-phenyl ester Nicotinic acid 5-ethoxycarbonylamino-2-hydroxy-4-(8-oxo-8H-pyrano[2,3-b]pyrazin-6-yl)-phenyl ester Nicotinic acid 3-ethoxycarbonylamino-4-(2-hydroxy-8-oxo-8H-pyrano[2,3-b]pyrazin-6-yl)-phenyl ester Nicotinic acid 3-ethoxycarbonylamino-4-(3-hydroxy-8-oxo-8H-pyrano[2,3-b]pyrazin-6-yl)-phenyl ester s) [5-Hydroxy-2-(4-oxo-4H-chromen-2-yl)-phenyl]-carbamic acid ethyl ester

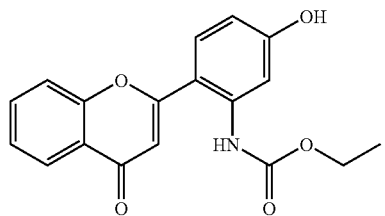

and its derivatives, including but not limited to:
[3,5-Dihydroxy-2-(4-oxo-4H-chromen-2-yl)-phenyl]-carbamic acid ethyl ester
[4,5-Dihydroxy-2-(4-oxo-4H-chromen-2-yl)-phenyl]-carbamic acid ethyl ester
[5-Hydroxy-2-(5-hydroxy-4-oxo-4H-chromen-2-yl)-phenyl]-carbamic acid ethyl ester
[5-Hydroxy-2-(6-hydroxy-4-oxo-4H-chromen-2-yl)-phenyl]-carbamic acid ethyl ester
[5-Hydroxy-2-(7-hydroxy-4-oxo-4H-chromen-2-yl)-phenyl]-carbamic acid ethyl ester
[5-Hydroxy-2-(8-hydroxy-4-oxo-4H-chromen-2-yl)-phenyl]-carbamic acid ethyl ester
[5-Hydroxy-2-(5,6-dihydroxy-4-oxo-4H-chromen-2-yl)-phenyl]-carbamic acid ethyl ester
[5-Hydroxy-2-(5,7-dihydroxy-4-oxo-4H-chromen-2-yl)-phenyl]-carbamic acid ethyl ester
[5-Hydroxy-2-(5,8-dihydroxy-4-oxo-4H-chromen-2-yl)-phenyl]-carbamic acid ethyl ester
[5-Hydroxy-2-(6,7-dihydroxy-4-oxo-4H-chromen-2-yl)-phenyl]-carbamic acid ethyl ester
[5-Hydroxy-2-(6,8-dihydroxy-4-oxo-4H-chromen-2-yl)-phenyl]-carbamic acid ethyl ester
[5-Hydroxy-2-(5,8-dihydroxy-4-oxo-4H-chromen-2-yl)-phenyl]-carbamic acid ethyl ester t) Carbonic acid ethyl ester 5-hydroxy-2-(4-oxo-4H-chromen-2-yl)-phenyl ester

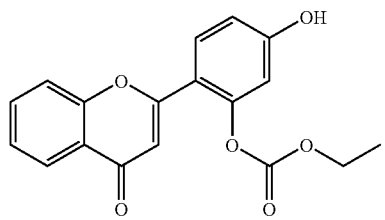

and its derivatives, including but not limited to:
Carbonic acid 3,5-dihydroxy-2-(4-oxo-4H-chromen-2-yl)-phenyl ester ethyl ester
Carbonic acid 4,5-dihydroxy-2-(4-oxo-4H-chromen-2-yl)-phenyl ester ethyl ester
Carbonic acid ethyl ester 5-hydroxy-2-(5-hydroxy-4-oxo-4H-chromen-2-yl)-phenyl ester
Carbonic acid ethyl ester 5-hydroxy-2-(6-hydroxy-4-oxo-4H-chromen-2-yl)-phenyl ester
Carbonic acid ethyl ester 5-hydroxy-2-(7-hydroxy-4-oxo-4H-chromen-2-yl)-phenyl ester
Carbonic acid ethyl ester 5-hydroxy-2-(8-hydroxy-4-oxo-4H-chromen-2-yl)-phenyl ester
Carbonic acid ethyl ester 5-hydroxy-2-(5,6-dihydroxy-4-oxo-4H-chromen-2-yl)-phenyl ester
Carbonic acid ethyl ester 5-hydroxy-2-(5,7-dihydroxy-4-oxo-4H-chromen-2-yl)-phenyl ester
Carbonic acid ethyl ester 5-hydroxy-2-(5,8-dihydroxy-4-oxo-4H-chromen-2-yl)-phenyl ester
Carbonic acid ethyl ester 5-hydroxy-2-(6,7-dihydroxy-4-oxo-4H-chromen-2-yl)-phenyl ester
Carbonic acid ethyl ester 5-hydroxy-2-(6,8-dihydroxy-4-oxo-4H-chromen-2-yl)-phenyl ester
Carbonic acid ethyl ester 5-hydroxy-2-(7,8-dihydroxy-4-oxo-4H-chromen-2-yl)-phenyl ester u) [5-Hydroxy-2-(4-oxo-4H-chromen-2-yl)-phenyl]-acetic acid ethyl ester

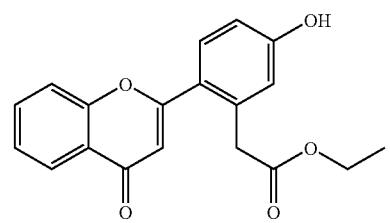

and its derivatives, including but not limited to:
[3,5-Dihydroxy-2-(4-oxo-4H-chromen-2-yl)-phenyl]-acetic acid ethyl ester
[4,5-Dihydroxy-2-(4-oxo-4H-chromen-2-yl)-phenyl]-acetic acid ethyl ester
[5-Hydroxy-2-(5-hydroxy-4-oxo-4H-chromen-2-yl)-phenyl]-acetic acid ethyl ester
[5-Hydroxy-2-(6-hydroxy-4-oxo-4H-chromen-2-yl)-phenyl]-acetic acid ethyl ester
[5-Hydroxy-2-(7-hydroxy-4-oxo-4H-chromen-2-yl)-phenyl]-acetic acid ethyl ester
[5-Hydroxy-2-(8-hydroxy-4-oxo-4H-chromen-2-yl)-phenyl]-acetic acid ethyl ester
[5-Hydroxy-2-(5,6-dihydroxy-4-oxo-4H-chromen-2-yl)-phenyl]-acetic acid ethyl ester
[5-Hydroxy-2-(5,7-dihydroxy-4-oxo-4H-chromen-2-yl)-phenyl]-acetic acid ethyl ester
[5-Hydroxy-2-(5,8-dihydroxy-4-oxo-4H-chromen-2-yl)-phenyl]-acetic acid ethyl ester

[5-Hydroxy-2-(6,7-dihydroxy-4-oxo-4H-chromen-2-yl)-phenyl]-acetic acid ethyl ester v) Nicotinic acid 4-(4-oxo-4H-chromen-2-yl)-phenyl ester

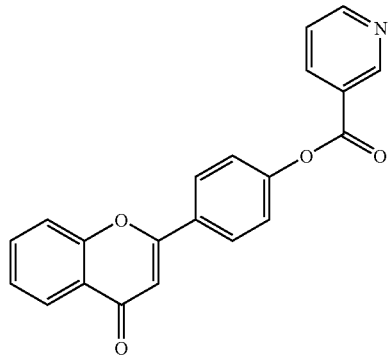

and its derivatives, including but not limited to:
Nicotinic acid 3-hydroxy-4-(4-oxo-4H-chromen-2-yl)-phenyl ester
Nicotinic acid 2-hydroxy-4-(4-oxo-4H-chromen-2-yl)-phenyl ester
Nicotinic acid 4-(5-hydroxy-4-oxo-4H-chromen-2-yl)-phenyl ester
Nicotinic acid 4-(6-hydroxy-4-oxo-4H-chromen-2-yl)-phenyl ester
Nicotinic acid 4-(7-hydroxy-4-oxo-4H-chromen-2-yl)-phenyl ester
Nicotinic acid 4-(8-hydroxy-4-oxo-4H-chromen-2-yl)-phenyl ester
Nicotinic acid 4-(5,6-dihydroxy-4-oxo-4H-chromen-2-yl)-phenyl ester
Nicotinic acid 4-(5,7-dihydroxy-4-oxo-4H-chromen-2-yl)-phenyl ester
Nicotinic acid 4-(5,8-dihydroxy-4-oxo-4H-chromen-2-yl)-phenyl ester
Nicotinic acid 4-(6,7-dihydroxy-4-oxo-4H-chromen-2-yl)-phenyl ester
Nicotinic acid 4-(6,8-dihydroxy-4-oxo-4H-chromen-2-yl)-phenyl ester
Nicotinic acid 4-(7,8-dihydroxy-4-oxo-4H-chromen-2-yl)-phenyl ester
Nicotinic acid 3-fluoro-4-(4-oxo-4H-chromen-2-yl)-phenyl ester
Nicotinic acid 2-fluoro-4-(4-oxo-4H-chromen-2-yl)-phenyl ester
Nicotinic acid 4-(5-fluoro-4-oxo-4H-chromen-2-yl)-phenyl ester
Nicotinic acid 4-(6-fluoro-4-oxo-4H-chromen-2-yl)-phenyl ester
Nicotinic acid 4-(7-fluoro-4-oxo-4H-chromen-2-yl)-phenyl ester
Nicotinic acid 4-(8-fluoro-4-oxo-4H-chromen-2-yl)-phenyl ester
Nicotinic acid 4-(5,6-difluoro-4-oxo-4H-chromen-2-yl)-phenyl ester
Nicotinic acid 4-(5,7-difluoro-4-oxo-4H-chromen-2-yl)-phenyl ester
Nicotinic acid 4-(5,8-difluoro-4-oxo-4H-chromen-2-yl)-phenyl ester
Nicotinic acid 4-(6,7-difluoro-4-oxo-4H-chromen-2-yl)-phenyl ester
Nicotinic acid 4-(6,8-difluoro-4-oxo-4H-chromen-2-yl)-phenyl ester
Nicotinic acid 4-(7,8-difluoro-4-oxo-4H-chromen-2-yl)-phenyl ester w) Nicotinic acid 3-ethoxycarbonylamino-4-(4-oxo-4H-chromen-2-yl)-phenyl ester

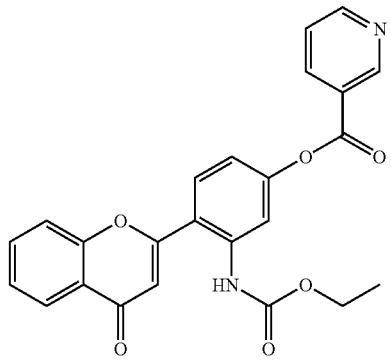

and its derivatives, including but not limited to:
Nicotinic acid 3-ethoxycarbonylamino-5-hydroxy-4-(4-oxo-4H-chromen-2-yl)-phenyl ester
Nicotinic acid 5-ethoxycarbonylamino-2-hydroxy-4-(4-oxo-4H-chromen-2-yl)-phenyl ester
Nicotinic acid 3-ethoxycarbonylamino-4-(5-hydroxy-4-oxo-4H-chromen-2-yl)-phenyl ester
Nicotinic acid 3-ethoxycarbonylamino-4-(6-hydroxy-4-oxo-4H-chromen-2-yl)-phenyl ester
Nicotinic acid 3-ethoxycarbonylamino-4-(7-hydroxy-4-oxo-4H-chromen-2-yl)-phenyl ester
Nicotinic acid 3-ethoxycarbonylamino-4-(8-hydroxy-4-oxo-4H-chromen-2-yl)-phenyl ester
Nicotinic acid 3-ethoxycarbonylamino-4-(5,6-dihydroxy-4-oxo-4H-chromen-2-yl)-phenyl ester
Nicotinic acid 3-ethoxycarbonylamino-4-(5,7-dihydroxy-4-oxo-4H-chromen-2-yl)-phenyl ester
Nicotinic acid 3-ethoxycarbonylamino-4-(5,8-dihydroxy-4-oxo-4H-chromen-2-yl)-phenyl ester
Nicotinic acid 3-ethoxycarbonylamino-4-(6,7-dihydroxy-4-oxo-4H-chromen-2-yl)-phenyl ester
Nicotinic acid 3-ethoxycarbonylamino-4-(6,8-dihydroxy-4-oxo-4H-chromen-2-yl)-phenyl ester
Nicotinic acid 3-ethoxycarbonylamino-4-(7,8-hydroxy-4-oxo-4H-chromen-2-yl)-phenyl ester
Nicotinic acid 3-ethoxycarbonylamino-5-fluoro-4-(4-oxo-4H-chromen-2-yl)-phenyl ester
Nicotinic acid 5-ethoxycarbonylamino-2-fluoro-4-(4-oxo-4H-chromen-2-yl)-phenyl ester
Nicotinic acid 3-ethoxycarbonylamino-4-(5-fluoro-4-oxo-4H-chromen-2-yl)-phenyl ester
Nicotinic acid 3-ethoxycarbonylamino-4-(6-fluoro-4-oxo-4H-chromen-2-yl)-phenyl ester
Nicotinic acid 3-ethoxycarbonylamino-4-(7-fluoro-4-oxo-4H-chromen-2-yl)-phenyl ester
Nicotinic acid 3-ethoxycarbonylamino-4-(8-fluoro-4-oxo-4H-chromen-2-yl)-phenyl ester Examples of isoflavanoid compounds of Formula 4 include, but are not limited to, the following compounds.

a) 3-(4-Hydroxy-phenyl)-chromen-4-one

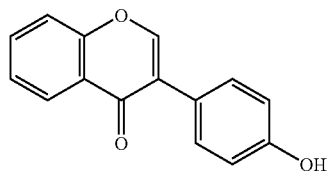

and its derivatives, including but not limited to:
3-(4-Hydroxy-phenyl)-pyrano[2,3-b]pyridin-4-one
3-(4-Hydroxy-phenyl)-pyrano[2,3-c]pyridin-4-one
3-(4-Hydroxy-phenyl)-pyrano[3,2-c]pyridin-4-one
3-(4-Hydroxy-phenyl)-pyrano[3,2-b]pyridin-4-one
3-(5-Hydroxy-pyridin-2-yl)-chromen-4-one
3-(6-Hydroxy-pyridin-3-yl)-chromen-4-one
3-(4-Hydroxy-phenyl)-benzo[e][1,2]oxazin-4-one
Nicotinic acid 4-(4-oxo-4H-chromen-3-yl)-phenyl ester
Nicotinic acid 4-(4-oxo-4H-pyrano[2,3-b]pyridin-3-yl)-phenyl ester
Nicotinic acid 4-(4-oxo-4H-pyrano[2,3-c]pyridin-3-yl)-phenyl ester
Nicotinic acid 4-(4-oxo-4H-pyrano[3,2-c]pyridin-3-yl)-phenyl ester
Nicotinic acid 4-(4-oxo-4H-pyrano[3,2-b]pyridin-3-yl)-phenyl ester
Nicotinic acid 6-(4-oxo-4H-chromen-3-yl)-pyridin-3-yl ester
Nicotinic acid 5-(4-oxo-4H-chromen-3-yl)-pyridin-2-yl ester b) [5-Hydroxy-2-(4-oxo-4H-chromen-3-yl)-phenyl]-carbamic acid ethyl ester

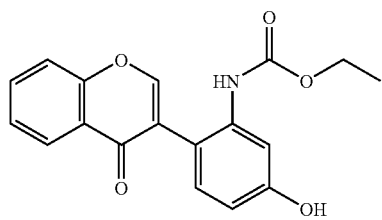

and its derivatives:
[5-Hydroxy-2-(4-oxo-4H-pyrano[2,3-b]pyridin-3-yl)-phenyl]-carbamic acid ethyl ester
[5-Hydroxy-2-(4-oxo-4H-pyrano[2,3-c]pyridin-3-yl)-phenyl]-carbamic acid ethyl ester
[5-Hydroxy-2-(4-oxo-4H-pyrano[3,2-c]pyridin-3-yl)-phenyl]-carbamic acid ethyl ester
[5-Hydroxy-2-(4-oxo-4H-pyrano[3,2-b]pyridin-3-yl)-phenyl]-carbamic acid ethyl ester
[6-Hydroxy-3-(4-oxo-4H-chromen-3-yl)-pyridin-2-yl]-carbamic acid ethyl ester
Nicotinic acid 3-ethoxycarbonylamino-4-(4-oxo-4H-chromen-3-yl)-phenyl ester
Nicotinic acid 3-ethoxycarbonylamino-4-(4-oxo-4H-pyrano[2,3-b]pyridin-3-yl)-phenyl ester
Nicotinic acid 3-ethoxycarbonylamino-4-(4-oxo-4H-pyrano[2,3-c]pyridin-3-yl)-phenyl ester
Nicotinic acid 3-ethoxycarbonylamino-4-(4-oxo-4H-pyrano[3,2-c]pyridin-3-yl)-phenyl ester
Nicotinic acid 3-ethoxycarbonylamino-4-(4-oxo-4H-pyrano[3,2-b]pyridin-3-yl)-phenyl ester
Nicotinic acid 6-ethoxycarbonylamino-5-(4-oxo-4H-chromen-3-yl)-pyridin-2-yl ester.

The following compounds were obtained from commercially available sources (such as Indofine Chemical Company, Inc.): 2-(4-hydroxyphenyl)-chromen-4-one; 6-hydroxy-2-(4-hydroxyphenyl)-4H-chromen-4-one; 5,7-dihydroxy-2-phenyl-4H-chromen-4-one; 5-hydroxy-2-(4-hydroxyphenyl)-4H-chromen-4-one; 7-hydroxy-2-(4-hydroxyphenyl)-4H-chromen-4-one; 7-hydroxy-2-phenyl-4H-chromen-4-one; 5-hydroxy-2-phenyl-4H-chromen-4-one; 2-phenyl-4H-chromen-4-one; 2-(3-hydroxyphenyl)-4H-chromen-4-one; 7-methoxy-2-(4-hydroxyphenyl)-4H-chromen-4-one; 2-(4-hydroxy-3-methoxyphenyl)-4H-chromen-4-one; 5,7-dihydroxy-2-(4-hydroxyphenyl)-4H-chromen-4-one; 5,7-dihydroxy-2-(4-hydroxyphenyl)-4H-chromen-4-one; and 3,5,7-trihydroxy-2-(3,4-dihydroxyphenyl)-4H-chromen-4-one.

Abbreviations used herein denote the following compounds, reagents and substituents: acetic acid (AcOH); 2,2'-azobisisobutyronitrile (AIBN); N-bromosuccinimide (NBS); N-tert-butoxycarbonyl (Boc); t-butyldimethylsilyl (TBDMS); m-chloroperoxybenzoic acid (mCPBA); dimethylaminopyridine (DMAP); dichloromethane (DCM); dimethylformamide (DMF); dimethylsulfoxide (DMSO); ethanol (EtOH); ethyl acetate (EtOAc); 1-ethyl-3-(3-dimethylaminopropyl)carbodiimide (EDCl); 1-hydroxybenzotriazole (HOBt); iodomethane (MeI); lithium hexamethyldisilazide (LHMDS); methanol (MeOH); methoxymethyl (MOM); tetrahydrofuran (THF).

Example 1

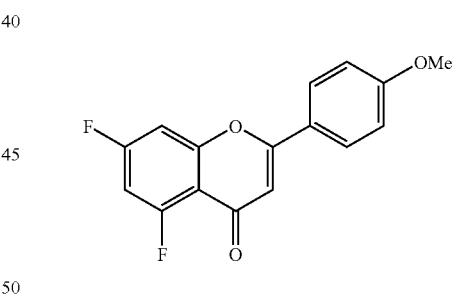

5,7-Difluoro-2-(4-methoxy-phenyl)-chromen-4-one

In a 100 mL 3-neck round-bottomed flask fitted with condenser and magnetic stirrer were placed dry THF (20 mL) and p-methoxy acetophenone (0.386 g, 2.57 mmol) under nitrogen. To this solution, LHMDS (2.69 mL as a 1M solution in THF, 2.57 mmol) was added drop wise at 25° C. After completion of addition, the mixture was stirred for 30 min at rt, then 2,4,6-trifluoro-benzoyl chloride (0.5 g, 2.57 mmol) in THF (5 mL) was added slowly at rt via syringe. The reaction mixture was stirred overnight at rt. The reaction was quenched with saturated NH$_4$Cl solution (10 mL). The organic layer was separated and aqueous layer was extracted with EtOAc. The combined organic layer was dries over Na$_2$SO$_4$, concentrated to give crude product, which was purified by column chromatography using 20% EtOAc in hexane, to give 215 mg of 1-(2,4,6-trifluoro-phenyl)-3-(4-methoxy-phenyl)-propane-1,3-dione (27%). 1-(2,4,6-trifluoro-phenyl)-3-(4-methoxy-phenyl)-propane-1,3-dione (100 mg) in DMSO (2 mL) was heated at 100-110° C. for 1 h. Then the reaction mixture was cooled to rt and diluted with water. The product was filtered and dried to give 62 mg of 5,7-difluoro-2-(4-methoxy-phenyl)-chromen-4-one (68%). MS (ES) m/z: 289.07 (M+1); $^{19}$F-NMR (DMSO-$d_6$): δ −101.9, −109.2.

Example 2

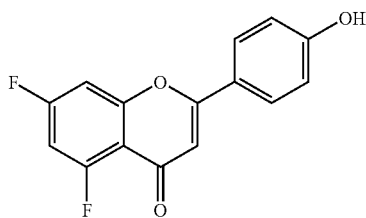

5,7-Difluoro-2-(4-hydroxyphenyl)-4H-chromen-4-one

In a 50 mL round-bottomed flask fitted with condenser and magnetic stirrer were placed 5,7-Difluoro-2-(4-methoxyphenyl)-4H-chromen-4-one (0.425 g, 1.47 mmol), hydroiodic acid (10 mL) and acetic acid (5 mL). The reaction mixture was heated 110° C. for 4 h. The reaction mixture was cooled to room temperature and diluted with water. The precipitate was filtered off, washed with water and dried to give the title compound (220 mg, 54%). Selected data for the title compound: MS (ES) m/z: 275.10 (M+1); $^{19}$F-NMR (DMSO-$d_6$): δ −106.2, −113.4.

Example 3

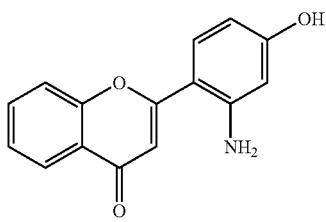

2-(2-Amino-4-hydroxy-phenyl)-4H-chromen-4-one

In a 100 mL round-bottomed flask fitted with condenser and magnetic stirrer were placed 2'-hydroxyacetophenone (2.76 g, 20.28 mmol), 2-nitro-4-methoxybenzoic acid (4.0 g, 20.28 mmol) and pyridine (60 mL). POCl$_3$ (3.11 g, 20.28 mmol) was added slowly on cooling. The reaction mixture was stirred for 24 h at rt under nitrogen. The reaction mixture was poured into ice-water and extracted with ethyl acetate. The organic layer was washed with water, dried and concentrated to give 2-acetylphenyl-4-methoxy-2-nitrobenzoate (6.24 g, 97%).

To a solution of 2-acetylphenyl-4-methoxy-2-nitrobenzoate (6.22 g, 19.71 mmol) in THF (100 mL), was added potassium t-butoxide (2.89 g, 23.65 mmol) and the reaction mixture was stirred for 24 h at rt under N$_2$. The reaction mixture was poured into a saturated aqueous solution of NH$_4$Cl. The organic layer was separated, washed with water, dried and concentrated to give the crude compound, which was purified by column chromatography using 50% ethyl acetate in hexane to give 1-(2-hydroxyphenyl)-3-(4-methoxy-2-nitrophenyl)propane-1,3-dione (5.92 g, 95%).

1-(2-Hydroxyphenyl)-3-(4-methoxy-2-nitrophenyl)propane-1,3-dione (5.92 g, 18.77 mmol) was dissolved in a mixture of 48% HCl (2 mL) and acetic acid (35 mL) and heated at 100° C. for 1 h. The reaction mixture was cooled to rt, diluted with water and extracted with ethyl acetate. The organic layer was washed with water, brine, dried and concentrated to give the crude compound, which was purified by column chromatography using 5% ethyl acetate in CH$_2$Cl$_2$ to give 2-(4-methoxy-2-nitrophenyl)-4H-chromen-4-one (3.92 g, 70%).

2-(4-Methoxy-2-nitrophenyl)-4H-chromen-4-one (1.5 g, 5.04 mmol) was dissolved in ethanol (30 mL) and heated at reflux. SnCl$_2$ (4.97 g, 26.23 mmol) was added. The mixture was heated under reflux for 20 min. The reaction mixture was cooled to rt diluted with water, neutralized and extracted with ethyl acetate to give the crude compound. This was purified by column chromatography using 3% MeOH in CH$_2$Cl$_2$ to give 2-(2-amino-4-methoxyphenyl)-4H-chromen-4-one (790 mg, 58%).

To a 50 mL round-bottomed flask fitted with condenser and magnetic stirrer was added 2-(2-amino-4-methoxyphenyl)-4H-chromen-4-one (770 mg, 2.88 mmol), hydroiodic acid (10 mL) and acetic acid (4 mL). The reaction mixture was heated to 110° C. for 8 h. The reaction mixture was cooled to rt and diluted with water. The precipitate was filtered off, washed with water and dried to give the crude compound, which was purified by column chromatography using 2% MeOH in CH$_2$Cl$_2$, to give 2-(2-amino-4-hydroxy-phenyl)-chromen-4-one (357 mg, 49%). MS (ES) m/z: 254.05 (M+1), 149.00, 134.01, and 121.00.

Example 4

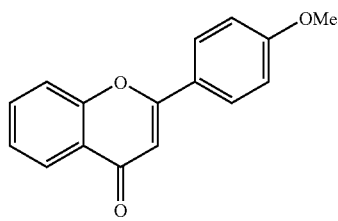

2-(4-Methoxy-phenyl)-4H-chromen-4-one

In a 50 mL round-bottomed flask fitted with condenser and magnetic stirrer were placed 2'-hydroxy acetophenone (1.0 g, 7.34 mmol) and pyridine (10 mL). To this mixture was added 4-methoxybenzoyl chloride (1.5 g, 8.81 mmol) and DMAP as a catalyst. The reaction was stirred for overnight at rt. The reaction mixture was poured into cold water and extracted with EtOAc. The combined organic layer was washed with water, brine, dried and solvent was removed afford 2-acetylphenyl 4-methoxybenzoate (1.9 g, 95%).

To solution of 2-acetylphenyl 4-methoxybenzoate (1.907 g, 7.05 mmol) in pyridine (10 mL) was added powdered KOH (1.49 g, 21.16 mmol). The reaction was stirred for 30 min at rt. The yellow viscous material was dissolved in water, neutralized and extracted to give crude product which was purified by column chromatography using 30% EtOAc in hexane to afford 450 mg (23%) of 1-(2-hydroxy-phenyl)-3-(4-methoxy-phenyl)-propane-1,3-dione.

To a solution of 1-(2-hydroxy-phenyl)-3-(4-methoxy-phenyl)-propane-1,3-dione (200 mg, 0.74 mmol) in dichloromethane (15 mL) was added BBr₃ (185 mg, 0.74 mmol, 1M solution in dichloromethane) slowly at 0° C., and then stirred for overnight at rt. Then MeOH was added at 0° C. to quench the unreacted BBr₃. The organic layer was washed with water, dried and concentrated to give a crude product, which was purified by column chromatography using 30% EtOAc in hexane to afford 50 mg (26%) of 2-(4-methoxy-phenyl)-4H-chromen-4-one. MS (ES) m/z: 253.08 (M+1), and 149.00.

Example 5

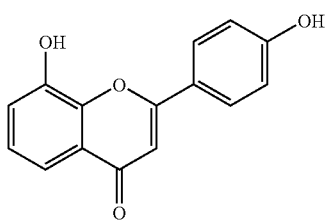

8-Hydroxy-2-(4-hydroxy-phenyl)-4H-chromen-4-one

To a solution of 4-methoxyacetophenone (2.0 g, 13.3 mmol) and methyl 2,3-dimethoxybenzoate (3.135 g, 15.98 mmol) in DMF (100 mL), was added a NaH (1.065 g, 26.63 mmol) and the reaction mixture was stirred for 24 h at rt under N₂. The reaction mixture was poured into ice water and products were extracted with EtOAc. The organic layer was separated, washed with water, dried and concentrated to afford 1-(2,3-dimethoxy-phenyl)-3-(4-methoxy-phenyl)-propane-1,3-dione (3.1 g, 74%).

1-(2,3-Dimethoxy-phenyl)-3-(4-methoxy-phenyl)-propane-1,3-dione (3.1 g, 9.86 mmol) was dissolved in mixture of HI (10 mL) and AcOH (10 mL) and heated at 110° C. for 4 days. The reaction mixture was cooled to rt, diluted with water and solids were filtered. The solid product was washed with water, dried and purified by column chromatography, using 30% EtOAc in dichloromethane to give 1.3 g (52%) of 8-hydroxy-2-(4-hydroxy-phenyl)-4H-chromen-4-one. MS (ES) m/z: 255.08 (M+1), and 154.15.

Example 6

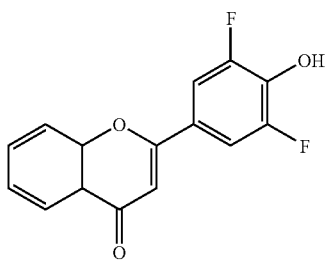

2-(3,5-Difluoro-4-hydroxyphenyl)chromen-4-one

To a solution of 2'-hydroxyacetophenone (0.68 g, 5 mmol) in 10 mL anhydrous pyridine was added 3,5-difluoro-4-methoxybenzoyl chloride (1.03 g, 5 mmol) and the reaction mixture was stirred at rt for 15 h under nitrogen atmosphere. The reaction mixture was poured into 100 mL 2N HCl. The solid was filtered off, washed with water and dried under vacuum to give a white solid (1.44 g, 94%). The compound (1.42 g, 4.63 mmol) was dissolved in 10 mL anhydrous pyridine. Powdered KOH (0.78 g, 13.9 mmol) was added and the reaction mixture was stirred at rt overnight under nitrogen. Water (50 mL) was added and the solid was isolated by filtration, and washed with water to give yellow solid (1.05 g, 74%). To a suspension of the yellow solid (0.82 g, 2.67 mmol) in 6 mL glacial AcOH was added 3 drops of conc. HCl and the reaction mixture was stirred at 110° C. for 2 h. The mixture was cooled to rt and 50 mL water was added. The solid was isolated by filtration, washed with water and dried under vacuum to give 2-(3,5-difluoro-4-methoxyphenyl)chromen-4-one as a white solid (0.61 g, 79%). 2-(3,5-Difluoro-4-methoxyphenyl)chromen-4-one was suspended in 15 mL hydroiodic acid. Glacial AcOH (6 mL) was added and the reaction mixture was stirred at 110° C. for 4 h. The mixture was cooled to rt. Water (100 mL) was added and the solid was isolated by filtration, washed with water and dried under vacuum. The crude compound was washed with 1:1 dichloromethane and MeOH (15 mL) to give 2-(3,5-difluoro-4-hydroxyphenyl)-4H-chromen-4-one (0.416 g, 73%) as a pale yellow solid. MS (ES) m/z: 275.04 (M+1); Mp. 275-276° C.

Example 7

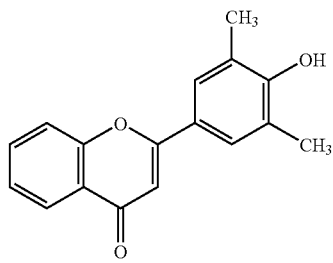

2-(4-Hydroxy-3,5-dimethylphenyl)-4H-chromen-4-one

To a solution of 2-hydroxyacetophenone (1.361 g, 10 mmol) in 20 mL anhydrous pyridine was added 3,5-dimethyl-4-methoxybenzoic acid (2.162 g, 12 mmol). The mixture was cooled to 0° C. and phosphorous oxychloride (1 mL) was added. A white precipitate was formed. The reaction mixture was stirred at rt for 2 h under nitrogen atmosphere. Then the reaction mixture was poured into 100 mL cold 2N HCl and extracted with EtOAc (2×200 mL). The combined organic layers were washed with water and brine and dried over anhydrous Na₂SO₄. The solvent was removed under vacuum to give a colorless liquid (2.89 g, 97%), which was used in the next step without further purification. The compound (2.88 g, 9.65 mmol) was dissolved in 10 mL anhydrous pyridine. Powdered potassium hydroxide (1.62 g, 28.95 mmol) was added and the reaction mixture was stirred at rt overnight under nitrogen. Water (100 mL) was added and the mixture was neutralized to pH 7 with conc. HCl. The yellow solid was filtered off, washed with water and dried under vacuum. Yield: 1.16 g, 40%. To a suspension of the yellow solid (1.14 g, 3.83 mmol) in 8 mL glacial AcOH was added 4 drops of conc. HCl and the reaction mixture was stirred at 110° C. for 2 h. The mixture was cooled to rt and water (50 mL) was added. The solid was isolated by filtration and washed with water and dried under vacuum to give 2-(4-methoxy-3,5-dimethyl phenyl)chromen-4-one (1.05 g, 98%) as a pale green solid. 2-(4-methoxy-3,5-dimethyl phenyl) chromen-4-one was suspended in 20 mL hydroiodic acid and 8 mL glacial AcOH was added. The reaction mixture was stirred at 110° C.

for 2 h. The mixture was cooled to rt. Water (100 mL) was added and the solid was isolated by filtration, washed with water and dried under vacuum. The crude compound was washed with 1:1 dichloromethane and methanol (20 mL) to give 0.763 g of 2-(4-hydroxy-3,5-dimethylphenyl)-4H-chromen-4-one (85%) as a pale yellow solid. MS (ES) m/z: 267.06 (M+1); Mp. 255-256° C.

Example 8

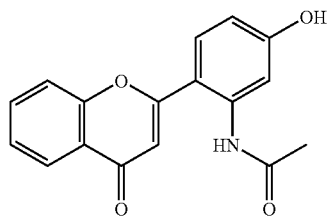

N-[5-Hydroxy-2-(4-oxo-4H-chromen-2-yl)-phenyl] acetamide

In a 50 mL round-bottomed flask fitted with condenser and magnetic stirrer were placed 2-(2-amino-4-hydroxy-phenyl)-chromen-4-one (150 mg, 0.592 mmol), Ac$_2$O (181 mg, 1.776 mmol), and pyridine (5 mL) and then the reaction mixture was stirred for 24 h at rt. The reaction mixture was poured into water and extracted with EtOAc. The organic layer washed with water, dried and concentrated to give the intermediate (228 mg, 99%). To a solution of the intermediate (228 mg, 0.676 mmol) in MeOH: THF (5 mL: 5 mL), K$_2$CO$_3$ (112 mg, 0.811 mmol) was added and stirred for 2 h at rt. Then the reaction mixture was neutralized by dilute HCl and extracted by EtOAc, the combined organic layers were washed with water, brine, dried and concentrated to give a crude product, which was purified by column chromatography using 2% MeOH in dichloromethane to afford N-[5-hydroxy-2-(4-oxo-4H-chromen-2-yl)-phenyl]acetamide (100 mg, 50%). MS (ES) m/z: 296.15 (M+1); Mp. 253-255° C.

Example 9

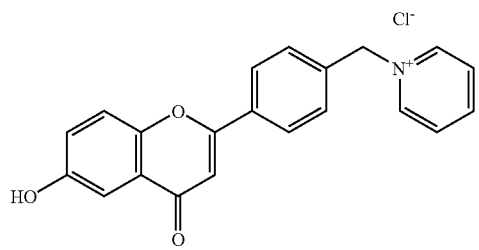

1-[4-(6-Hydroxy-4-oxo-4H-chromen-2-yl)benzyl] pyridinium chloride

In a 100 mL round-bottomed flask fitted with condenser and magnetic stirrer were placed 2'-hydroxy-5'-methoxyacetophenone (2.0 g, 12.03 mmol), 4-acetoxymethylbenzoic acid (2.4 g, 12.03 mmol) and pyridine (20 mL). POCl$_3$ (1.8 g, 12.03 mmol) was added slowly on cooling. The reaction mixture was stirred for 24 h at rt under nitrogen. The reaction mixture was poured into ice-water and extracted with EtOAc. The organic layer was washed with water, dried and concentrated to give the product (3.08 g, 72%). To a solution of this product (3.08 g, 8.99 mmol) in THF (50 mL), was added potassium t-butoxide (1.32 g, 10.07 mmol) and the reaction mixture was stirred for 24 h at rt under N$_2$. The reaction mixture was poured into saturated aqueous NH$_4$Cl. The organic layer was separated, washed with water, dried and concentrated to give the crude diketone (3.07 g, 99%). The diketone compound (3.07 g, 8.96 mmol) was dissolved in a mixture of 48% HCl (2 mL) and AcOH (20 mL) and heated at 100° C. for 1 h. The reaction mixture was cooled to rt, diluted with water and extracted with EtOAc. The organic layer was washed with water, brine, dried and concentrated to give cyclized product (1.38 g, 47%). To a solution of the cyclized product (1.2 g, 3.69 mmol) in THF (30 mL), K$_2$CO$_3$ (613 mg, 4.44 mmol) was added and the mixture was stirred overnight at rt. Then the reaction mixture was neutralized by dilute HCl and extracted by EtOAc, the combined organic layers were washed with water, brine, dried and concentrated to give a crude product (548 mg, 52%). A mixture of the 6-methoxy-flavone analogue (400 mg, 1.41 mmol) and pyridinium hydrochloride (8 g) was heated at 190° C. for 4 h. The reaction mixture was cooled to rt, diluted with water, neutralized with NaHCO$_3$ and filtered to give the crude product. This was purified by crystallization using MeOH/dichloromethane/EtOAc to give 200 mg of 1-[4-(6-hydroxy-4-oxo-4H-chromen-2-yl)benzyl]pyridinium chloride (51%). MS (ES) m/z: 330.89 (M), 329.86 (M−1); Mp. 243-247° C.

Example 10

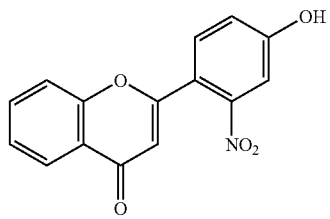

2-(4-Hydroxy-2-nitrophenyl)chromen-4-one

In a 100 mL round-bottomed flask fitted With condenser and magnetic stirrer were placed 2'-hydroxyacetophenone (2.76 g, 20.28 mmol), 2-nitro-4-methoxybenzoic acid (4.0 g, 20.28 mmol) and pyridine (60 mL). POCl$_3$ (3.11 g, 20.28 mmol) was added slowly on cooling. The reaction mixture was stirred for 24 h at rt under nitrogen. The reaction mixture was poured into ice-water and extracted with ethyl acetate. The organic layer was washed with water, dried and concentrated to give product (6.24 g, 97%). To a solution of the product (817 mg, 2.59 mmol) in THF (10 mL), was added potassium t-butoxide (380 mg, 3.11 mmol), and the reaction mixture was stirred for 24 h at rt under N$_2$. The reaction mixture was poured into a saturated aqueous solution of NH$_4$Cl. The organic layer was separated, washed with water, dried over Na$_2$SO$_4$ and concentrated to give the diketone (800 mg, 97%).

The diketone compound (800 mg, 2.53 mmol) was dissolved in a mixture of 48% HCl (1 mL) and acetic acid (7 mL) and heated at 100° C. for 1 h. The reaction mixture was cooled to rt, diluted with water and extracted with ethyl acetate. The organic layer was washed with water, brine, dried over Na$_2$SO$_4$ and concentrated to the crude product, which was purified by crystallization to give (500 mg, 67%) of cyclized product. The product (500 mg, 1.68 mmol) and pyridinium hydrochloride (8 g) were mixed and heated at 190° C. for 4 h. The reaction mixture was cooled to rt, diluted with water, neutralized by NaHCO$_3$ and filtered to give 2-(4-hydroxy-2-nitrophenyl)chromen-4-one (430 mg, 92%). MS (ES) m/z: 284.88 (M+1), 283.86 (M); Mp. 277-279° C.

Example 11

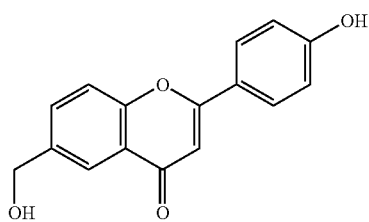

6-Hydroxymethyl-2-(4-hydroxyphenyl)chromen-4-one

A suspension of 2'-hydroxyacetophenone (5 g) and paraformaldehyde (1.9 g) in 20 mL of conc. HCl was stirred at 35° C. for 4 h, until the formation of a yellow precipitate. 2'-Hydroxy-5'-chloromethylacetophenone was filtered off, air dried and used for the next step without further purification. 2'-Hydroxy-5'-chloromethylacetophenone (6.8 g) was dissolved in 100 mL of dry MeOH and NaOMe (25 w % in MeOH, 15.9 g) was slowly added. The resulting solution was stirred at rt overnight. After the reaction, 1M HCl was slowly added to neutralize the reaction mixture. The reaction mixture was dried by direct addition of anhydrous MgSO$_4$ and concentrated by evaporation of the MeOH. The residue was loaded on a column with 20% EtOAc/Hexane as an eluent to isolate 2'-hydroxy-5'-methoxymethylacetophenone (4.9 g, 74%).

A mixture of 2'-hydroxy-5'-methoxymethylacetophenone (1.2 g) and 20 mL of pyridine was stirred for 15 min, before the addition of 4-methoxybenzoyl chloride (1.14 g). The formed solution was stirred at rt overnight. HCl (1 M) was slowly added to neutralize the reaction solution. Then 50 mL of water was added, and the resulting solution was extracted by EtOAc (3×50 mL). The combined organic layers were dried over MgSO$_4$ and evaporated under vacuum. The residue was passed through a silica gel column quickly with 40% EtOAc/hexane as an eluent to afford benzoate (1.46 g, 70%). To the solution of benzoate (2.3 g) in dry THF (30 mL) was slowly added NaH (0.92 g, 60% in mineral oil). The solution was heated to reflux overnight. The solution was cooled to rt and neutralized by adding 1M HCl. Water (50 mL) was added and the resulting solution was extracted with EtOAc (3×50 mL). After drying the combined organic layers over MgSO$_4$ and evaporation of solvent, the product was assayed by $^1$H-NMR and the crude diketone was used directly in the next step reaction without further purification.

A mixture of the diketone (1.1 g), 30 mL of AcOH and 3 mL of conc. HCl was stirred at 105° C. for 15 min. Then water (30 mL) was added and the resulting solution was extracted by EtOAc (3×30 mL). The combined organic layers were dried over MgSO$_4$, evaporated under vacuum and purified by column chromatography on silica gel (40% EtOAc/Hexane) to afford the cyclized compound (0.68 g, 66%). To the solution of the cyclized compound (0.6 g) in dichloromethane (20 mL), 10 mL of 1 M BBr$_3$ were added slowly. The resulting black solution was stirred at rt for 24 h. After the reaction, 50 mL of water was slowly added to the stirring solution. Then 30 mL of EtOAc and Na$_2$CO$_2$ powder was added. After the neutralization, conc. HCl was used to acidify the solution to pH 2. The mixture was extracted with EtOAc (2×20 mL). The combined organic layers were concentrated and purified by column chromatography on silica gel (5% MeOH/dichloromethane) to afford 6-bromomethyl-2-(4-hydroxyphenyl)chromen-4-one (0.4 g, 60%).

To a solution of 6-bromomethyl-2-(4-hydroxyphenyl)chromen-4-one (250 mg, 0.754 mmol) in dioxane:DMF (10:2, 12 mL), was added potassium acetate (500 mg, 3.77 mmol). The mixture was heated at 100° C. for 3 h. The reaction mixture was diluted with water and extracted with EtOAc. The combined organic layers were washed with water, brine, dried over Na$_2$SO$_4$ and concentrated to give crude product (225 mg, 96%). To a solution of the crude product (220 mg, 0.711 mmol) in MeOH:THF (5 mL:5 mL) was added K$_2$CO$_3$ (216 mg, 1.56 mmol) and the mixture was stirred for 24 h at rt. Then the reaction mixture was neutralized by dilute HCl and extracted by EtOAc, the combined organic layers were washed with water, brine, dried and concentrated to give a crude product, which was purified by column chromatography using 5% MeOH in dichloromethane, to afford 6-hydroxymethyl-2-(4-hydroxyphenyl) chromen-4-one (80 mg, 42%). MS (ES) m/z: 269.88 (M+1), 268.85 (M); Mp. 246-247° C.

Example 12

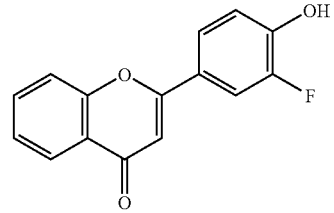

2-(3-Fluoro-4-hydroxyphenyl)chromen-4-one

To a solution of 2'-hydroxyacetophenone (1.36 g, 10 mmol) in 20 mL anhydrous pyridine was added 3-fluoro-4-methoxybenzoyl chloride (1.89 g, 10 mmol) and the reaction mixture was stirred at rt for 15 h under a nitrogen atmosphere. The reaction mixture was poured into 200 mL of 2 N HCl. The formed solid was isolated by filtration, washed with water and dried under vacuum to give a white solid (2.76 g, 95.7%). The compound (2.68 g, 9.3 mmol) was dissolved in 10 mL anhydrous pyridine. Powdered potassium hydroxide (1.57 g, 27.9 mmol) was added and the reaction mixture was stirred at rt overnight under nitrogen. Water (100 mL) was added, the solid was isolated by filtration and washed with water to give a yellow solid (1.83 g, 68%). The compound (1.78 g, 6.17 mmol) was suspended in 15 mL glacial AcOH. Five drops of conc. HCl was added and the reaction mixture was stirred at 110° C. for 2 h, then cooled to rt. Water (100 mL) was added. The formed solid was separated by filtration, washed with water and dried under vacuum to give 2-(3-fluoro-4-methoxyphenyl)chromen-4-one as a white solid (1.62 g, 97%). 2-(3-

Fluoro-4-methoxyphenyl)chromen-4-one (1.6 g, 5.92 mmol) was suspended in 40 mL of HI. Glacial AcOH (15 mL) was added and the reaction mixture was stirred at 110° C. for 4 h, then cooled to rt. Water (200 mL) was added, and the solid was isolated by filtration, washed with water and dried under vacuum. The crude compound was washed with 1:1 dichloromethane and methanol (15 mL) to give 1.1 g of 2-(3-fluoro-4-hydroxyphenyl)chromen-4-one (72%) as a pale yellow solid. MS (ES) m/z: 257.91 (M+1), 256.88 (M); Mp. 275-276° C.

Example 13

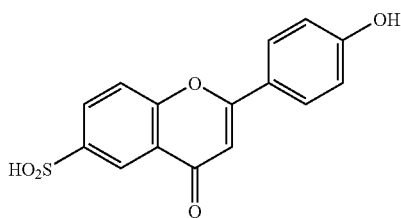

2-(4-Hydroxyphenyl)-4-oxo-4H-chromene-6-sulfonic acid

To a solution of 2'-hydroxyacetophenone (5.43 g, 40 mmol) in cyclohexane (28 mL) was added dimethylcarbonate (28 mL). The mixture was stirred under nitrogen and heated to 60° C. Chlorosulfonic acid was added over a period of 15 min. Liberated HCl was removed by trapping with solid NaOH. On completion of the addition, the reaction mixture was heated to 70° C. for 1 h and then cooled to rt. The solid was filtered off, washed with a mixture of dimethyl carbonate and cyclohexane (1:1, 20 mL) and dried under vacuum to give 3-acetyl-4-hydroxybenzene sulfonic acid as yellow solid (4.5 g, 52%). 3-Acetyl-4-hydroxybenzene sulfonic acid (2.16 g, 10 mmol) was suspended in 20 mL anhydrous pyridine. 4-Methoxybenzoyl chloride (3.4 g, 20 mmol) was added slowly at rt. Stirring continued under nitrogen for 15 h. Excess pyridine was removed under reduced pressure. The solid obtained was dried under vacuum. This material was used without further purification. This crude compound (~10 mmol) was dissolved in 10 mL anhydrous pyridine. Powdered KOH (2.8 g, 50 mmol) was added and the reaction mixture was stirred at rt for 14 h under nitrogen. Water (10 mL) was added and the mixture was concentrated to dryness. The crude product was taken in 10 mL of glacial AcOH. Five drops of concentrated HCl was added and the reaction mixture was stirred at 110° C. for 4 h, then cooled to rt. The yellow solid was isolated by filtration, washed with AcOH and dried under vacuum to give 2-(4-methoxy phenyl)-4-oxo-4H-chromen-6-sulfonic acid (0.475 g, 14%) as yellow solid. The product (0.375 g, 1.13 mmol) was suspended in HI (7 mL). Glacial AcOH (3 mL) was added and the reaction mixture was stirred at 110° C. for 2 h, then cooled to rt. The solid was isolated by filtration, washed with AcOH and dried under vacuum. The crude compound was triturated with ether to afford 2-(4-hydroxyphenyl)-4-oxo-4H-chromene-6-sulfonic acid (0.2 g, 55%) as yellow solid. MS (ES) m/z: 319.88 (M+1), 318.85 (M); $^{13}$C-NMR (DMSO-$d_6$): δ 177.5, 163.7, 161.7, 156.1, 146.1, 132.1, 129.1, 123.1, 122.3, 122.2, 118.7, 116.6, 105.5.

Example 14

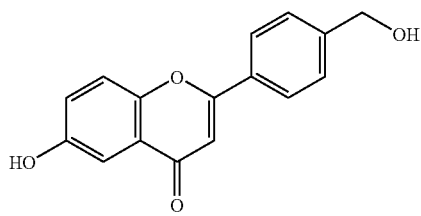

6-Hydroxy-2-(4-hydroxymethylphenyl)chromen-4-one

In a 100 mL round-bottomed flask fitted with condenser and magnetic stirrer were placed 2'-hydroxy-5'-acetoxyacetophenone (2.63 g, 13.54 mmol), 4-acetoxymethyl benzoic acid (2.63 g, 13.54 mmol) and pyridine (20 mL). POCl$_3$ (2.07 g, 13.54 mmol) was added slowly on cooling. Then the reaction mixture was stirred for 24 h at rt under nitrogen. The reaction mixture was poured into ice water and extracted with EtOAc. The organic layer was washed with water, dried and concentrated to give product (3.0 g, 60%). A solution of this product (3.0 g, 8.10 mmol) in THF (50 mL), was added potassium t-butoxide (1.187 g, 9.72 mmol) and the reaction mixture was stirred for 24 h at rt under N$_2$. The reaction mixture was poured into saturated aqueous solution of NH$_4$Cl. The organic layer was separated, washed with water, dried and concentrated to give crude diketone (3.0 g, 99%). The mentioned diketone (3.0 g, 8.10 mmol) was taken into a mixture of 48% HCl (2 mL) and AcOH (25 mL) and heated at 100° C. for 1 h. The reaction mixture was cooled to rt, diluted with water and extracted with EtOAc. The organic layer was washed with water, brine, dried and concentrated to give the di-acetyl flavone (1.2 g, 74%). To a solution of the di-acetyl flavone (228 mg, 0.676 mmol) in methanol:THF (5 ml:5 mL), K$_2$CO$_3$ (112 mg, 0.811 mmol) was added and stirred for 2 h at rt, then the reaction mixture was neutralized by dilute HCl and extracted with EtOAc. The combined organic layers were washed with water, brine, dried and concentrated to give a crude product, which was purified by column chromatography using 2% MeOH in dichloromethane, to give 100 mg of 6-hydroxy-2-(4-hydroxymethylphenyl)chromen-4-one (50%). MS (ES) m/z: 269.90 (M+1), 268.91 (M); Mp. 262-265° C.

Example 15

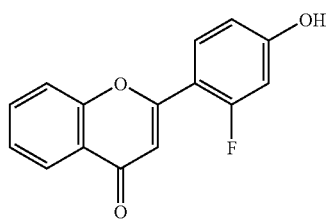

2-(2-Fluoro-4-hydroxyphenyl)chromen-4-one

To a solution of 2-fluoro-4-hydroxybenzoic acid (1.87 g, 12 mmol) in 30 mL pyridine was added acetic anhydride (1.84 g, 18 mmol) and catalytic amount of DMAP and the reaction mixture was stirred at rt for 15 h. The pyridine was removed under reduced pressure; the residue was dissolved in EtOAc (100 mL), washed with 1N HCl (20 mL), water (20 mL) and dried over anhydrous $Na_2SO_4$. Removal of solvent gave 2-fluoro-4-acetoxybenzoic acid in 57% yield (1.35 g). To a suspension of 2-fluoro-4-acetoxybenzoic acid (1.33 g, 6.71 mmol) in 10 mL anhydrous dichloromethane was added oxalyl chloride (2.56 g, 20.13 mmol). Two drops of DMF was added and the reaction mixture was stirred at rt for 3 h. The solvent and excess oxalyl chloride were removed under reduced pressure to give 1.48 g of 2-fluoro-4-acetoxybenzoyl chloride which was used in next step without purification. To a solution of 2'-hydroxyacetophenone (0.93 g, 6.83 mmol) in 15 mL anhydrous pyridine was added 2-fluoro-4-acetoxybenzoyl chloride (1.48 g, 6.83 mmol) and the reaction mixture was stirred at rt for 15 h under nitrogen atmosphere. Then the reaction mixture was poured into 100 mL 2N HCl, extracted with EtOAc (200 mL). The crude compound was purified by column chromatography (Silica Gel 230-400 mesh; 20% EtOAc in hexanes as eluent) to give 4-acetoxy-2-fluorobenzoic acid 2-acetyl phenyl ester (1.14 g, 53%). The ester compound (0.74 g, 2.34 mmol) was dissolved in 10 mL anhydrous THF. Potassium tert-butoxide (0.53 g, 4.68 mmol) was added in portions and stirred at rt under nitrogen for 1 h. A yellow solid was formed. The reaction mixture was quenched with 15 mL saturated aqueous ammonium chloride. EtOAc (100 mL) was added and the organic phase was separated and dried over anhydrous $Na_2SO_4$. Removal of solvent gave crude product (0.725 g) which was used in next step without further purification. This crude compound (0.72 g, 2.62 mmol) was dissolved in 10 mL glacial AcOH, conc. HCl (1 mL) was added and the reaction mixture was stirred at 110° C. for 4 h. The reaction mixture was cooled to rt. The solid was isolated by filtration, washed with AcOH and dried under vacuum to give 126 mg (21%) over 2 steps. MS (ES) m/z: 256.89 (M), 255.86 (M−1); Mp. 287-289° C.

Example 16

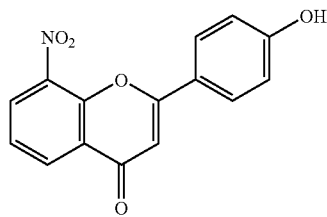

2-(4-Hydroxyphenyl)-8-nitro-4H-chromen-4-one

In a 250 mL round-bottomed flask fitted with condenser and magnetic stirrer were placed 2-hydroxy-3-nitro-acetophenone (1.0 g, 5.52 mmol), 4-methoxybenzoyl chloride (0.94 g, 5.52 mmol) and pyridine (20 mL). The reaction mixture was stirred for 24 h at rt under nitrogen. The reaction mixture was poured into ice-water and extracted with EtOAc. The organic layer was washed with water, dried and concentrated to give crude product (1.7 g, 99%). To a solution of the crude product (1.56 g, 4.95 mmol) in THF (50 mL), was added potassium t-butoxide (666 mg, 5.94 mmol) and the reaction mixture was stirred for 16 h at rt under $N_2$. The reaction mixture was poured into a saturated solution of $NH_4Cl$. The organic layer was separated, washed with water, dried and concentrated to give the crude diketone (1.5 g, 99%). The diketone (1.5 g, 4.76 mmol) was dissolved in a mixture of 48% HCl (1 mL) and AcOH (15 mL) and heated at 100° C. for 1 h. The reaction mixture was cooled to rt, diluted with water and extracted with EtOAc. The organic layer was washed with water, brine, dried and concentrated to give cyclized product, which was purified by crystallization to give 760 mg of compound in 54% yield. A mixture of the cyclized compound (360 mg, 1.21 mmol) and pyridinium hydrochloride (5 g) was heated at 190° C. for 3 h. The reaction mixture was cooled to rt, diluted with water, neutralized with $NaHCO_3$ and filtered to give crude product, which purified by chromatography using 5% MeOH in dichloromethane to give 196 mg of 2-(4-hydroxyphenyl)-8-nitro-4H-chromen-4-one (57%). MS (ES) m/z: 284.88 (M+1), 283.88 (M); Mp. 299-301° C.

Example 17

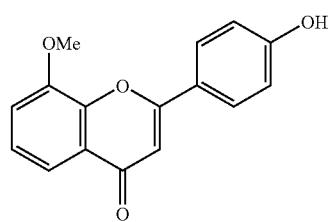

2-(4-Hydroxyphenyl)-8-methoxy-4H-chromen-4-one

In a 250 mL dry flask was charged with 2-hydroxy-3-methoxybenzoic acid (6.0 g, 36.0 mmol) and anhydrous THF (20 mL) under $N_2$. Methyl lithium in an ether solution (1.6 M, 73.5 mL, 117.6 mmol) was added dropwise over 20 min. The reaction mixture was heated to reflux for 20 h. After cooling the mixture was poured into 25 mL of brine with 6 N HCl and extracted with 100 mL of EtOAc. The organic layer was further washed with brine three times and dried over sodium sulfate. The solvent was evaporated and the residue was purified by column (hexane:EtOAc 2.5:1) to give 1-(2-hydroxy-3-methoxy-phenyl)-ethanone (4.3, 71.8%). 1-(2-Hydroxy-3-methoxy-phenyl)-ethanone (1.0 g, 6.0 mmol), 4-acetoxybenzoic acid (1.08 g, 6.0 mmol) and phosphorus oxychloride (0.923 g, 6.0 mmol) in 10 mL pyridine were stirred at rt overnight. The reaction mixture was poured into water (100 mL) and the isolated solid was washed with water. The solid was dissolved in dichloromethane and purified by column chromatography (hexane:EtOAc 2:1) to give the intermediate (1.05 g, 53.13%). Potassium tert-butoxide (0.4 g, 3.5 mmol) was added to this intermediate (1.05 g, 3.2 mmol) in 20 mL anhydrous THF. The reaction mixture was stirred for 4 h at rt. The mixture was poured into water (100 mL) with 1 mL AcOH (adjusted pH to 6-7.0). The solid was further rinsed with water and dissolved in dichloromethane. The organic layer was wash with brine and dried over sodium sulfate. The crude compound was treated with AcOH and two drops of concentrated HCl solution and heated to 110° C. for 1 h. The AcOH was evaporated and the solid residue was dissolved in MeOH and potassium carbonate (3.8 mmol) was added. The reaction mixture was stirred for 1 hour at rt. The reaction mixture was neutralized with AcOH and the solvent was evaporated. The residue was poured into water and the solid was collected by filtration and purified by column to give 150 mg of 2-(4-hydroxyphenyl)-8-methoxy-4H-chromen-4-one (17.4%). MS (ES) m/z: 269.93 (M+1), 268.91 (M); Mp. 281-283° C.

Example 18

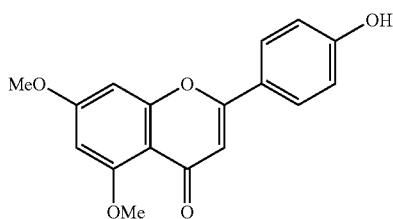

2-(4-Hydroxyphenyl)-5,7-dimethoxy-4H-chromen-4-one

To a solution of 4',6'-dimethoxy-2'-hydroxy acetophenone (1.96 g, 10 mmol) in 20 mL anhydrous pyridine was added 4-acetoxy benzoic acid (2.16 g, 12 mmol). The mixture was cooled to 0° C. and phosphorous oxychloride (1 mL) was added. A white precipitate was formed. The reaction mixture was stirred at rt for 2 h under nitrogen atmosphere. The reaction mixture was poured into 100 mL cold 2 N HCl. The mixture was extracted with EtOAc (2×200 mL). The combined organic layers were washed with water and brine and dried over anhydrous Na$_2$SO$_4$. The solvent was removed under vacuum to give a gummy solid product (3.36 g, 94%), which was used in next step without further purification. The gummy product (3.35 g, 9.35 mmol) was dissolved in 30 mL anhydrous THF. Potassium tert-butoxide (2.1 g, 18.7 mmol) was added in portions and the mixture was stirred at rt under nitrogen for 15 h. A yellow solid was formed. The reaction was quenched with saturated aqueous ammonium chloride solution (30 mL). EtOAc (100 mL) was added and the organic layer was separated and dried over anhydrous Na$_2$SO$_4$. Removal of solvent gave fluffy solid (2.52 g) which was used in next step without further purification. The fluffy solid (1.0 g, 2.79 mmol) was dissolved in glacial AcOH (8 mL). Concentrated HCl (5 drops) was added and the reaction mixture was stirred at 110° C. for 2.5 h. The mixture was cooled to rt and water (50 mL) was added. The solid was filtered off, washed with water and dried under vacuum. The crude compound was purified by column chromatography (Silica Gel 230-400 mesh; 30% EtOAc in hexanes as eluent) to give 204 mg of 2-(4-hydroxyphenyl)-5,7-dimethoxy-4H-chromen-4-one (25%) as an off-white solid. MS (ES) m/z: 299.94 (M+1), 298.93 (M); Mp. 301-303° C.

Example 19

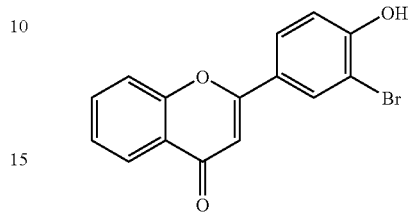

2-(3-Bromo-4-hydroxyphenyl)-4H-chromen-4-one

To a solution of 3-bromo-4-hydroxy-benzoic acid (3.0 g, 13.83 mmol) in dichloromethane (100 mL) and pyridine (20 mL) was added acetyl chloride (1.1 mL, 15.20 mmol) and the resulting mixture was stirred at rt for 1 h. The reaction was quenched with water (50 mL) and acidified with HCl (1 N) to adjust pH=1~2. The mixture was extracted with dichloromethane (3×100 mL) and concentrated to afford 4-acetoxy-3-bromo-benzoic acid (3.6 g, 100%). To a solution of 4-acetoxy-3-bromo-benzoic acid (3.60 g, 13.83 mmol) in dichloromethane (100 mL) at rt was added oxalyl chloride (1.8 mL, 20.75 mmol) and DMF (0.5 mL), sequentially. The resulting mixture was stirred at rt for 1 h. The mixture was concentrated to afford the acid chloride. To a solution of the freshly prepared acid chloride in dichloromethane (100 mL) were added 2'-hydroxyacetophenone (2.5 mL, 20.75 mmol) and triethylamine (3.9 mL, 27.66 mmol). This mixture was stirred at rt for 2 h. The reaction was quenched with water (100 mL) and extract with dichloromethane (3×150 mL). The combined organic layers were concentration to afford an oily residue, which was purified by column chromatography using 30% EtOAc in hexane to give the phenol ester (4.5 g, 86%). A solution of the phenol ester (4.0 g, 10.61 mmol) in THF (100 mL) was mixed with potassium t-butoxide (1.6 g, 14.32 mmol) and stirred at 60° C. for 1.5 h. This mixture was cooled to rt, diluted with water (100 mL) and acidified with HCl (1 N) to adjust pH=5~6. The mixture was extract with dichloromethane (3×100 mL) and the combined organic layers were concentration to give a yellow solid residue. The residue was purified by column chromatography using 30% EtOAc in hexane to give the diketone (2.3 g, 58%). A solution of the diketone (1.50 g, 3.98 mmol) in AcOH (100 mL) and HCl (conc., 2 mL) was stirred at reflux for 16 h. This mixture was cooled to rt, diluted with water (100 mL), extracted with dichloromethane (3×100 mL) and concentrated. The residue was purified by column chromatography using 50% EtOAc in hexane to give the flavone acetate (0.4 g, 28%). A solution of the flavone acetate (0.53 g, 1.48 mmol) in MeOH (80 mL) and water (20 mL) was mixed with potassium carbonate (1.10 g, 8.00 mmol) and was stirred at rt for 1 h. The solid was filtered off, washed with water, hexanes, and dichloromethane sequentially to give 390 mg of product (83%) as a light yellow solid. MS (ES) m/z: 318.84+316.84 (two isotopes of M); Mp. 273.5-274.9° C.

Example 20

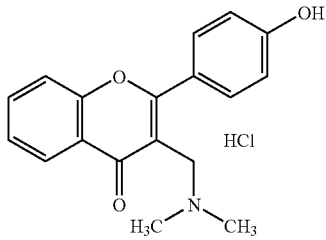

3-((Dimethylamino)methyl)-2-(4-hydroxyphenyl)-4H-chromen-4-one hydrochloride

A 100 mL dry flask was charged with 2'-hydroxy propiophenone (10.0 g, 67 mmol), 4-acetoxybenzoic acid (12.0 g, 67 mmol), phosphorus oxychloride (6.7 mL, 73 mmol), pyridine (25 mL) and anhydrous dichloromethane (10 mL) sequentially. The reaction mixture was stirred at rt for 3 h then poured into 150 mL of cold water. EtOAc (3×100 mL) was used to extract the compound out of the aqueous layer. The combined organic layers were washed with sodium bicarbonate, brine and dried over sodium sulfate. The residue was purified by column chromatography (hexane:EtOAc 2:1) to afford 14.6 g of the corresponding phenol ester (77%). To a solution of the phenol ester (14.0 g, 51.5 mmol) in THF (200 mL) was added potassium tert-butoxide (8.64 g, 77.2 mmol) and the reaction mixture was stirred at rt for 16 h. The reaction was quenched by adding water (100 mL), then extracted with dichloromethane (3×100 mL). The combined organic layers were concentrated to afford a solid residue. This residue was dissolved in AcOH (160 mL) and concentrated HCl (5 mL) and the mixture was stirred at reflux for 8 h. The reaction was quenched by adding water (100 mL). The reaction mixture was extracted with dichloromethane (3×100 mL) and concentrated to afford a solid residue. This solid was re-dissolved in MeOH (200 mL) and water (200 mL) and the solution was mixed with potassium carbonate (16 g) and stirred at rt for 2 h. The MeOH was removed and the aqueous layer was acidified with HCl (1 N) to pH=5. The solid was filtered off and further washed with water, EtOAc and dichloromethane to afford the flavone analog (7.5 g, 58% over two step). A solution of the flavone (6.9 g, 27.4 mmol) in acetic anhydride (50 mL) was stirred at reflux for 16 h. The mixture was cooled to rt and poured into ice water (300 mL). The mixture was extracted with dichloromethane (3×100 mL) and concentrated to afford a light yellow solid as the corresponding flavone acetate (6.8 g, 84%). To a solution of the flavone acetate (6.8 g, 23.1 mmol) in carbon tetrachloride (200 mL) at reflux was added NBS (4.12 g, 23.1 mmol) and benzoyl peroxide (0.56 g, 2.31 mmol). The reaction was stirred at reflux for 4 h and then quenched with HCl (0.5 N, 100 mL). The reaction mixture was extracted with dichloromethane (3×100 mL) and the combined organic layers were concentrated to afford 3-bromomethyl-2-(4-hydroxyphenyl)-4H-chromen-4-one as a light yellow compound (8.6 g, 100%).

A solution of 3-((dimethylamino)methyl)-2-(4-hydroxyphenyl)-4H-chromen-4-one hydrochloride (0.3 g, 0.8 mmol) in DMF (20 mL) was mixed with dimethylamine solution in THF (2 mL, 4 mmol) and was stirred at 45° C. for 24 h. The reaction mixture was extract with EtOAc (3×100 mL) and concentrated to an oily residue. This residue was re-dissolved in MeOH (50 mL) and water (50 mL), mixed with potassium carbonate (1 g), and stirred at rt for 0.5 h. The mixture was extracted with dichloromethane (3×50 mL) and concentrated to afford an oil. This oil was re-dissolved in dichloromethane (10 mL) and mixed with HCl in ether (10 mL, 20 mmol) and stirred at rt for 1 h. The resulting solid was filtered and washed with dichloromethane and hexanes to give 3-((dimethylamino)methyl)-2-(4-hydroxyphenyl)-4H-chromen-4-one hydrochloride a light yellow solid product (0.24 g, 90%). MS (ES) m/z: 295.98 (M); Mp. 271.5-272.3° C.

Example 21

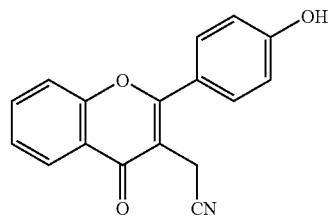

2-(2-(4-Hydroxyphenyl)-4-oxo-4H-chromen-3-yl)acetonitrile

A solution of 3-bromomethyl-2-(4-hydroxyphenyl)-4H-chromen-4-one (0.3 g, 0.8 mmol) in DMF (15 mL), water (15 mL), and NaCN (0.12 g, 2.4 mmol) was stirred at 45° C. for 24 h. The reaction mixture was extracted with EtOAc (3×100 mL) and concentrated to afford a solid residue. This residue was re-dissolved in MeOH (50 mL) and water (50 mL) and was mixed with potassium carbonate (1 g) and stirred at rt for 0.5 h. MeOH was removed, the aqueous layer was acidified with HCl (1 N) to pH=5. The solid was filtered off and then purified by column chromatography (hexane:EtOAc 1:2). The resulting solid was re-crystallized from dichloromethane and hexanes to give 2-(2-(4-hydroxyphenyl)-4-oxo-4H-chromen-3-yl)acetonitrile as a light yellow solid product (0.14 g, 63%). MS (ES) m/z: 278.94 (M+1), 277.93 (M); Mp. 258.2-259.5° C.

Example 22

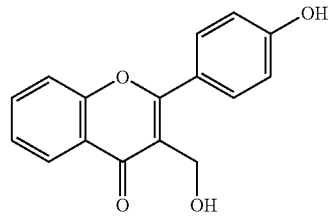

3-(Hydroxymethyl)-2-(4-hydroxyphenyl)-4H-chromen-4-one

A solution of 3-bromomethyl-2-(4-hydroxyphenyl)-4H-chromen-4-one (0.50 g, 1.5 mmol) and sodium acetate (1.24 g, 15.0 mmol) in AcOH (20 mL) was heated to reflux for 15 h. AcOH was removed and the residue was poured into water and extracted with EtOAc (100 mL). The organic phase was further washed with brine and dried over sodium sulfate. The residue was mixed with potassium carbonate (0.52 g) and MeOH (10 mL) and stirred for 2 h. AcOH (1.0 mL) was added and MeOH was removed. The residue was poured into water and the solid was washed additionally with water and hexane to give 3-(hydroxymethyl)-2-(4-hydroxyphenyl)-4H-chromen-4-one (0.265 g, 62.6%). MS (ES) m/z: 269.94 (M+1), 268.94 (M); Mp. 234-235° C.

Example 23

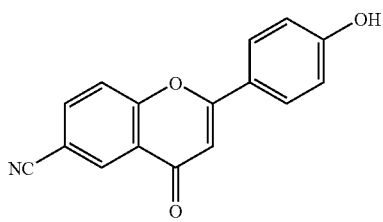

2-(4-Hydroxyphenyl)-4-oxo-4H-chromene-6-carbonitrile

2-Acetyl-4-cyanophenol (0.78 g, 4.84 mmol), 4-acetoxybenzoic acid (0.872 g, 4.84 mmol) and phosphorus oxychloride (0.5 mL) and pyridine (2.0 mL) were mixed in anhydrous dichloromethane (10 mL). The reaction mixture was stirred overnight at rt and then poured into cold water and extracted with dichloromethane (150 mL). The organic layer was washed with sodium bicarbonate, brine and dried over sodium sulfate followed by concentration. The crude compound (1.40 g, 89.5%) was obtained after evaporation of the solvent. The crude compound (1.4 g, 4.33 mmol) was dissolved into dry THF (20 mL) and potassium tert-butoxide (0.51 g, 4.55 mmol) was added and the reaction mixture was stirred at rt for 2 h. The solvent was removed, followed by addition of water (50 mL) and EtOAc (150 mL) was used to extract out the compound. The organic layer was washed with brine and dried over sodium sulfate. The crude product (1.20 g) and 4 drops of sulfuric acid were added to AcOH (15 mL). The reaction mixture was heated to 110° C. for 1 h. AcOH was removed and sodium bicarbonate solution was added followed by extraction with EtOAc. The organic layer was washed with brine and dried over sodium sulfate and concentrated. The crude and potassium carbonate (1.1 g) was added to MeOH (20 mL). The reaction mixture was stirred for 2 h. AcOH (1.0 mL) was added and MeOH was removed. The residue was purified by preparative HPLC to give 70 mg of 2-(4-hydroxyphenyl)-4-oxo-4H-chromene-6-carbonitrile. MS (ES) m/z: 264.91 (M+1), 263.90 (M); Mp. 296-298° C.

Example 24

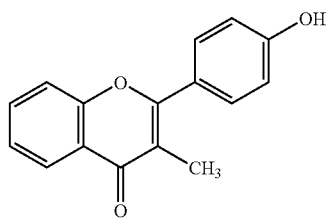

2-(4-Hydroxyphenyl)-3-methyl-4H-chromen-4-one

A 100 mL dry flask was charged with 2'-hydroxy propiophenone (10.0 g, 0.067 mol), 4-acetoxybenzoic acid (12.0 g, 0.067 mol), POCl$_3$ (6.7 mL, 0.073 mol), pyridine (25 mL) and anhydrous dichloromethane (10 mL). The reaction mixture was kept at rt with stirring for 3 hours then poured into 150 mL of cold water. The mixture was extracted with EtOAc (150 mL) and the organic layer was washed with sodium bicarbonate, brine and dried over sodium sulfate. The crude compound was purified by column chromatography (hexane: EtOAc 2:1) to give the intermediate (14.6 g, 70.2%). The intermediate (14.0 g, 44.8 mmol) was dissolved in dry THF (150 mL) and potassium tert-butoxide (5.28 g, 47.0 mmol) was added. The reaction mixture was stirred at rt for 2 h. The mixture was concentrated and water (50 mL) was added, followed by extraction with EtOAc (150 mL). The organic layer was washed with brine and dried over sodium sulfate. The crude compound (11.0 g, 35.2 mmol) was dissolved into AcOH (30 mL) and 37% HCl (2.0 mL) was added. The reaction was carried out at 110° C. for 2 h. AcOH was removed and 7.0 g potassium carbonate and 40 mL methanol were added followed by stirring overnight. AcOH (5.0 mL) was added to the mixture and methanol was removed. Water (50 mL) was added to the residue. The mixture was stirred for a while to obtain the solid, which was filtered off and further washed with water and EtOAc to give 3.70 g of 2-(4-hydroxyphenyl)-3-methyl-4H-chromen-4-one (41.7%). MS (ES) m/z: 253.89 (M+1), 252.90 (M); Mp. 241-242° C.

Example 25

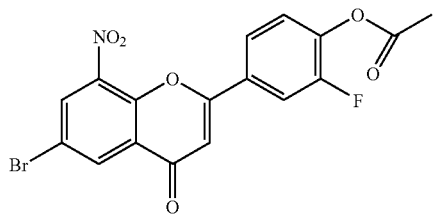

4-(6-Bromo-8-nitro-4-oxo-4H-chromen-2-yl)-2-fluorophenyl acetate

To a solution of 2'-hydroxy-5'-bromoacetophonone (10 g, 46.5 mmol) in carbon tetrachloride (60 mL) at reflux was added 70% nitric acid (5.2 mL, 79.6 mmol). The reaction mixture was stirred at reflux for 40 min. and then cooled to rt. The resulting solid was filtered off and washed with water and hexanes to provide 2'-hydroxy-3'-nitro-5'-bromoacetophonone (10.19 g, 84%). To a solution of 3-fluoro-4-hydroxybenzoic acid (3.0 g, 19.2 mmol) in pyridine (20 mL) and dichloromethane (50 mL) was added acetyl chloride (1.8 mL, 25 mmol) and the reaction mixture was stirred at rt for 1 h. The reaction mixture was washed with HCl (1 N, 2×100 mL), and concentrated to afford 3-fluoro-4-acetoxybenzoic acid (3.18 g, 83%). To a solution of 3-fluoro-4-acetoxybenzoic acid (3.18 g, 16.1 mmol) in dichloromethane (100 mL) was added oxalyl chloride (2.1 mL, 24.0 mmol) and DMF (0.2 mL) sequentially. The resulting mixture was stirred at rt for 1 h and then concentrated to afford the corresponding acid chloride. A mixture of the acid chloride, 2'-hydroxy-3'-nitro-5'-bromoacetophonone (4.17 g, 16.1 mmol) and triethylamine (8.9 mL, 64.2 mmol) in dichloromethane (100 mL) was stirred at rt for 1 h and then concentrated. The residue was re-dissolved in THF (100 mL) and mixed with potassium tert-butoxide (4.0 g, 35.3 mmol). The reaction was stirred at rt for 16 h and then quenched by adding water (100 mL). The mixture was extracted with dichloromethane (3×100 mL) and concentration to afford the crude diketone as a yellow solid. This solid was re-dissolved in AcOH (100 mL) and HCl (conc., 5 mL) and the mixture was stirred at reflux for 20 h. The reaction was quenched with water (100 mL), extracted with dichloromethane (3×100 mL) and concentrated. A solution of the resulting residue in MeOH (50 mL) and water (50 mL) was mixed with potassium carbonate (2 g) and stirred at rt for 2 h. MeOH was removed and the aqueous layer was acidified with HCl (1 N) to pH=5. The solid was filtered off and washed with water, acetone, and dichloromethane sequentially to provide a solid of the flavone analog (1.85 g, 30% five steps combined). To a solution of the flavone analog (1.85 g, 4.87 mmol) in pyridine (50 mL) and dichloromethane (100 mL) at rt was added acetyl chloride (1.1 mL, 14.6 mmol) and the reaction mixture was stirred at rt for 16 h. The reaction mixture was washed with HCl (1 N, 2×100 mL), and concentrated to afford a solid residue, which was purified by column chromatography (hexane:EtOAc 2:1). The resulting solid was re-crystallized from EtOAc and hexanes to afford 4-(6-bromo-8-nitro-4-oxo-4H-chromen-2-yl)-2-fluorophenyl acetate (1.1 g, 54%) as a light yellow solid. MS (ES) m/z: 423.78, 421.77; Mp. 236.2-238.5° C.

mL) was stirred overnight at rt. The reaction mixture was neutralized by addition of AcOH and the solvent was removed. The residue was poured into water and the solid was collected and purified by column chromatography (hexane: EtOAc 2:1) to give 155 mg of 2-(4-hydroxyphenyl)-3-(methoxymethyl)-4H-chromen-4-one (35.0%). MS (ES) m/z: 283.95 (M+1), 282.93 (M); Mp. 237-239° C.

Example 27

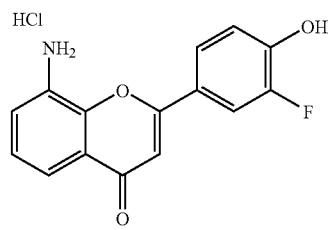

8-Amino-2-(3-fluoro-4-hydroxyphenyl)-4H-chromen-4-one hydrochloride

A Parr Bottle charged with a solution of 4-(6-bromo-8-nitro-4-oxo-4H-chromen-2-yl)-2-fluorophenyl acetate (0.8 g, 1.90 mmol) in THF (350 mL) and palladium carbon (10% on carbon, 0.2 g) was subjected for hydrogenation at 50 psi at rt for 16 h. The reaction mixture was passed through a Celite pad and the filtrate was concentrated. The resulting solid was filtered off and washed with dichloromethane to afford the aminoflavone analog as a brown solid (0.5 g, 85%). A solution of the aminoflavone analog (0.5 g, 1.60 mmol) in MeOH (50 mL) and water (20 mL) was mixed with potassium carbonate (1 g) and stirred at rt for 1 h. The MeOH was removed and the aqueous layer was neutralized with HCl (1 N). The resulting solid was filtered off, washed with MeOH, dichloromethane, and hexanes sequentially to provide the hydrolyzed product (0.204 g, 48%). To a solution of the hydrolyzed analog (0.106 g, 0.391 mmol) in MeOH (20 mL) was added HCl ether solution (5 mL, 10 mmol) and the reaction mixture was stirred at rt for 1 h. The MeOH was removed, and the resulting solid was filtered off and washed with a mixture of MeOH-dichloromethane (10:1) to afford 82 mg of 8-amino-2-(3-fluoro-4-hydroxyphenyl)-4H-chromen-4-one hydrochloride (68%). MS (ES) m/z: 271.97; Mp. 256.4-258.5° C.

Example 26

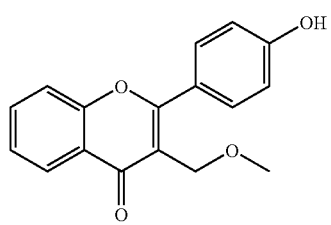

2-(4-Hydroxyphenyl)-3-(methoxymethyl)-4H-chromen-4-one

A mixture of 3-bromomethyl-2-(4-hydroxyphenyl)-4H-chromen-4-one (0.52 g, 1.57 mmol), sodium methoxide (1.36 mL, 6.28 mmol, 25% in MeOH) and anhydrous MeOH (10

Example 28

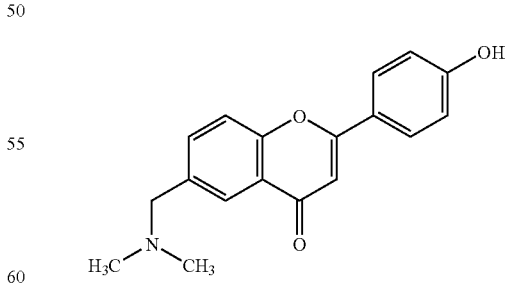

6-((Dimethylamino)methyl)-2-(4-hydroxyphenyl)-4H-chromen-4-one

Dimethylamine (1 M solution in THF, 1.2 mL) was added to 6-bromomethyl-2-(4-hydroxyphenyl)chromen-4-one (206 mg, 0.62 mmol) dissolved in dry THF (10 mL). The reaction mixture was stirred at rt for 17 hr. Most of the solvent was then removed in vacuo and the yellowish residue was suspended in 20 mL of water. The resulting suspension was stirred at rt for 30 min and the solid was removed by filtration, washed with water, ether, and air-dried to afford 6-((dimethylamino)methyl)-2-(4-hydroxyphenyl)-4H-chromen-4-one (125 mg, 68%). MS (ES) m/z: 296.98 (M+1), 295.97 (M); Mp. 99-102° C.

Example 29

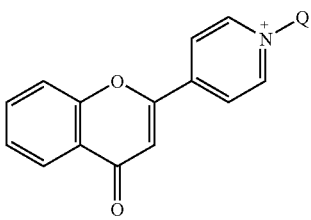

2-(1-Oxy-pyridin-4-yl)-chromen-4-one

To a solution of 2-pyridin-4-yl-chromen-4-one (0.3 g, 1.35 mmol) in 15 mL anhydrous dichloromethane was added m-chloroperbenzoic acid (57-86%) (0.33 g, 1.35 mmol) at 0° C. and the mixture was stirred for 10 min. under nitrogen. The ice-bath was removed and the stirring was continued at rt for 4 h. A white precipitate was formed. The reaction mixture was diluted with dichloromethane (50 mL) and washed with 0.5 N aq. NaOH solution (12 mL). The organic layer was dried over anhydrous $Na_2SO_4$. The solvent was removed and triturated with ether to afford 2-(1-oxy-pyridin-4-yl)-chromen-4-one (0.27 g, 84%). MS (ES) m/z: 239.89 (M); Mp. 258-259° C.

Example 30

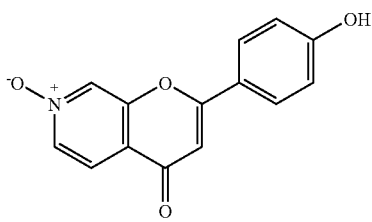

2-(4-Hydroxyphenyl)-4-oxo-4H-pyrano[2,3-c]pyridine 7-oxide

A mixture of 2-(4-hydroxyphenyl)-pyrano[2,3-c]pyridin-4-one (0.50 g, 2.09 mmol), acetyl chloride (0.164 g, 2.09 mmol) and anhydrous pyridine (2.5 mL) was stirred at rt overnight. The mixture was then poured into water (100 mL) and stirred for 30 min. The solid was filtered and further washed with water and dry to give the ester (0.586 g, 99%). The ester (0.230 g, 0.82 mmol) and 3-chloroperoxybenzoic acid (0.242 g, 0.98 mmol) were added to dichloromethane (10 mL) and the reaction mixture was stirred at rt for 2 weeks. The mixture was concentrated and potassium carbonate (0.60 g) and MeOH (10 mL) was added and the reaction mixture was stirred for 1 h. AcOH was added to adjust pH to 6.0-7.0, and the solvent was removed. The residue was poured into water. The solid was collected by filtration and washed with EtOAc to give 120 mg (57.4%) of 2-(4-hydroxyphenyl)-4-oxo-4H-pyrano[2,3-c]pyridine 7-oxide. MS (ES) m/z: 255.90 (M); Mp. 307-308° C.

Example 31

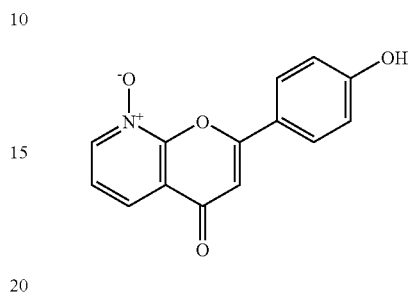

2-(4-Hydroxyphenyl)-4-oxo-4H-pyrano[2,3-b]pyridine 8-oxide

In a 50 mL round-bottomed flask fitted with condenser and magnetic stirrer were placed 2-(4-hydroxy-phenyl)-pyrano [2,3-b]pyridin-4-one (1.5 g, 6.27 mmol), $Ac_2O$ (700 mg, 6.89 mmol) and a catalytic amount of DMAP (50 mg) in pyridine (10 mL) and the reaction mixture was stirred for 16 h at rt. The reaction mixture was poured into water and extracted with ethyl acetate. The organic layer washed with water, dried and concentrated to give a 2-(4-acetoxyphenyl)-pyrano[2,3-b]pyridin-4-one (930 mg, 53%). To a stirred solution of the 4-acetoxy compound (930 mg, 3.30 mmol) in $CH_2Cl_2$ (50 mL), mCPBA (1.9 g, 11.3 mmol) was added and the reaction mixture was stirred at rt for 5 days. The reaction mixture was diluted with $CH_2Cl_2$ and washed with $NaHCO_3$ solution. The organic layer was separated, washed with water, brine, dried and concentrated to give crude product, which was purified by column chromatography, using 5% methanol in $CH_2Cl_2$ to give 168 mg of N-oxide product in 17% yield. To a solution of the acetoxy N-oxide (168 mg, 0.565 mmol) in methanol: THF (10 mL: 10 mL), $K_2CO_3$ (156 mg, 1.13 mmol) was added and the mixture was stirred for 2 h at rt. The reaction mixture was neutralized by dilute HCl. The solid was isolated by filtration, washed with water and dried to give 2-(4-hydroxyphenyl)-4-oxo-4H-pyrano[2,3-b]pyridine 8-oxide (150 mg, 100%). MS (ES) m/z: 255.90 (M); Mp. 314-315° C.

Example 32

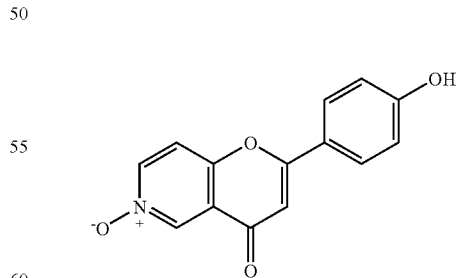

2-(4-Hydroxyphenyl)-4-oxo-4H-pyrano[3,2-c]pyridine 6-oxide

A solution of 2-(4-hydroxyphenyl)-pyrano[3,2-c]pyridin-4-one (1.75 g, 7.32 mmol) in acetic anhydride (50 mL) was stirred at reflux for 16 h. The reaction mixture was cooled to rt, quenched with water (100 mL), extracted with CH$_2$Cl$_2$ (3×100 mL). The combined organic layers were concentrated. The resulting residue was purified by column chromatography (hexane: ethyl acetate 1:1 to 1:3) to provide 1.3 g of the corresponding acetate (63%). A solution of the acetate (0.4 g, 1.42 mmol) and mCPBA (1.0 g, 4.70 mmol) in CH$_2$Cl$_2$ (50 mL) was stirred at rt for 11 days. The CH$_2$Cl$_2$ was removed by concentration. The residue was re-dissolved in MeOH (150 mL) and water (120 mL) and was mixed with potassium carbonate (1.0 g). The mixture was stirred at rt for 1 hour and neutralized with HCl (1 N). The resulting solid was filtered off, washed with water, MeOH, and CH$_2$Cl$_2$ sequentially to afford a light yellow solid of 2-(4-hydroxyphenyl)-4-oxo-4H-pyrano[3,2-c]pyridine 6-oxide (0.21 g, 58%). MS (ES) m/z: 255.96 (M); 322.8-323.4° C.

Example 33

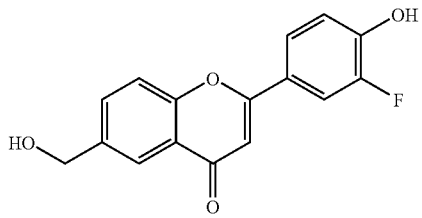

2-(3-Fluoro-4-hydroxyphenyl)-6-(hydroxymethyl)-4H-chromen-4-one

In a 100 mL round-bottomed flask fitted with condenser and magnetic stirrer were placed 2-hydroxy-5-methoxymethyl acetophenone (1.62 g, 9.014 mmol), 4-methoxy-3-fluoro benzoyl chloride (1.7 g, 9.014 mmol) and pyridine (20 mL). The reaction mixture was stirred for 16 h at rt under nitrogen. The reaction mixture was poured into ice-water. The solids were filtered off, washed with water and dried to give the intermediate (2.33 g, 78%). To a solution of this intermediate (2.33 g, 7.01 m mol) in THF (50 mL), was added potassium t-butoxide (945 mg, 8.42 mmol) and the reaction mixture was stirred for 16 h at rt under N$_2$. The reaction mixture was poured into saturated solution of NH$_4$Cl. The organic layer was separated, washed with water, dried and concentrated to give crude intermediate diketone (2.3 g, 98.7%).

The diketone compound (2.3 g, 6.92 mmol) was taken into a mixture of HCl (1 mL) and acetic acid (15 mL) and heated at 100° C. for 1 h. The reaction mixture was cooled to rt, diluted with water and extracted with ethyl acetate. The organic layer was washed with water, brine, dried and concentrated to give 1.75 g of the intermediate in 80.6% yield. In a 100 mL dry round-bottomed flask fitted with condenser and magnetic stirrer were placed this intermediate (925 mg, 2.94 mmol) in CH$_2$Cl$_2$ (30 mL). BBr$_3$ (2.21 g, 8.83 mmol, 1M solution in CH$_2$Cl$_2$) was added slowly at 0° C. The reaction mixture was stirred for 16 h at rt under nitrogen. The reaction mixture was quenched by carefully adding methanol. The solvent was removed under reduced pressure and the resulting solid was washed with water and dried to give 1.0 g of crude 3'-fluoro-4'-methoxy-5-bromo methyl flavone in 97% yield. To a solution of 5-bromomethyl flavone (1.0 g, 2.86 mmol) in DMF (20 mL), potassium acetate (845 mg, 8.60 mmol) was added. The mixture was heated at 100° C. for 1 h. The reaction mixture was diluted with water and extracted with ethyl acetate. The combined organic layers were washed with water, brine, dried over Na$_2$SO$_4$ and concentrated to give crude acetyl flavone (810 mg, 86%). To a solution of the acetyl flavone (810 mg, 2.47 mmol) in methanol (15 mL), K$_2$CO$_3$ (1.02 g, 7.41 mmol) was added and the reaction mixture was stirred for 2 h at rt. The solvent was removed and the product was taken in to water and neutralized by dilute HCl. The solid was separated by filtration, washed with water and dried to give 2-(3-fluoro-4-hydroxyphenyl)-6-(hydroxymethyl)-4H-chromen-4-one in 38% yield. MS (ES) m/z: 286.96 (M); Mp. 256-258° C.

Example 34

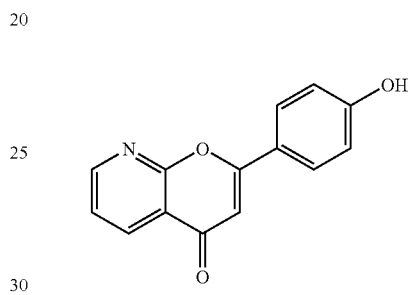

2-(4-Hydroxy-phenyl)-pyrano[2,3-b]pyridin-4-one

In a 500 mL dry round bottom flask with reflux condenser and magnetic stirrer was placed with 2-chloro-3-ethyl nicotinate (40.0 g, 215.5 mmol) in methanol (200 mL). CH$_3$ONa in methanol (25%, 65 mL, 301.7 mmol) was added slowly and the reaction mixture was refluxed for 16 h. The reaction was cooled to rt, quenched by addition of a saturated aqueous NH$_4$Cl solution. The aqueous mixture was extracted with ethyl acetate. The combined organic layers were washed well with water, brine, dried over Na$_2$SO$_4$ and concentrated to give 35 g of 2-methoxy-3-methyl nicotinate with 97% yield. Sodium hydride (60% in oil, 9.21 g, 230.3 mmol) was added to a dry 500 mL round bottom flask followed by 100 mL DMF. 4-Methoxyacetophenone (31.45 g, 209.44 mmol) in 50 mL dry DMF was added dropwise at 0° C. over 30 min. The reaction mixture was stirred for 1 h at rt. 2-Methoxynicotinic acid methyl ester (35 g, 209.44 mmol) was dissolved in 50 mL dry DMF and added slowly, keeping the temperature at 0° C. The mixture was stirred for 16 h at rt, then quenched by addition of a saturated aqueous NH$_4$Cl solution and diluted with water. The solid was filtered off, washed with water and dried to give 56.7 g diketo product in 95% yield.

The diketo compound (56.7 g, 198.9 mmol) was added to a 1 L round bottom flask together with pyridinium hydrochloride (345 g). The mixture was heated at 190° C. for 5 h. The reaction mixture was cooled to rt and diluted with water. The solid was isolated by filtration and purified by column chromatography using 5% methanol in CH$_2$Cl$_2$ to give 2-(4-hydroxy-phenyl)-pyrano[2,3-b]pyridin-4-one (23.25 g, 48.8%).

MS (ES) m/z: 240.07 (M+1); $^{13}$C-NMR (DMSO-$d_6$): δ 178.2, 164.2, 161.8, 160.8, 153.9, 136.3, 129.2, 123.2, 121.8, 116.8, 116.75, 116.74, 105.7.

Example 35

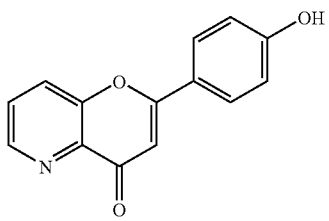

2-(4-Hydroxy-phenyl)-pyrano[3,2-b]pyridin-4-one

In a 500 mL round-bottom flask fitted with condenser and magnetic stirrer were placed MeOH (250 mL), 3-hydroxypyridine-2-carboxylic acid (10.0 g, 71.9 mmol) and concentrated $H_2SO_4$ (3 mL). The reaction mixture was heated at 64° C. for 24 hs. The reaction mixture was cooled to rt. The solvent was removed under reduced pressure; the residue was partitioned between EtOAc (150 mL) and water (20 mL). Solid sodium carbonate was added to adjust pH to 6. The organic layer was separated, dried over $Na_2SO_4$, concentrated to give 3.5 g of crude 3-hydroxypyridine-2-carboxylic acid methyl ester (32%).

In a 50 mL round-bottom flask fitted with magnetic stirrer were placed 3-hydroxypyridine-2-carboxylic acid methyl ester (3.5 g, 22.80 mmol), $K_2CO_3$ (3.46 g, 25.0 mmol), MeI (4.87 g, 34.3 mmol) and DMF (20 mL). The reaction mixture was stirred for 18 h at rt under nitrogen. The reaction mixture was diluted with EtOAc (30 mL) and water (10 mL). The organic layer was separated and aqueous layer was extracted with EtOAc. The combined organic extracts were dried over $Na_2SO_4$ and concentrated to give the crude product. The crude product was purified by column chromatography using 30% EtOAc in hexane to give 2.1 g of 3-methoxypyridine-2-carboxylic acid methyl ester (54%).

In 100 mL round-bottom flask fitted with magnetic stirrer were placed the NaH (1.62 g of 60% suspension in mineral oil, 40 mmol) and the solution of t3-methoxypyridine-2-carboxylic acid methyl ester (3.5 g, 20 mmol) in anhydrous DMF (20 mL). The mixture was stirred for 15 min at rt under $N_2$, then the solution of 4-methoxyacetophenone (3.3 g, 22 mmol) was added via syringe. The reaction mixture was stirred overnight at rt, then 10% aqueous solution of $NaHSO_4$ was used to adjust pH to 7. The organic layer was separated and aqueous layer was extracted with EtOAc. The combined organic extracts were dried over $Na_2SO_4$ and concentrated to give the crude product. The crude product was purified by column chromatography using 30% EtOAc in hexane to give 4.68 g of 1-(4-methoxyphenyl)-3-(3-methoxypyridin-2-yl)propane-1,3-dione (80%).

In 50 mL round-bottom flask fitted with magnetic stirrer were placed 1-(4-methoxyphenyl)-3-(3-methoxypyridin-2-yl) propane-1,3-dione (4.68 g, 16 mmol) and 45% aqueous solution of HBr (25 mL). The reaction mixture was refluxed for 3 h, then cooled down to rt. Solid $NaHCO_3$ was used to adjust pH to 7, followed by EtOAc (30 mL). The organic layer was separated and aqueous layer was extracted with EtOAc (2×30 mL). The combined organic extracts were dried over $Na_2SO_4$, concentrated to give the crude product, which was purified by column chromatography using 30% MeOH in EtOAc to give 125 mg of 2-(4-hydroxy-phenyl)-pyrano[3,2-b]pyridin-4-one (3.2%). MS (ES) m/z: 240.09 (M+1), and 149.06.

Example 36

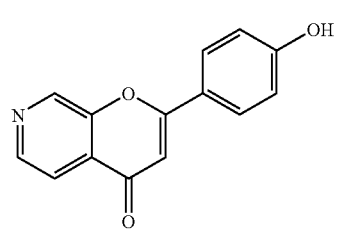

2-(4-Hydroxyphenyl)-pyrano[2,3-c]pyridin-4-one

A 50 mL flask was charged with 5.0 g (0.0354 mol) 3-fluoroisonicotinic acid and thionyl chloride (3.88 mL, 0.053 mol). The mixture was heated to reflux for 1 h, then the excess thionyl chloride was evaporated under vacuum. Anhydrous methanol was added to the residue and the mixture was heated to reflux for one hour. The reaction mixture was poured into sodium bicarbonate solution and pH was adjusted to 7.0. The mixture was extracted with EtOAc and the organic layer was dry over sodium sulfate. The organic solvent was evaporated yielding the product (4.80 g, 88%). A 50 mL dry flask was charged with methyl 3-fluoroisonicotinitate (3.50 g, 0.0227 mol), 4-methoxyacetophenone (3.60 g, 0.024 mol) and 10 mL dry DMF under nitrogen. Sodium hydride (1.82 g, 60% in oil) was added and the reaction was stirred for 30 min, then poured into ammonium chloride solution and extracted with EtOAc and dried over sodium sulfate. The solution was concentrated and the residue was pass through a column (EtOAc: hexane 1:3) to give the product (3.50 g, 54.0%). A 50 mL flask was charged with this product (0.5 g, 1.75 mmol) and pyridine hydrogen chloride (2.02 g, 17.5 mmol) and heat to 190° C. for 4 h. The mixture was poured into a sodium bicarbonate solution and the solid was collected by filtration, washed with EtOAc and methanol to give 2-(4-hydroxyphenyl)-pyrano[2, 3-c]pyridin-4-one as a yellow product (0.36 g, 86%). MS (ES) m/z: 240.90 (M+1), 239.89 (M); Mp. 294-296° C.

Example 37

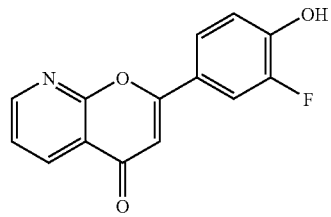

2-(3-Fluoro-4-hydroxyphenyl)pyrano[2,3-b]pyridine-4-one

Methyl 2-methoxynicotinate was synthesized from ethyl 2-chloronicotinate with sodium methoxide as in Example 34.

A 50 mL flask was charged with methyl 2-methoxynicotinate (2.50 g, 0.015 mol), 10 mL dry DMF and 60% NaH (0.745 g, 0.0186 mol) with magnetic stirring. 3'-Fluoro-4'-methoxyacetophenone (2.60 g, 0.0155 mol) in 6 mL anhydrous DMF was added over 5-10 min. After addition, the reaction mixture was stirred for 30 min. The mixture was poured into 50 mL NH₄Cl solution, the yellow solid was filtered and further washed with water and purified by column chromatography (hexane:EtOAc 4:1) to get (3.0 g, 66.4%) of product. A 50 mL flask was charged with this product (0.8 g, 2.64 mmol) and pyridine hydrogen chloride (3.04 g, 26.4 mmol) and heated to 190° C. for 4 h. The mixture was poured into sodium bicarbonate solution and the solid was collected by filtration, washed with EtOAc and MeOH and passed through a column (methanol:dichloromethane 1:4) to afford 400 mg of 2-(3-fluoro-4-hydroxyphenyl)pyrano[2,3-b]pyridine-4-one (59%). MS (ES) m/z: 257.85 (M); Mp. 267-268° C.

Example 38

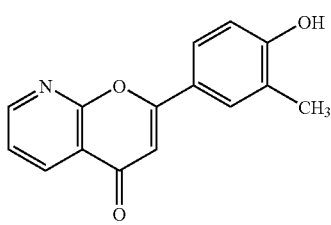

2-(4-Hydroxy-3-methylphenyl)-4H-pyrano[2,3-b]pyridine-4-one

Methyl 2-methoxynicotinate was synthesized from ethyl 2-chloronicotinate with sodium methoxide as described in Example 34. A 100 mL dry flask was charged with 2-methylanisole (7.92 g, 65 mmol), acetyl chloride (5.1 mL, 71 mmol), aluminum chloride (9.45 g, 71 mmol) and 40 mL of anhydrous dichloromethane. The reaction mixture was kept at reflux for 2 h, then poured into 15 mL of HCl (3 N) and extracted with 100 mL ether. The organic layer was further washed with sodium bicarbonate to pH 6-7, then further washed with brine and dried over sodium sulfate. The solvent was evaporated and the residue was dried under high vacuum to yield the intermediate (10.0 g, 93.85%). A 100 mL dry flask was charged with methyl 2-methoxynicotinate (2.50 g, 15 mmol), 10 mL anhydrous DMF and NaH (0.9 g, 22.5 mmol, 60% in oil). The intermediate (2.58 g, 15.7 mmol) in 3 mL anhydrous DMF was added and the reaction was stirred for 2 hours. The mixture was poured into 120 mL of water with 3 mL AcOH. The yellow solid was further wash with water and passed through a column (hexane:EtOAc 3:1) to give the methoxy intermediate (3.4 g, 75.7%). A 50 mL flask was charged with the methoxy intermediate (1.0 g, 3.3 mmol) and pyridine hydrogen chloride (4.0 g, 33 mmol) and heated to 190° C. for 3 h. The mixture was poured into a sodium bicarbonate solution and the solid was collected by filtration, washed with EtOAc and MeOH (20 mL each) to give 2-(4-hydroxy-3-methylphenyl)-4H-pyrano[2,3-b]pyridine-4-one (0.58 g, 69.4%). MS (ES) m/z: 254.0 (M+1); Mp. 300-302° C.

Example 39

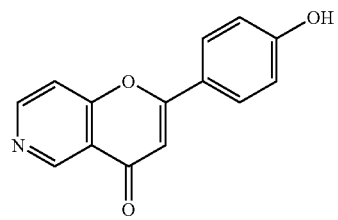

2-(4-Hydroxyphenyl)-4H-pyrano[3,2-c]pyridin-4-one

A solution of 4-chloropicolinic acid (3.0 g, 19.04 mmol) in EtOH (100 mL) was mixed with H₂SO₄ (conc., 5 mL) and was stirred at reflux for 48 h. The reaction mixture was cooled to rt and neutralized with NaOH (1 N) to adjust pH=8~9. The mixture was extract with dichloromethane (3×100 mL) and concentration to afforded ethyl 4-ethoxypicolinate (3.44 g, 93%).

To a solution of ethyl 4-ethoxypicolinate (3.44 g, 17.43 mmol) and 4-methoxy acetophenone (2.62 g, 17.43 mmol) in THF (100 mL) and DMSO (50 mL) was added NaH (1.4 g, 34.80 mmol). The resulting mixture was stirred at 95° C. for 6 h. The reaction mixture was cooled to rt and quenched with water (100 mL). The mixture was extract with EtOAc (3×150 mL) and concentration to a yellow solid. The solid was washed with hexanes to afford the diketone (3.6 g, 69%).

The diketone (1 g, 3.34 mmol) was mixed with pyridine hydrochloride (10 g). This mixture was stirred at 190° C. under N₂ for 12 h. The mixture was then diluted with EtOAc (30 mL) and poured into a beaker of 200 mL ice water. NaOH (1 N) was used to adjust pH=9. The solid was then filtered off and washed with water, hexanes, dichloromethane, EtOAc sequentially to afford the brownish solid 2-(4-hydroxyphenyl)-4H-pyrano[3,2-c]pyridin-4-one (0.39 g, 49%). MS (ES) m/z: 240.92 (M+1), 239.89 (M); Mp. 306-308° C.

Example 40

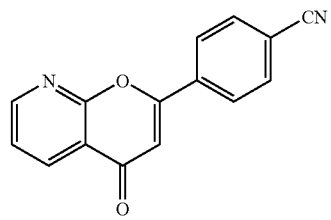

4-(4-Oxo-4H-pyrano[2,3-b]pyridine-2-yl)benzonitrile

Methyl 2-methoxynicotinitate was synthesized from Ethyl 2-chloronicotinitate with sodium methoxide as described in Example 34. A dry 50 mL flask was charged with methyl 2-methoxynicotinitate (2.50 g, 14.9 mmol) and 4-acetylbenzonitrile (2.25 g, 15.9 mmol) and anhydrous DMF (10 mL).

NaH (0.745 g, 18.6 mmol, 60% in oil) was added and the reaction mixture was stirred for 30 min. then poured into 100 mL water and AcOH (2 mL) to adjust pH to 6-7.0. The yellow solid was further washed with water and dissolved in dichloromethane. The organic solution was washed with brine and dried over sodium sulfate. The solvent was removed and the residue was purified by column chromatography (hexane: EtOAc 3:1) to give the intermediate (1.7 g, 40.7%). A 50 mL flask was charged with the intermediate (0.7 g, 2.49 mmol) and pyridine hydrogen chloride (2.87 g, 24.9 mmol) and heat to 190° C. for 1 h. The mixture was poured into a sodium bicarbonate solution and the solid was collected and purified by column chromatography (hexane:EtOAc:dichloromethane 1:1:1, then dichloromethane:methanol 1:1) to give 320 mg (51.7%) of 4-(4-oxo-4H-pyrano[2,3-b]pyridine-2-yl) benzonitrile. MS (ES) m/z: 249.80 (M+1), 248.90 (M); Mp. 250-252° C.

Example 41

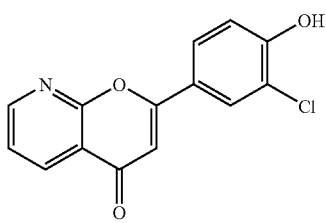

2-(3-Chloro-4-hydroxyphenyl)-4H-pyrano[2,3-b]pyridine-4-one

Sodium methoxide (18 mL, 25 wt % in methanol) was added slowly to a solution of ethyl-2-chloronicotinate (11.134 g 60 mmol) in 60 mL anhydrous methanol. The reaction mixture was stirred under reflux for 15 h, then cooled to rt. Methanol was removed in vacuo. The residue was dissolved in EtOAc (200 mL) and saturated aqueous ammonium chloride (50 mL) was added. The organic layer was separated and dried over anhydrous Na$_2$SO$_4$. The solvent was removed to give ethyl-2-methoxynicotinate (8.58 g, 79%). Sodium hydride (60% in mineral oil, 0.48 g, 12 mmol) was dissolved in anhydrous DMF (10 mL). A solution of 3'-chloro-4'-methoxy acetophenone (1.85 g, 10 mmol) in anhydrous DMF (5 mL) was added drop-wise at 0° C. under nitrogen. The mixture was stirred at 0° C. for 5 min. and then at rt for 30 min. The mixture was cooled to 0° C. A solution of ethyl 2-methoxy nicotinate (1.81 g, 10 mmol) in anhydrous DMF (5 mL) was added slowly. The ice bath was removed and the mixture was stirring at rt under nitrogen for 20 h. Water (20 mL) was added and the mixture was extracted with EtOAc (2×100 mL). The combined organic layers were washed with brine and dried over anhydrous Na$_2$SO$_4$. Removal of solvent gave a dark colored solid. Triturating with ether gave a yellow solid (1.64 g, 51%). The yellow solid (1.36 g, 4.21 mmol) and pyridinium hydrochloride (7.3 g, 63.2 mmol) were mixed together and stirred at 190° C. for 2 h, then cooled to rt. Water (100 mL) was added. The solid was separated by filtration, washed with water and dried under vacuum. The crude compound was purified by column chromatography (Silica Gel 230-400 mesh; 5% methanol in dichloromethane as an eluent to afford 2-(3-chloro-4-hydroxyphenyl)-4H-pyrano[2,3-b]pyridine-4-one (0.385 g, 33% yield) as yellow solid. MS (ES) m/z: 275.94+273.92 (two isotopes of M); Mp. 259-262° C.

Example 42

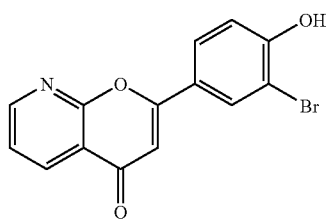

2-(3-Bromo-4-hydroxyphenyl)-4H-pyrano[2,3-b]pyridin-4-one

Sodium methoxide (18 mL, 25 wt % in methanol) was added slowly to a solution of ethyl-2-chloronicotinate (11.14 g 60 mmol) in anhydrous methanol (60 mL). The reaction mixture was stirred under reflux for 15 h, then cooled to rt. The methanol was removed in vacuo. The residue was dissolved in EtOAc (200 mL) and sat. ammonium chloride solution (50 mL) was added. The organic layer was separated and dried over anhydrous Na$_2$SO$_4$. Removal of solvent gave ethyl-2-methoxynicotinate (8.58 g, 79%) as yellow oil. Sodium hydride (0.21 g, 60% in mineral oil, 5.16 mmol) was mixed with anhydrous DMF (5 mL). A solution of 3'-bromo-4'-methoxyacetophenone (0.99 g, 4.3 mmol) in anhydrous DMF (3 mL) was added drop-wise at 0° C. under nitrogen. The mixture was stirred at 0° C. for 5 min. and then at rt for 30 min. The mixture was cooled to 0° C. A solution of ethyl 2-methoxy nicotinate (1.81 g, 10 mmol) in anhydrous DMF (3 mL) was added slowly. The ice bath was removed and the stirring continued at rt under nitrogen for 20 h. Water (20 mL) was added and the mixture was extracted with EtOAc (2×100 mL). The organic layer was washed with brine and dried over anhydrous Na$_2$SO$_4$. Removal of the solvent gave a dark solid. Triturating with ether gave a yellow solid (1.32 g, 84%). The solid (1.31 g, 3.6 mmol) and pyridinium hydrochloride (6.24 g, 54 mmol) were mixed together and stirred at 190° C. for 3 h, The reaction mixture was then cooled to rt, followed by the addition of water (200 mL). The solid was isolated by filtration, washed with water and dried under vacuum. The crude compound was purified by column chromatography (Silica Gel 230-400 mesh; 5:4:1 hexanes, EtOAc and methanol as an eluent) to give 2-(3-bromo-4-hydroxyphenyl)-4H-pyrano[2,3-b]pyridin-4-one (0.453 g, 40%) of as yellow solid. MS (ES) m/z: 317.84, 239.9; Mp. 267-272° C.

Example 43

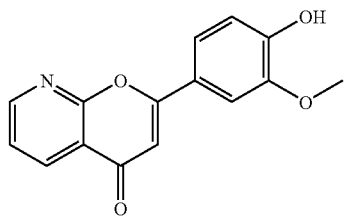

2-(4-Hydroxy-3-methoxyphenyl)-4H-pyrano[2,3-b]pyridine-4-one

A solution of ethyl 2-chloronicotinitate (6.0 g, 0.0323 mol) in anhydrous methanol (10 mL) at rt was added sodium methoxide (10 mL, 25% in methanol). The reaction mixture was stirred for half hour then heated to reflux for one hour. The mixture was poured into water and extracted with ethyl acetate and the organic layer was washed with water until neutral, dried over sodium sulfate, and concentrated to give methyl 2-methoxynicotinate (5.2 g, 96.3%).

A 100 mL dry flask was charged with acetovanillone (4.16 g, 0.025 mol) and anhydrous DMF (10 mL). Sodium hydride (1.05 g, 0.0263 mol, 60% in mineral oil) was added and the reaction mixture was stirred at rt followed by the dropwise addition of benzyl bromide (3.1 mL, 0.0263 mol). The reaction was carried out at rt for 2 h, then poured into water. Ethyl acetate (150 mL) was used to extract out the compound and the organic layer was washed with water (2×100 mL), brine, dried over sodium sulfate, and concentrated to give the benzyl intermediate (6.21 g, 96%), which was subsequently used without further purification.

A 100 mL dry flask was charged with methyl 2-methoxynicotinitate (2.2 g, 0.0131 mol), the benzyl intermediate (3.37 g, 0.0131 mol) and anhydrous DMF (10 mL). Sodium hydride (0.524 g, 0.0131 mol, 60% in mineral oil) was added and the reaction mixture was stirred for 2 hours at rt. The reaction mixture was poured into water and extracted with ethyl acetate (150 mL). The organic layer was washed with water (2×100 mL), brine (100 mL), dried over sodium sulfate, and concentrated to give the intermediate (5.0 g, 97.6%). This intermediate (4.0 g, 0.0102 mol) and pyridine hydrochloride (12.0 g, 0.102 mol) were mixed and heated to 170-190° C. for 20 min. The reaction mixture was cooled and poured into water (100 mL). The mixture was extracted with ethyl acetate (3×200 mL), and the combined organic layers were washed with brine (3×100 mL), dried over sodium sulfate, and concentrated. The solid was further purified by refluxing with methanol (40 mL). The solution was cooled and filtered to yield 2-(4-hydroxy-3-methoxyphenyl)-4H-pyrano[2,3-b]pyridine-4-one (250 mg, 9.1%). MS (ES) m/z: 270.92, 269.91; Mp. 253-255° C.

Example 44

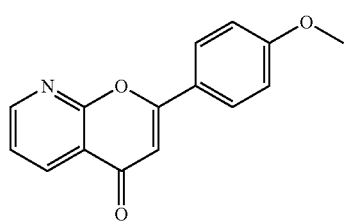

2-(4-Methoxyphenyl)-4H-pyrano[2,3-b]pyridine-4-one

In a 500 mL dry round bottom flask with reflux condenser and magnetic stirrer was placed with 2-chloro-3-ethyl nicotinate (40.0 g, 215.5 mmol) in methanol (200 mL), and sodium methoxide (65 mL, 301.7 mmol, 25% in methanol) was added slowly and the reaction mixture was refluxed for 16 h. The reaction mixture was cooled to rt and the reaction was quenched by addition of saturated aqueous $NH_4Cl$ solution, followed by extraction with ethyl acetate. The combined organic layers were washed well with water, brine, dried over $Na_2SO_4$ and concentrated to give 2-methoxy-3-methyl nicotinate (35 g, 97%). To a dry 500 mL round bottom flask was added NaH (9.21 g 230.3 mmol, 60% in mineral oil) in DMF (100 mL). 4-Methoxyacetophenone (31.45 g, 209.44 mmol) in dry DMF (50 mL) was added dropwise at 0° C. over 30 minutes. The reaction mixture was stirred for 1 h at rt. Then 2-methoxynicotinic acid methyl ester (35 g, 209.44 mmol) dissolved in dry DMF (50 mL) was added slowly on cooling. The mixture was stirred for 16 h at rt. The reaction was quenched by addition of saturated $NH_4Cl$ solution and diluted with water. The solid was filtered off, washed with water and dried to give the diketo product (56.7 g, 95%). Polyphosphoric acid (8.0 g) was heated at 90° C. and the diketo compound (1.0 g, 3.50 mmol) was added slowly and heated at 90° C. for 1 h. The reaction mixture was cooled to rt and diluted with water. The solid was isolated by filtration, washed with water and dried to give 2-(4-methoxyphenyl)-4H-pyrano[2,3-b]pyridine-4-one (570 mg, 64%). MS (ES) m/z: 254.89 (M+1), 253.90 (M); Mp. 269-270° C.

Example 45

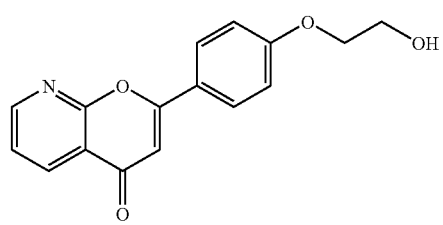

2-(4-(2-Hydroxyethoxy)phenyl)-4H-pyrano[2,3-b]pyridine-4-one

In a 100 mL dry round bottom flask with reflux condenser and magnetic stirrer was placed 2-(4-hydroxy-phenyl)-pyrano[2,3-b]pyridin-4-one (1.0 g, 4.18 mmol) in EtOH (10 mL) and acetonitrile (50 mL). 2-Chloroethanol (2.05 g, 25.0 mmol) was added slowly and the reaction mixture was refluxed for 48 h. The reaction mixture was cooled to rt and concentrated under reduced pressure. The crude product was purified by column chromatography, using 2% MeOH in dichloromethane to afford 2-(4-(2-hydroxyethoxy)phenyl)-4H-pyrano[2,3-b]pyridine-4-one (380 mg, 32% yield). MS (ES) m/z: 284.94 (M+1), 283.95 (M); Mp. 157-159° C.

Example 46

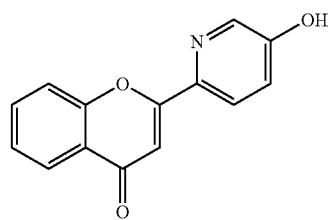

2-(5-Hydroxy-pyridin-2-yl)-chromen-4-one

In a 100 mL round-bottomed flask fitted with condenser and magnetic stirrer were placed 5-amino-2-cyano pyridine (1.0 g, 8.38 mmol), conc. $H_2SO_4$ (4.2 mL), water (15 mL) and the mixture was cooled to 0° C. A solution of $NaNO_2$ (636 mg, 9.22 mmol) in water (5.7 mL) was added slowly at 0° C. Then the reaction mixture was stirred for 30 min at 0° C. The reaction mixture was poured into a boiling mixture of water (11 mL) and $H_2SO_4$ (1 mL) and stirred for 30 min. The mixture was cooled and extracted with EtOAc. The organic layer was washed with water, dried and concentrated to give 2-cyano-5-hydroxy pyridine (900 mg, 89%).

2-Cyano-5-hydroxy pyridine (200 mg, 1.66 mmol), DMF (10 mL) and $K_2CO_3$ (253 mg, 1.83 mmol), and MeI (354 mg, 2.49 mmol) were combined at rt and the reaction mixture was stirred for 24 h at rt. The reaction mixture was poured into water and extracted with EtOAc. The organic layer was separated, washed with water, dried and concentrated to give 2-cyano-5-methoxy pyridine (175mg, 78%).

2-Cyano-5-methoxy pyridine (170 mg, 1.26 mmol) was dissolved in 6N HCl (4 mL) and refluxed for 16 h. The reaction mixture was cooled to rt and diluted with water, neutralized and extracted with EtOAc. The organic layer was washed with water, brine, dried and concentrated to give a crude (290 mg).

In a 100 mL round-bottomed flask fitted with condenser and magnetic stirrer were placed 2'-hydroxy acetophenone (3.56 g, 26.14 mmol), 5-methoxy-2 nicotinic acid (4.0 g, 26.14 mmol) and pyridine (50 mL). $POCl_3$ (4 g, 26.14 mmol) was added slowly on cooling. Then the reaction mixture was stirred for 24 h at rt under $N_2$. The reaction mixture was poured into ice-water and extracted with EtOAc. The organic layer was washed with water, dried and concentrated to give 2-acetylphenyl 5-methoxypyridine-2-carboxylate (1.76 g, 24%).

To a solution of 2-acetylphenyl 5-methoxypyridine-2-carboxylate (1.76 g, 6.49 mmol) in THF (30 mL), was added potassium t-butoxide (952 mg, 7.79 mmol) and the reaction mixture was stirred for 24 h at rt under $N_2$. The reaction mixture was poured into saturated solution of $NH_4Cl$. The organic layer was separated, washed with water, dried and concentrated to give crude product which was purified by using column chromatography using 50% EtOAc in hexane to give 1-(2-hydroxy-phenyl)-3-(4-methoxy-pyridin-2-yl)-propane-1,3-dione (870 mg, 49%).

1-(2-Hydroxy-phenyl)-3-(4-methoxy-pyridin-2-yl)-propane-1,3-dione (870 mg, 3.21 mmol) was dissolved in a mixture of 48% HCl (1 mL) and AcOH (10 mL) and heated at 100° C. for 1 h. The reaction mixture was cooled to rt, diluted with water and extracted with EtOAc. The organic layer was washed with water, brine, dried and concentrated to give 2-(5-methoxy-pyridin-2-yl)-chromen-4-one (794 mg, 98%).

2-(5-Methoxy-pyridin-2-yl)-chromen-4-one (790 mg, 3.12 mmol) in HI (10 mL) and AcOH (4 mL) was heated at reflux for 6 h. Reaction mixture was cooled to rt, diluted with water, neutralized and extracted with EtOAc to give crude product. This was purified by column chromatography using 5% MeOH in dichloromethane to give (270 mg, 36%) of 2-(5-Hydroxy-pyridin-2-yl)-chromen-4-one. MS (ES) m/z: 240.09 (M+1).

Example 47

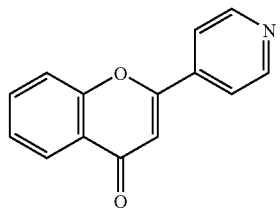

2-Pyridin-4-yl-chromen-4-one

2-Hydroxyacetophenone (1.36 g, 10 mmol) and isonicotinyl chloride hydrochloride (1.78 g, 10 mmol) were dissolved in 20 mL anhydrous pyridine and stirred at rt for 15 h under nitrogen. Water (20 mL) was added and neutralized to pH 6 with 4N HCl. The formed solid was filtered off, washed with water and dried to give isonicotinic acid-2-acetyl phenyl ester as a white powder (2.32 g, 96%). To a solution of isonicotinic acid-2-acetyl phenyl ester (2.2 g, 9.12 mmol) in 20 mL anhydrous pyridine was added powdered potassium hydroxide (1.54 g, 27.36 mmol) and stirred at rt for 15 h under nitrogen. Water (50 mL) was added and the pH was adjusted to pH 6 with 4N HCl. The solid formed was filtered off, washed with water and dried to give a yellow powder (0.66 g). The aqueous phase was extracted with EtOAc. The organic layer was washed with brine, dried over anhydrous $Na_2SO_4$, and concentrated to give a yellow solid (1.32 g, 60%). The compound (0.64 g, 2.654 mmol) was suspended in 6 mL glacial AcOH. Three drops of conc. HCl was added and the mixture was stirred at 110° C. for 3 h. The mixture was cooled to rt. Water (20 mL) was added and the mixture was neutralized to pH 6-7 with a 2 N NaOH solution. The white precipitate formed was filtered off, washed with water and dried under vacuum to give 2-pyridin-4-yl-chromen-4-one (0.56 g, 94.5%). MS (ES) m/z: 224.89 (M+1), 223.92 (M); Mp. 144-145° C.

Example 48

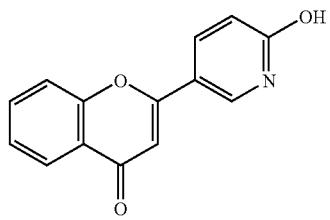

2-(6-Hydroxypyridin-3-yl)-chromen-4-one

In a 100 mL round-bottomed flask fitted with condenser and magnetic stirrer were placed 2'-hydroxy acetophenone (2.0 g, 14.69 mmol), 2-methoxy-5-pyridine carboxylic acid (2.0 g, 14.69 mmol) and pyridine (20 mL). $POCl_3$ (2.25 g, 14.69 mmol) was added slowly on cooling. The reaction mixture was stirred for 24 h at rt under nitrogen. The reaction mixture was poured into ice-water and extracted with EtOAc. The organic layer was washed with water, dried and concentrated to give product (2.82 g, 70%). To a solution of this product (2.8 g, 10.33 mmol) in THF (50 mL) was added potassium t-butoxide (1.51 g, 12.4 mmol) and the reaction mixture was stirred for 3 h at rt under $N_2$. The reaction mixture was poured into a saturated aqueous solution of $NH_4Cl$. The organic layer was separated, washed with water, dried and concentrated to give crude diketone (2.8 g, 99%). The diketone (2.8 g, 10.33 mmol) was dissolved in a mixture of 36% HCl (2 mL) and AcOH (25 mL) and heated at 100° C. for 1 h. The reaction mixture was cooled to rt, diluted with water and extracted with EtOAc. The organic layer was washed with water, brine, dried and concentrated to give the crude cyclized product (1.96 g, 74%). A mixture of the cyclized product (500 mg, 1.97 mmol) and pyridinium hydrochloride (5 g) was heated at 190° C. for 1 h. The reaction mixture was cooled to rt, diluted with water, neutralized with $NaHCO_3$ and filtered to give 2-(6-hydroxypyridin-3-yl)-chromen-4-one (480 mg, 98%). MS (ES) m/z: 240.92 (M+1), 239.89 (M); Mp. 296-297° C.

Example 49 dimethoxy-2-(4'-hydroxy-phenyl)-quinolin-4-one. MS (ES) m/z: 298.21 (M+1), and 284.20.

Example 50

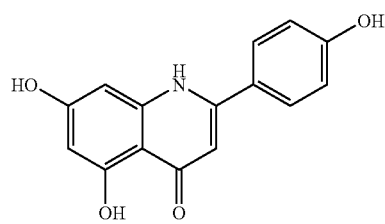

5,7-Dihydroxy-2-(4-hydroxyphenyl)-quinolin-4(H)-one

In a 50 mL round-bottomed flask fitted with condenser and magnetic stirrer, 5,7-dimethoxy-2-(4'-hydroxy-phenyl)-quinolin-4-one (1.0 g, 3.36 mmol) and 48% HBr (15 mL) were taken. The mixture was heated to reflux for 5 h. The reaction mixture was cooled to rt, and the water was removed under reduced pressure to give a crude product, which was purified by column chromatography using DCM:EtOAc:MeOH (6:3:1) to give 100 mg of 5,7-dihydroxy-2-(4-hydroxyphenyl)-quinolin-4(H)-one (11%). MS (ES) m/z: 270.13 (M+1).

Example 51

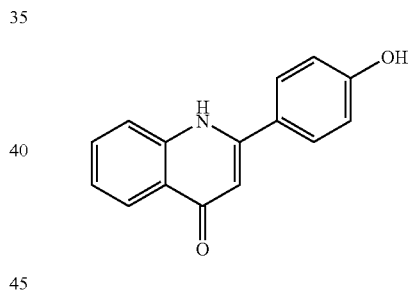

2-(4-Hydroxy-phenyl)-1H-quinolin-4-one

In a 50 mL round-bottomed flask fitted with condenser and magnetic stirrer were placed 2-amino acetophenone (1.0 g, 7.39 mmol), THF (15 mL) and $Et_3N$ (2.39 g, 23.64 mmol). To the solution p-methoxy benzoyl chloride (1.32 g, 7.76 mmol) in THF (15 mL) was added slowly at 0° C. and stirred for 30 min at 0° C. Then the reaction mixture was stirred for 24 h at rt under nitrogen. The reaction mixture was poured into ice water. The crude product was collected and crude product was purified by column chromatography using 25% EtOAc in hexane to give 1.865 g of N-(2-acetylphenyl)-4-methoxybenzamide (93%).

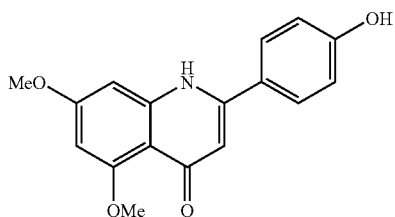

5,7-Dimethoxy-2-(4'-hydroxy-phenyl)-quinolin-4-one

In a 50 mL round-bottomed flask fitted with condenser and magnetic stirrer, 3,5-dimethoxy aniline (1.0 g, 6.52 mmol) and polyphosphoric acid (12 g) were taken. The mixture was heated 90-100° C. Then 4-hydroxy benzoyl methyl ester (1.26 g, 6.52 mmol) was added slowly over 1.5 h. After addition reaction mixture was heated for further 2 h. The reaction mixture was cooled to rt, and diluted with water. The precipitates were filtered to give a crude product, which was heated at 100° C. in concentrated HCl (10 mL) for 3 h. Then cooled the reaction mixture to rt and filtered the precipitates. The product was purified by column chromatography using 10% MeOH in dichloromethane to give 50 mg of 5,7-

To a suspension of N-(2-acetylphenyl)-4-methoxybenzamide (0.865 g, 3.2 mmol) in t-butanol (12 mL), was added potassium t-butoxide (1.57 g, 12.8 mmol). The reaction mixture was heated at 70° C. for 24 h under $N_2$. The mixture was cooled to rt and poured into 30 mL of saturated $NH_4Cl$. The solids were collected and purified by column chromatography using 10% MeOH in DCM to give 398 mg of 1-(2-aminophenyl)-3-(4-methoxy-phenyl)-propane-1,3-dione (49%).

1-(2-Amino-phenyl)-3-(4-methoxy-phenyl)-propane-1,3-dione (375 mg, 1.49 mmol) was dissolved in 48% HBr (15 mL) and refluxed for 16 h. The solvent was removed at reduced pressure. The solids were taken into water and neutralized by NaHCO₃. Solids were collected and purified by column chromatography using 5% MeOH in DCM to give 350 mg of 2-(4-hydroxy-phenyl)-1H-quinolin-4-one (98%). MS (ES): m/z: 238.1 (M+1).

Example 52

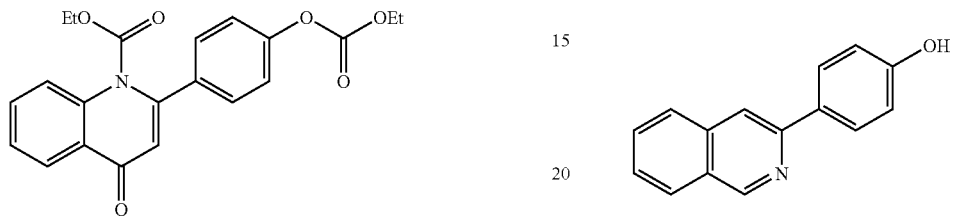

2-(4-Ethoxycarbonyloxy-phenyl)-4-oxo-4H-quinoline-1-carboxylic acid ethyl ester

In a 50 mL round-bottomed flask fitted with condenser and magnetic stirrer were placed 2-(4-hydroxy-phenyl)-1H-quinolin-4-one (250 mg, 1.054 mmol), DCM (30 mL), ethylchloroformate (252 mg, 2.32 mmol) and Et₃N (234 mg, 2.32 mmol) and stirred for overnight at rt. Solvent was removed and crude product was purified by column chromatography using DCM to gave 240 mg of 2-(4-ethoxycarbonyloxy-phenyl)-4-oxo-4H-quinoline-1-carboxylic acid ethyl ester (50%). MS (ES) m/z: 382.23 (M+1), 324.21, and 310.18.

Example 53

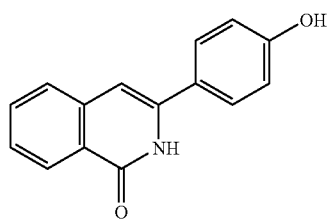

3-(4-Hydroxyphenyl)-2H-isoquinolin-1-one

To a solution of n-methyl-o-toluamide (2.0 g, 13.4 mmol) in THF (30 mL), n-butyl lithium (12.3 mL, 30.8 mmol, 2.5 M solution in hexane) was added slowly under N₂ with cooling (ice-salt bath) maintaining the temperature below 20° C. After addition, the mixture was stirred for 1 h at 0° C., then cooled to −50° C. A solution of 4-methoxy benzonitrile (2.14 g, 16.08 mmol) in THF (5 mL) was added quickly. The cooling bath was removed and the reaction was allowed to warm to rt. A saturated aqueous NH₄Cl solution was added during cooling, and the solid was isolated by filtration to give the methoxy compound (2.2 g, 65%). The methoxy compound (750 mg, 2.98 mmol) was dissolved in a 50 mL flask and pyridinium hydrochloride (10 g) was added. The mixture was heated at 190° C. for 2 h, then cooled to rt. The reaction was then diluted with water, neutralized with NaHCO₃ and the solid was isolated by filtration to give 600 mg of 3-(4-hydroxyphenyl)-2H-isoquinolin-1-one (84%). MS (ES) m/z: 238.92 (M+1), 237.89 (M); Mp. 239-241° C.

Example 54

4-Isoquinolin-3-yl-phenol

To a solution of 2-bromobenzaldehyde (1.85 g, 10 mmol) and 4-methoxyphenyl acetylene (1.58 g, 12 mmol) in 40 mL of triethylamine were added dichlorobis(triphenylphosphine) palladium(II) (140 mg, 2 mol %) and copper(I) iodide (20 mg, 1 mol %). The reaction mixture was heated at 50° C. under nitrogen for 3 h. The reaction mixture was cooled to room temperature and the ammonium salt was removed by filtration. The filtrate was concentrated under reduced pressure. Purification of the crude compound by column chromatography (SilicaGel 230-400 mesh; 10% ethyl acetate in hexanes as eluent) afforded of 2-(4-methoxy phenylethynyl)benzaldehyde (2.1 g, 89%).

2-(4-Methoxyphenylethynyl)benzaldehyde (2.06 g, 8.73 mmol) and t-butylamine (3.83 g, 52.4 mmol) were stirred under nitrogen for 24 h at room temperature. The resulting mixture was extracted with ether and the organic layer was dried over anhydrous Na₂SO₄, concentrated to give the imine (2.4 g, 94%) which was used in the next step without further purification. To a solution of this imine (2.39 g, 8.2 mmol) in 100 mL anhydrous DMF was added (0.156 g, 0.82 mmol) copper(I) iodide and flushed with nitrogen. The reaction mixture was heated at 100° C. for 4 h. The mixture was cooled to room temperature, and diluted with ether (200 mL). The organic layer was washed with saturated aqueous ammonium chloride (3×100 mL). The organic layer was dried over anhydrous Na₂SO₄ and concentrated to give the crude compound as a dark coloured solid. Purification by column chromatography (SilicaGel 230-400 mesh; 10% ethylacetate in hexanes as eluent) afforded 3-(4-methoxyphenyl)isoquinoline (1.064 g, 55%) as a white solid. The 3-(4-methoxyphenyl)isoquinoline (1.05 g, 4.47 mmol) was suspended in 30 mL hydroiodic acid and 12 mL of acetic acid was added. The reaction mixture was stirred at 110° C. for 2 h, then cooled to room temperature. The precipitate formed was filtered off, washed with acetic acid (2×5 mL) and dried under vacuum to give a yellow solid. The crude compound was purified by triturating with 5% methanol in ether to give 4-isoquinolin-3-yl-phenol (0.83 g, 84%) as a white powder. MS (ES) m/z: 222.89 (M+1), 221.86 (M); Mp. 218-219° C.

Example 55

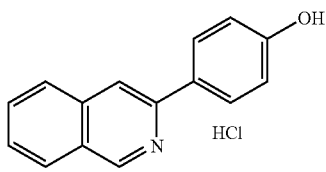

4-(Isoquinolin-3-yl)phenol hydrochloride

HCl (0.4 mL, 2 N) was added to 4-isoquinolin-3-yl-phenol (0.044 g, 0.2 mmol) and the solution was heated at 60° C. for 10 min, resulting in a yellow solid. The reaction mixture was evaporated to dryness to give 4-(isoquinolin-3-yl)phenol hydrochloride (0.45 g, 77%). MS (ES) m/z: 222.96 (M+1), 221.95 (M); $^{13}$C-NMR (DMSO-$d_6$): δ 180.2, 149.9, 138.8, 130.0, 129.6, 129.5, 127.8, 126.7, 116.7.

Example 56

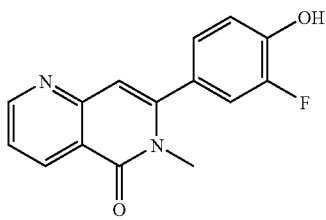

7-(3-Fluoro-4-hydroxyphenyl)-6-methyl-1,6-naphthyridin-5(6H)-one

A suspension of 2-methyl nicotinic acid (1.5 g, 10.94 mmol) in DCM (30 mL), triethylamine (1.16 g, 11.48 mmol) and oxlyl chloride (2.77 g, 21.87 mmol) were stirred at rt for 16 h. The solvent and excess of oxalyl chloride were removed at reduced pressure. The solid was dissolved in DCM (10 mL) and methylamine hydrochloride (1.02 g, 32.81 mmol) was added on cooling followed by stirring at rt for 4 h. The solvent was removed and the crude product was purified by chromatography by using 5% MeOH in DCM to give 1.4 g of the amide product (95%). To a solution of the amide (1.35 g, 8.99 mmol) in THF (25 mL), was slowly added n-butyl lithium (8.3 mL, 20.68 mmol, 2.5 M solution in hexane) under N$_2$ with cooling (ice-salt bath), maintaining the temperature below 20° C. After addition, the mixture was stirred for 1 h at 0° C. The mixture was cooled to −50° C. and a solution of 4-methoxy-3-fluoro benzonitrile (1.63 g, 10.79 mmol) in THF (10 mL) was added quickly. The cooling bath was removed and the mixture was allowed to warm to rt. Saturated NH$_4$Cl solution was added under cooling, and the layers were separated. The organic layer was washed with water, brine, and dried over Na$_2$SO$_4$. After concentration, the crude product was purified by chromatography using 5% MeOH in DCM to give 918 mg of the enamine (34%). To a suspension of the enamine (400 mg, 1.33 mmol) in EtOH (15 mL) was added conc. HCl (2 mL). The mixture was heated at 80° C. for 2 h. The reaction mixture was cooled to rt and the solvent was removed to give 400 mg of crude methoxy compound (94%). In a 50 mL flask were placed the methoxy compound (400 mg, 1.40 mmol) and pyridinium hydrochloride (6 g), followed by heating of the mixture at 190° C. for 4 h. The flask was then cooled to rt, diluted with water, neutralized with NaHCO$_3$ and the solid was filtered to afford 160 mg of 7-(3-fluoro-4-hydroxyphenyl)-6-methyl-1,6-naphthyridin-5(6H)-one (42%). MS (ES) m/z: 271.97 (M+1), 270.96 (M); Mp. 182-184° C.

Example 57

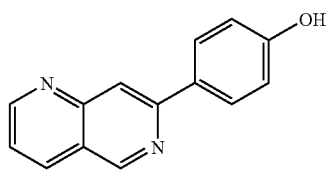

4-(1,6-Naphthyridin-7-yl)phenol

To a solution of 2-bromo-3-pyridinecarboxaldehyde (1.86 g, 10 mmol) and 4'-methoxy phenylacetylene (1.58 g, 12 mmol) in triethylamine (40 mL) were added dichlorobis (triphenylphosphine) palladium(II) (140 mg, 2 mol %) and copper (I) iodide (20 mg, 1 mol %). The reaction mixture was heated at 50° C. under nitrogen for 3 h, then cooled to room temperature. The ammonium salt was removed by filtration. The filtrate was concentrated under reduced pressure leaving 2-(4-methoxy phenylethynyl)pyridine-3-carboxaldehyde (2.35g, 99%) as yellow solid. 2-(4-Methoxyphenylethynyl) pyridine-3-carboxaldehyde (2.28 g, 9.60 mmol) and tert-butylamine (3.83 g, 60 mmol) were stirred under nitrogen for 24 h at rt. The resulting mixture was extracted with ether and dried over anhydrous Na$_2$SO$_4$. Removal of solvent gave the imine (2.72 g, 97%) which was used in next step without further purification. To a solution of this imine (2.7 g, 9.23 mmol) in 50 mL anhydrous DMF was added (0.190 g, 0.1 mmol) copper (I) iodide. The reaction mixture was heated at 100° C. for 4 h, then cooled to room temperature and diluted with ether (200 mL). The organic layer was washed with sat. aqueous ammonium chloride solution (3×100 mL). The organic layer was dried over anhydrous Na$_2$SO$_4$. Removal of solvent gave the crude compound as a dark colored solid. Purification by column chromatography (Silica Gel 230-400 mesh; 30% ethyl acetate in hexanes as eluent) afforded 7-(4-methoxy phenyl)[1,6]naphthridine (0.730 g, 33%) as a brown solid. To a solution of 7-(4-methoxyphenyl) [1,6]naphthridine (0.485 g, 2.05 mmol) in anhydrous N-methyl -2-pyrrolidinone (5 mL) was added thiophenol (0.25 g, 2.26 mmol) and potassium carbonate (0.028 g, 0.205 mmol). The reaction mixture was stirred at 190° C. for 1 h under nitrogen. The reaction mixture was cooled to room temperature. The crude compound was adsorbed onto silica gel and purified by column chromatography (Silica Gel 230-400 mesh; 20-70% ethyl acetate in hexanes as fluent) to give 4-(1,6-naphthyri-

Example 58

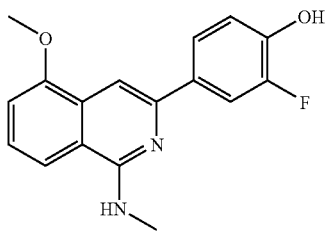

2-Fluoro-4-(5-methoxy-1-(methylamino)isoquinolin-3-yl)phenol

To a suspension of 2-methyl-3-methoxy benzoic acid (2.0 g, 12.03 mmol) in $CH_2Cl_2$ (30 mL), oxalyl chloride (3.05 g, 24.07 mmol) was added and stirred at room temperature for 16 h. The solvent and excess of oxalyl chloride were removed at reduced pressure. The solid was dissolved in $CH_2Cl_2$ (10 mL) and methyl amine (1.12 g, 36.1 mmol) was added on cooling and the mixture was stirred at room temperature for 4 h. The solvent was removed and the crude product was purified by chromatography using 5% methanol in $CH_2Cl_2$ to give the amide product (1.67 g, 78%). To a solution of the amide (946 mg, 5.28 mmol) in THF (20 mL) was added n-butyl lithium (4.85 mL, 12.14 mmol, 2.5 M solution in hexane) was added slowly under $N_2$ with cooling (ice-salt bath) maintaining temperature below −20° C. After completion of addition, the mixture was stirred for 1 h at 0° C., then cooled to −50° C. and a solution of 4-O-TBDMS-3-fluoro benzonitrile (1.46 g, 5.8 mmol) in THF (10 mL) was added quickly. The cooling bath was removed and the reaction mixture was allowed to warm to room temperature. Saturated $NH_4Cl$ solution was added under cooling. The organic layer was washed with water, brine, dried over $Na_2SO_4$ and concentrated to give the crude product, which was purified by chromatography using 5% methanol in $CH_2Cl_2$, to give two products: An enamine (260 mg) and a cyclized product (450 mg). To a suspension of the enamine (400 mg, 1.33 mmol) in ethanol (15 mL), conc. HCl (2 mL) was added and heated at 80° C. for 2 h. The reaction mixture was cooled to room temperature and the solvent was removed and neutralized by $NaHCO_3$ to give 2-fluoro-4-(5-methoxy-1-(methylamino)isoquinolin-3-yl)phenol (150 mg, 83%). MS (ES) m/z: 300.01 (M+1), 299.00 (M); Mp. 185-187° C.

Example 59

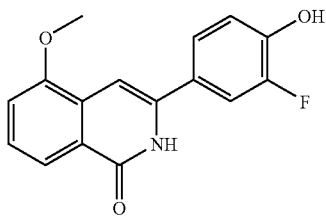

3-(3-Fluoro-4-hydroxyphenyl)-5-methoxyisoguino-lin-1(2H)-one

To a suspension of 2-methyl-3-methoxy benzoic acid (2.0 g, 12.03 mmol) in DCM (30 mL), oxalyl chloride (3.05 g, 24.07 mmol) was added and stirred at rt for 16 h. The solvent and excess of oxylyl chloride were removed at reduced pressure. The solid was dissolved in DCM (10 mL) and methyl amine (1.12 g, 36.1 mmol) was added on cooling and the mixture was stirred at rt for 4 h. The solvent was removed and the crude product was purified by chromatography using 5% MeOH in DCM to give the amide product (1.67 g, 78%). To a solution of the amide (946 mg, 5.28 mmol) in THF (20 mL) was added n-butyl lithium (4.85 mL, 12.14 mmol, 2.5 M solution in hexane) was added slowly under $N_2$ with cooling (ice-salt bath) maintaining temperature below −20° C. After completion of addition, the mixture was stirred for 1 h at 0° C., then cooled to −50° C. and a solution of 4-O-TBDMS-3-fluoro benzonitrile (1.46 g, 5.8 mmol) in THF (10 mL) was added quickly. The cooling bath was removed and the reaction mixture was allowed to warm to rt. Saturated $NH_4Cl$ solution was added under cooling. The organic layer was washed with water, brine, dried over $Na_2SO_4$ and concentrated to give the crude product, which was purified by chromatography using 5% MeOH in DCM, to give two products: an enamine (260 mg) and a cyclized product (450 mg). To a suspension of the cyclized product (450 mg, 1.1 mmol) in EtOH (15 mL), conc. HCl (2 mL) was added and heated at 60° C. for 3 h. The reaction mixture was cooled to rt and the solvent was removed and purified by chromatography using 5% MeOH in DCM to give 85 mg of product (26%). MS (ES) m/z: 286.11; Mp. 289-291° C.

Example 60

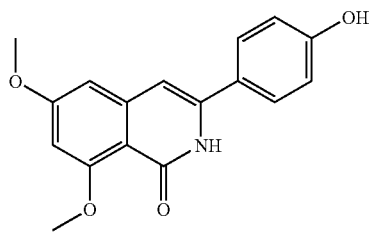

3-(4-Hydroxyphenyl)-6,8-dimethoxyisoquinolin-1(2H)-one

To a suspension of 2-methyl-4,6-dimethoxy benzoic acid (2.8 g, 14.27 mmol) in $CH_2Cl_2$ (30 mL), oxalyl chloride(3.62 g, 28.54 mmol) was added and the mixture was stirred at rt for 16 h. The solvent and excess of oxalyl chloride were removed at reduced pressure. The solid was dissolved in $CH_2Cl_2$ (10 mL) and methyl amine hydrochloride (1.33 g, 42.81 mmol) was added on cooling and the mixture was stirred at rt for 4 h. The solvent was removed and the crude product was purified by chromatography by using 5% methanol in $CH_2Cl_2$, to give 1.3 g of the amide intermediate in 43% yield. To a solution of the amide intermediate (1.29 g, 6.16 mmol) in THF (30 mL), n-butyl lithium (5.6 mL, 14.18 mmol, 2.5 M solution in hexane) was added slowly under $N_2$ with cooling( ice-salt bath) maintaining the temperature below 20° C. The mixture was stirred for 1 h at 0° C., then cooled to −50° C. and a solution of 4-O-TBDMS-benzonitrile (1.58 g, 6.78 mmol) in THF (10 mL) was added quickly. The cooling bath was removed and allowed to warm to rt and stirred for 16 h at rt. Saturated aqueous NH$_4$Cl solution was added with cooling, and the layers were separated. The organic layer was washed with water, brine, dried over Na$_2$SO$_4$ and concentrated to give the crude intermediate, which was purified by chromatography using 5% methanol in CH$_2$Cl$_2$, to give two products (1) 678 mg of isoquinoline in 26% yield and (2) 780 mg of quinalone product in 27% yield. To a suspension of the above quinalone product (2) (780 mg, 1.65mmol) in ethanol (20 mL), conc. HCl (2 ml) was added and the mixture was heated at 70° C. for 2 h. The reaction mixture was cooled to rt and the solvent was removed and purified by chromatography using 5% methanol in CH$_2$Cl$_2$ to give 3-(4-hydroxyphenyl)-6,8-dimethoxyisoquinolin-1(2H)-one (215 mg, 44%). MS (ES) m/z: 297.93 (M); Mp. 245-247° C.

Example 61

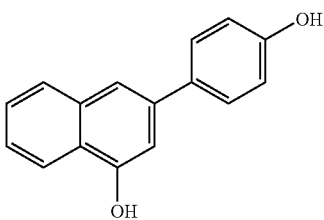

3-(4-Hydroxyphenyl)naphthalene-1-ol

A 100 mL flask equipped with a condenser was charged with phenylacetyl chloride (5.8 mL 0.0435 mol) and 4-methoxyphenylacetylene (3.2 g, 0.024 mol). The condenser was connected to a drying tube. The flask was heated for 16 h at 180° C. under nitrogen using an oil bath. The cooled dark brown mixture was poured into 30 mL water and DCM was added. The pH was adjusted to 7.0 by a NaOH solution. The DCM was evaporated and the residue was passed through a column (hexane:EtOAc:DCM 14:1:1) to give 3.4 g (38.2%) of product. A 50 mL flask was charged with the product (0.91 g), 0.138 g KOH, water (0.3 mL) and MeOH (10 mL). The mixture was stirred for 12 h at rt, followed by neutralization with HCl to pH 7.0. The aqueous phase was extracted with EtOAc and purified via column chromatography (hexane: EtOAc 10:1) to yield 0.42 g of product (68%). The product 3-(4-methoxy)phenyl-1-naphthol (0.290 g) and 57% HI (8 mL) were added to a 50 mL flask with reflux condenser. The flask was heated to 110° C. for 7 h, then cool to rt. The pH was adjusted to 7.0 with NaHCO$_3$ solution and extracted with EtOAc. The organic layer was further washed with brine and dried with sodium sulfate. The residue was washed with DCM to give 234 mg of 3-(4-hydroxyphenyl)naphthalene-1-ol (73.6%). MS (ES) m/z: 236.09 (M), 235.05 (M–1).

Example 62

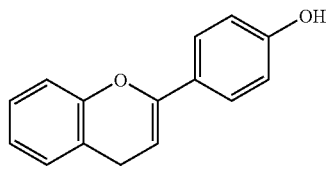

4-(4H-Chromen-2-yl)-phenol

A suspension of aluminum chloride (680 mg, 5.1 mmol) in dry THF (50 mL) was cooled to 0° C. under nitrogen. LAH (580 mg, 15.5 mmol) was added to the above solution and the resulting mixture was stirred for 20 min at 0° C., and then at rt for additional 20 min, and cooled down to –50° C. 4'-Hydroxyflavone (400 mg, 1.7 mmol) dissolved in 60 mL of THF was added slowly. The reaction mixture was stirred at –50° C. for 2 h and then for 2 h at rt. The reaction was quenched by careful addition of water (traces, to decompose LiAlH$_4$) and the solvent was removed under reduced pressure. The crude product was initially purified by crystallization from MeOH, and then further purified by column chromatography (silica gel, 5-20% EtOAc/hexane) and repeated crystallization from MeOH to afford 109 mg of 4-(4H-chromen-2-yl)-phenol (29%). MS (ES) m/z: 225.10 (M+1), 149.04.

Example 63

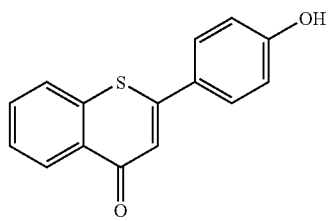

2-(4-Hydroxy-phenyl)-thiochromen-4-one

In a 50 mL round-bottomed flask fitted with condenser and magnetic stirrer, thiophenol (4.0 g, 36.30 mmol) and polyphosphoric acid (6 g) were heated at 90-100° C. Then 4-methoxybenzoyl AcOH methyl ester (4.03 g, 18.15 mmol) was added slowly during 1.5 h. After addition, reaction mixture was heated for an additional 2 h. The reaction mixture was then cooled to the rt, diluted with water and precipitates were filtered to give the crude product, which was purified by column chromatography using 30% EtOAc in hexane to afford 2-(4-methoxyphenyl)-thiochromen-4-one (2.05 g, 43%).

In a 50 mL round-bottomed flask fitted with condenser and magnetic stirrer, 2-(4-methoxyphenyl)-thiochromen-4-one (500 mg, 1.86 mmol) and DCM (20 mL) were taken. The mixture was cooled to 0° C. and BBr$_3$ (933 mg, 3.72 mmol, 1M solution in DCM) was added slowly at 0° C. Then the reaction mixture was stirred for overnight at rt under N$_2$. The unreacted BBr$_3$ was carefully quenched by addition of MeOH under cooling. Solvent was removed under reduced pressure to give crude product, which was purified by column chromatography using 5% MeOH in DCM to afford 2-(4-hydroxy-phenyl)-thiochromen-4-one (380 mg, 80%). MS (ES) m/z: 255.02 (M+1).

Example 64

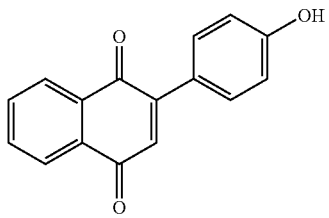

2-(4-Hydroxy-phenyl)-[1,4]naphthoquinone

To a mixture of 2-bromo-1,4-naphthoquinone (1.0 g, 4.22 mmol), 4-hydroxyphenylboronic acid (640 mg, 4.64 mmol), potassium phosphate (3.135 g, 14.76 mmol), tricyclohexylphosphine (118 mg, 0.422 mmol), toluene (20 mL) and water (1 mL) was added palladium acetate (47 mg, 0.21 mmol) under N$_2$. The reaction mixture was heated to 100° C. for 3 h. The reaction was cooled to rt and water was added. The mixture was extracted with EtOAc, and the combined organic extracts were washed with water and brine. The organic phase was separated, dried and concentrated to give crude product. Purification by column chromatography, using 10% EtOAc in hexane, gave 480 mg of 2-(4-hydroxy-phenyl)-[1,4]naphthoquinone (45%). MS (ES) m/z: 251.03 (M+1).

Example 65

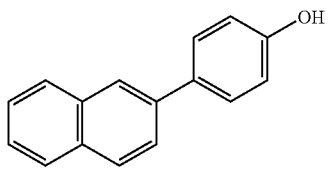

4-Naphthalen-2-yl-phenol

To a mixture of 2-bromonaphthalene (4.0 g, 19.32 mmol), 4-hydroxyphenylboronic acid (2.9 g, 21.24 mmol), potassium phosphate (14.35 g, 67.61 mmol), tricyclohexyl phosphine (542 mg, 1.93 mmol), toluene (80 mL) and water (4 mL) was added palladium acetate (217 mg, 0.965 mmol) under N$_2$. The reaction mixture was heated to 100° C. for 24 h and then cooled to rt. Water was added and the mixture was extracted with EtOAc. The organic layer was separated, washed with water, brine, dried and concentrated to give crude product. Purification by column chromatography using 10% EtOAc in hexane afforded 105 mg of 4-naphthalen-2-yl-phenol. MS (ES) m/z: 220.07 (M) and 219.04 (M−1).

Example 66

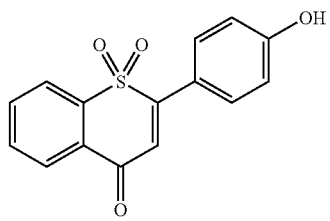

2-(4-Hydroxy-phenyl)-1,1-dioxo-1H-1λ$^6$-thiochromen-4-one

In a 50 mL round-bottomed flask fitted with condenser and magnetic stirrer were placed 2-(4-hydroxy-phenyl)-thiochromen-4-one (1.298 g, 5.1 mmol), Ac$_2$O (625 mg, 6.12 mmol), Et$_3$N (619 mg, 6.12 mmol) and catalytic amount of DMAP in DCM (10 mL) and the reaction mixture was stirred for 24 h at rt. The reaction mixture was poured into water and extracted with EtOAc. The organic layer washed with water, dried and concentrated to afford the 2-(4-acetoxy-phenyl)-thiochromen-4-one (1.4 g, 96%).

To a stirred solution of 2-(4-acetoxy-phenyl)-thiochromen-4-one (800 mg, 2.69 mmol) in DCM (260 mL), m-CPBA (665 mg, 2.69 mmol) was added and the reaction mixture was stirred at rt for 48 h. The reaction mixture was diluted with DCM and washed with NaHCO$_3$ solution. The organic layer was separated, washed with water, brine, dried and concentrated to give crude product, which was purified by column chromatography, using EtOAc:hexane:DCM (1:2:7) to give 260 mg of 2-(4-acetoxy-phenyl)-1,1-dioxo-1H-1λ$^6$-thiochromen-4-one.

To a solution of 2-(4-acetoxy-phenyl)-1,1-dioxo-1H-1λ$^6$-thiochromen-4-one (260 mg, 0.79 mmol) in MeOH:THF (5 mL: 5 mL), K$_2$CO$_3$ (133 mg, 0.95 mmol) was added and stirred for 2 h at rt Then the reaction mixture was neutralized by dilute HCl and extracted by EtOAc, the combined organic layer was washed with water, brine, dried and concentrated to give a crude product, which was purified by column chromatography using 50% EtOAc in hexane, to give 134 mg (59%) of 2-(4-hydroxy-phenyl)-1,1-dioxo-1H-1λ$^6$-thiochromen-4-one. MS (ES) m/z: 286.05 (M), 285.01 (M−1); Mp. 222-224° C.

Example 67

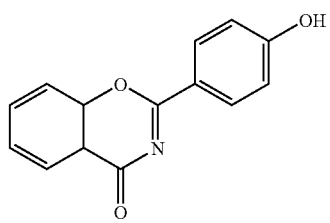

2-(4-Hydroxyphenyl)benzo[e][1,3]oxazin-4-one

Salicylamide (6.85 g, 50 mmol) and 4-acetoxybenzoyl chloride (10.9 g, 55 mmol) were dissolved in 35 mL anhydrous xylene. Anhydrous pyridine (0.5 mL) was added and the reaction mixture was refluxed under nitrogen for 12 h. Water was removed by a Dean-Stark apparatus. The mixture was cooled to rt, and the xylene was removed under vacuum. Acetone (100 mL) was added and the mixture was stirred for 10 min. The solid was filtered off, washed with acetone and dried under vacuum to give the crude compound (3.0 g). The crude compound (1.5 g) was purified by column chromatography (SilicaGel 70-230 mesh; 2-5% MeOH in DCM as eluent) to give 770 mg of 2-(4-hydroxyphenyl)benzo[e][1,3]oxazin-4-one (12%) as pale yellow solid. MS (ES) m/z: 240.02; Mp. 273-275° C.

Example 68

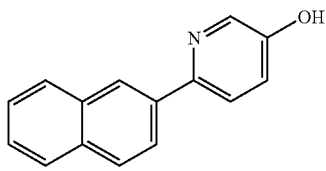

6-Naphthalen-2-yl-pyridin-3-ol

To a solution of 2-bromo-5-hydroxypyridine (1.04 g, 6 mmol) in 25 mL anhydrous THF was added 2-naphthylboronic acid (1.03 g, 6 mmol) and 2 M aq. sodium carbonate (9 mL, 18 mmol). To this reaction mixture was added palladium tetrakistriphenylphosphine (0.7 g, 0.6 mmol) and the mixture was stirred at rt for 15 h under nitrogen. The reaction mixture was diluted with EtOAc, the organic layer was washed with water (50 mL), brine (50 mL) and dried over anhydrous Na$_2$SO$_4$. Removal of solvent gave a white powder which was purified by column chromatography (Silica Gel 230-400 mesh; 3% MeOH in DCM) to give 6-naphthalen-2-yl-pyridin-3-ol (0.225 g, 17%). MS (ES) m/z: 222.96 (M+1), 221.93 (M); Mp. 168-169° C.

Example 69

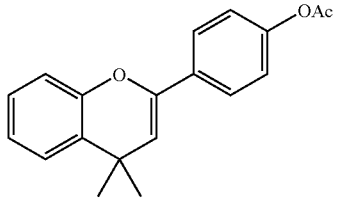

4-(4,4-Dimethyl-4H-chromen-2-yl)phenyl acetate

To a suspension of 4'-hydroxy flavone (500 mg, 2.098 mmol) in toluene (15 mL) was cooled to 0° C. under N$_2$. The apparatus was evacuated and filled with N$_2$ three times and trimethylaluminum solution (2M in toluene, 5.02 mL, 10.05 mmol) was added over 30 min. The resulting mixture was allowed to warm to rt over 3 h and stirred for 14 h at rt. The reaction mixture was quenched by addition of 2 N HCl with cooling, and extracted with EtOAc. The combined organic layers were washed with water, brine, dried over Na$_2$SO$_4$ and concentrated to give crude product, which was purified by chromatography using neutral Al$_2$O$_3$, to give the dimethyl product (150 mg, 28%). In a 50 mL round-bottomed flask fitted with condenser and magnetic stirrer were placed dimethyl product (150 mg, 0.59 mmol), Ac$_2$O (67 mg, 0.65 mmol), DCM (10 mL) and Et$_3$N (66 mg, 0.65 mmol) then the reaction mixture was stirred for 24 h at rt. The reaction mixture was poured into water and extracted with EtOAc. The organic layer was washed with water, dried and concentrated to give 150 mg of 4-(4,4-dimethyl-4H-chromen-2-yl)phenyl acetate (85%). MS (ES) m/z: 295.95 (M+1), 294.92 (M); Mp. 84-86° C.

Example 70

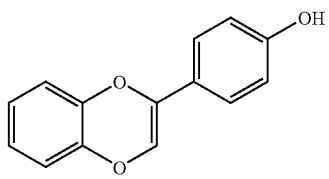

4-(Benzo[b][1,4]dioxin-2-yl)phenol

A mixture of 4-(benzo[b][1,4]dioxin-2-yl)phenyl acetate (270 mg, 1.0 mmol) in MeOH:THF (5 mL: 3 mL) and K$_2$CO$_3$ (167 mg, 1.2 mmol) was stirred for 30 min at rt. The solvent was removed under reduced pressure and water was added. The solution was neutralized by dilute HCl and the solid was isolated by filtration, washed well with water and dried to give 175 mg of 4-(benzo[b][1,4]dioxin-2-yl)phenol (77%). MS (ES) m/z: 225.97 (M), 224.93 (M−1); Mp. 137-140° C.

Example 71

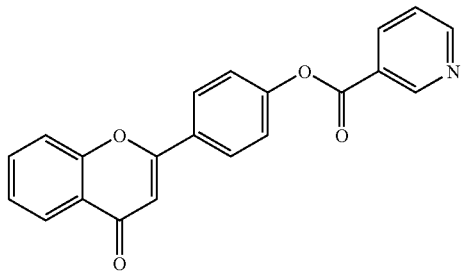

4-(4-oxo-4H-chromen-2-yl)-phenyl nicotinate

In a 50 mL round-bottomed flask fitted with condenser and magnetic stirrer were placed 2-(4-hydroxyphenyl)chromen-4-one (100 mg, 0.419 mmol), pyridine (5 mL) and nicotinoyl chloride (223 mg, 1.25 mmol). The reaction mixture was stirred for 24 h at rt under nitrogen. The solvent was removed under reduced pressure and crude product was purified by column chromatography using 50% EtOAc in hexane to give 100 mg of 4-(4-oxo-4H-chromen-2-yl)phenyl nicotinate (69%). MS (ES) m/z: 344.09 (M+1).

Example 72

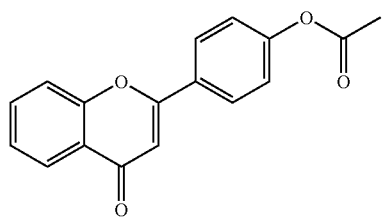

4-(4-oxo-4H-chromen-2-yl)phenyl acetate

In a 50 mL round-bottomed flask fitted with condenser and magnetic stirrer were placed 2-(4-hydroxyphenyl)chromen-4-one (150 mg, 0.63 mmol), Ac$_2$O (96 mg, 0.94 mmol), Et$_3$N (96 mg, 0.94 mmol) and catalytic amount of DMAP in DCM (2 mL) and then the reaction mixture was stirred for 24 h at rt. The reaction mixture was poured into water and extracted with EtOAc. The organic layer washed with water, dried and concentrated to gave 160 mg of acetic acid 4-(4-oxo-4H-chromen-2-yl)phenyl acetate (91%). MS (ES) m/z: 281.15 (M+1), and 239.12.

Example 73

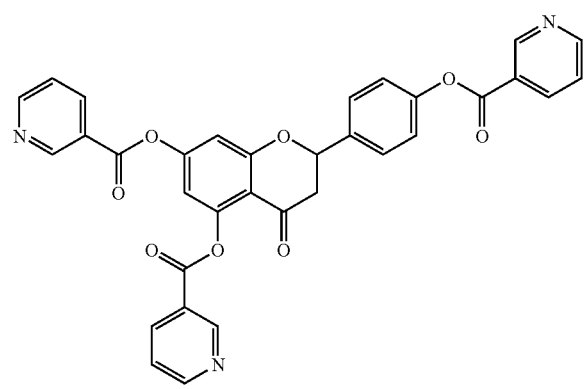

2-(4-(Nicotinoyloxy)phenyl)-4-oxochroman-5,7-diyl dinicotinate

In a 500 mL round-bottomed flask fitted with magnetic stirrer were placed naringenin (4',5,7-trihydroxyflavanone (5 g, 18.37 mmol)), DMF (80 mL) and nicotinic acid (9 g, 73.46 mmol). EDCl (14 g, 73.46 mmol) and DMAP (1 g) were added. The reaction mixture was stirred for 24 h at rt under nitrogen. The solid was filtered and washed with DMF. Crystallization from DCM-MeOH gave 5.2 g of the product. The filtrate was evaporated under reduced pressure and the residue was dissolved in DCM, which was washed with water and evaporated. The crude product was purified by column chromatography using toluene-acetone (2:1) to give 3.0 g of 2-(4-(nicotinoyloxy)phenyl)-4-oxochroman-5,7-diyl dinicotinate (76%). MS (ES) m/z: 588.25 (M+1), 294.75, and 196.83.

Example 74

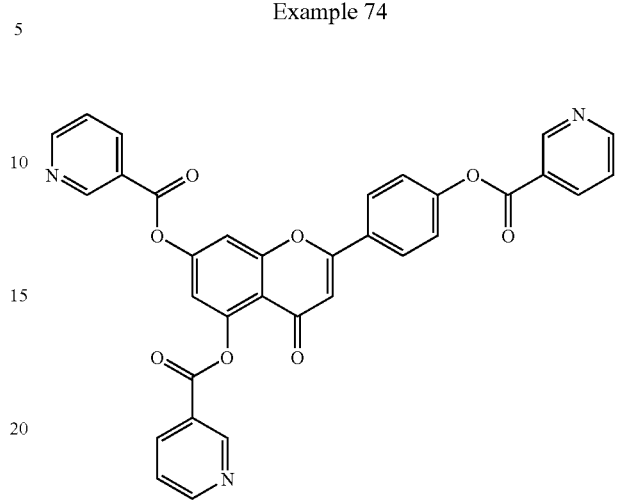

2-(4-Nicotinoyloxy)phenyl)-oxo-4H-chromene-5,7-diyl dinicotinate

In a 500 mL round-bottomed flask fitted with magnetic stirrer were placed apigenin (4',5,7-trihydroxyflavone (5 g, 18.50 mmol)) and pyridine (250 mL). The mixture was cooled at −10° C. and nicotinoyl chloride HCl (16.5 g, 92.70 mmol) was added. Then the reaction mixture was stirred for 24 h at rt under nitrogen. The solvent was removed under reduced pressure and the residue was dissolved in chloroform, which was washed with water and evaporated. The crude product was purified by crystallization from DCM-MeOH to give 7.5 g of 2-(4-nicotinoyloxy)phenyl)-oxo-4H-chromene-5,7-diyl dinicotinate (69%). MS (ES) m/z: 586.17 (M+1), 481.11, 293.70.

Example 75

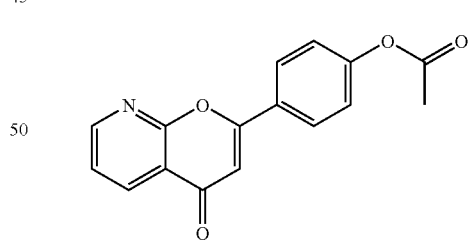

4-(4-Oxo-4H-pyrano[2,3-b]pyridine-2-yl)phenyl acetate

In a 50 mL round-bottomed flask fitted with condenser and magnetic stirrer were placed 2-(4-hydroxy-phenyl)-pyrano[2,3-b]pyridin-4-one (212 mg, 0.89 mmol), Ac$_2$O (99 mg, 0.97 mmol), and pyridine (5 mL). The reaction mixture was stirred for 24 h at room temperature. The reaction mixture was poured into water and extracted with EtOAc. The organic layer washed with water, dried and concentrated to afford 4-(4-oxo-4H-pyrano[2,3-b]pyridine-2-yl)phenyl acetate (240 mg, 96%). MS (ES) m/z: 282.89 (M+1), 281.92 (M); Mp. 167-169° C.

Example 76

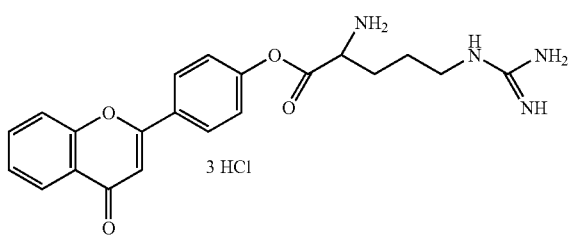

2-Amino-5-guanidino-pentanoic acid 4-(4-oxo-4H-chromen-2-yl)phenyl ester trihydrochloride To a solution of 4'-hydroxy flavone (277 mg, 1.16 mmol) in DMF (6 mL) were added diisopropyl ethylamine (451 mg, 4.49 mmol), EDCl (245 mg, 1.28 mmol), Boc-Argenine (580 mg, 1.22 mmol) and HOBt (157 mg, 1.16 mmol) and the mixture was stirred at rt for 24 h under $N_2$. The reaction mixture was diluted with water and the solid was filtered off. The solid product was dissolved in diethyl ether and the organic layer was washed with water, brine, dried over $Na_2SO_4$ and concentrated to give the Boc-protected product (730 mg, 90%). To a solution of the Boc-protected product (200 mg, 0.287 mmol) in DCM (15 mL), HCl gas was bubbled through for 6 h at 0° C. The solid was filtered off and washed with DCM to give 133 mg of 2-amino-5-guanidino-pentanoic acid 4-(4-oxo-4H-chromen-2-yl)phenyl ester trihydrochloride (69%). MS (ES) m/z: 394.93 (M−Arg), 238.86.

Example 77

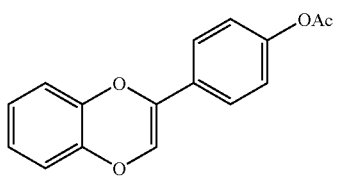

4-(Benzo[b][1,4]dioxin-2-yl)phenyl acetate

To a solution of 1,4-benzodioxane (5 g, 36.72 mmol) in $CCl_4$ (200 mL), NBS (14.38 g, 80.79 mmol) and AIBN (500 mg) were added under $N_2$. The mixture was heated at reflux for 12 h. The reaction mixture was cooled to rt. The solution was evaporated to give the crude product, which was purified by chromatography on neutral $Al_2O_3$ using 10% EtOAc in hexane to give the di-bromo compound (9.34 g, 86%). To a stirred solution of 2,3-dibromo-2,3-dihydro-1,4-benzodioxine (9.84 g, 33.45 mmol) in $Et_2O$ (150 mL), was added potassium t-butoxide (4.5 g, 40.14 mmol) under $N_2$. The mixture was stirred for 3 h at rt. The solid was filtered off and the solution was concentrated to give the crude product, which purified by chromatography on neutral $Al_2O_3$ using 10% EtOAc in hexane to give 2-bromodioxane (6.8 g, 95%). To a mixture of 2-bromodioxane (1.0 g, 4.69 mmol), 4-(4,4,5,5-tetramethyl-1,3-dioxaborolan-2-yl)phenyl acetate (1.23 g, 4.69 mmol), sodium bicarbonate (1.18 g, 14.07 mmol), THF (50 mL) and water (7 mL) was added tetrakis-triphenyl phosphine palladium (271 mg, 0.23 mmol) under $N_2$. The reaction mixture was heated to 110° C. for 5 h and then cooled to rt. Water was added and the mixture was extracted with EtOAc. The organic layer was separated, washed with water, brine, dried and concentrated to give crude product, which was purified by column chromatography, using 20% EtOAc in hexane to give 775 mg of 4-(benzo[b][1,4]dioxin-2-yl)phenyl acetate (62%). MS (ES) m/z: 269.92 (M+1), 268.91 (M); Mp. 123-125° C.

Example 78

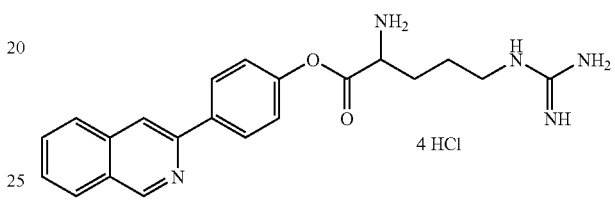

4-(Isoquinolin-3-yl)phenyl 2-amino-5-guanidinopentanoate tetrahydrochloride

HCl (0.4 mL, 2 N) was added to 4-isoquinolin-3-yl-phenol (0.133 g, 0.6 N) in anhydrous DMF (5 mL). To this mixture were added HOBt (0.081 g, 0.6 mmol), Boc-Arg-(Boc)$_2$-OH (0.285 g, 0.6 mmol), and EDCl (0.115 g, 0.6 mmol). N,N-Diisopropylethylamine (0.233 g, 1.8 mmol) was added and the mixture was stirred at rt for 24 h. Water (15 mL) was added and the white precipitate was filtered off, washed with water and dried under vacuum to give 0.3 g (74%) of the Boc-arginine derivative. The Boc derivative compound (0.3 g,) was dissolved in anhydrous dichloromethane (10 mL). HCl gas was bubbled into the solution at 0° C. for 4 h. A yellow precipitate was formed. The solvent was removed and the resulting sold was dried under vacuum. Triturating with ether gave 200 mg of 4-(isoquinolin-3-yl)phenyl 2-amino-5-guanidinopentanoate tetrahydrochloride (86%). MS (ES) m/z: 222.96 (M+1−Arg), 221.99 (M−Arg); Mp. 198-201° C.

Example 79

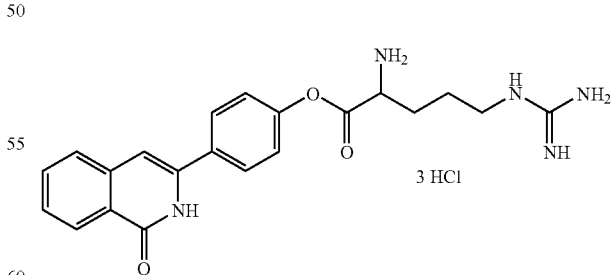

4-(1-Oxo-1,2-dihydroisoquinolin-3-yl)phenyl 2-amino-5-guanidinopentanoate trihydrochloride 3-(4-Hydroxyphenyl)-2H-isoquinolin-1-one (150 mg, 0.63 mmol) in DMF (5 mL), diisopropyl ethyl amine (245 mg, 1.89 mmol), EDCl (133 mg, 0.696 mmol), Boc-argenine (330 mg, 0.696 mmol) and HOBt (94 mg, 0.696 mmol) were stirred and stirred at rt for 24 h under nitrogen. The reaction mixture was diluted with water and the solid was collected by filtration. The solid was purified by column chromatography using 5% MeOH in DCM to give the tri-Boc ester product (375 mg 85%). HCl gas was bubbled through a solution of the tri-Boc ester (325 mg, 0.468 mmol) in DCM (10 mL) for 6 h at 0° C. The solid was filtered off and washed with DCM to give 170 mg of 4-(1-oxo-1,2-dihydroisoquinolin-3-yl)phenyl 2-amino-5-guanidinopentanoate trihydrochloride (72%). MS (ES) m/z: 237.25 (M−Arg); $^{13}$C-NMR (DMSO-d$_6$): δ 168.8, 163.4, 157.7, 151.0, 139.8, 139.5, 133.4, 132.8, 128.9, 127.4, 127.3, 127.25, 125.6, 122.6, 104.2, 55.6, 52.5, 27.7, 25.0.

Example 80

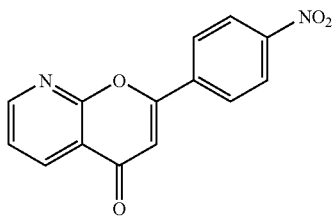

2-(4-Nitrophenyl)-4H-pyrano[2,3-b]pyridine-4-one

To a stirred solution of 2-methoxynicotinic acid (2.3 g, 15 mmol) in 75 mL anhydrous THF was added N-methyl morpholine (1.52 g, 15 mmol). The reaction mixture was cooled to −10° C. Ethylchloroformate (1.63 g, 15 mmol) was added dropwise at −10° C. The reaction mixture was stirred at −10° C. for 15 min. and then at rt for 10 h. Water (50 mL) was added, and the solution was extracted with ethyl acetate. The organic layer was separated, dried (Na$_2$SO$_4$), and concentrated to give a colorless liquid in 97% yield (3.29 g). To a solution of this colorless liquid (3.28 g, 14.57 mmol) and 4'-nitroacetophenone (2.477 g, 15 mmol) in anhydrous THF (75 mL) was added lithium bis(trimethylsilyl)amide 1.0M solution in THF (18 mL) at −30° C. over a period of 45 min. Stirring continued at −30° C. for 30 min. The reaction mixture was allowed to warm to rt. The stirring was continued for another 15 h at rt, and the reaction mixture was then diluted with ethyl acetate (200 mL). Saturated NH$_4$Cl solution (50 mL) was added. The organic layer was separated and dried over anhydrous Na$_2$SO$_4$. Removal of solvent gave the crude product which was triturated with ether to give 1-(2-methoxy pyridine-3-yl)-3-(4-nitrophenyl)propane-1,3-dione as yellow solid in 62% yield (2.79 g).

1-(2-methoxy pyridine-3-yl)-3-(4-nitrophenyl) propane-1,3-dione (2.16 g, 7.193 mmol) and pyridinium hydrochloride (12.47 g, 107.9 mmol) were mixed together and stirred at 190° C. for 2 h under nitrogen atmosphere. The reaction mixture was cooled to rt. Water (100 mL) was added, the solid was separated by filtration, washed with water and dried under vacuum. The crude compound was purified by column chromatography (SilicaGel 230-400 mesh; 2-5% methanol in CH$_2$Cl$_2$ as eluent) to give 2-(4-nitrophenyl)-4H-pyrano[2,3-b]pyridine-4-one as a brown solid in 43% yield (0.82 g). MS (ES) m/z: 268.88 (M); Mp. 261-263° C.

Example 81

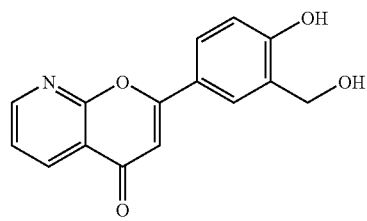

2-(4-Hydroxy-3-(hydroxymethyl)phenyl)-4H-pyrano[2,3-b]pyridine-4-one 2-(4-Hydroxy-3-methyl phenyl)-4H-pyrano[2,3-b]pyridine-4-one (0.91 g, 0.0036 mol), acetic anhydride (1.2 g, 0.0117 mol), DMAP (0.05 g) and triethylamine (10 mL) were added to a 50 ml flask and stirred overnight at rt. The solvent was removed and ethyl acetate (100 mL) was added and washed with water (80 mL), brine and dried over sodium sulfate. After the majority of the ethyl acetate was removed, hexane was added and the solid was isolated by filtration to give the acetylated intermediate (0.978 g, 92.0%).

The acetylated intermediate (0.50 g, 0.0017 mol) was dissolved into dry carbon tetrachloride (20 mL) and NBS (0.317 g, 0.00178 mol) was added. The reaction mixture was heated to reflux under a lamp for 3 h. After cooling the solid was filtered off and further washed with hot water to remove the succinimide. The methyl bromide was isolated by crystallization from DCM/Hexane (0.497 g, 78.2%).

The methyl bromide (0.49 g (0.0013 mol) and sodium acetate (1.07 g, 0.0131 mol) were mixed in acetic acid (20 mL) and heated to reflux for 16 hours. Acetic acid was removed and the residue was poured into water and extracted with ethyl acetate. The organic layer was washed with water, brine and dried in sodium sulfate. The solvent was removed and 0.50 g of the crude diacetylated compound was isolated. The diacetylated compound (0.50 g), potassium carbonate (0.45 g), and methanol (10 mL) were mixed and stirred for 3 hours. Acetic acid (2 mL) was added and the pH was adjusted to 5. The organic solvent was removed and the crude mixture was purified by column chromatography (DCM:MeOH 20:1) and then recrystallized to give 2-(4-hydroxy-3-(hydroxymethyl)phenyl)-4H-pyrano[3,2-b]pyridine-4-one (70 mg, 19.8%). MS (ES) m/z: 269.92 (M); Mp. 226-227° C.

Example 82

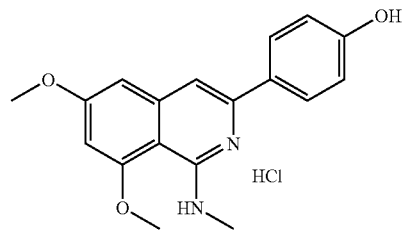

4-(6,8-Dimethoxy-1-(methylamino)isoquinolin-3-yl)phenol hydrochloride

To a suspension of 2-methyl-4,6-dimethoxy benzoic acid (2.8 g, 14.27 mmol) in $CH_2Cl_2$ (30 mL), oxalyl chloride (3.62 g, 28.54 mmol) was added and the mixture was stirred at rt for 16 h. The solvent and excess of oxalyl chloride were removed at reduced pressure. The solid was dissolved in $CH_2Cl_2$ (10 mL) and methyl amine hydrochloride (1.33 g, 42.81 mmol) was added on cooling and the mixture was stirred at rt for 4 h. The solvent was removed and the crude product was purified by chromatography by using 5% methanol in $CH_2Cl_2$, to give 1.3 g of the amide intermediate in 43% yield.

To a solution of the amide intermediate (1.29 g, 6.16 mmol) in THF (30 mL) under $N_2$ was slowly added n-butyl lithium (5.6 mL, 14.18 mmol, 2.5 M solution in hexane) with cooling (ice-salt bath), maintaining the temperature below 20° C. The mixture was stirred for 1 h at 0° C., then cooled to −50° C. and a solution of 4-O-TBDMS-benzonitrile (1.58 g, 6.78 mmol) in THF (10 mL) was added quickly. The cooling bath was removed and allowed to warm to rt and stirred for 16 h at rt. Saturated aqueous $NH_4Cl$ solution was added with cooling, and the layers were separated. The organic layer was washed with water, brine, dried over $Na_2SO_4$ and concentrated to give the crude intermediate, which was purified by chromatography using 5% methanol in $CH_2Cl_2$, to give two products: (1) 678 mg of isoquinoline in 26% yield and (2) 780 mg of quinalone product in 27% yield.

To a suspension of the isoquinoline (678 mg, 1.59 mmol) in ethanol (20 mL), conc. HCl (2 mL) was added and the mixture was heated at 80° C. for 2 h. The reaction mixture was cooled to rt, solvent was removed and the solid was washed well with ethyl acetate to give 4-(6,8-dimethoxy-1-(methylamino)isoquinolin-3-yl)phenol hydrochloride (445 mg, 80%). MS (ES) m/z: 312.04 (M+1); Mp. 250-253° C.

Example 83

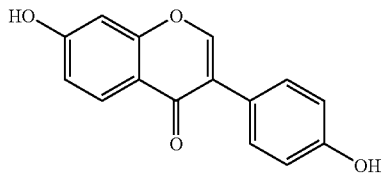

7-Hydroxy-3-(4-hydroxyphenyl)-chromen-4-one

In a solution of 1-(2,4-dihydroxyphenyl)-2-(4-hydroxyphenyl)-ethanone (2 mmol) in DMF (6 mL), freshly distilled $BF_3.OEt_2$ (6.3 mL) was added under argon. The mixture was heated at 50° C., and a solution of methanesulphonyl chloride (1 mL) in dry DMF (1.5 mL) was added slowly. After reaction at 80° C. for 1 h, the mixture was cooled to rt and poured into a large volume of ice cold aq. sodium acetate (12 g/100 mL), then extracted with EtOAc, and the organic layer was dried and concentrated. The residue was purified by column chromatography on silica gel using a mixture of DCM and MeOH to give 7-hydroxy-3-(4-hydroxyphenyl)-chromen-4-one.

Example 84

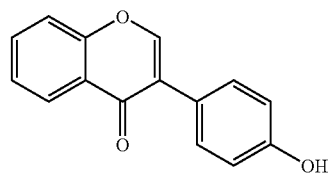

3-(4-Hydroxyphenyl)-4H-chromen-4-one

To a mixture of 3-bromochromone (1.5 g, 6.66 mmol), 4-methoxy phenyl boronic acid (1.01 g, 6.66 mmol), sodium carbonate (2.12 g, 20.0 mmol), toluene (40 mL) and water (10 mL) was added tetrakis-triphenyl phosphine palladium (385 mg, 0.33 mmol) under $N_2$. The reaction mixture was heated to 110° C. for 5 h and then cooled to rt. Water was added and the mixture was extracted with EtOAc. The organic layer was separated, washed with water, brine, dried and concentrated to give crude product, which was purified by column chromatography, using 20% EtOAc in hexane to give, 885 mg of 4'-methoxychromone product in 52% yield. A mixture of the above mentioned 4'-methoxychromone (400 mg, 1.58 mmol) and pyridinium hydrochloride (5 g) was heated at 190° C. for 4 h. The reaction mixture was cooled to rt, diluted with water, neutralized with $NaHCO_3$ and filtered to give 314 mg of 3-(4-hydroxyphenyl)-4H-chromen-4-one (83%). MS (ES) m/z: 239.95 (M+1), 238.99 (M); Mp. 237-238° C.

Example 85

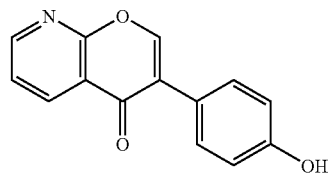

3-(4-Hydroxyphenyl)-4H-pyrano[2,3-b]pyridine-4-one

Methyl 4-methoxyphenylacetate (5.58 g, 0.031 mol) was added to anhydrous toluene (75 mL) and the reaction mixture was kept at −70° C. Diisobutylaluminum hydride (1.0 M, 34 mL) in toluene was added over 25 min. The reaction mixture was stirred for another 20 min then a sodium-potassium-tartrate solution (100 mL) was added to the reaction mixture. The organic layer was separated and the water layer was extracted with ether. The combined organic layers were washed with water, brine, and dried over sodium sulfate. The crude compound was purified by column chromatography (hexane:EtOAc 4:1) to yield 4-methoxyphenylacetaldehyde (0.90 g, 19.3%). A mixture of 4-methoxyphenylacetaldehyde (0.40 g, 2.66 mmol), morpholine (0.232 g, 2.66 mmol), and benzotriazole (0.304 g, 2.56 mmol) in ether (20 mL) with 3 Å molecular sieves was stirred at rt overnight. The molecular sieves were removed by filtration and the solvent was removed. The crude product was used for next step reaction without further purification. Sodium hydride (0.125 g, 5.2 mmol, 60% in mineral oil) was added to the crude product with anhydrous THF (20 mL). The reaction mixture was stirred at reflux for 3 h. THF was removed and the residue was poured into cold water (60 mL) and extracted with hexane (2×80 mL). The organic layer was dried over sodium sulfate and the solvent was removed to give the enamine (0.60 g). 2-Chloropyridine-3-carbonylchloride (0.44 g, 2.5 mmol) in dry DCM (5 mL) was added to the enamine (0.60 g), followed by triethylamine (0.5 mL) in anhydrous DCM (15 mL) at −70° C. The reaction mixture was allowed to warm to rt overnight. The mixture was then poured into water, and the organic phase was washed with sodium bicarbonate and brine. The crude residue was purified by column chromatography (EtOAc:MeOH 5:1) to the desired intermediate (0.45 g). The intermediate (0.45 g, 1.25 mmol) was stirred in HCl (8.0 mL, 6 N) overnight at rt. The desired compound was filtered off and washed with large amounts of water. The crude product (0.24 g, 1.18 mmol) was mixed with pyridine hydrochloride (1.4 g) and heated to 180-190° C. for 3 h. The mixture was poured into water and stirred for 30 min. The solid was filtered off and further washed with water and hexane to give 140 mg of 3-(4-hydroxyphenyl)-4H-pyrano[2,3-b]pyridine-4-one (49.6%). MS (ES) m/z: 239.90; Mp. 262-264° C.

Example 86

ApoA-I Promoter Induction in Caco-2 Intestinal Cells

To examine the effects of compounds of the invention to increase ApoA-I expression, Caco-2 cells, an intestinal cell line derived from human epithelial intestinal cells, were grown under conditions recommended by the ATCC and summarized in United States Patent Application Publication No. 20040033480 ("Wong"), incorporated herein by reference. Wong demonstrates that resveratrol increases ApoA-I promoter activity by 2.5-times over untreated control. This study similarly demonstrates that compounds of the present invention induce ApoA-I promoter activity.

Briefly, the promoter region of the gene encoding human ApoA-I was isolated and ligated upstream of the firefly luciferase gene to construct the reporter plasmid pAI.474-Luc. This reporter plasmid and pRSV-β-galactosidase (as a control for transfection efficiency) were co-transfected to Caco-2 cells. The Caco-2 cells were then incubated in a MEM selection media containing 20% fetal calf serum supplemented with G418 (final concentration: 0.5 mg/mL, Gibco) to give established strains that stably express from the reporter gene. The strains were seeded in 6-well culture plates and incubated for 48 hours at 37° C. under 5% carbon dioxide. Cells were starved for 24 hrs in MEM selection media containing 0.5% FBS. Then, a solution of a compound of the invention in DMSO or other appropriate solvent was added to the wells at a final concentration of 0 to 100 μM in MEM selection media containing 0.5% FBS.

After further incubation for 48 hours, the cells were harvested and lysed using Reporter Lysis Buffer (PROMEGA E3971), and 50 μL of luciferase assay reagent (PROMEGA E4550 Luciferase Reporter 1000 assay system) was added to measure luciferase activity with a luminometer (Fluoroskan Ascent FL from Thermo electron Corporation). Luciferase activity was normalized to lysate protein concentrations, measured using Bradford Reagent (BioRad Protein Assay reagent Cat #500-0006). The luciferase activity of cells treated with various concentrations of test compounds was compared to that of solvent control sample (i.e., solvent without any compound of the present invention added) and untreated control sample. An increase in luciferase activity compared to control samples indicated that the compound of the invention increased the expression of ApoA-I. The results provided in Table 2 are based on values obtained at 15 μM concentrations.

TABLE 2

Induction of ApoA-I Promoter in Caco-2 Intestinal Cells

| Compound | ApoA-I Promoter Induction |
|---|---|
| Resveratrol | increased |
| 5,7-Dihydroxy-2-(4-hydroxyphenyl)-chroman-4-one | increased |
| 5,7-Dihydroxy-2-(4-hydroxyphenyl)-4H-chromen-4-one | increased |
| 5,7-Dihydroxy-2-phenyl-4H-chromen-4-one | increased |
| 5-Hydroxy-2-(4-hydroxyphenyl)-4H-chromen-4-one | increased |
| 7-Hydroxy-2-(4-hydroxyphenyl)-4H-chromen-4-one | increased |
| 5-Hydroxy-2-phenyl-4H-chromen-4-one | increased |
| 2-(4-Hydroxyphenyl)-chromen-4-one | increased |
| 7-Hydroxy-2-phenyl-4H-chromen-4-one | increased |
| 2-Phenyl-4H-chromen-4-one | increased |
| 6-Hydroxy-2-(4-hydroxyphenyl)-4H-chromen-4-one | increased |
| 2-(3-Hydroxyphenyl)-4H-chromen-4-one | increased |
| 2-(4-Hydroxy-3-methoxyphenyl)-4H-chromen-4-one | increased |
| 4-(4-Oxo-4H-chromen-2-yl)-phenyl nicotinate (Example 71) | increased |
| 2-(4-Nicotinoyloxy)phenyl)-oxo-4H-chromene-5,7-diyl dinicotinate (Example 74) | increased |
| 5,7-Difluoro-2-(4-hydroxyphenyl)-4H-chromen-4-one (Example 2) | increased |
| 5,7-Difluoro-2-(4-methoxy-phenyl)-chromen-4-one (Example 1) | no increase |
| 2-(4-Hydroxy-phenyl)-1H-quinolin-4-one (Example 51) | no increase |
| 2-(4-Hydroxy-phenyl)-pyrano[2,3-b]pyridin-4-one (Example 34) | increased |
| 2-(4-Hydroxy-phenyl)-pyrano[3,2-b]pyridin-4-one (Example 35) | increase |
| 2-(5-Hydroxy-pyridin-2-yl)-chromen-4-one (Example 46) | increased |
| 4-(4-Oxo-4H-chromen-2-yl)phenyl acetate (Example 72) | increased |
| 2-Pyridin-4-yl-chromen-4-one (Example 47) | increased |
| 4-(4-Oxo-4H-pyrano[2,3-b]pyridine-2-yl)phenyl acetate (Example 75) | increased |
| 2-(6-Hydroxypyridin-3-yl)chromen-4-one (Example 48) | no increase |
| 2-(4-Hydroxyphenyl)-pyrano[2,3-c]pyridin-4-one(Example 36) | increased |
| 2-(4-Hydroxyphenyl)-4H-pyrano[3,2-c]pyridin-4-one | increased |

TABLE 2-continued

Induction of ApoA-I Promoter in Caco-2 Intestinal Cells

| Compound | ApoA-I Promoter Induction |
|---|---|
| (Example 39) | |
| 3-(4-Hydroxyphenyl)-2H-isoquinolin-1-one (Example 53) | increased |
| 4-Isoquinolin-3-yl-phenol (Example 54) | increased |
| 4-(1,6-Naphthyridin-7-yl)phenol (Example 57) | increased |
| 2-Amino-5-guanidino-pentanoic acid 4-(4-oxo-4H-chromen-2-yl)phenyl ester trihydrochloride (Example 76) | increased |
| 4-(Benzo[b][1,4]dioxin-2-yl)phenyl acetate (Example 77) | increased |
| 2-(4-Methoxy-phenyl)-4H-chromen-4-one (Example 4) | increased |
| 8-Hydroxy-2-(4-hydroxy-phenyl)-4H-chromen-4-one (Example 5) | increased |
| 2-(4-Hydroxy-3,5-dimethylphenyl)chromen-4-one (Example 7) | increased |
| 4-Naphthalen-2-yl-phenol (Example 65) | increased |
| 2-(3-Fluoro-4-hydroxyphenyl)pyrano[2,3-b]pyridine-4-one (Example 37) | increased |
| 2-(4-Hydroxyphenyl)-8-methoxy-4H-chromen-4-one (Example 17) | increased |
| 2-(4-Hydroxyphenyl)-5,7-dimethoxy-4H-chromen-4-one (Example 18) | increased |
| 2-(3-Chloro-4-hydroxyphenyl)-4H-pyrano[2,3-b]pyridine-4-one (Example 41) | increased |
| 2-(4-Hydroxyphenyl)-4-oxo-4H-pyrano[2,3-c]pyridine 7-oxide (Example 30) | no increase |
| 2-(3-Bromo-4-hydroxyphenyl)-4H-chromen-4-one (Example 19) | increased |
| 4-(Isoquinolin-3-yl)phenyl 2-amino-5-guanidinopentanoate tetrahydrochloride (Example 78) | increased |
| 3-(3-Fluoro-4-hydroxyphenyl)-5-methoxyisoquinolin-1(2H)-one (Example 59) | increased |
| 3-(4-Hydroxyphenyl)-6,8-dimethoxyisoquinolin-3-yl)phenol hydrochloride (Example 60) | increased |
| 4-(4-Oxo-4H-pyrano[2,3-b]pyridine-2-yl)benzonitrile (Example 40) | increased |
| 3-((Dimethylamino)methyl)-2-(4-hydroxyphenyl)-4H-chromen-4-one hydrochloride (Example 20) | no increase |
| 4-(1-Oxo-1,2-dihydroisoquinolin-3-yl)phenyl 2-amino-5-guanidinopentanoate trihydrochloride (Example 79) | increased |
| 2-(4-Hydroxyphenyl)-4-oxo-4H-pyrano[2,3-b]pyridine 8-oxide (Example 31) | no increase |
| 7-(3-Fluoro-4-hydroxyphenyl)-6-methyl-1,6-naphthyridin-5(6H)-one (Example 56) | no increase |
| 4-(6-Bromo-4-oxo-4H-chromen-2-yl)-2-fluorophenyl acetate (Example 25) | increased |
| 2-(2-(4-Hydroxyphenyl)-4-oxo-4H-chromen-3-yl)acetonitrile (Example 21) | increased |
| 2-(3-Bromo-4-hydroxyphenyl)-4H-pyrano[2,3-b]pyridin-4-one (Example 42) | increased |
| 5,7-Dihydroxy-2-(4-hydroxyphenyl)-quinolin-4(1H)-one (Example 50) | increased |
| 2-(4-(2-Hydroxyethoxy)phenyl)-4H-pyrano[2,3-b]pyridine-4-one (Example 45) | increased |
| 2-(4-Methoxyphenyl)-4H-pyrano[2,3-b]pyridine-4-one (Example 44) | increased |
| 2-(4-Hydroxyphenyl)-3-(methoxymethyl)-4H-chromen-4-one (Example 26) | increased |
| 2-(4-Hydroxy-3-methoxyphenyl)-4H-pyrano[2,3-b]pyridine-4-one (Example 43) | increased |
| 2-(4-Nitrophenyl)-4H-pyrano[2,3-b]pyridin-4-one (Example 80) | no increase |
| 2-(4-Hydroxyphenyl)-4-oxo-4H-pyrano[3,2-c]pyridine 6-oxide (Example 32) | no increase |
| 2-(4-Hydroxy-3-(hydroxymethyl)phenyl)-4H-pyrano[2,3-b]pyridin-4-one (Example 81) | increased |
| 4-(Benzo[b][1,4]dioxin-2-yl)phenol (Example 70) | increased |
| 2-(4-Hydroxyphenyl)benzo[e][1,3]oxazin-4-one (Example 67) | increased |
| 4-(4,4-Dimethyl-4H-chromen-2-yl)phenyl acetate (Example 69) | increased |
| 2-(4-Hydroxy-3-methylphenyl)-4H-pyrano[2,3-b]pyridine-4-one (Example 38) | increased |
| 2-(3-Fluoro-4-hydroxyphenyl)-6-(hydroxymethyl)-4H-chromen-4-one (Example 33) | increased |
| 4-(6,8-Dimethoxy-1-(methylamino)isoquinolin-3-yl)phenol hydrochloride (Example 82) | increased |
| 3-(4-hydroxyphenyl)-4H-pyrano[2,3-b]pyridine-4-one (Example 85) | increased |
| 5,7-Dihydroxy-3-(4-hydroxyphenyl)-chromen-4-one | increased |
| 3-(4-Hydroxyphenyl)-4H-chromen-4-one (Example 84) | increased |

The results of these assays indicate that an electron donating group in the "B"-ring, in particular the 4' position, following the flavonoid nomenclature, or R7 position in Formula I and IV, generally improves ApoA-I promoter activity. For example, a comparison of the results of 5-hydroxy-2-phenyl-4H-chromen-4-one to 5-hydroxy-2-(4-hydroxyphenyl)-4H-chromen-4-one demonstrated that the 4' hydroxyl plays a role in the increase in ApoA-I promoter activity. These studies further demonstrated that a nitrogen atom in the "A"-ring, following the flavonoid nomenclature of Formula I and IV, does not suppress the activity of the 4' hydroxyflavone; however, the nitrogen atom does improve the pharmacokinetic properties, for example, increasing the solubility as discussed below in connection with the solubility assays. Unexpectedly, the presence of an oxygen in the C1 position and nitrogen in the 8 position improves ApoA-I promoter activity. The presence of a carbon at position C1 and nitrogen in the 3 and/or 8 positions also appears to enhance ApoA-I promoter activity.

Example 87

Kinetics of ApoA-I Promoter Induction

Whereas the preceding studies showed that the compounds of the invention stimulate ApoA-I promoter activity, the duration of action was unclear. Accordingly, the kinetics of induction of the ApoA-I promoter were assessed.

Caco-2 cells transfected with pAI.474-Luc were treated with compounds of the invention at selected time points varying from 4 to 72 hours. This construct pAI.474-Luc contained the human ApoA-I promoter fused to the reporter gene, firefly luciferase (Luc). Wong demonstrated that when the test compound is resveratrol a significant stimulation of ApoA-I promoter activity in Caco-2 cells was observed at 4, 8, 16 and 24 hours following administration, but maximal stimulation was observed following 16 hours of exposure.

5,7-dihydroxy-2-(4-hydroxyphenyl)-4H-chromen-4-one was found to have a significant effect on ApoA-I promoter activity at 16, 24, 28 and 72 hours following its administration. Further, maximal stimulation appeared following 48 hour exposure. 4'-hydroxyflavone had a significant effect on stimulation of ApoA-I promoter activity in Caco-2 cells at 16, 24, and 48 hours following the administration. Maximal stimulation appeared following 48 hour exposure to the compound.

Example 88

Confirmation of ApoA-I Induction in Caco-2 Intestinal Cells

This experiment will measure the ability of a test compound to stimulate transcriptional activity of the endogenous Apo-A1 promoter in the Caco-2 cells. Such simulation will result in an increase in expression of ApoA-I protein, which is ultimately responsible for antiatherogenic activity. A test compound, such as, for example, 5,7-dihydroxy-2-(4-hydroxyphenyl)-4H-chromen-4-one, which has demonstrated an increase in the activity of the ApoA-I promoter in the pAI.474-Luc construct, may be tested in this assay to confirm its effect on the activity of the ApoA-I gene endogenous to the Caco-2 cells. The Caco-2 cells are cultured as described in Wong and exposed to media containing 5,7-dihydroxy-2-(4-hydroxyphenyl)-4H-chromen-4-one or other test compound at a concentration of 5, 7.5, 10, 15 or 20 µM for 24 or 48 hours. Longer exposure of the cells to the test compound is utilized to allow adequate time for the ApoA-I protein to be secreted into the media from the Caco-2 cells, and detected. Conditioned media exposed to the cells for 24 or 48 hours is assayed for its content of ApoA-I protein using Western blot analysis and enzyme-linked immunoassay (ELISA).

Results should show an increase in the amount of ApoA-I protein in the conditioned media from cells treated with test compound as compared to untreated cells. The results of these studies will demonstrate that a test compound augments expression of the ApoA-I gene and is, therefore, antiatherogenic. Increased expression of the ApoA-I gene augments reverse cholesterol transport and thereby facilitates the removal of cholesterol from the body.

Example 89

ApoA-I Promoter Induction in HepG2 Liver Cells

This study determined whether compounds of the invention have an effect on ApoA-I promoter activity expression in HepG2 cells, a liver cell line. Cells were grown under conditions recommended by the ATCC and summarized by Wong.

The promoter region of the gene encoding human ApoA-I was isolated and ligated upstream the structure gene of firefly luciferase to construct a reporter plasmid (pAI.474-Luc). The reporter plasmid, along with pRSV-β-galactosidase (as a control for transfection efficiency), were co-transfected into HepG2 cells. The cells were then incubated in an MEM selection media containing 20% fetal calf serum supplemented with G418 (final concentration: 0.5 mg/mL, Gibco) to give established strains that stably express from the reporter gene. The strains were seeded to a 6-well culture plates and incubated for 48 hours at 37° C. under 5% carbon dioxide. Cells were starved for 24 hrs in MEM selection media containing 0.5% FBS. Then, a solution of the compounds of the invention in DMSO (or other appropriate solvent) was added to the wells at a final concentration of 0 to 100 µM in MEM selection media containing 0.5% FBS.

After further incubation for 48 hours, the cells were harvested and lysed using Reporter Lysis Buffer (PROMEGA E3971), and 50 µL of luciferase assay reagent (PROMEGA E4550 Luciferase Reporter 1000 assay system) were added to measure luciferase activity with a luminometer (Fluoroskan Ascent FL from Thermo electron Corporation). Luciferase activity was normalized to lysate protein concentrations, measured using Bradford Reagent (Biorad Protein Assay reagent Cat #500-0006). An increase in luciferase activity compared to untreated and or control samples indicates that the compound of the invention increases the expression of ApoA-I. The results provided in Table 3 are based on average values at 15 µM concentrations.

TABLE 3

Induction of ApoA-I Promoter in HepG2 liver cells

| Compound | ApoA-I Promoter Induction |
| --- | --- |
| 6-Hydroxy-2-(4-hydroxymethylphenyl)chromen-4-one (Example 14) | increased |
| 4',5-dihydroxyflavone | increased |
| 5,7-dihydroxy-2-(4-hydroxyphenyl)-chroman-4-one | increased |
| 3,5,7-trihydroxy-2-(3,4-dihydroxyphenyl)-chromen-4-one | increased |
| 5,7-dihydroxy-2-(4-hydroxyphenyl)-4H-chomen-4-one | increased |
| 2-(4-(nicotinoyloxy)phenyl)-4-oxochroman-5,7-diyl dinicotinate (Example 73) | no increase |
| 2-(4-nicotinoyloxy)phenyl)-oxo-4H-chromene-5,7-diyl dinicotinate (Example 74) | increased |

TABLE 3-continued

Induction of ApoA-I Promoter in HepG2 liver cells

| Compound | ApoA-I Promoter Induction |
|---|---|
| 4-(4-oxo-4H-chromen-2-yl)phenyl nicotinate (Example 71) | increased |
| 2-(4-hydroxy-phenyl)-pyrano[2,3-b]pyridin-4-one (Example 34) | increased |
| 2-(2-amino-4-hydroxy-phenyl)-chromen-4-one (Example 3) | increased |
| 3-(4-hydroxyphenyl)-2H-isoquinolin-1-one (Example 53) | increased |
| 4-isoquinolin-3-yl-phenol (Example 54) | increased |
| 6-hydroxymethyl-2-(4-hydroxyphenyl)chromen-4-one (Example 11) | increased |
| 2-(3-fluoro-4-hydroxyphenyl)chromen-4-one (Example 12) | increased |
| 4'-hydroxyflavone | increased |

Example 90

ApoA-I Protein Expression in HepG2 Cells

This study confirmed that compounds of the invention have an effect on ApoA-I protein secretion in HepG2 (liver) cells by measuring whether stimulation of transcriptional activity of the endogenous ApoA-I promoter in the HepG2 cells increased the abundance and secretion of ApoA-I protein.

The HepG2 cell line was obtained from the ATCC and cultured in MEM media supplemented with 10% FBS (Gibco), with 1 mM sodium pyruvate, 0.1 mM MEM non-essential amino acid, 2 mM L-glutamine, 100 U/ml penicillin, 100 µg/ml streptomycin and 5 µg/ml plasmocin. Cells were maintained at 37° C. in an atmosphere of 5% $CO_2$ Cells were grown to 85% confluency prior to initiating the experiment.

Cells were plated and allowed to adhere overnight in a phenol red-free DMEM containing 10% of Charcoal/Dextran treated FBS (Hyclone), with 1 mM sodium pyruvate, 0.1 mM MEM non-essential amino acid, 2 mM L-glutamine, 100 U/ml penicillin, 100 µg/ml streptomycin and 5 µg/ml plasmocin. The medium was removed, and cells were washed in 1×PBS. Cells were then starved in phenol red-free DMEM (serum free) for a period of 24 hours. Cells were then mock treated (untreated, DMSO), or treated with compound of the invention diluted in phenol red-free DMEM (serum free) media at a concentration of 7.5 µM. Cells and media were harvested at 0, 6 and 24 hours following compound treatment.

Medium was removed from cells at the desired times and applied to a solid phase capture sandwich in an ELISA assay according to manufacturer's instructions (Total human Apo-lipoprotein ELISA Assay-Alercheck). FIG. 1 shows results from an ELISA analysis to measure ApoA-I protein content from conditioned media from HepG2 Cells untreated, treated with diluent and treated with compound at 0, 6 and 24 hours after exposure. When HepG2 cells were treated for 6 and 24 hours with compound 2-(4-Hydroxy-phenyl)-pyrano[2,3-b]pyridin-4-one (Example 34), 2-(4-hydroxyphenyl )-3-methyl-4H-chromen-4-one (Example 24), 4-(1,6-naphthyridin-7-yl)phenol (Example 57) and 2-(4-methoxyphenyl)-4H-pyrano[2,3-b]pyridine-4-one (Example 44), the ApoA-I content in the medium increased significantly when compared with untreated cells and cells treated with solvent.

While not wishing to be limited to a theory, the time course experiment indicates that the rate at which ApoA-I levels increase in the medium of HepG2 cells treated with 2-(4-Hydroxy-phenyl)-pyrano[2,3-b]pyridin-4-one (Example 34), 2-(4-hydroxyphenyl)-3-methyl-4H-chromen-4-one (Example 24), 4-(1,6-naphthyridin-7-yl)phenol (Example 57) and 2-(4-methoxyphenyl)-4H-pyrano[2,3-b]pyridine-4-one (Example 44) is starting at ~6 hours after the addition of compound to the medium. This may suggest that the mechanism responsible for the increase in ApoA-I production by hepatic cells involves the induction of the ApoA-I gene at the transcriptional level.

Accordingly, representative compounds of the invention activate promoter activity for ApoA-I, leading to an increase in transcription, as demonstrated in Example 86 and 89 and increase in synthesis of ApoA-I, as demonstrated in Example 90. Thus, the compounds of the invention and pharmaceutically acceptable salt or hydrate thereof, can be expected to elevate ApoA-I protein expression level, in intestinal and liver cells and be useful for elevating plasma ApoA-I levels in a patient to whom the compounds are administered.

Example 91

Solubility Analysis

To evaluate the solubility of illustrative compounds of the invention, 1 mg of compound was added to 1 mL of PBS and sonicated for 1 hour at room temperature using the Branson 3210 Sonicator in triplicate and incubated in a water bath at 25° C. for 3 hrs. Samples were then centrifuged at 14,000 rpm for 6 minutes at room temperature. The supernatant was diluted with acetonitrile and was removed for analysis. Analysis was performed using HPLC-UV with 7-point standard curve to determine the concentration. The average concentration calculated is regarded as the solubility (µM). Table 4 shows the results of these experiments.

TABLE 4

Solubility Analysis

| Compound | Solubility (PBS) (µM) |
|---|---|
| 5,7-dihydroxy-2-(4-hydroxyphenyl)-4H-chomen-4-one | 3.37* |
| 3-(4-hydroxyphenyl)-2H-isoquinolin-1-one (Example 53) | 44.89 |
| 4-(6,8-dimethoxy-1-(methylamino)isoquinolin-3-yl)phenol hydrochloride (Example 82) | 66.83 |
| 2-(4-hydroxyphenyl)-4H-pyrano[3,2-c]pyridine-4-one (Example 39) | 31.60 |
| 4'-hydroxyflavone | 5.04 |
| 2-(3-chloro-4-hydroxyphenyl)-4H-pyrano[2,3-b]pyridine-4-one (Example 41) | 84.37 |
| 2-(3-bromo-4-hydroxyphenyl)-4H-pyrano[2,3-b]pyridin-4-one (Example 42) | 52.59 |
| 2-(3-fluoro-4-hydroxyphenyl)pyrano[2,3-b]pyridine-4-one (Example 37) | 194.50 |
| 3-(4-Hydroxyphenyl)-6,8-dimethoxyisoquinolin-1(2H)-one (Example60) | 58.24 |
| 2-(4-hydroxy-3-methoxyphenyl)-4H-pyrano[2,3-b]pyridine-4-one (Example 43) | 47.09 |
| 2-(4-(2-hydroxyethoxy)phenyl)-4H-pyrano[2,3-b]pyridine-4-one (Example 45) | 334.05 |
| 2-(4-hydroxy-3-(hydroxymethyl)phenyl)-4H-pyrano[2,3-b]pyridin-4-one (Example 81) | 48.54 |
| 2-(3-fluoro-4-hydroxyphenyl)-6-(hydroxymethyl)-4H-chromen-4-one (Example 33) | 51.42 |

*S. P. Ng et al., "Evaluation of the first-pass glucoronidation of select flavones in the gut by Caco2 monolayer model," J. Pharm. Pharmaceut. Sci. 8(1):1-9 (2005)

These experiments indicate that the solubility of representative compounds of the invention is significantly better than that of naturally occurring polyphenols, such as apigenin with a solubility of 3.27 µM. The poor bioavailability of naturally occurring polyphenols is partially attributed to poor solubility. As such, solubility is unlikely to affect the validity of any in vitro tests performed on the compounds of the invention, and formulation of these compounds for in vivo work should not be technically difficult to one skilled in the art. Accordingly, the compounds of the invention and pharmaceutically acceptable salts and hydrates thereof, are suitable for human use due to the unexpected utility of improved solubility.

Example 92

Caco-2 Permeability

The Caco-2 cell drug transport model is widely used for screening compounds in drug discovery to assess intestinal transport and predict absorption rates. For example, the fraction of drug absorbed in human could be determined by in vivo human permeability or predicted by in vitro Caco-2 permeability; if compound permeability in Caco-2 cells reaches $13.3-18.1 \times 10^{-6}$ cm/s, it is predicted that in vivo, permeability in humans would reach $2 \times 10^{-4}$ cm/s, and the predicted fraction of drug absorbed would be >90%, which is defined as highly permeable. (D. Sun et al., "In vitro testing of drug absorption for drug 'developability' assessment: forming an interface between in vitro preclinical data and clinical outcome," *Curr. Opin. Drug Discov. Devel.* 7(1):75-85 (2004). Therefore, in vitro absorption testing is a highly valuable tool for comparison of structural analogues for improved intestinal absorption, and to identify compounds within the decision-making process for clinical studies at early-stage drug discovery and development.

Figure 2:
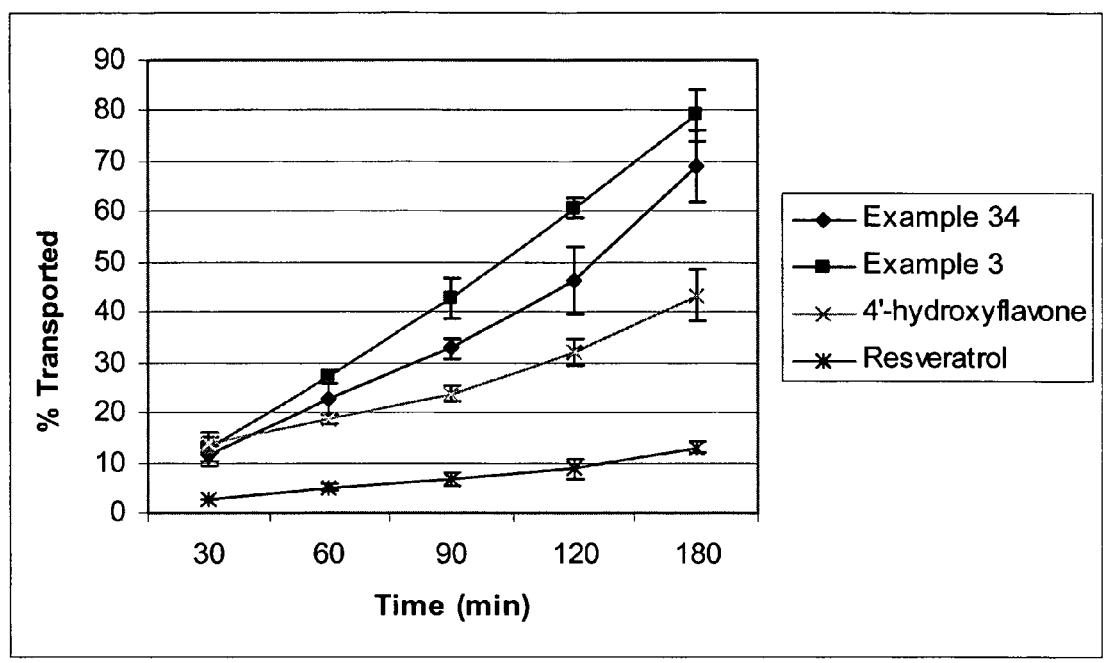
FIG. 2 shows permeability of Caco-2 cells to 4'-hydroxyflavone, 2-(4-hydroxy-phenyl)-pyrano[2,3-b]pyridin-4-one, and 2-(2-amino-4-hydroxy-phenyl)-chromen-4-one over time (expressed as percent transported Paap (cm/s)).

The method of B. Hai-Zhi et al., "High-throughput Caco-2 cell permeability screening by cassette dosing and sample pooling approaches using direct injection/on-line guard cartridge extraction/tandem mass spectrometry," *Rapid Communications in Mass Spectrometry* 14:523-528 (2000) may be used with obvious modifications to someone skilled in the art. FIG. 2 and Table 5 show the results of permeability of representative compounds of the invention in an in vitro Caco-2 intestinal transport model over time, and compared to resveratrol and 5,7-dihydroxy-2-(4-hydroxyphenyl)-4H-chomen-4-one (apigenin).

TABLE 5

Permeability Analysis

| Compound | % Transported Paap (cm/s) |
|---|---|
| Propanol | $1.01 \times 10^{-5}$ |
| 2-(2-amino-4-hydroxy-phenyl)-chromen-4-one (Example 3) | $7.42 \times 10^{-6}$ |
| 7-methoxy-2-(4-hydroxyphenyl)-4H-chromen-4-one | $6.92 \times 10^{-6}$ |
| 2-pyridin-4-yl-chromen-4-one (Example 47) | $6.48 \times 10^{-6}$ |
| 2-(4-hydroxy-phenyl)-pyrano[2,3-b]pyridin-4-one (Example 34) | $6.36 \times 10^{-6}$ |
| 4-(1,6-naphthyridin-7-yl)phenol (Example 57) | $5.34 \times 10^{-6}$ |
| 4'-hydroxyflavone | $4.31 \times 10^{-6}$ |
| 4-isoquinolin-3-yl-phenol (Example 54) | $4.11 \times 10^{-6}$ |
| Resveratrol | $3.34 \times 10^{-6}$ |
| 4-(4-oxo-4H-chromen-2-yl)phenyl acetate (Example 72) | $2.65 \times 10^{-6}$ |
| 2-(3-fluoro-4-hydroxyphenyl)pyrano[2,3-b]pyridine-4-one (Example 37) | $2.06 \times 10^{-6}$ |
| 2-(4-hydroxy-phenyl)-pyrano[3,2-b]pyridin-4-one (Example 35) | $1.98 \times 10^{-6}$ |
| 3-(4-hydroxyphenyl)-2H-isoquinolin-1-one (Example 53) | $1.76 \times 10^{-6}$ |
| 2-(3-chloro-4-hydroxyphenyl)-4H-pyrano[2,3-b]pyridine-4-one (Example 41) | $1.76 \times 10^{-6}$ |
| 5,7-dihydroxy-2-(4-hydroxyphenl)-4H-chomen-4-one | $1.50 \times 10^{-6}$ |
| 2-(5-hydroxy-pyridin-2-yl)-chromen-4-one (Example 46) | $1.23 \times 10^{-6}$ |
| 2-(4-hydroxyphenyl)-4H-pyrano[3,2-c]pyridine-4-one (Example 39) | $1.21 \times 10^{-6}$ |
| 2-(3-bromo-4-hydroxyphenyl)-4H-pyrano[2,3-b]pyridin-4-one (Example 42) | $9.59 \times 10^{-7}$ |
| 2-(4-hydroxy-3,5-dimethylphenyl)chromen-4-one | $6.95 \times 10^{-7}$ |

TABLE 5-continued

Permeability Analysis

| Compound | % Transported Paap (cm/s) |
|---|---|
| (Example 7) 2-(4-hydroxy-3-methylphenyl)-4H-pyrano[2,3-b]pyridine-4-one (Example 38) | $5.96 \times 10^{-7}$ |
| 2-(3,5-difluoro-4-hydroxyphenyl)chromen-4-one (Example 6) | $5.31 \times 10^{-7}$ |
| 5,7-dihydroxy-2-phenyl-4H-chromen-4-one | $1.22 \times 10^{-7}$ |

These experiments indicate that the permeability of representative compounds of the invention are equivalent to or greater than naturally occurring polyphenols, such as 5,7-dihydroxy-2-(4-hydroxyphenyl)-4H-chomen-4-one (apigenin) with a permeability of $1.50 \times 10^{-6}$ or resveratrol with a permeability $3.34 \times 10^{-6}$. Accordingly, the compounds of the invention and pharmaceutically acceptable salts and hydrates thereof, are potentially suitable for human use due to the permeability of intestinal cells to these compounds.

Example 93

Transgenic Mice

To test whether the efficacy of compounds of the invention observed in vitro extended to an in vivo model, transgenic mice carrying multiple copies of the human ApoA-I gene (C57BI/6-tgn(apoa1)1 rub, Jackson Laboratory, Bar Harbor, Me.) were exposed to representative compounds of the invention. The exogenous human ApoA-I gene in these mice enables them to express the human ApoA-I protein under the control of this promoter.

Seven to eight week old male mice, transgenic for human ApoA-I were housed five per cage (10"×20"×8" with aspen chip bedding) with pelleted Rodent chow [Purina 5001] and water available at all times. After an acclimation period of 1 week, animals were individually identified by numbering on tail and weighed. Mice were pre bled via the retro-orbital plexus, and 150 μl of blood was collected in 1.5 ml Eppendorf tube containing 1 μl of heparin and chilled on ice. Plasma was collected after centrifuging the whole blood at 14000 rpm [TOMY high speed micro-refrigerated centrifuge NTX-150] for 10 minutes at 4° C. and frozen at −80° C. Plasma was analyzed for: human ApoA-I by a human ApoA-I enzyme-linked Immunoassay [Direct Sandwich ELISA Calbiochem Cat#178422, Calbiochem Cat#178452, lot #B9076, Calbiochem Cat #178470 conjugated to Horse Radish Peroxidase (Cedarlane Cat#80220)]; total cholesterol [Ponte scientific reagents: # C7509-STD, #L7580-18, # C7510]; and triglyceride [Pointe Scientific Reagents: # 7532-STD, # L7580-18, #7532]. All samples were measured in triplicates and expressed as mg/dl. Mice were grouped based on the above plasma parameters and having an average body weight of 25 gm.

Two days following pre-bleed, mice were dosed by oral gavage daily for 14 days using a 20 gauge, 11/2" curved disposable feeding needle [Popper & Sons]; when BID, mice were gavaged morning and afternoon (8 am and 5 pm); when SID mice were gavaged in morning (8 am). Compounds were prepared each day in vehicle. Test article(s), a positive control fenofibrate, and vehicle were dosed at volume of 5 mL/kg of body weight as a suspension (0.1 mL/20 g mouse). Fenofibrate was obtained commercially [SIGMA #F 6020]. Mice weights were recorded on day 1, 4, 7, 10, 12, and 15. On day 15, mice were weighed and fasted for 4 hours, sacrificed by inhalation of $CO_2$ and blood was obtained via cardiac puncture (0.7-1.0 ml). Plasma was collected and frozen at −80° C. Samples were assayed for ApoA-I, total cholesterol, triglyceride and HDL-C by HPLC [Polaris 200 with an auto sampler Prostar 410 from Varian on a Superose 6 10/30 column from Amersham]. Samples were sent for NMR analysis [LipoScience] to identify particle size and subclass for lipoproteins. During necropsy, liver, brown fat, and the whole of small and large intestines were collected, cleaned with cold PBS and frozen at −80° C. for further analysis of compound levels. Variation between studies, in ApoA-I changes, was observed. Therefore, a relative comparison between individual(s) in the study groups was used.

Experiment A

4'-hydroxyflavone (10 mg/kg of body weight), 4-(4-oxo-4H-chromen-2-yl)phenyl nicotinate (Example 71) (10 mg/kg of body weight) and fenofibrate (100 mg/kg of body weight) were BID administered to hApoA-I transgenic mice daily for fourteen days by oral gavage in 0.5% Methylcellulose (w/v)/1% Tween 80 (w/v). Plasma was assayed for ApoA-I (FIG. 3A), HDL cholesterol and total cholesterol (FIG. 3B) and percent weight gain (FIG. 3C).

Figure 3A:
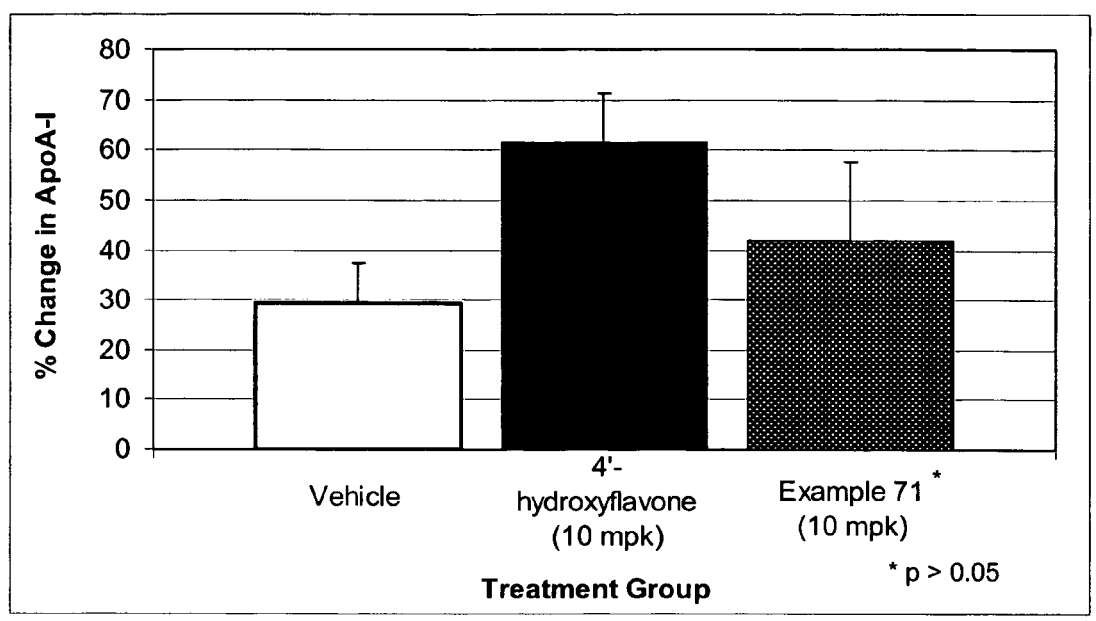
FIG. 3(A) shows the effect of 4'-hydroxyflavone, and 4-(4-oxo4H-chromen-2-yl)phenyl nicotinate on ApoA-I levels in hApoA-I transgenic mice (expressed as net percent change in ApoA-I).
Figure 3B:
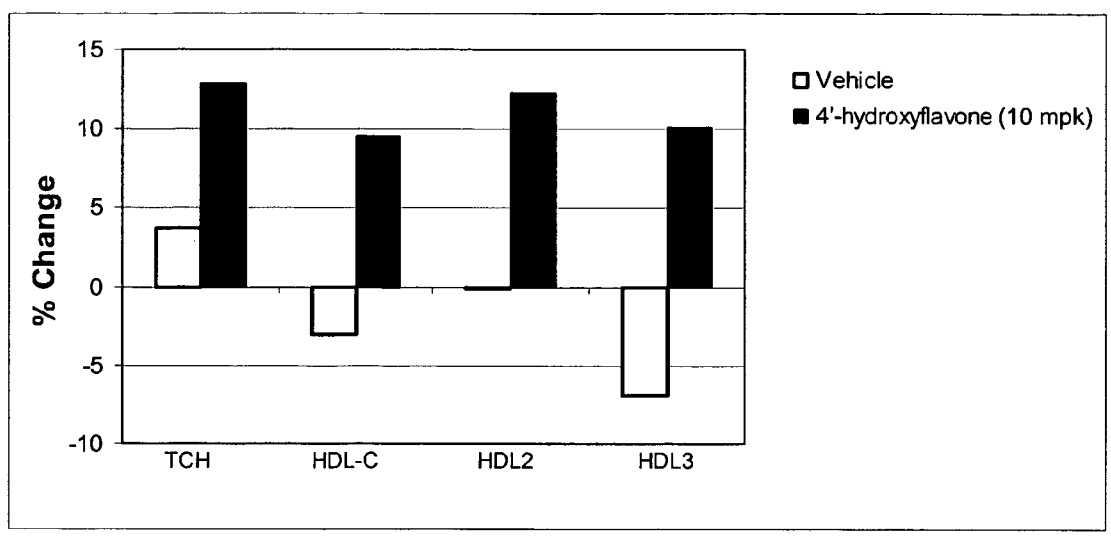
FIG. 3(B) shows the change in HDL-C, large HDL (HDL2), small HDL (HDL3) and total cholesterol (TC) levels in hApoA-I transgenic mice following administration of 4'-hydroxyflavone.
Figure 3C:
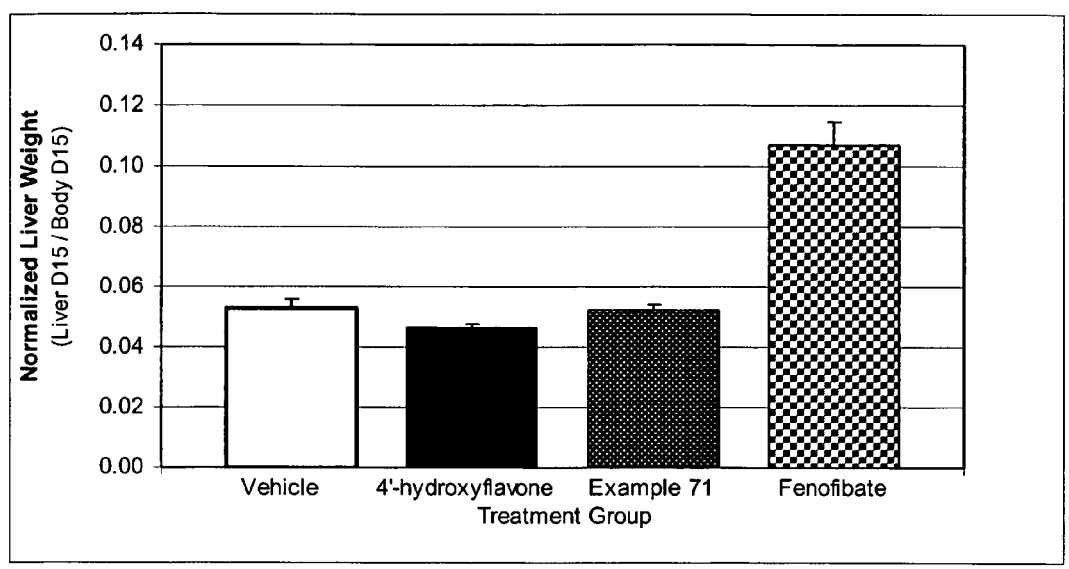
FIG. 3(C) graphically depicts the change in liver weight in hApoA-I transgenic mice following administration of 4'-hydroxyflavone, 4-(4-oxo4H-chromen-2-yl)phenyl nicotinate, and fenofibrate.

In the hApoA-I transgenic mice, 4'-hydroxyflavone and 4-(4-oxo-4H-chromen-2-yl)phenyl nicotinate (Example 71) increased plasma ApoA-I with a net % change over vehicle of 32.44 and 12.82, respectively, after two weeks of treatment (FIG. 3A). Study group treated 4'-hydroxyflavone was selected for full lipoprotein cholesterol profile analysis using NMR. Lipoprotein cholesterol profiles demonstrated that treatment with 4'-hydroxyflavone resulted in a marked alteration in the distribution of cholesterol among lipoproteins (FIG. 3B). In particular, 4'-hydroxyflavone caused a marked elevation in HDL cholesterol after two weeks of treatment (12.6% net % change). Notably, one adverse effect of fenofibrate treatment is liver weight gain, largely due to increased hepatic peroxisome proliferation. This was confirmed, as shown in FIG. 3C, that fenofibrate in male, day 15, hApoA-I transgenic mice caused a significant increase in liver weight gain when normalized to body weight, compared to vehicle. 4'-hydroxyflavone and 4-(4-oxo-4H-chromen-2-yl)phenyl nicotinate (Example 71) showed minor changes relative to vehicle. The lack of change in body weight in mice suggests that the compounds of the invention may not act as peroxisomal proliferator activator receptor alpha ligands. These results indicate that the compounds of the invention are useful for increasing plasma ApoA-I and elevating circulating HDL, without the adverse side effect associated with liver weight gain in a patient to whom the compound is administered.

Experiment B

4'-hydroxyflavone (3 mg/kg of body weight), 4'-hydroxyflavone (10 mg/kg of body weight), 4'-hydroxyflavone (30 mg/kg of body weight), 2-(4-Hydroxy-phenyl)-pyrano[2,3-b]pyridin-4-one (10 mg/kg of body weight), and fenofibrate (100 mg/kg of body weight) were BID administered to hApoA-I transgenic mice daily for fourteen days by oral gavage in 0.5% methylcellulose (w/v)/1% Tween 80 (w/v). In this experiment plasma was assayed for ApoA-I.

In the hApoA-I transgenic mice, 4'-hydroxyflavone at 10 mpk and 2-(4-Hydroxy-phenyl)-pyrano[2,3-b]pyridin-4-one (Example 71) at 10 mpk increased plasma ApoA-I with a net % change over vehicle 31.24 and 3.75, respectively, after two weeks of treatment. This trend is consistent with results observed in Experiment A, that is 4'-hydroxyflavone and 4-(4-oxo-4H-chromen-2-yl)phenyl nicotinate (Example 71) elevate the levels of circulating ApoA-I protein in a mammalian system. A lack of statistically significant change in ApoA-I at 3 and 30 mpk over vehicle suggests that the therapeutically effective amount of 4'-hydroxyflavone may be between 3 and 30 mpk and, more preferably, 10 mpk to observe an increase in ApoA-I.

Experiment C

In a number of different experiments following protocols similar to Experiments A and B, representative compounds of the invention and fenofibrate (positive control) were administered daily at various doses to 7-8 week old hApoA-I transgenic mice for 14 days BID or SID by oral gavage in a dosing vehicle (Control 1 was 0.5% MC & 1% Tween 80 and Control 3 was F-101).

Table 6 below shows the effect of these compounds, and fenofibrate on the percent change in plasma ApoA-I, relative to pretreatment values, in hApoA-I transgenic mice. All mice were treated BID for 14 days.

TABLE 6

In Vivo Effect on ApoA-I Expression

| Compound | Dose (mg/kg) | Volume (ml/kg) | N | ApoA-I (% change) |
|---|---|---|---|---|
| Control 1 | 0 | 5 | 8 | 11.94 |
| 2-(4-Hydroxy-phenyl)-pyrano[2,3-b]pyridin-4-one (Example 34) | 3 | 5 | 8 | 18.87 |
| 2-(4-Hydroxy-phenyl)-pyrano[2,3-b]pyridin-4-one (Example 34) | 10 | 5 | 8 | 36.64* |
| 2-(4-Hydroxy-phenyl)-pyrano[2,3-b]pyridin-4-one (Example 34) | 30 | 5 | 8 | 47.46* |
| Control 1 | 0 | 5 | 4 | 3.42 |
| 2-(3-Fluoro-4-hydroxyphenyl)pyrano[2,3-b]pyridine-4-one (Example 37) | 10 | 5 | 8 | 14.45 |
| Fenofibrate | 30 | 5 | 4 | 127.42* |
| Control 3 | 0 | 5 | 4 | (6.32) |
| 2-(4-Hydroxy-phenyl)-1H-quinolin-4-one (Example 51) | 10 | 5 | 8 | 32.81* |
| 2-(4-Hydroxy-phenyl)-pyrano[2,3-b]pyridin-4-one (Example 34) | 10 | 5 | 8 | 30.94* |
| 2-(4-Hydroxy-phenyl)-pyrano[3,2-b]pyridin-4-one (Example 35) | 10 | 5 | 8 | (0.97) |
| 2-(5-Hydroxy-pyridin-2-yl)-chromen-4-one (Example 46) | 10 | 5 | 8 | 5.62 |
| 2-Pyridin-4-yl-chromen-4-one (Example 47) | 10 | 5 | 8 | 22.73* |
| Fenofibrate | 30 | 5 | 3 | 74.40* |
| Control 3 | 0 | 5 | 4 | 1.11 |
| 3-(4-Hydroxyphenyl)-2H-isoquinolin-1-one (Example 53) | 10 | 5 | 8 | 13.22 |
| 2-(6-Hydroxypyridin-3-yl)-chromen-4-one (Example 48) | 10 | 5 | 8 | 4.94 |
| 2-(4-Hydroxyphenyl)pyrano[2,3-c]pyridin-4-one (Example 36) | 10 | 5 | 8 | 17.01 |
| 2-(4-Hydroxyphenyl)-4H-pyrano[3,2-c]pyridine-4-one (Example 39) | 10 | | 8 | 11.20 |
| 4-(1,6-Naphthyridin-7-yl)phenol (Example 57) | 10 | 5 | 8 | 9.49 |
| Fenofibrate | 30 | 5 | 4 | 68.94* |

*p < 0.05

These results demonstrate that compounds of the invention activate the human ApoA-I transgene in mice, leading to an increase in circulating ApoA-I. Thus, the compounds of the invention and pharmaceutically acceptable salt or hydrate thereof, can be expected to elevate ApoA-I protein level and to be useful for elevating plasma ApoA-I levels in a patient to whom the compounds are administered.

Example 94

Measurement of AGCCCCCGC Sequence Element Induction

Caco-2 or HepG2 cells are exposed to effective concentrations of compounds of the invention. The cells are first transfected using standard techniques with a reporter construct comprising one or more copies of the nine nucleotides, 5'-AGCCCCCGC-3' acting as an enhancer element (Kilbourne et al., *J. Biol. Chem.* 270:7004 (1995)), operably linked to a promoter (for example, the thymidine kinase (TK) promoter), operably linked to a reporter gene (for example luciferase, CAT, or the ApoA-I gene) along with pRSV-β-galactosidase, which monitors transfection efficiency (as taught in Wong). Compounds of the invention are then dissolved in appropriate solvent (for example, DMSO) and then added to the culture media for 16 hours. At the end of the treatment, the cells are harvested, and the reporter gene activity is measured using standard assays. Increased or decreased reporter gene activity indicates that compounds of the invention have the ability to modulate transcription from promoters that contain the nine nucleotide sequence 5'-AGCCCCCGC-3', which is believed to comprise an egr-1 responsive element.

Example 95

Measurement of Antioxidant Effectiveness

The antioxidant performance of compounds of the invention is demonstrated by measuring the extent of low density lipoprotein hydroxyperoxide by copper catalyzed autoxidation using a published dye based color assay. FOX Assay, Zadeh, *Methods in Enzymology*, 300:58 (1999). Samples containing only LDL and copper sulfate without test materials, serve as a positive control for comparison with identical mixtures containing test materials.

Human Low Density Lipoprotein (Sigma Chemical Company L2139) in phosphate buffered saline pH 7.4 is mixed with copper sulfate. Incubation with effective amounts of compounds of the invention at 25° C. or 37° C. open to air effects oxidation, and the mixture is sampled at time zero and between 3 and 20 hours of incubation for measurement of hydroperoxide in the FOX assay. Samples are read in a microtitre plate reader. Decreased hydroperoxide as measured by the FOX assay reveals the anti-oxidant activity of compounds of the invention and their usefulness for the treatment or prevention of disorders, diseases or conditions associated with oxidation or benefiting from the administration of anti-oxidants. An example of such a condition that would benefit from the treatment of anti-oxidants is cardiovascular disease.

Example 96

Measurement of Antioxidant Activity by LDL Oxidation Assay

The method of Esterbauer (Esterbauer, H. et al *Free Radic Res Commun* 6:67 (1989)) may be used, with some modification as follows: the compound is dissolved with an appropriate solubilizing agent in a phosphate buffer solution (PBS, 0.15 M NaCl-0.05 M Na Phosphate Buffer-pH 7.4). The exact concentration is noted (approximately 30-60 µL/mL of extract to be measured). To 100 µL of this solution is added to 900 µL of an oxidizing buffer (made from human LDL, 120 µL of 5 mg/mL solution with d=1.019-1.063 g/mL, purchased from PerImmune, Rockville, Md.) and copper sulfate (20 µL of 10 mM aqueous solution) in 8 mL PBS). A blank sample made with 100 µL PBS and 900 µL oxidizing buffer is also prepared. Each solution is then transferred to a 1 cm quartz cuvette, and the cuvette is placed into thermostat (37° C.). An HP-8452A Diode Array Spectrophotometer measures optical density at 234 nm (OD sub 234), making a measurement every 5 minutes. The lag time for oxidation is calculated as the maximum of the first derivative of the optical density curve. A standard containing ascorbic acid is run with each assay.

Example 97

Effects on LDL-Cholesterol, HDL-Cholesterol and Triglyceride Levels in Male Sprague-Dawley Rats Compounds of the invention are administered daily at a dose of 100 mg/kg to chow fed male Sprague-Dawley rats for seven days in the morning by oral gavage in 1.5% carboxymethylcellulose/0.2% Tween-20 (dosing vehicle). Animals are weighed daily. Animals are allowed free access to rodent chow and water throughout the study. After the seventh dose, animals are sacrificed in the evening and blood serum is assayed for lipoprotein cholesterol profiles, serum triglycerides, total cholesterol VLDL, LDL, and HDL cholesterol, and the ratio of HDL cholesterol to that of VLDL plus LDL cholesterol, apolipoproteins AI, C-II, C-III, and E by immunoelectrophoresis, and percent weight gain.

Blood serum is assayed for total cholesterol and triglycerides, lipoprotein cholesterol profiles, VLDL plus LDL cholesterol combined (also referred to as ApoB containing lipoprotein cholesterol or non-HDL cholesterol), HDL cholesterol, and the ratio of HDL cholesterol to that of VLDL plus LDL cholesterol, serum glucose, and non-esterified fatty acids, and percent weight gain.

Example 98

Effects on LDL-Cholesterol, HDL-Cholesterol and Triglyceride Levels in Obese Female Zucker Rats Compounds of the invention and troglitazone are administered daily at various doses to 1 0-week old chow fed obese female Zucker rats for 14 days in the morning by oral gavage in 1.5% carboxymethylcellulose/0.2% Tween-20 (dosing vehicle). Animals are weighed daily. Animals are allowed free access to rodent chow and water throughout the study. Blood glucose is determined after a 6-hour fast in the afternoon without anesthesia from a tail vein. Serum is also prepared from a blood sample subsequently obtained from the orbital venous plexus (with $O_2/CO_2$ anesthesia) prior to and after one week treatment and used lipid and insulin determinations. At two weeks, blood glucose is again determined after a 6-hour fast without anesthesia from a tail vein. Soon thereafter, animals are sacrificed by $CO_2$ inhalation in the evening and cardiac blood serum is collected and assessed for various lipids and insulin. Body weight is determined daily prior to dosing and at the time of euthanasia.

Blood serum is assayed for serum non-HDL cholesterol, HDL-cholesterol, triglyceride and body weight (relative to pretreatment values) in fasted (6 hours) chow-fed obese female Zucker rats. Blood glucose and serum insulin levels are determined from fasted rats just prior to and following one and two weeks of treatment. Blood glucose is maintained at slightly elevated levels for 10-12 week old obese Zucker rats during treatment with all doses, with the exception of the doses, whereby the compounds show a tendency to lower blood glucose. Percent liver to body weight is determined after two weeks of treatment at the time of sacrifice.

Example 99

Effects on Lipoprotein Cholesterol Profile in LDL Receptor-Deficient Mice

Homozygous familial hypercholesterolemia is a rare human disease (affecting about 1/1,000,000) characterized by absent or defective LDL receptors, markedly elevated serum LDL cholesterol levels and very early and severe onset of atherosclerosis. The more common form of this disease in humans, heterozygous familial hypercholesterolemia, occurs in about one in every 500 humans. Patients with the heterozygous form of this disease also present with elevated LDL levels and early onset of atherosclerosis.

The effect of the compounds of the invention on LDL levels in a murine model of homozygous familial hypercholesterolemia (Ishibashi et al., *J. Clin. Invest.* 92:883 (1993); Ishibashi et al., *J. Clin. Invest.* 93:1885 (1994)) is studied. LDL receptor-deficient mice have elevated LDL cholesterol relative to wild type mice when fed a chow diet. When fed cholesterol-enriched diets, these mice develop atherosclerosis.

Example 100

Effect on Synthesis of Non-Saponified and Saponified Lipids in Hepatocytes Isolated From Male Sprague-Dawley Rats A male Sprague-Dawley rat is anesthetized by administration of sodium pentobarbitol by intraparitoneal injection at 50 mg/kg. In situ perfusion of the liver is performed as follows. The abdomen of the animal was opened, the portal vein canulated, and the liver perfused with WOSH solution (149 mM NaCl, 9.2 mM Na HEPES, 1.7 mM fructose, 0.5 mM EGTA, 0.029 mM phenol red, 10 U/ml heparin, pH 7.5) at a flow rate of 30 ml/min for 6 minutes. To digest the liver, DSC solution (6.7 mM KCl, 143 mM NaCl, 9.2 mM Na HEPES, 5 mM $CaCl_2—2H_2O$, 1.7 mM fructose, 0.029 mM Phenol red, 0.2% BSA, 100 U/ml collagenase Type I, 93 U/ml hyaluronidase, 160 BAEE/ml trypsin inhibitor, pH 7.5) is perfused through the liver at a flow rate of 30 ml/min for 6 minutes at a temperature of 37° C. After digestion, cells are dispersed in a solution of DMEM containing 2 mM GlutMax-1, 0.2% BSA, 5% FBS, 12 nM insulin, 1.2 µM hydrocortisone to stop the digestion process. The crude cell suspension is filtered through three layers of stainless steel mesh with pore sizes of 250, 106, and 75 µm respectively. Filtered cells are centrifuged at 50×g for two minutes and the supernatant discarded. The resulting cell pellet is resuspended in DMEM and centrifuged again. This final cell pellet is resuspended in DMEM+HS solution (DMEM containing 2 mM GlutMax-1, 20 nM delta-aminolevulinic acid, 17.4 mM MEM non-essential amino acids, 20% FBS, 12 nM insulin, 1.2 µM hydrocortisone) and plated to form monolayer cultures at a density of $100×10^3$ cells/cm² on collagen coated culture dishes. Four hours after initial plating, media is changed to DMEM+ (DMEM containing 2 mM GlutMax-1, 20 nM delta-aminolevulinic acid, 17.4 mM MEM non-essential amino acids, 10% FBS, 12 nM insulin, 1.2 µM hydrocortisone) and remained on cells overnight.

To test the effect of compounds of the invention on synthesis rates of non-saponified and saponified lipids, the monolayer cultures are exposed to 1 µM of lovastatin or 100 µM of test compound in DMEM+containing 1 µCi/ml $^{14}C$-acetate. Control cells are exposed to the same media lacking lovastatin or the test compounds. All are exposed to 0.1% DMSO. Metabolic labeling with $^{14}C$-acetate continued for 2 hr at 37° C. After labeling, cells are washed twice with 1 ml of PBS followed by lysing in 1 ml of deionized water. Cells are scraped from the dishes, transferred to glass tubes and sonicated. 2.5 ml of 2:1 chloroform/methanol mixture was added followed by 1.5 ml of Phosphate Buffered Saline (PBS). To correct for extraction efficiency in the upcoming extractions, 3000 dpm of $^3H$-cholesterol was added to each tube. Tubes are shaken for 30 min. to extract lipids into the organic phase followed by centrifugation for 10 minutes at 1000×g to separate the organic and aqueous phases. The lower organic phase containing total lipids is removed and placed in a new tube. The organic solution is evaporated under $N_2$. The dry lipid extract was resuspended in 1 ml of 93% ethanol containing 1 M KOH and placed at 70° C. for 2.5 hours. After the reaction and cooling, 2 ml of hexane and 2.5 ml of water is added to each tube followed by rigorous shaking for 10 min. Tubes are centrifuged for 10 min. at 1000×g and the organic (top) layer containing the non-saponified lipids is transferred to a new tube followed by evaporation of the organic solvent under $N_2$. The aqueous phase containing the saponified lipids is also transferred to a new tube. The non-saponified lipid extract, after drying, is resuspended in toluene and an aliquot of the suspension is added to a scintillation cocktail for radioactive counting. The number of $^{14}C$ counts representing the incorporation of $^{14}C$-acetate into non-saponified lipids is corrected for extraction efficiency, based on the recovery of $^3H$ counts extracted. To isolate saponified lipids, 1.5 ml of aqueous phase solution is mixed with 400 µl of 1 M HCl, and then lipids are extracted by the addition of 2.5 ml of 2:1 chloroform:methanol, 1.5 ml of PBS, and 1 ml of water followed by rigorous shaking and isolation of the organic phase. The organic phase from this extraction is evaporated under $N_2$ and resuspended in toluene. Its radioactivity is counted using scintillant to provide the rate of $^{14}C$-acetate incorporation into saponified lipid.

Example 101

Measurement and Comparison of HDL, LDL, VLDL and Triglyceride Levels in Humans

Compounds of the invention are administered daily to human subjects. Other dietary uptake is monitored and held constant between individuals. Blood samples are taken on the day 0, prior to commencing the administration of the compounds, and once weekly for 3 to 6 months. Blood serum is assayed for total cholesterol and triglycerides, lipoprotein cholesterol profiles, VLDL plus LDL cholesterol combined (also referred to as ApoB containing lipoprotein cholesterol or non-HDL cholesterol), HDL cholesterol, $HDL_2$ and $HDL_3$ cholesterol fractions, and the ratio of HDL cholesterol to that of VLDL plus LDL cholesterol, utilizing standard, commercially available cholesterol tests, such as the VAP test (Atherotech Inc, Birmingham, Ala.) which can reproducibly measure these parameters from a small sample of human blood. Alternatively, $HDL_2$ and HDL3 can be measured from blood by the method of Kulkarni et al., *J. Lipid Res.* 38:2353 (1997) or by the method of Gidez et al., *J. Lipid Res.* 23:1206 (1982). Compounds of the invention which increase total HDL, increase $HDL_2$, decrease total LDL, decrease VLDL, decrease triglyceride, or increase the HDL/total cholesterol or HDL/LDL ratios as determined in such a blood test are useful for the treatment of cholesterol or lipid associated disorders.

Example 102

Measurement of Atherosclerotic Lesion Size Using Proteoglycan-Binding-Defective LDL A nucleic acid construct may be used to generate mice expressing a proteoglycan-binding-defective LDL. The transgenic mice are fed a diet containing 1.2% cholesterol, 0.5% bile salts, and 20% fat for 17 weeks. The mice are then sacrificed, and the aortas are perfusion fixed and analyzed with the en face procedure, in which the entire aorta is pinned out flat, stained with Sudan IV, and analyzed with a morphometric image-analysis system (Image-1/AT) to quantitate the extent of atherosclerosis.

Example 103

Determination of ACAT Inhibition

The activity of compounds of the invention as inhibitors of ACAT may be determined by known methods, for example, those taught in U.S. Pat. No. 6,165,984, incorporated herein by reference and summarized below.

First, rats are sacrificed by decapitation and the livers excised. 1 g of each of the livers is homogenized in 5 ml of homogenization medium (0.1 M $KH_2PO_4$, pH 7.4, 0.1 mM EDTA and 10 mM β-mercaptoethanol). The homogenate is centrifuged at 3,000×g for 10 min. at 4° C. and the supernatant thus obtained is centrifuged at 15,000×g for 15 min. at 4° C. to obtain a supernatant. The supernatant is put into an ultracentrifuge tube (Beckman) and centrifuged at 100,000×g for 1 hour at 4° C. to obtain microsomal pellets, which are then suspended in 3 ml of the homogenization medium and centrifuged at 100,000×g for 1 hour at 4° C. The pellets thus obtained are suspended in 1 ml of the homogenization medium. The concentration of proteins in the resulting suspension is determined by Lowry's method and then adjusted to 4 to 8 mg/ml. The resulting suspension is stored in a deep freezer (Biofreezer, Form a Scientific Inc.).

6.67 μl of 1 mg/ml cholesterol solution in acetone is mixed with 6 μl of 10% Triton WR-1339 (Sigma Co.) in acetone and, then, acetone is removed from the mixture by evaporation using nitrogen gas. Distilled water is added to the resulting mixture in an amount to adjust the concentration of cholesterol to 30 mg/ml. To 10μl of the resulting aqueous cholesterol solution is added 10 μl of 1 M $KH_2PO_4$ (pH 7.4), 5 μl of 0.6 mM bovine serum albumin (BSA), 10 μl of microsome solution obtained in (Step 1) and 55 μl of distilled water (total 90 μl). The mixture is pre-incubated in a waterbath at 37° C. for 30 min.

10 μl of $(1-^{14}C)$ oleoyl-CoA solution (0.05 μCi, final concentration: 10 μM) is added to the pre-incubated mixture and the resulting mixture is incubated in a waterbath at 37° C. for 30 min. To the mixture is added 500 μl of isopropanol:heptane mixture (4:1(v/v)) 300 μl of heptane and 200 μl of 0.1 M $KH_2PO_4$ (pH 7.4), and the mixture is mixed violently by using a vortex and then allowed to stand at a room temperature for 2 min. 200 μl of the resulting supernatant is put in a scintillation bottle and 4 ml of scintillation fluid (Lumac) is added thereto. The mixture is assayed for radioactivity with liquid scintillation counter. ACAT activity is calculated as picomoles of cholesteryl oleate synthesized per min. per mg protein (pmoles/min/mg protein).

Example 104

Determination of Inhibition of HMG-CoA Reductase

The potency of inhibition of HMG-CoA reductase by compounds of the invention may be determined using known methods, such as that taught in U.S. Pat. No. 5,877,208, incorporated herein by reference and summarized below.

Rats are sacrificed by decapitation and the livers are excised and immediately placed in an ice-cold homogenization medium (50 mM $KH_2PO_4$ (pH 7.0), 0.2M sucrose, 2 mM dithiothreitol (DTT). The livers are homogenized in the homogenization medium (2 ml medium/g of the liver) with a Waring blender for 15 sec. (three strokes with a motor-driven Teflon pestle in a Potter-Elvehjem type glass homogenizer). The homogenate is centrifuged at 15,000×g for 10 min. and the supernatant thus obtained is centrifuged at 100,000×g for 75 min. to obtain microsomal pellets, which are then resuspended in the homogenization medium containing 50 mM EDTA and centrifuged at 100,000×g for 60 min. The supernatant containing the microsome is used as an enzyme source.

The activity of HMG-COA reductase is determined by employing radiolabeled $^{14}C$ HMG-COA, in accordance with the method of Shapiro et al. (Shapiro et al *Biochemica et Biophysica Acta* 370:369 (1974)) as follows. The enzyme in the supernatant containing the microsome obtained in (Step 1) is activated at 37° C. for 30 min. Added to a reaction tube is 20 μl of HMG-CoA reductase assay buffer (0.25M $KH_2PO_4$ (pH 7.0), 8.75 mM EDTA, 25 mM DTT, 0.45M KCl and 0.25 mg/ml BSA), 5 μl of 50 mM NADPH, 5 μl of radiolabeled $^{14}C$ HMG-CoA (0.05 μCi/tube, final conc. 120 μM), and 10 μl of activated microsomal enzyme (0.03-0.04 mg), and the mixture is incubated at 37° C. for 30 min. The reaction is terminated by adding 10 μl of 6M HCl to the mixture, and the mixture is incubated at 37° C. for 15 min. to allow complete lactonization of the product. The precipitate is removed by centrifugation at 10,000×g for 1 min. and the supernatant is applied to a Silica gel 60G TLC plate (Altech, Inc., Newark, U.S.A.) and then developed with benzene:acetone (1:1, v/v). The appropriate region is removed by scraping with a disposable cover slips and assayed for radioactivity with 1450 Microbeta liquid scintillation counter (Wallacoy, Finland). Enzyme activities are calculated as picomoles mevalonic acid synthesized per min. per mg protein (pmoles/min/mg protein). Control rats show a relatively high HMG-CoA reductase activity, while the HMG-CoA activities observed with rats fed compounds of the invention are lower than that of the control group.

Example 105

Method of Determining the ABCA-1 Activating Ability

This test will demonstrate the effectiveness of compounds of the invention on ABCA-1 gene expression, using a known method, as taught in U.S. Pat. No. 6,548,548, incorporated herein by reference. Briefly, the pGL3 luciferase reporter vector system (Promega, Madison, Wis.) is used to create a recombinant plasmid to measure reporter gene expression under control of the ABCA-1 promoter.

Plasmid pGL3-Basic (Promega, Madison, Wis.; Cat. #E1751) is used as a control plasmid containing the promoterless luciferase gene. The reporter construct containing the ABCA-1 promoter and luciferase gene is made by cloning a genomic fragment from the 5' flanking region of the ABCA-1 gene (hAPR1 5' promoter, corresponding to nucleotides 1080-1643 of SEQ ID NO: 3 as disclosed in U.S. Pat. No. 6,548,548) into the SacI site of the GL3-Basic plasmid to generate plasmid GL-6a. Next, plasmid GL-6a is digested with SpeI and Acc65I. A BsiWI-SpeI fragment excised from a lambda subclone, representing the ABCA-1 genomic sequence corresponding to nucleotides 1-1534 of SEQ ID NO: 3 is ligated into the remaining vector/ABCA-I promoter fragment produced by this digestion. The resultant plasmid, pAPR1, encodes the luciferase reporter gene under transcriptional control of 1.75 kb of the human ABCA-1 promoter sequence.

The control or pAPR1 plasmid wisas transfected into confluent cultures of RAW 264.7 cells maintained in DMEM containing 10% fetal bovine serum. Each well of a 12 well dish is transfected for 5 hours with either pGL3-Basic, pGL3-Promoter or pAPR1 DNA (1 µg), luciferase plasmid DNA (1 µg), and 12 µl of Geneporter reagent (Gene Therapy Systems, San Diego, Calif.; Cat. #T201007). In addition, 0.1 µg of pCMVβ plasmid DNA (Clontech, Palo Alto, Calif., Cat. #6177-1) is added as a control for transfection efficiency. After 5 hours, the culture medium is replaced with serum-free DMEM/BSA in the presence or absence of acetylated LDL (100 µg/ml) and incubated for 24 hours.

Following transfection, the cells in each well are lysed in 70 µl of 1× cell lysis reagent (Promega, Madison, Wis., Cat. #E3971), subjected to one freeze-thaw cycle, and the lysate cleared by centrifugation for 5 minutes at 12,000×g. After centrifugation, 100 µl of luciferase assay reagent (Promega, Madison, Wis.; Cat. #E1501) is added to 10 µl of lysate. The luciferase activity of each lysate is measured as light units using a luminometer. Additionally, the β-galactosidase activity of each lysate is measured using the chemiluminescent assay reagents supplied in the Galacto-light kit according to the manufacturer's instructions (Tropix Inc., Bedford, Mass.: Cat. #BL100G). The normalized luciferase activity for each lysate is determined by dividing the luciferase activity value by the determined β-galactosidase value and reported as relative light units.

Example 106

Measurement of Reduced Hypertension In Vivo

A pressure transducer is connected to the right carotid artery via a catheter containing heparinized saline. The mean arterial pressure and heart rate are recorded. The rats are anesthetized with nembutal at an initial dose of 35 mg/kg body weight with additional smaller injections as necessary. The compounds are dissolved in a pharmaceutical carrier (such as Abbott's 5% dextrose USP) and injected into the rats via a catheter in the right femoral vein. Positive controls that may be employed include sodium nitroprusside and $NaNO_2$, while $NaNO_3$ may be employed as a negative control. The results will show that the compounds provided for in the invention are potent anti-hypertensives, that decreases blood pressure significantly. The peak value of the blood pressure decrease should take a short time to reach, for example, approximately one minute, after injection and the blood pressure should start to rise again soon thereafter and should have totally recovered within about approximately 10 to 15 minutes.

Example 107

Measurement of the Reduction of Degree of Restenosis After Arterial Injury in High Cholesteric Rabbits The procedure of Tomaru, as described in U.S. Pat. No. 5,595,974 and further described by Goodman in U.S. Pat. No. 6,022,901, both herein incorporated by reference, may be used to evaluate the utility of the compounds of the invention to preventing restenosis in high cholesteric rabbits.

Example 108

Use in Preventing Restenosis in Humans

The procedure of Tardif et al., *New England J. Med.* 337: 365 (1997)) may be carried out as described by Goodman in U.S. Pat. No. 6,022,901, incorporated herein by reference, to examine the ability of compounds of the invention to prevent restenosis in humans.

Example 109

Measurement of Platelet Anti-Aggregating Activity

Platelet anti-aggregating activity may be evaluated in vitro on human platelets stimulated by thrombin in accordance with the method described by Bertele et al., *Science* 220:517 (1983).

Example 110

Measurement of the Influence on ADP-Induced Aggregation of Platelets in Rabbits

Aggregation of platelet testing: Rabbit blood is sampled by cardiac puncture from rabbit with silicon-coated syringe. The blood is mixed with 3.8% sodium citrate at 9:1 and spun at 1,000 rpm for 6 minutes. 1 ml of the platelet-rich plasma is transferred to a silicon-coated 2 ml cell, mixed and read for transmittance (Ti), with a spectrophotometer. 0.02 ml of ADP (10 mu.M) is added, stirred, and read for transmittance of the platelet-containing-plasma once per minute and the maximal transmittance (Tm) is obtained within 10 minutes. Spin the blood sample at 3000 rpm for 45 minutes and read for transmittance.

Example 111

Measurement of the Effect on Collagen Induced Thrombo-cytopenia In Vivo

Male rats (Charles River, CRL:CD(SD), 400-450×g) are anesthetized with Sodium pentabarbital (65 mg/kg, Vet Labs, Limited, Inc., Lenexa, Kans.). Two incisions are made to expose both jugular veins. Using an infusion pump (Harvard Apparatus, South Natick, Mass.) and a 5 cc syringe with a 19 gauge butterfly, the test compound or vehicle is infused into the left jugular vein at a rate of 0.39 ml/min for 3 minutes. After 2 minutes of compound/vehicle infusion, collagen (60 µg/kg) (Helena Laboratories, Beaumont, Tex.) is injected with a 1 ml syringe into the right jugular vein. The body cavity is opened and the vena cava is exposed for blood sampling. One minute after the collagen injection, compound infusion is stopped and blood is sampled from the vena cava (within 30 sec) with a 3 cc syringe containing 0.3 mg of 4.5% EDTA/Tris (0.1M) (pH 7.35) plus 150 μM indomethacin. Platelet rich plasma (PRP) is prepared by centrifuging the blood at 126×g for 10 min. 5 μl of PRP is counted in 20 ml of Isoton.® III in a Coulter Counter. Percent inhibition of collagen induced aggregation is calculated by comparison of the number of platelets counted in treated animals with numbers for animals receiving no collagen and with counts from animals receiving vehicle and collagen. Estimation of potency is based on inhibition of collagen-induced thrombocytopenia.

Example 112

Measurement of In Vivo Anti-Psoriatic Effectiveness

A topical formulation comprising a compound of the invention is administered to the affected area of human patients suffering from psoriasis. A control formulation, containing none of the compound of the invention, is applied to a comparable area of the patient. The effectiveness of the compound is determined by analyzing the improvement in inflammation and decrease in proliferative cells at the site at which the compound is applied compared to the site at which control formulation is applied at 3 and 7 days following administration.

Example 113

Measurement of Protein Kinase Inhibition

A compound of the invention is mixed with radio-labeled ATP, an appropriate protein kinase and an appropriate substrate in an appropriate buffer. Following incubation the reaction is stopped by spotting onto filter paper and a scintillation counter employed to quantify the difference in ATP addition to the substrate, which measures the amount of protein kinase inhibition, when compared to control.

Example 114

Measurement of Inhibition of Neutrophil Activation

A compound of the invention is tested using the protocol of Tudan, *Biochem. Pharmacol.* 58:1869 (1999). This test demonstrates the ability of the test compound to inhibit the activation of neutrophils caused by crystals and by chemoattractants such as fMLP.

Example 115

Measurement of Inhibition of TPA-Induced Inflammation

A compound of the invention is tested by a modified method of Marks et al., *Cancer Res.* 36:2636 (1976) to demonstrate the compound's effectiveness against inflammation induced by application of 12-O-tetradecanoylphorbol-13-acetate (TPA). The compound is applied to an ear of a mouse, followed by application of TPA. Four hours later a biopsy punch of the mouse ear is weighed to measure edema, compared to a biopsy punch of the other ear which received no compound.

Example 116

Measurement of the Inhibition of Carrageenan-Induced Inflammation

A compound of the invention is tested by the method of Slowing et al., *J Wrhnoph Exol.* 43:9 (1994) in Wistar rats. Animals receive intradermal injections of Freund's adjuvant into the tail. Seven days later, the test compound is administered, followed one hour later by a suspension of carrageenan in saline solution into the left hind paw. Paw volume is measured by water plethysmography and compared to control.

Example 117

Measurement of Cancer Chemopreventative Activity

C3H/10T1/2 clone 8 cells (ATCC) are treated with a compound of the invention by the method of Mondal et al., *Cancer Res.* 36:2254 (1976). The cells in culture are treated with 3-methylcholanthrene for 24 hours, followed by washing a five days of incubation in fresh medium. TPA is subsequently added to the medium, with or without the test compound. Seven weeks after confluency is reached, fixation with methanol and staining with Giemsa reveals Type II and III transformed foci, which are scored to demonstrate effectiveness of inhibition of two-stage transformation by the test compound.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for increasing expression of ApoA-I in a mammal comprising administering a therapeutically effective amount of a compound of Formula I:

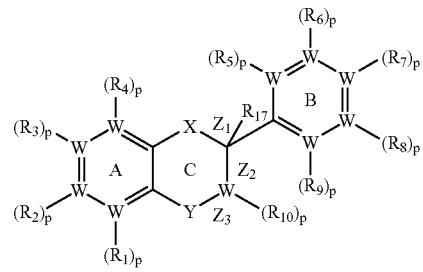

Formula I wherein:
X is O;
Y is CO;
$R_1$, $R_3$, $R_4$, $R_5$, $R_6$, $R_8$, $R_9$, and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone;
$R_2$ is selected from alkoxy, aryloxy, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, ketone, nitro, phosphate, sulfide, sulfinyl, sulfonyl, sulfonic acid, sulfonamide and thioketone;
$R_7$ is selected from alkoxy, aryloxy, alkyl, alkenyl, alkynyl, amide, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone;

R₁₀ is selected from alkyl, aryloxy, alkenyl, alkynyl, amide, amino, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone;

each W is independently selected from C and N, wherein if W is N, then p is 0 and if W is C, then p is 1;

at least one W is N;

$Z_1$ and $Z_3$ are each a single bond; and $Z_2$ is a double bond;

and pharmaceutically acceptable salts and hydrates thereof.

2. The method of claim 1, wherein the therapeutically effective amount of the compound of Formula I is administered with a pharmaceutically acceptable carrier in a pharmaceutically acceptable composition.

3. The method of claim 1, further comprising treating a cardiovascular, cholesterol or lipid related disorder.

4. A method for increasing expression of ApoA-I in a mammal comprising administering a therapeutically effective amount of a compound selected from:

5,7-Difluoro-2-(4hydroxyl-phenyl)-chromen-4-one,
2-(3,5-Difluoro-4-hydroxyphenyl)chromen-4-one,
2-(4-Hydroxy-3,5-dimethylphenyl)chromen-4-one,
2-(5-Methoxy-pyridin-2-yl)-chromen-4-one,
2-(5-Hydroxy-pyridin-2-yl)-chromen-4-one,
2-(6-Hydroxy-pyridin-3-yl)-chromen-4-one,
2-(4-Methoxy-phenyl)-thiochromen-4-one,
2-(4-Hydroxy-phenyl)-thiochromen-4-one,
2-(4-Hydroxyphenyl)-3-methyl-4H-chromen-4-one,
4-(6-Bromo-4-oxo-4H-chromen-2-yl)-2-fluorophenyl acetate,
1-(2-Nitro-4-methoxy-phenyl)-chromen-4-one,
2-(4-Hydroxy-2-nitrophenyl)chromen-4-one,
2-(2-Amino-4-methoxy-phenyl)-chromen-4-one,
2-(2-Amino-4-hydroxy-phenyl)-chromen-4-one,
N[5-Hydroxy-2-(4-oxo-4H-chromen-2-yl)-phenyl]acetamide,
6-Hydroxy-2-(4-hydroxymethylphenyl)chromen-4-one,
2-(2-Fluoro-4-hydroxyphenyl)chromen-4-one,
2-(4-Hydroxyphenyl)-8-nitro-4H-chromen-4-one,
2-(4-Hydroxyphenyl)-8-methoxy-4H-chromen-4-one,
2-(4-Hydroxyphenyl)-5,7-dimethoxy-4H-chromen-4-one,
2-(3-Bromo-4-hydroxyphenyl)-4H-chromen-4-one,
2-(4-Hydroxyphenyl)-4-oxo-4H-chromene-6-carbonitrile,
2-(4-Methoxy-phenyl)-chromen-4-one,
2-(3-Fluoro-4-hydroxyphenyl)chromen-4-one,
2-(4-Hydroxyphenyl)-4-oxo-4H-chromene-6-sulfonic acid,
6-Hydroxymethyl-2-(4-hydroxyphenyl)chromen-4-one,
6-((Dimethylamino)methyl)-2-(4-hydrophenyl)-4H-chromen-4-one,
8-Hydroxy-2-(4-hydroxy-phenyl)-chromen-4-one,
2-(4-Hydroxy-phenyl)-chromen-4-one,
7-Hydroxy-2-(4-hydroxy-phenyl)-chromen-4-one,
5-Hydroxy-2-(4-hydroxy-phenyl)-chromen-4-one,
5,7-Djihydroxy-2-(4-hydroxy-phenyl)-chromen-4-one,
5,7-Dihydroxy-2-phenyl-chromen-4-one,
5-Hydroxy-2-phenyl-chromen-4-one,
2-(4-Acetoxy-phenyl)-thiochromen-4-one,
2-(4-Acetoxy-phenyl)-1,1-dioxo-1H-1$\lambda^6$-thiochromen-4-one,
2-(4-Hydroxy-phenyl)-1,1-dioxo-1H-1$\lambda^6$-thiochromen-4-one,
5,7-Dimethoxy-2-(4'-hydroxy-phenyl)-quinolin-4-one,
5,7-Dihydroxy-2-(4-hydroxy-phenyl)-quinolin-4-one,
2-(4-Hydroxy-phenyl)-pyrano[3,2-b]pyridin-4-one,
2-(4-Methoxyphenyl)-4H-pyrano[2,3-b]pyridine-4-one,
2-(4-Hydroxy-phenyl)-pyrano[2,3-b]pyridin-4-one,
2-(4-(2-Hydroxyethoxy)phenyl)-4H-pyrano[2,3-b]pyridine-4-one,
2-(3-Fluoro-4-hydroxyphenyl)pyrano[2,3-b]pyridine-4-one,
2-(4-Hydroxy-3-methylphenyl)-4H-pyrano[2,3-b]pyridine-4-one,
4-(4-Oxo-4H-pyrano[2,3-b]pyridine-2-yl)benzonitrile,
2-(3-Chloro-4-hydroxyphenyl)-4H-pyrano[2,3-b]pyridine-4-one,
2-(3-Bromo-4-hydroxyphenyl)-4H-pyrano[2,3-b]pyridin-4-one,
2-(4-Hydroxy-3-methoxyphenyl)-4H-pyrano[2,3-b]pyridine-4-one,
2-(4-Hydroxy-phenyl)-pyrano[2,3-c]pyridin-4-one,
2-(4-hydroxy-phenyl)-pyrano[3,2-c]pyridin-4-one,
2-(2-(4-Hydroxyphenyl)-4-oxo-4H-chromen-3-yl)acetonitrile,
3-(Hydroxymethyl)-2-(4-hydroxyphenyl)-4H-chromen-4-one,
2-(4-Hydroxyphenyl)-3-(methoxymethyl)-4H-chromen-4-one,
3-(4-Hydroxyphenyl)-2H-isoquinolin-1-one,
3-(3-Fluoro-4-hydroxyphenyl)-5-methoxyisoquinolin-1(2H)-one,
2-Fluoro-4-(5-methoxy-1-(methylamino)-isoquinolin-3-yl)phenol,
4-Naphthalen-2-yl-phenol,
6-Naphthalen-2-yl-pyridin-3-ol,
3-(4-Hydroxyphenyl)-naphthalene-1-ol,
4-Isoquinolin-3-yl-phenol,
4-(1,6-Naphthyridin-7-yl)phenol,
2-(4-Hydroxy-phenyl)-[1,4]naphthoquinone,
4-(Benzo[b][1,4]dioxin-2-yl)phenyl acetate,
4-(Benzo[b][1,4]dioxin-2-yl)phenol,
4-(4H-Chromen-2-yl)-phenol,
2-(4-Hydroxyphenyl)benzo[e][1,3]oxazin-4-one,
6-Naphthalen-2-yl-pyridin-3-ol,
2-(4-Ethoxycarbonyloxy-phenyl)-4-oxo-4H-quinoline-1-carboxylic acid ethyl ester,
Nicotinic acid 4-(4-oxo-4H-chromen-2-yl)-phenyl ester,
Acetic acid 4-(4-oxo-4H-chromen-2-yl)-phenyl ester,
4-(4-oxo-4H-pyrano[2,3-b]pyridine-2-yl)phenyl acetate,
2-Amino-5-guanidino-pentanoic acid 4-(4-oxo-4H-chromen-2-yl)phenyl ester,
4-(Isoquinolin-3-yl)phenyl 2-amino-5-guanidinopentanoate,
4-(1-Oxo-1,2-dihydroisoquinolin-3-yl)phenyl 2-amino-5-guanidinopentanoate, and
2-(4-(Nicotinoyloxy)phenyl)-4-oxo-4H-chromene-5,7-diyl dinicotinate.

5. A method for increasing expression of ApoA-I in a mammal comprising administering a therapeutically effective amount of the compound 4-isoquinolin-3-yl-phenol.

6. A method for increasing expression of ApoA-I in a mammal comprising administering a therapeutically effective amount of a compound of Formula VII:

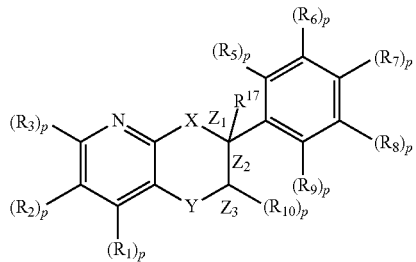

Formula VII wherein:
X is O;
Y is CO;

$R_1$, $R_2$, $R_3$, $R_5$, $R_6$, $R_7$, $R_8$, $R_9$, $R_{10}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or two adjacent substituents selected from $R_1$, $R_2$, $R_3$, $R_5$, $R_6$, $R_7$, $R_8$, $R_9$, and $R_{10}$ are connected in a 5 or 6-membered ring to form a bicyclic aryl or bicyclic heteroaryl;

$Z_1$ and $Z_3$ are single bonds, and $Z_2$ is a double bond;

and pharmaceutically acceptable salts and hydrates thereof.

7. The method of claim 6, wherein the compound of Formula I is 2-(4-hydroxy-phenyl)-pyrano[2,3-b]pyridin-4-one.

8. The method of claim 6, further comprising treating a cardiovascular, cholesterol or lipid related disorder.

* * * * *

UNITED STATES PATENT AND TRADEMARK OFFICE
CERTIFICATE OF CORRECTION

| | |
|---|---|
| PATENT NO. | : 8,093,273 B2 |
| APPLICATION NO. | : 11/255103 |
| DATED | : January 10, 2012 |
| INVENTOR(S) | : Norman C. W. Wong et al. |

It is certified that error appears in the above-identified patent and that said Letters Patent is hereby corrected as shown below:

Claim 4, col. 231, line 23,

"5,7-Difluoro-2-(4hydroxyl-phenyl)-chromen-4-one," should read

--5,7-Difluoro-2-(4-hydroxyl-phenyl)-chromen-4-one,--.

Claim 4, col. 231, lines 38-39,

"N[5-Hydroxy-2-(4-oxo-4H-chromen-2-yl)-phenyl]acetamide," should read

--N-[5-Hydroxy-2-(4-oxo-4H-chromen-2-yl)-phenyl]acetamide,--.

Claim 4, col. 231, line 60,

"7-Djihydroxy-2-(4-hydroxy-phenyl)-chromen-4-one," should read

--7-Dihydroxy-2-(4-hydroxy-phenyl)-chromen-4-one,--.

Signed and Sealed this
Twenty-seventh Day of March, 2012

David J. Kappos
*Director of the United States Patent and Trademark Office*